(12) United States Patent
Fang et al.

(10) Patent No.: US 12,344,671 B2
(45) Date of Patent: Jul. 1, 2025

(54) BLOOD-BRAIN BARRIER TRANSMIGRATING THERAPEUTIC COMPOUNDS AND USES THEREOF

(71) Applicant: National Research Council of Canada, Ottawa (CA)

(72) Inventors: Hung Fang, Ottawa (CA); Danica Stanimirovic, Ottawa (CA); Arsalan Haqqani, Kanata (CA); Will Costain, Ottawa (CA); Gregory Hussack, Ottawa (CA)

(73) Assignee: National Research Council of Canada, Ottawa (CA)

( * ) Notice: Subject to any disclaimer, the term of this patent is extended or adjusted under 35 U.S.C. 154(b) by 1244 days.

(21) Appl. No.: 17/050,075

(22) PCT Filed: Apr. 23, 2019

(86) PCT No.: PCT/CA2019/050499
§ 371 (c)(1),
(2) Date: Oct. 23, 2020

(87) PCT Pub. No.: WO2019/204912
PCT Pub. Date: Oct. 31, 2019

(65) Prior Publication Data
US 2021/0253715 A1  Aug. 19, 2021

Related U.S. Application Data

(60) Provisional application No. 62/661,869, filed on Apr. 24, 2018.

(51) Int. Cl.
| A61K 47/68 | (2017.01) |
| A61P 21/00 | (2006.01) |
| C07K 14/765 | (2006.01) |
| C07K 16/28 | (2006.01) |
| A61K 9/00 | (2006.01) |
| A61K 39/00 | (2006.01) |

(52) U.S. Cl.
CPC ...... *C07K 16/2863* (2013.01); *A61K 47/6843* (2017.08); *A61P 21/00* (2018.01); *C07K 14/765* (2013.01); *A61K 9/0019* (2013.01); *A61K 2039/505* (2013.01)

(58) Field of Classification Search
None
See application file for complete search history.

(56) References Cited

U.S. PATENT DOCUMENTS

| 5,693,761 A | 12/1997 | Queen et al. |
| 5,766,886 A | 6/1998 | Studnicka et al. |
| 5,821,123 A | 10/1998 | Studnicka |
| 5,859,205 A | 1/1999 | Adair et al. |
| 5,869,619 A | 2/1999 | Studnicka |
| 6,054,297 A | 4/2000 | Carter et al. |
| 6,180,370 B1 | 1/2001 | Queen et al. |
| 7,943,129 B2 | 5/2011 | Muruganandam et al. |
| 2013/0034572 A1 | 2/2013 | Stanimirovic et al. |

FOREIGN PATENT DOCUMENTS

| EP | 0519596 A1 | 12/1992 |
| EP | 626390 | 11/1994 |
| WO | 9504069 | 2/1995 |
| WO | 02057445 | 7/2002 |
| WO | 2003046560 | 6/2003 |
| WO | 2004076670 | 9/2004 |
| WO | 2007036021 | 4/2007 |
| WO | 2011/044542 A1 | 4/2011 |
| WO | 2011044542 | 4/2011 |
| WO | 2011061629 | 5/2011 |
| WO | 2011127580 A1 | 10/2011 |
| WO | 2013098651 | 7/2013 |
| WO | 2014136065 | 9/2014 |
| WO | 2015/131256 | 9/2015 |
| WO | 2015/131258 A1 | 9/2015 |
| WO | 2015131257 | 9/2015 |
| WO | 2015131258 | 9/2015 |
| WO | 2015/191934 A1 | 12/2015 |
| WO | 2018007950 | 1/2018 |
| WO | 2018/031424 A1 | 2/2018 |

OTHER PUBLICATIONS

De Pascalis et al. (2002). Journal of Immunology. 169:3076-3084.*
MacCallum et al. (1996). J. Mol. Biol. 262:732-745.*
Rudikoff et al. (1982). PNAS. 79:1979-1983.*
Arbabi Ghahroudi, M., Desmyter, A., Wyns, L., Hamers, R., and Muyldermans, S. (1997). Selection and identification of single domain antibody fragments from camel heavy-chain antibodies. FEBS Lett. 414: 521-526.
Artursson, P., and Karlsson, J. (1991). Correlation between oral drug absorption in humans and apparent drug permeability coefficients in human intestinal epithelial (Caco-2) cells. Biochem. Biophys. Res. Commun. 175: 880-5.
Balestrino, R., and Schapira, A.H. V (2018). Glucocerebrosidase and Parkinson Disease: Molecular, Clinical, and Therapeutic Implications. The Neuroscientist. 24(5) 540-559. DOI: 10.1177/1073858417748875.

(Continued)

*Primary Examiner* — Christine J Saoud
*Assistant Examiner* — Jon M Lockard
(74) *Attorney, Agent, or Firm* — Benoit & Cote Inc.; Mathieu Miron

(57) ABSTRACT

The present invention relates to a compound comprising an antibody or a fragment thereof operable to transmigrate across the blood-brain barrier (BBB), and a polypeptide related to the treatment of lysosomal storage disease (LSD), for the treatment of α-synucleinopathies, or both. The present invention also relates to pharmaceutical compositions and methods for 5 treating LSDs, treating, α-synucleinopathies, or both.

23 Claims, 23 Drawing Sheets
Specification includes a Sequence Listing.

(56) References Cited

OTHER PUBLICATIONS

Bell, A., Wang, Z.J., Arbabi-Ghahroudi, M., Chang, T.A., Durocher, Y., Trojahn, U., et al. (2010). Differential tumor-targeting abilities of three single-domain antibody formats. Cancer Lett. 289: 81-90.

Chothia, C., and Lesk, A.M. (1987). Canonical structures for the hypervariable regions of immunoglobulins. J. Mol. Biol. 196: 901-917.

Davies, J., and Riechmann, L. (1996). Affinity improvement of single antibody VH domains: residues in all three hypervariable regions affect antigen binding. Immunotechnology 2: 169-79.

De Kruif, J. and Logtenberg, T. (1996). Leucine zipper dimerized bivalent and bispecific scFv antibodies from a semi-synthetic antibody phage display library. J. Biol. Chem. 271: 7630-7634.

Dumoulin, M., Conrath, K., Meirhaeghe, A. Van, Meersman, F., Heremans, K., Frenken, L.G.J., et al. (2002). Single-domain antibody fragments with high conformational stability. Protein Sci. 11: 500-15.

Eisenberg, D., Schwarz, E., Komaromy, M., and Wall, R. (1984). Analysis of membrane and surface protein sequences with the hydrophobic moment plot. J. Mol. Biol. 179: 125-42.

Fluttert, M., Dalm, S., and Oitzl, M.S. (2000). A refined method for sequential blood sampling by tail incision in rats. Lab. Anim. 34: 372-8.

Garberg, P., Ball, M., Borg, N., Cecchelli, R., Fenart, L., Hurst, R.D., et al. (2005). In vitro models for the blood-brain barrier. Toxicol. In Vitro 19: 299-334.

Hamers-Casterman, C., Atarhouch, T., Muyldermans, S., Robinson, G., Hammers, C., Songa, E.B., et al. (1993). Naturally occurring antibodies devoid of light chains. Nature 363: 446-448.

Haqqani, A.S., Caram-Salas, N., Ding, W., Brunette, E., Delaney, C.E., Baumann, E., et al. (2013). Multiplexed evaluation of serum and CSF pharmacokinetics of brain-targeting single-domain antibodies using a NanoLC-SRM-ILIS method. Mol. Pharm. 10: 1542-56.

Haqqani, A.S., Kelly, J.F., and Stanimirovic, D.B. (2008a). Quantitative protein profiling by mass spectrometry using Isotope-coded affinity tags. Methods Mol. Biol. 439: 225-240.

Haqqani, A.S., Kelly, J.F., and Stanimirovic, D.B. (2008b). Quantitative protein profiling by mass spectrometry using label-free proteomics. Methods Mol. Biol. 439: 241-256.

Hussack, G., Hirama, T., Ding, W., MacKenzie, R., and Tanha, J. (2011b). Engineered single-domain antibodies with high protease resistance and thermal stability. PLoS One 6: e28218.

Iqbal, U., Trojahn, U., Albaghdadi, H., Zhang, J., O'Connor-McCourt, M., Stanimirovic, D., et al. (2010). Kinetic analysis of novel mono- and multivalent VHH-fragments and their application for molecular imaging of brain tumours. Br. J. Pharmacol. 160: 1016-28.

Jespers, L., Schon, O., Famm, K., and Winter, G. (2004). Aggregation-resistant domain antibodies selected on phage by heat denaturation. Nat. Biotechnol. 22: 1161-1165.

Kabat, E.A., and Wu, T.T. (1991). Identical V region amino acid sequences and segments of sequences in antibodies of different specificities. Relative contributions of VH and VL genes, minigenes, and complementarity-determining regions to binding of antibody-combining sites. J. Immunol. 147: 1709-1719.

Kim, D.Y., Kandalaft, H., Ding, W., Ryan, S., Faassen, H. Van, Hirama, T., et al. (2012). Disulfide linkage engineering for improving biophysical properties of human VH domains. Protein Eng. Des. Sel. 25: 581-589.

Hussack, G., Arbabi-Ghahroudi, M., Faassen, H. Van, Songer, J.G., Ng, K.K.S., MacKenzie, R., et al. (2011a). Neutralization of Clostridium difficile toxin A with single-domain antibodies targeting the cell receptor binding domain. J. Biol. Chem. 286: 8961-8976.

Li, S., Zheng, W., KuoLee, R., Hirama, T., Henry, M., Makvandi-Nejad, S., et al. (2009). Pentabody-mediated antigen delivery induces antigen-specific mucosal immune response. Mol. Immunol. 46: 1718-1726.

Lin, D., Alborn, W.E., Slebos, R.J.C., and Liebler, D.C. (2013). Comparison of protein immunoprecipitation-multiple reaction monitoring with ELISA for assay of biomarker candidates in plasma. J. Proteome Res. 12: 5996-6003.

Merritt, E.A., and Hol, W.G. (1995). AB5 toxins. Curr. Opin. Struct. Biol. 5: 165-171.

Mitsui, J., Matsukawa, T., Sasaki, H., Yabe, I., Matsushima, M., Dürr, A., et al. (2015). Variants associated with Gaucher disease in multiple system atrophy. Ann. Clin. Transl. Neurol. 2: 417-26.

Nicaise, M., Valerio-Lepiniec, M., Minard, P., and Desmadril, M. (2004). Affinity transfer by CDR grafting on a honimmunoglobulin scaffold. Protein Sci. 13: 1882-1891.

Nielsen, U.B., Adams, G.P., Weiner, L.M., and Marks, J.D. (2000). Targeting of bivalent anti-ErbB2 diabody antibody fragments to tumor cells is independent of the intrinsic antibody affinity. Cancer Res. 60: 6434-6440.

Pardridge, W.M. (1995). Transport of small molecules through the blood-brain barrier: biology and methodology. Adv. Drug Deliv. Rev. 15: 5-36.

Puschmann, A., Bhidayasiri, R., and Weiner, W.J. (2012). Synucleinopathies from bench to bedside. Parkinsonism Relat. Disord. 18 Suppl 1: S24-7.

Nuttall, S.D., Krishnan, U. V, Doughty, L., Pearson, K., Ryan, M.T., Hoogenraad, N.J., et al. (2003). Isolation and characterization of an IgNAR variable domain specific for the human mitochondrial translocase receptor Tom70. Eur. J. Biochem. 270: 3543-3554.

Ridgway, J.B.B., Presta, L.G., and Carter, P. (1996). 'Knobs-into-holes' engineering of antibody C H 3 domains for heavy chain heterodimerization. Protein Eng. 9: 617-621.

Samuels, B.L., Mick, R., Vogelzang, N.J., Williams, S.F., Schilsky, R.L., Safa, A.R., et al. (1993). Modulation of vinblastine resistance with cyclosporine: A phase I study. Clin. Pharmacol. Ther. 54: 421-429.

Watanabe, T., Tsuge, H., Oh-Hara, T., Naito, M., Tsuruo, T., Gigante, M., et al. (1995). Comparative study on reversal efficacy of SDZ PSC 833, cyclosporin A and verapamil on multidrug resistance in vitro and in vivo. Acta Oncol. 34: 235-41.

Zhang, J., Tanha, J., Hirama, T., Khieu, N.H., To, R., Tong-Sevinc, H., et al. (2004b). Pentamerization of single-domain antibodies from phage libraries: A novel strategy for the rapid generation of high-avidity antibody reagents. J. Mol. Biol. 335: 49-56.

To, R., Hirama, T., Arbabi-Ghahroudi, M., MacKenzie, R., Wang, P., Xu, P., et al. (2005). Isolation of monomeric human VHs by a phage selection. J. Biol. Chem. 280: 41395-41403.

Ying, T., Chen, W., Gong, R., Feng, Y., and Dimitrov, D.S. (2012). Soluble monomeric IgG1 Fc. J. Biol. Chem. 287: 19399-408.

Yun, S.P., Kim, D., Kim, S., Kim, S., Karuppagounder, S.S., Kwon, S.-H., et al. (2018). α-Synuclein accumulation and GBA deficiency due to L444P GBA mutation contributes to MPTP-induced parkinsonism. Mol. Neurodegener. 13: 1.

Zhang, J., Li, Q., Nguyen, T.D., Tremblay, T.L., Stone, E., To, R., et al. (2004a). A pentavalent single-domain antibody approach to tumor antigen discovery and the development of novel proteomics reagents. J. Mol. Biol. 341: 161-169.

Zhu, X., Wang, L., Liu, R., Flutter, B., Li, S., Ding, J., et al. (2010). COMBODY: One-domain antibody multimer with improved avidity. Immunol. Cell Biol. 88: 667-675.

Zunke, F., Moise, A.C., Belur, N.R., Gelyana, E., Stojkovska, I., Dzaferbegovic, H., et al. (2017). Reversible Conformational Conversion of α-Synuclein into Toxic Assemblies by Glucosylceramide. Neuron 97: 92-107.e10.

Ribecco-Lutkiewicz, M., Sodja, C., Haukenfrers, J., Haqqani, A.S., Ly, D., Zachar, P., et al. (2018). A novel human induced pluripotent stem cell blood-brain barrier model: Applicability to study antibody-triggered receptor-mediated transcytosis. Sci. Rep. 8: 1873.

Gottesman, M.M., and Pastan, I. (1993). Biochemistry of Multidrug Resistance Mediated by the Multidrug Transporter. Annu. Rev. Biochem. 62: 385-427.

Henry, K.A. et al., Identification of cross-reactive single-domain antibodies against serum albumin using next-generation DNA sequencing; Protein Engineering, Design & Selection, Aug. 27, 2015, vol. 28, No. 10, pp. 379-383, ISSN 1741-0134, Tables I-III R28, M79.

International Search Report of PCT/CA2019/050499; Jul. 24, 2019; Misener, Stephen.

(56) References Cited

OTHER PUBLICATIONS

Kan Shih-Hsin et al: "Insulin-like growth factor II peptide fusion enables uptake and lysosomal delivery of alpha-N-acetylglucosaminidase to mucopolysaccharidosis type IIIB fibroblasts", Biochemical Journal, Published By Portland Press On Behalf of the Biochemical Society, GB, vol. 458, No. par 2, Mar. 1, 2014 (Mar. 1, 2014), pp. 281-289, XP009177918, ISSN: 0264-6021, DOI: 10.1042/BJ20130845, figure 7.

Qing-Hiu Zhou et al: "Brain-Penetrating IgG-Iduronate 2-Sulfatase Fusion Protein for the Mouse", Drug Metabolism and Disposition, Feb. 1, 2012 (Feb. 1, 2012), pp. 329-335, XP055239284, DOI: 10.1124/dmd.111.042903.

The Extended European Search Report 19792686.8, National Research Council of Canada, May 6, 2022.

Communication pursuant to Article 94(3) EPC, 19792686.8-1111, Apr. 22, 2024.

Danica B Stanimirovic et al: "Blood & ndash; brain barrier models: in vitro to in vivo translation in preclinical development of CNS-targeting biotherapeutics", Expert Opinion On Drug Discovery, vol. 10, No. 2, Nov. 12, 2014 (Nov. 12, 2014), pp. 141-155, XP055395138, London, GB.

Tersrappen Georg C et al: "Strategies for delivering therapeutics across the blood-brain barrier", Nature Reviews Drug Discovery, Nature Publishing Group, GB, vol. 20, No. 5, Mar. 1, 2021 (Mar. 1, 2021), pp. 362-383, XP037444970.

Ruben J. Boado et al: "Insulin Receptor Antibody– Sulfamidase Fusion Protein Penetrates the Primate Blood– Brain Barrier and Reduces Glycosoaminoglycans in Sanfilippo Type A Cells", Molecular Pharmaceutics, vol. 11, No. 8, Aug. 4, 2014 (Aug. 4, 2014), pp. 2928-2934, XP055406273, US.

Abulrob A et al: "The blood-brain barrier transmigrating single domain antibody: mechanisms of transport and antigenic epitopes in human brain endothelial cells", Jounral of Neurochemistry, Wiley-Blackwell Publishing Ltd, GB, vol. 95, No. 4, Nov. 1, 2005 (Nov. 1, 2005), pp. 1201-1214, XP003010699.

* cited by examiner

| | M7(PM)2 | M8(PM)2 | M6PM | M7PM | M8PM | M5 | M6 | M7 | M8 | M9 | %Bi | %Mono | %Neutrals |
|---|---|---|---|---|---|---|---|---|---|---|---|---|---|
| P454 A3#1 | 4 | 29 | 5 | 23 | 24 | 6 | 4 | 1 | 2 | 3 | 33 | 52 | 15 |
| P454 A3#1 | 5 | 34 | 6 | 27 | 28 | | | | | | 39 | 61 | |
| P454 A3#1 4°C | 3 | 37 | 2 | 19 | 30 | 4 | | | 5 | | 40 | 51 | 9 |
| P454 A3#1 4°C | 3 | 41 | 2 | 21 | 33 | | | | | | 44 | 56 | |
| P454 A3#1 -80°C | 3 | 35 | 2 | 19 | 30 | 4 | | | 7 | | 38 | 51 | 11 |
| P454 A3#1 -80°C | 3 | 39 | 3 | 21 | 34 | | | | | | 43 | 57 | |
| | M5P2 | M6P2 | M3P | M4P | M5P | M6P | | | | | | | |
| P454 A4#2 | 11 | 37 | 27 | 17 | 8 | 0 | | | | | 48 | 52 | |
| P454 A7#1 | 13 | 35 | 27 | 17 | 9 | 0 | | | | | 48 | 52 | |

Figure 4

| Parameter | Units | IDS-C1 | IGF1R3H5-IDS | IGF1R3H5-IDS-HSA | IGF1R3H5-IDS-R28 | IGF1R3H5-IDS-M79 |
|---|---|---|---|---|---|---|
| | | | 2-Compartment population PK analysis | | | |
| V | mL/kg | 38.9 ± 6.17 | 42.4 ± 5.47 | 65.7 ± 3.71 | 58.6 ± 2.58 | 64.9 ± 2.89 |
| V2 | mL/kg | 142 ± 16.0 | 134 ± 13.7 | 152 ± 12.0 | 123 ± 11.8 | 166 ± 10.9 |
| CL | mL/min/kg | 0.924 ± 0.054 | 0.5159 ± 0.0335 | 0.0705 ± 0.0132 | 0.0458 ± 0.0062 | 0.0527 ± 0.0091 |
| CL2 | mL/min/kg | 1.78 ± 0.189 | 1.96 ± 0.166 | 1.12 ± 0.108 | 0.595 ± 0.0599 | 0.745 ± 0.155 |
| AUC | nmol*min/mL | 84.2 ± 4.93 | 151 ± 9.8 | 1219 ± 228 | 1702 ± 125 | 1477 ± 254 |
| Cmax | nmol/mL | 2.00 ± 0.31704 | 1.84 ± 0.237 | 1.31 ± 0.0738 | 1.33 ± 0.108 | 1.20 ± 0.0535 |
| VSS | mL/kg | 181 ± 18.1 | 176 ± 14.7 | 218 ± 12.0 | 181 ± 27.8 | 231 ± 9.19 |
| Alpha_hl | min | 8.87 ± 1.28 | 9.84 ± 1.36 | 27.6 ± 3.38 | 44.6 ± 3.27 | 41.8 ± 9.24 |
| Beta_hl | min | 182 ± 20.7 | 275 ± 35.3 | 2209 ± 503 | 2846 ± 650 | 3142 ± 670 |

Figure 17

|                  | SERUM          |                |         | CSF       | AUC      |           |
|------------------|----------------|----------------|---------|-----------|----------|-----------|
|                  | $t_{1/2}\alpha$ | $t_{1/2}\beta$ | AUC     | AUC       | RATIO    |           |
| IDS-C1           | 9.0            | 217.8          | 55.7    | 34.3      | 0.62     | $\times 10^{-3}$ |
| IGF1R3H5-IDS     | 12.3           | 381.3          | 115.6   | 310.4     | 2.69     | $\times 10^{-3}$ |
| IGF1R3H5-IDS-HSA | 24.9           | 6847           | 442.4   | 1455      | 3.29     | $\times 10^{-3}$ |
| IGF1R3H5-IDS-R28 | 35.9           | 2333           | 902.7   | 1796      | 1.99     | $\times 10^{-3}$ |
| IDS-R28          | 11.6           | 263.9          | 295.7   |           |          |           |
|                  | min            | min            | μM·min  | nM·min    |          |           |

Figure 20

BLOOD-BRAIN BARRIER TRANSMIGRATING THERAPEUTIC COMPOUNDS AND USES THEREOF

CROSS-REFERENCE TO RELATED APPLICATIONS

This application is a U.S. National Phase application under 35 U.S.C. § 371 of PCT/CA2019/050499, filed Apr. 23, 2019, which claims priority from and the benefit of U.S. Provisional Patent Application 62/661,869 filed Apr. 24, 2018, the specifications of which are hereby incorporated by reference in their entireties.

REFERENCE TO AN ELECTRONIC SEQUENCE LISTING

The contents of the electronic sequence listing (P4314US01SequenceListing.txt; Size: 302 429 bytes; and Date of Creation: Apr. 23, 2021) is herein incorporated by reference in its entirety.

FIELD OF THE INVENTION

The present invention relates to enabling blood-brain barrier (BBB) transmigration of proteins or functional fragments thereof involved in lysosomal storage disease (LSD). The present invention relates to enabling blood-brain barrier (BBB) transmigration of proteins or functional fragments thereof involved in α-synucleinopathies using a BBB-transmigrating antibody or fragment thereof, and uses thereof. More specifically, the present invention describes a fusion protein comprising of IGF1R3H5 and IDS (iduronate-2-sulfatase) or GCase (acid beta-glucosidase or glucocerebrosidase), and uses thereof.

BACKGROUND OF THE INVENTION

Lysosomal storage diseases (LSDs) are a group of approximately 50 rare inherited metabolic disorders that result from defects in lysosomal function. LSDs are usually a consequence of deficiency of a single enzyme required for the metabolism of lipids, glycoproteins and mucopolysaccharides. Individually, LSDs occur with incidences of less than 1:100,000; however, as a group the incidence is about 1:5,000-1:10,000. Most of these disorders are autosomal recessively inherited such as Gaucher's disease and Niemann-Pick disease, type C; however a few are X-linked recessively inherited, such as Fabry disease and Hunter syndrome (MPS II). Disease is caused by excessive accumulation of non-processed material in cells and tissues resulting in gross abnormalities in development and mental retardation when the CNS is affected.

There are no cures for lysosomal storage diseases and treatment is mostly symptomatic, although bone marrow transplantation and enzyme replacement therapy (ERT) have been tried with some success. ERT (injection of recombinantly produced active enzyme that is affected by the disease) has been successful in treating peripheral symptoms (by improving enzyme activity in peripheral tissues such as liver and heart) but is ineffective for treating central (brain) symptoms, because enzymes cannot cross the BBB after systemic injection and thus cannot reach neuronal tissues.

Lysosomal enzymes are known to contribute to the pathology of certain complex neurodegenerative diseases, including Parkinson's disease (PD), Multiple Systems Atrophy (MSA) and Dementia with Lewy Bodies (DLB). In particular there is an abundance of reports implicating glucocerebrosidase in the above mentioned synucleinopathies (Mitsui et al., 2015; Balestrino and Schapira, 2018), which arise from the accumulation of abnormal aggregates of α-synuclein (Puschmann et al., 2012). The involvement of glucocerebrosidase in synucleinopathies is supported by the observed increase in the incidence of PD and MSA in Gaucher's patients, as well as the contribution of glucocerebrosidase to MPTP-induced parkinsonism (Yun et al., 2018) and the promotion of toxic assemblies of α-synuclein (Zunke et al., 2017).

While the characteristics of the BBB protect the brain from pathogens and toxins, they equally prevent the entry of most therapeutics. In fact, less than 5% of small molecule therapeutics and virtually none of the larger therapeutics can cross the BBB in pharmacologically relevant concentrations (i.e., sufficient to engage a central nervous system (CNS) target and elicit a pharmacologic/therapeutic response) unless they are specifically 'ferried', that is, coupled to a transporter molecule. Due to the lack of effective 'carriers' to transport molecules across the BBB, numerous drugs against neurodegenerative diseases have been 'shelved' or eliminated from further development as they cannot be delivered to the brain in sufficient amounts.

Peptides, antibodies and proteins (such as enzymes) have to be 'ferried' across the BBB using 'carriers' that recognize BBB receptors that undergo receptor-mediated transcytosis or other forms of vesicular transport through brain endothelial cells. Antibodies against such receptors have been developed as 'Trojan horses' to deliver biologics across the BBB.

Enzyme replacement therapy with IDS (iduronate-2-sulfatase) is used to treat peripheral symptoms in mucopolysaccharidosis type II (MPS II; also known as Hunter syndrome) patients. Likewise, ERT with recombinant glucocerebrosidase is used to treat peripheral symptoms in Gaucher patients. Creating a fusion protein consisting of a 'Trojan horse' antibody that crosses the BBB and a payload (such as IDS or GCase) is expected to enable ERT in the brain. An example is a fusion protein consisting of the Insulin receptor antibody (IgG) expressed in fusion with 2 molecules of IDS at its C-terminus end (developed by Armagen). This fusion protein has a MW of ~300 kDa and demonstrates side effects due to insulin receptor engagement (hypoglycemia). Furthermore, the fusion molecule is not optimized for lysosomal targeting in cells and neurons.

Therefore, there is a need for additional therapeutics for enzyme or protein replacement therapy of LSDs that mitigate the disadvantages of current therapies.

There is also a need for or additional therapeutics for enzyme or protein replacement therapy of α-synucleinopathies that mitigate the disadvantages of current therapies.

SUMMARY OF THE INVENTION

According to an embodiment, there is provided a compound comprising an antibody or a fragment thereof operable to transmigrate the blood-brain barrier (BBB), and a polypeptide related to the treatment of lysosomal storage disease (LSD).

According to another embodiment, there is provided a compound comprising
an antibody or a fragment thereof operable to transmigrate the blood-brain barrier (BBB),
and
a polypeptide related to the treatment of α-synucleinopathies.

The antibody or fragment thereof may bind TMEM30A or IGF1R.

The antibody or fragment thereof may comprises
a complementarity determining region (CDR) 1 sequence GFKITHYTMG (SEQ ID NO:1); CDR2 sequence RITWGGX$_1$X$_2$TX$_3$YSNSVKG, where X$_1$ is D or K, X$_2$ is N or D, and X$_3$ is F, I or L (SEQ ID NO:2); and CDR3 sequence GSTSTAX$_4$PLRVDY, where X$_4$ is T or K (SEQ ID NO:3);
a complementarity determining region (CDR) 1 sequence EYPSNFYA (SEQ ID NO:6); CDR2 sequence VSRDGLTT (SEQ ID NO:7); and CDR3 sequence AIVITGVWNKVDVNSRSYHY (SEQ ID NO:8); or
a complementarity determining region (CDR) 1 sequence GRTIDNYA (SEQ ID NO:11); CDR2 sequence IDWGDGGX, where X is A or T (SEQ ID NO:12), where X is A or T;
and CDR3 sequence AMARQSRVNLDVARYDY (SEQ ID NO:13).

The antibody or fragment thereof may comprise an amino acid sequence selected from the group consisting of:

(SEQ ID NO: 5)
X$_1$VQLVESGGGLVQPGGSLRLSCAASGFKITHYTMGWX$_2$RQAPGKX$_3$X$_4$

EX$_5$VSRITWGGDNTFYSNSVKGRFTISRDNSKNTX$_6$YLQMNSLRAEDT

AVYYCAAGSTSTATPLRVDYWGQGTLVTVSS, wherein X$_1$=D or E, X$_2$=F or V, X$_3$=E or G, X$_4$=R or L, X$_5$=F or W, and X$_6$=L or V;

(SEQ ID NO: 9)
X$_1$VX$_2$LX$_3$ESGGGLVQX$_4$GGSLRLSCX$_5$ASEYPSNFYAMSWXRQAPGK

X$_7$X$_8$EX$_9$VX$_{10}$GVSRDGLTTLYADSVKGRFTX$_{11}$SRDNX$_{12}$KNTX$_{13}$X$_{14}$L

QMNSX$_{15}$X$_{16}$AEDTAVYYCAIVITGVWNKVDVNSRSYHYWGQGTX$_{17}$V

TVSS, wherein X$_1$ is E or Q; X$_2$ is K or Q; X$_3$ is V or E; X$_4$ is A or P; X$_5$ is V or A; X$_6$ is F or V; X$_7$ is E or G; X$_8$ is R or L; X$_9$ is F or W; X$_{10}$ is A or S; X$_{11}$ is M or I; X$_{12}$ is A or S; X$_{13}$ is V or L; X$_{14}$ is D or Y; X$_{15}$ is V or L; X$_{16}$ is K or R; and X$_{17}$ is Q or L; and
X$_1$VX$_2$LX$_3$ESGGGLVQX$_4$GGSLRLSCAASGRTIDN-YAMAWX$_5$RQAPGKX$_6$X$_7$EX$_8$VX$_9$TIDWGDGG-X$_{10}$RYANS-VKGRFTISRDNX$_{11}$KX$_{12}$TX$_{13}$YLQMNX$_{14}$LX$_{15}$X$_{16}$EDT AVYX$_{17}$CAMARQSRVNLDVARYDYWGQGTX$_{18}$VTVSS (SEQ ID NO:14), wherein X$_1$ is E or Q; X$_2$ is K or Q; X$_3$ is V or E; X$_4$ is A or P; X$_5$ is V or S; X$_6$ is D or G; X$_7$ is L or R; X$_8$ is F or W; X$_9$ is A or S; X$_{10}$ is A or T; X$_{11}$ is A or S; X$_{12}$ is G or N; X$_{13}$ is M or L; X$_{14}$ is N or R; X$_{15}$ is E or R; X$_{16}$ is P or A; X$_{17}$ is S or Y; and X$_{18}$ is Q or L;
or a sequence substantially identical thereto operable to transmigrate across the BBB.

The antibody or fragment thereof may be a single chain Fab (scFab), a single chain Fv (scFv), or a single domain antibody (sdAb).

The polypeptide related to the treatment of LSD, or for the treatment of α-synucleinopathy may be selected from the group consisting of Type I sulfatases, a glucosidase or a glucocerebrosidase.

The polypeptide related to the treatment of LSD, or for the treatment of α-synucleinopathy may be iduronate-2-sulfatase (IDS) (SEQ ID NO:24), acid-beta-glucosidase (GCase) (SEQ ID NO: 68), acid-beta-glucosidase mut1 (GCase-mut1) (SEQ ID NO:26).

The antibody or fragment thereof may be linked to the polypeptide.

The antibody or fragment thereof may be linked to the polypeptide with a linker sequence.

The linker sequence in any one of SEQ ID NO: 30, 31, 32, 33, 34, 35, 36, 37, 39, 41, 42, 43, 44, 47, 48, 49, 50, 52, 53, 54, 55, 56, 57, 58. 59, 60, 61, 62, 64, 65, or 70 may be (GGGGS)$_n$, wherein n≥1, or any suitable linker.

The compound may be glycosylated.

The polypeptide related to the treatment of LSD, or for the treatment of α-synucleinopathy may be glycosylated polypeptide.

The glycosylated polypeptide may be glycosylated with one or more N-glycans.

The N-glycans of the glycosylated polypeptide may contain one or more mannose 6-phosphate residues.

The glycosylated polypeptide may contain monophosphorylated N-glycans, bi-phosphorylated N-glycans or a combination thereof.

The compound may further comprise human serum albumin (HSA) (SEQ ID NO:67), human serum albumin K573P (HSA (K573P)) (SEQ ID NO:28), or an albumin targeting moiety.

The albumin targeting moiety may be an antibody or a fragment thereof capable of targeting albumin.

The albumin targeting moiety may be a single domain antibody (sdAb) comprising:
a CDR1 sequence GRTFIAYA (SEQ ID NO:16), CDR2 sequence ITNFAGGTT (SEQ ID NO: 17), and CDR3 sequence AADRSAQTMRQVRPVLPY (SEQ ID NO:18);
a CDR1 sequence GSTFSSSS (SEQ ID NO:20), CDR2 sequence ITSGGST (SEQ ID NO: 21), and CDR3 sequence NVAGRNWVPISRYSPGPY (SEQ ID NO:22);
an amino acid sequence (SEQ ID NO: 19)
QVQLVESGGGLVQAGGSLRLSCVASGRTFIAYAMGWFRQAPGKEREFVA

AITNFAGGTTYYADSVKGRFTISRDNAKTTVYLQMNSLKPEDTALYYCA

ADRSAQTMRQVRPVLPYWGQGTQVTVSS;

or
an amino acid sequence (SEQ ID NO: 23)
QVKLEESGGGLVQAGGSLKLSCAASGSTFSSSSVGWYRQAPGQQRELVA

AITSGGSTNTADSVKGRFTMSRDNAKNTVYLQMRDLKPEDTAVYYCNVA

GRNWVPISRYSPGPYWGQGTQVTVSS.

The compound may be any one of the following compounds:
1) a compound comprising an antibody or fragment thereof having CDR 1 sequence EYPSNFYA (SEQ ID NO:6), CDR2 sequence VSRDGLTT (SEQ ID NO:7), CDR3 sequence AIVITGVWNKVDVNSRSYHY (SEQ ID NO:8), IDS (SEQ ID NO: 24); and human serum albumin (HSA) (SEQ ID NO:67) or human serum albumin K573P (HSA (K573P)) (SEQ ID NO:28);
2) a compound comprising an antibody or fragment thereof having CDR 1 sequence EYPSNFYA (SEQ ID NO:6), CDR2 sequence VSRDGLTT (SEQ ID NO:7), a CDR3 sequence AIVITGVWNKVDVNSRSYHY (SEQ ID NO:8), IDS (SEQ ID NO:24), and a CDR1 sequence GRTFIAYA (SEQ ID NO:16), CDR2 sequence ITNFAGGTT (SEQ ID NO: 17), and CDR3 sequence AADRSAQTMRQVRPVLPY (SEQ ID NO:18);
3) a compound comprising an antibody or fragment thereof having CDR 1 sequence EYPSNFYA (SEQ ID NO:6), CDR2 sequence VSRDGLTT (SEQ ID NO:7); CDR3 sequence AIVITGVWNKVDVNSRSYHY (SEQ ID NO:8), IDS (SEQ ID NO:24), and a CDR1 sequence GSTFSSSS (SEQ ID NO:20), CDR2 sequence ITSGGST (SEQ ID NO: 21), and CDR3 sequence NVAGRNWVPISRYSPGPY (SEQ ID NO:22);
4) IGF1R3H5-IDS-HSA (K573P) (SEQ ID NO:35);
5) IGF1R3H5-IDS-R28 (SEQ ID NO:36); and
6) IGF1R3H5-IDS-M79 (SEQ ID NO:37).

According to another embodiment, there is provided a composition comprising the compound of the present invention and a pharmaceutically acceptable diluent, carrier, or excipient.

According to another embodiment, there is provided a compound of the present invention or a composition of the present invention, for the treatment of LSD in the brain in a subject in need thereof.

According to another embodiment, there is provided a compound of the present invention or a composition of the present invention, for the treatment of α-synucleinopathy in the brain in a subject in need thereof.

According to another embodiment, there is provided a method of delivering a polypeptide related to LSD across the BBB, comprising administering the compound according to the present invention or a composition according to the present invention to a subject in need thereof.

According to another embodiment, there is provided a method of delivering a polypeptide related to α-synucleinopathy across the BBB, comprising administering the compound according to the present invention or a composition according to the present invention to a subject in need thereof.

The administering may be intravenous (iv), subcutaneous (sc), or intramuscular (im).

According to another embodiment, there is provided a use of the compound according to the present invention or a composition according to the present invention related to the treatment of LSD in the brain in a subject in need thereof.

According to another embodiment, there is provided a use of the compound according to the present invention or a composition according to the present invention related to the treatment of α-synucleinopathy in the brain in a subject in need thereof.

The compound may be for use intravenously (iv), subcutaneously (sc), or intramuscularly (im).

The LSD may be a sphingolipidose, a mucopolysaccharidoses, a glycoproteinose, an oligosaccharidose, a glycogenose, a lipidose or a neuronal ceroid lipofuscinoses.

The α-synucleinopathy may be Parkinson Disease (PD), dementia with Lewy Bodies or Multiple System Atrophy (MSA).

According to another embodiment, there is provided a nucleic acid vector comprising a nucleotide sequence encoding a compound of the present invention.

According to another embodiment, there is provided a cell comprising the nucleic acid vector of the present invention for expressing the compound of the present invention.

According to another embodiment, there is provided a cell for expressing the compound of the present invention.

BRIEF DESCRIPTION OF THE DRAWINGS

These and other features of the invention will now be described by way of example, with reference to the appended drawings, wherein:

FIG. 4 shows the results of an N-glycan analysis with results presented as percentage area under the peak for each N-glycan structure detected using DSA-FACE.

FIG. 17 shows the results of a WinNonlin analysis of in vivo serum PK data in rats for IDS-C1, IGF1R3H5-IDS, IGF1R3H5-IDS-HSA, IGF1R3H5-IDS-R28 and IGF1R3H5-IDS-M79.

FIG. 20 shows the results of a Prism analysis of in vivo serum and CSF PK data in rats for IDS-C1, IGF1R3H5-IDS, IGF1R3H5-IDS-HSA, IGF1R3H5-IDS-R28, and IDS-R28. The analysis shows that IGF1R3H5 increases brain exposure of IDS by increasing the AUC ratio. The data also demonstrates that HSA or R28 increases total brain exposure (CSF AUC) by increasing the serum half-life. The data also shows that the serum PK of IGF1R3H5-IDS-R28 was extended relative to IDS-R28.

DETAILED DESCRIPTION OF THE INVENTION

Figure 1:
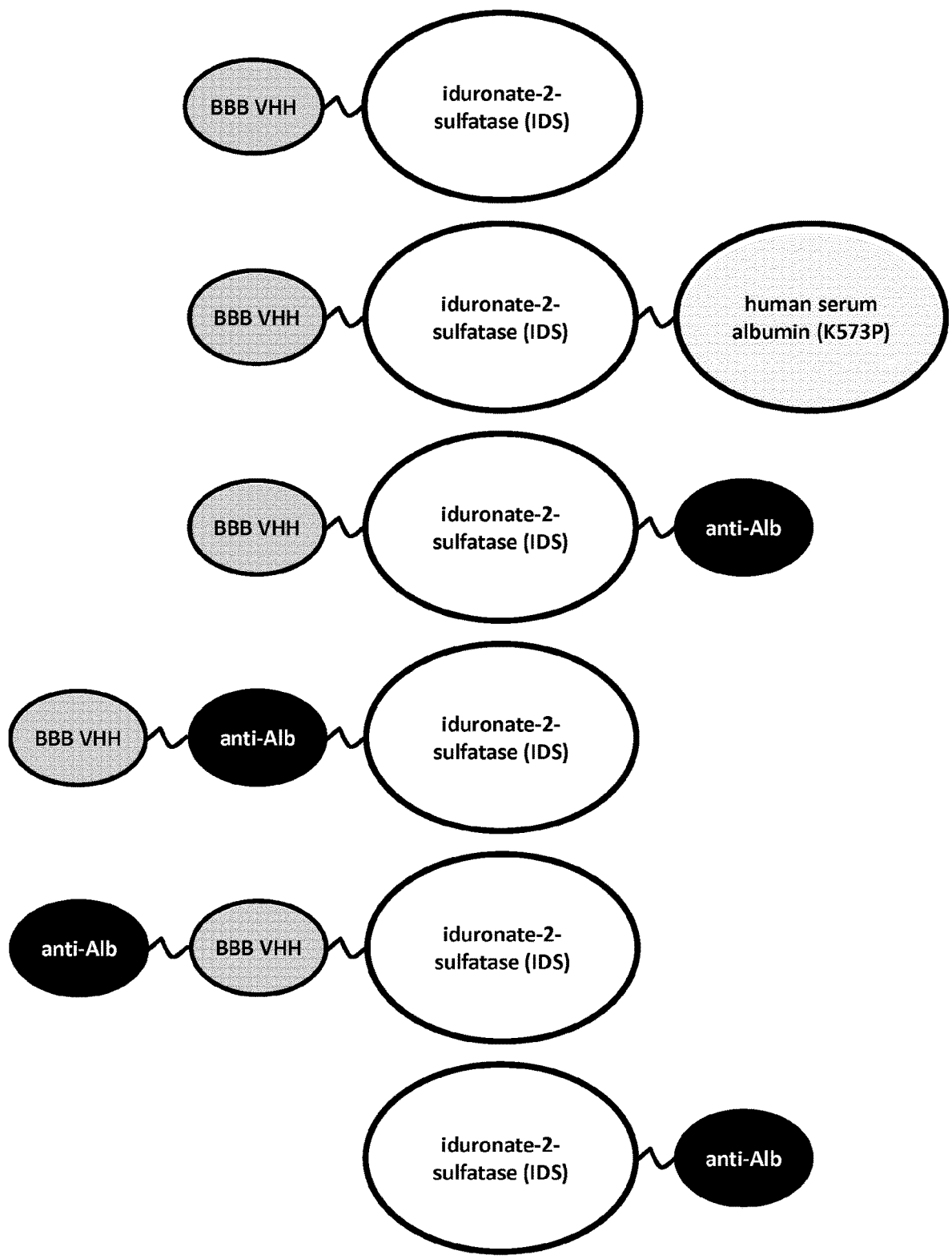
FIG. 1 depicts the arrangement of some of the constructs utilized herein. "BBB VHH" indicates BBB penetrating single domain antibodies (IGF1R3H5 or IGF1R5H2 or FC5). "anti-Alb" indicates anti albumin single domain antibodies (R28 VHH or M79 VHH) or Alb1 or Alb8.

In a first embodiment, there is disclosed a compound comprising an antibody or a fragment thereof operable to transmigrate the blood-brain barrier (BBB), and a polypeptide related to the treatment of lysosomal storage disease (LSD).

In another embodiment, there is disclosed a compound comprising an antibody or a fragment thereof operable to transmigrate the blood-brain barrier (BBB), and a polypeptide related to the treatment of α-synucleinopathy.

As used herein the term "polypeptide" refers to enzymes, proteins, or functional fragments thereof, that are related to the treatment of LSD, α-synucleinopathy, or both.

The present invention provides isolated or purified fusion proteins comprising an antibody or fragment thereof and a polypeptide related to LSD, related to α-synucleinopathy, or both, wherein the antibody or fragment specifically binds to an Insulin-Like Growth Factor 1 Receptor (IGF1R) epitope or a TMEM30A epitope, and wherein the antibody or fragment thereof is operable to transmigrate the blood-brain barrier, along with a polypeptide related to the treatment of LSD, to the treatment of α-synucleinopathy, or both.

The antibody or fragment thereof as described herein is capable of transmigration across the blood brain barrier. The brain is separated from the rest of the body by a specialized endothelial tissue known as the blood-brain barrier (BBB). The endothelial cells of the BBB are connected by tight junctions and efficiently prevent many therapeutic compounds from entering the brain.

In addition to low rates of vesicular transport, one specific feature of the BBB is the existence of enzymatic barrier(s) and high level(s) of expression of ATP-dependent transporters on the abluminal (brain) side of the BBB, including P-glycoprotein (Gottesman and Pastan, 1993; Watanabe et al., 1995), which actively transport various molecules from the brain into the blood stream (Samuels et al., 1993). Only small (<500 Daltons) and hydrophobic (Pardridge, 1995) molecules can more readily cross the BBB. Thus, the ability of the antibody or fragment thereof as described above to specifically bind the surface receptor, internalize into brain endothelial cells, and undergo transcytosis across the BBB by evading lysosomal degradation is useful in the neurological field.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_H2$, $C_H3$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al. (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the Kabat scheme (i.e. CDR1, 2 and 3, for each variable region).

An "antibody fragment" as referred to herein may include any suitable antigen-binding antibody fragment, or simply, antigen-binding fragment known in the art. The antibody fragment may be a naturally-occurring antibody fragment, or may be obtained by manipulation of a naturally-occurring antibody or by using recombinant methods. For example, an antibody fragment may include, but is not limited to an Fv, single-chain Fv (scFv; a molecule consisting of $V_L$ and $V_H$ connected with a peptide linker), Fab, F(ab')$_2$, single-domain antibody (sdAb; a fragment composed of a single $V_L$ or $V_H$), and multivalent presentations of any of these. Antibody fragments such as those just described may require linker sequences, disulfide bonds, or other types of covalent bond to link different portions of the fragments; those of skill in the art will be familiar with the requirements of the different types of fragments and various approaches for their construction.

In a non-limiting example, the antibody fragment may be an sdAb derived from naturally-occurring sources. Heavy chain antibodies of camelid origin (Hamers-Casterman et al., 1993) lack light chains and thus their antigen binding sites consist of one domain, termed $V_HH$. sdAb have also been observed in shark and are termed $V_{NAR}$ (Nuttall et al., 2003). Other sdAb may be engineered based on human Ig heavy and light chain sequences (Jespers et al., 2004; To et al., 2005). As used herein, the term "sdAb" includes those sdAb directly isolated from $V_H$, $V_HH$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAb possess desirable properties for antibody molecules, such as high thermostability, high detergent resistance, relatively high resistance to proteases (Dumoulin et al., 2002) and high production yield (Arbabi Ghahroudi et al., 1997); they can also be engineered to have very high affinity by isolation from an immune library (Li et al., 2009) or by in vitro affinity maturation (Davies and Riechmann, 1996). Further modifications to increase stability, such as the introduction of non-canonical disulfide bonds (Hussack et al., 2011a, 2011b; Kim et al., 2012), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

The present invention further encompasses an antibody or fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to other human antibody fragment framework regions (Fv, scFv, Fab) or to other proteins of similar size and nature onto which CDR can be grafted (Nicaise et al., 2004). In such a case, the conformation of the one or more than one hypervariable loop(s) is likely preserved, and the affinity and specificity of the sdAb for its target (i.e., IGF1R) is likely minimally affected. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would also be amply familiar with methods of preparing such humanized antibody fragments and humanizing amino acid positions.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, His5, or His6), or a combination thereof. In another example, the additional sequence may be a biotin recognition site such as that described by Cronan et al. in WO 95/04069 or Voges et al. in WO/2004/076670.

As is also known to those of skill in the art, linker sequences may be used in conjunction with the antibody or fragment thereof, the polypeptide related to treatment of lysosomal storage disease (LSD) or treatment of α-synucleinopathies, the additional sequences or tags, or may serve as a detection/purification tag. As used herein, the term "linker sequences" is intended to mean short peptide sequences that occur between protein domains. Linker sequences are often composed of flexible residues like glycine and serine so that the adjacent protein domains are free to move relative to one another. The linker sequence can be any linker sequence known in the art that would allow for the antibody and polypeptide of a compound, of the present invention to be operably linked for the desired function. The linker may be any sequence in the art (either a natural or synthetic linker) that allows for an operable fusion comprising an antibody or fragment linked to a polypeptide. For example, the linker sequence may be a linker sequence L such as $(GGGGS)_n$, wherein n equal to or greater than 1, or from about 1 to about 5, or from about 1 to 15, or n may be any number of linker that would allow for the operability of the compound of the present invention. In another example, the linker may be an amino acid sequence, for example, an amino acid sequence that comprises about 3 to about 40 amino acids, or about 5 to about 40 amino acids, or about 10 to about 40 amino acids, or about 15 to about 40 amino acids, or about 20 to about 40 amino acids, or about 25 to about 40 amino acids, or about 30 to about 40 amino acids, or about 35 to about 40 amino acids, or about 3 to about 35 amino acids, or about 5 to about 35 amino acids, or about 10 to about 35 amino acids, or about 15 to about 35 amino acids, or about 20 to about 35 amino acids, or about 25 to about 35 amino acids, or about 30 to about 35 amino acids, or about 3 to about 30 amino acids, or about 5 to about 30 amino acids, or about 10 to about 30 amino acids, or about 15 to about 30 amino acids, or about 20 to about 30 amino acids, or about 25 to about 30 amino acids, or about 3 to about 25 amino acids, or about 5 to about 25 amino acids, or about 10 to about 25 amino acids, or about 15 to about 25 amino acids, or about 20 to about 25 amino acids, or about 3 to about 20 amino acids, or about 5 to about 20 amino acids, or about 10 to about 20 amino acids, or about 15 to about 20 amino acids, or about 3 to about 15 amino acids, or about 5 to about 15 amino acids, or about 10 to about 15 amino acids, or about 15 to about 20 amino acids, or about 3 to about 10 amino acids, or about 5 to about 10 amino acids, or about 3 to about 5 amino acids, or about 3, 5, 10, 15, 20, 25, 30, 35, or 40 amino acids.

The antibody or fragment thereof of the present invention may also be in a multivalent display format, also referred to herein as multivalent presentation. Multimerization may be achieved by any suitable method known in the art. For example, and without wishing to be limiting in any manner, multimerization may be achieved using self-assembly molecules such as those described in Zhang et al. (2004a, 2004b) and WO2003/046560, where pentabodies are produced by expressing a fusion protein comprising the antibody or fragment thereof of the present invention and the pentamerization domain of the B-subunit of an AB5 toxin family (Merritt and Hol, 1995). A multimer may also be formed using the multimerization domains described by Zhu et al. (2010); this form, referred to herein as a "combody" form, is a fusion of the antibody or fragment of the present invention with a coiled-coil peptide resulting in a multimeric molecule (Zhu et al., 2010). Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielsen et al., 2000), c-jun/Fos interaction (De Kruif and Logtenberg, 1996), "Knob into holes" interaction (Ridgway et al., 1996).

Another method known in the art for multimerization is to dimerize the antibody or fragment thereof using an Fc domain, for example, but not limited to human Fc domains. The Fc domains may be selected from various classes including, but not limited to, IgG, IgM, or various subclasses including, but not limited to IgG1, IgG2, etc. In this approach, the Fc gene is inserted into a vector along with the sdAb gene to generate a sdAb-Fc fusion protein (Bell et al., 2010; Iqbal et al., 2010); the fusion protein is recombinantly expressed, then purified. For example, and without wishing to be limiting in any manner, multivalent display formats may encompass chimeric or humanized formats of antibodies and VHH of the present invention linked to an Fc domain, or bi- or tri-specific antibody fusions with two or three antibodies and VHH recognizing unique epitopes. Such antibodies are easy to engineer and to produce, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse Fc2b fragment or human Fc1 fragment (Bell et al., 2010; Iqbal et al., 2010). The antibody or fragment thereof may be fused to the N-terminus or C-terminus of the Fc fragment.

Each subunit of the multimers described above may comprise the same or different antibodies or fragments thereof of the present invention, which may have the same or different specificity. Additionally, the multimerization domains may be linked to the antibody or antibody fragment using a linker sequence, as required. As defined above, the linker sequence can be any linker known in the art that would allow for the compound of the present invention to be prepared and be operable for the desired function. For example, such a linker sequence should be of sufficient length and appropriate composition to provide flexible attachment of the two molecules, but should not hamper the antigen-binding properties of the antibody.

For example, and without wishing to be limiting in any manner, the isolated or purified antibody or fragment thereof operable to transmigrate the BBB may be an antibody or fragment thereof which comprises:

a complementarity determining region (CDR) 1 sequence GFKITHYTMG (SEQ ID NO: 1); CDR2 sequence RITWGGX$_1$X$_2$TX$_3$YSNSVKG, where X$_1$ is D or K, X$_2$ is N or D, and X$_3$ is F, I or L (SEQ ID NO:2); and CDR3 sequence GSTSTAX$_4$PLRVDY, where X$_4$ is T or K (SEQ ID NO:3);

a complementarity determining region (CDR) 1 sequence EYPSNFYA (SEQ ID NO: 6); CDR2 sequence VSRDGLTT (SEQ ID NO:7); and CDR3 sequence AIVITGVWNKVDVNSRSYHY (SEQ ID NO:8); or a complementarity determining region (CDR) 1 sequence GRTIDNYA (SEQ ID NO: 11); CDR2 sequence IDWGDGGX (SEQ ID NO: 12), where X is A or T; and CDR3 sequence AMARQSRVNLDVARYDY (SEQ ID NO:13).

According to an embodiment, the antibody or fragment thereof comprises an amino acid sequence selected from the group consisting of:

```
                                          (SEQ ID NO: 5)
X1VQLVESGGGLVQPGGSLRLSCAASGFKITHYTMGWX2RQAPGKX3X4

EX5VSRITWGGDNTFYSNSVKGRFTISRDNSKNTX6YLQMNSLRAEDT

AVYYCAAGSTSTATPLRVDYWGQGTLVTVSS,
``` wherein $X_1$=D or E, $X_2$=F or V, $X_3$=E or G, $X_4$=R or L, $X_5$=F or W, and $X_6$=L or V;

(SEQ ID NO: 9)
$X_1$VX$_2$LX$_3$ESGGGLVQX$_4$GGSLRLSCX$_5$ASEYPSNFYAMSWXRQAPGK

X$_7$X$_8$EX$_9$VX$_{10}$GVSRDGLTTLYADSVKGRFTX$_{11}$SRDNX$_{12}$KNTX$_{13}$X$_{14}$L

QMNSX$_{15}$X$_{16}$AEDTAVYYCAIVITGVWNKVDVNSRSYHYWGQGTX$_{17}$V

TVSS, wherein $X_1$ is E or Q; $X_2$ is K or Q; $X_3$ is V or E; $X_4$ is A or P; $X_5$ is V or A; $X_6$ is F or V; $X_7$ is E or G; $X_8$ is R or L; $X_9$ is F or W; $X_{10}$ is A or S; $X_{11}$ is M or I; $X_{12}$ is A or S; $X_{13}$ is V or L; $X_{14}$ is D or Y; $X_{15}$ is V or L; $X_{16}$ is K or R; and $X_{17}$ is Q or L; and $X_1$VX$_2$LX$_3$ESGGGLVQX$_4$GGSLRLSCAASGRTIDN-YAMAWX$_5$RQAPGKX$_6$X$_7$EX$_8$VX$_9$TIDWGDG-GX$_{10}$RYANSVKGRFTISRDNX$_{11}$KX$_{12}$TX$_{13}$YLQ-MNX$_{14}$LX$_{15}$X$_{16}$EDT AVYX$_{17}$CAMARQSRVNLDVARY-DYWGQGTX$_{18}$VTVSS (SEQ ID NO:14), wherein $X_1$ is E or Q; $X_2$ is K or Q; $X_3$ is V or E; $X_4$ is A or P; $X_5$ is V or S; $X_6$ is D or G; $X_7$ is L or R; $X_8$ is F or W; $X_9$ is A or S; $X_{10}$ is A or T; $X_{11}$ is A or S; $X_{12}$ is G or N; $X_{13}$ is M or L; $X_{14}$ is N or R; $X_{15}$ is E or R; $X_{16}$ is P or A; $X_{17}$ is S or Y; and $X_{18}$ is Q or L;

or a sequence substantially identical thereto operable to transmigrate across the blood-brain barrier BBB.

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the sdAb while maintaining the CDR sequences listed above and the overall structure of the CDR of the antibody or fragment; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence at least 95%, 98%, or 99% identical to that of the antibodies described herein.

The present invention provides a compound comprising an antibody or fragment thereof that transmigrates the blood brain barrier (BBB). An antibody or fragment of the present invention may bind to, for example, transmembrane protein 30A (TMEM30A), as described in WO 2007/036021, or to an Insulin-Like Growth Factor 1 Receptor (IGF1R) epitope, or isoforms, variants, portions, or fragments thereof.

According to an embodiment, the compound of the present invention comprises a polypeptide related to the treatment of LSDs. According to an embodiment, the compound of the present invention comprises a polypeptide related to the treatment of α-synucleinopathies. According to another embodiment, the compound of the present invention comprises a polypeptide related to the treatment of both LSD and α-synucleinopathies. Non-limiting examples of such polypeptides include polypeptides that are operable for the treatment of, without wishing to be limiting, sphingolipidoses, mucopolysaccharidoses, glycoproteinoses/oligosaccharidoses, glycogenosis (e.g. type II), lipodoses or neuronal ceroid lipofuscinoses. In embodiments, such polypeptides may be selected from the group consisting of Type I sulfatases or a glucosidase.

According to embodiments, for example and without wishing to be limiting in any manner, the peptide related to the treatment of LSD may be iduronate-2-sulfatase (IDS):

SETQANSTTDALNVLLIIVDDLRPSLGCYGDKLVRSPNIDQLASHSLLF
QNAFAQQAVCAPSRVSFLTGRRPDTTRLYDFNSYWRVHAGNFSTIPQYF
KENGYVTMSVGKVFHPGISSNHTDDSPYSWSFPPYHPSSEKYENTKTCR
GPDGELHANLLCPVDVLDVPEGTLPDKQSTEQAIQLLEKMKTSASPFFL
AVGYHKPHIPFRYPKEFQKLYPLENITLAPDPEVPDGLPPVAYNPWMDI
RQREDVQALNISVPYGPIPVDFQRKIRQSYFASVSYLDTQVGRLLSALD

-continued

DLQLANSTIIAFTSDHGWALGEHGEWAKYSNFDVATHVPLIFYVPGRTA

SLPEAGEKLFPYLDPFDSASQLMEPGRQSMDLVELVSLFPTLAGLAGLQ

VPPRCPVPSFHVELCREGKNLLKHFRFRDLEEDPYLPGNPRELIAYSQY

PRPSDIPQWNSDKPSLKDIKIMGYSIRTIDYRYTVWVGFNPDEFLANFS

DIHAGELYFVDSDPLQDHNMYNDSQGGDLFQLLMP.

referred to herein as IDS (SEQ ID NO: 24), or sequences substantially identical thereto.

According to another embodiment, for example and without wishing to be limiting in any manner, the peptide related to the treatment of LSD, to the treatment of α-synucleinopathy, or both, may be acid-beta-glucosidase (GCase)

ARPCIPKSFGYSSVVCVCNATYCDSFDPPTFPALGTFSRYESTRSGRRM

ELSMGPIQANHTGTGLLLTLQPEQKFQKVKGFGGAMTDAAALNILALSP

PAQNLLLKSYFSEEGIGYNIIRVPMASCDFSIRTYTYADTPDDFQLLNF

SLPEEDTKLKIPLIHRALQLAQRPVSLLASPWTSPTWLKTNGAVNGKGS

LKGQPGDIYHQTWARYFVKFLDAYAEHKLQFWAVTAENEPSAGLLSGYP

FQCLGFTPEHQRDFIARDLGPTLANSTHHNVRLLMLDDQRLLLPHWAKW

VLTDPEAAKYVHGIAVHWYLDFLAPANATLGETHRLFPNTMLFASEACV

GSKFWEQSVRLGSWDRGMQYSHSIITNLLYHVVGWTDWNLALNPEGGPN

WVRNFVDSPIIVDITKDTFYKQPMFYHLGHFSKFIPEGSQRVGLVASQK

NDLDAVALMHPDGSAVVVVLNRSSKDVPLTIKDPAVGFLETISPGYSIH

TYLWRRQ, referred to herein as GCaseMut1 (SEQ ID NO: 26), or sequences substantially identical thereto.

GCasemut1 differs from wild-type human GCase in that it lacks the first 39 amino acids (signal peptide) and has 2 amino acid substitutions.

The compounds of the present invention and/or the polypeptide related to the treatment of LSD, to the treatment of α-synucleinopathy, or both may be hyperglycosylated and hyperphosphorylated to increase cellular uptake into neurons and its lysosomal localization. Therefore, according to another embodiment, the compound of the present invention, and particularly the polypeptide related to the treatment of LSD, to the treatment of α-synucleinopathy, or both may be a glycosylated polypeptide. In embodiments, the glycosylated polypeptide may be glycosylated with one or more N-glycans. According to another embodiment, the glycosylated polypeptide may further be a phosphorylated polypeptide, and for example, the phosphorylation may be a mannose-6-phosphate. In embodiments, the mannose-6-phosphate may be attached to an N-glycan. Also, for example the glycosylated and phosphorylated polypeptide may contain monophosphorylated or bisphosphorylated N-glycans, or a combination thereof.

To generate the glycosylated or glycosylated and phosphorylated compounds and/or the polypeptide related to the treatment of the LSD, to the treatment of α-synucleinopathy, or both, of the present invention, the compounds may be expressed in yeast expression systems that synthesize high levels of phosphorylated N-glycans, such as those described in WO2011061629, and the strain *Yarrowia lipolytica* strain OXYY5632 mentioned below.

According to another embodiment, the compounds of the present invention may also comprise elements to improve the half-life of the compounds in serum. According to an embodiment, for example and without wishing to be limiting in any manner, the compounds of the present invention may further comprise human serum albumin (HSA).

DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGPKLVAASQAALGL, referred to herein as HSA (K573P) (SEQ ID NO:28).

HSA (K573P) differs from mature wild-type human HSA in that it has the K573P substitution.

According to another embodiment, the elements to improve the half-life of the compounds in serum may be an albumin targeting moiety. As used herein, the term "albumin targeting moiety" is intended to mean any compound that can bind to serum albumin and particularly to human serum albumin. For example, the albumin targeting moiety may be an anti-albumin or anti-HSA antibody or a fragment thereof.

According to an embodiment, for example and without wishing to be limiting in any manner, the albumin targeting moiety may be a CDR1 sequence GRTFIAYA (SEQ ID NO:16); a CDR2 sequence ITNFAGGTT (SEQ ID NO:17); and a CDR3 sequence AADRSAQTMRQVRPVLPY (SEQ ID NO:18);

a CDR1 sequence GSTFSSSS (SEQ ID NO:20); a CDR2 sequence ITSGGST (SEQ ID NO: 21); and a CDR3 sequence NVAGRNWVPISRYSPGPY (SEQ ID NO:22); or an amino acid sequence (SEQ ID NO: 19)
QVQLVESGGGLVQAGGSLRLSCVASGRTFIAYAMGWFRQAPGKEREFVA

AITNFAGGTTYYADSVKGRFTISRDNAKTTVYLQMNSLKPEDTALYYCA

ADRSAQTMRQVRPVLPYWGQGTQVTVSS;

or
an amino acid sequence (SEQ ID NO: 23)
QVKLEESGGGLVQAGGSLKLSCAASGSTFSSSSVGWYRQAPGQQRELVA

AITSGGSTNTADSVKGRFTMSRDNAKNTVYLQMRDLKPEDTAVYYCNVA

GRNWVPISRYSPGPYWGQGTQVTVSS.

According to another embodiment, for example and without wishing to be limiting in any manner, the compounds of the present invention may comprise
1) a compound comprising an antibody or fragment thereof having CDR 1 sequence EYPSNFYA (SEQ ID NO:6), CDR2 sequence VSRDGLTT (SEQ ID NO:7), CDR3 sequence AIVITGVWNKVDVNSRSYHY (SEQ ID NO:8), IDS (SEQ ID NO: 24), and human serum albumin (HSA) (SEQ ID NO:67);
2) a compound comprising an antibody or fragment thereof having CDR 1 sequence EYPSNFYA (SEQ ID NO:6), CDR2 sequence VSRDGLTT (SEQ ID NO:7), a CDR3 sequence AIVITGVWNKVDVNSRSYHY (SEQ ID NO:8), IDS (SEQ ID NO:24), and an albumin targeting moiety comprising CDR1 sequence GRTFIAYA (SEQ ID NO:16), CDR2 sequence ITNFAGGTT (SEQ ID NO:17), and CDR3 sequence AADRSAQTMRQVRPVLPY (SEQ ID NO:18);
3) a compound comprising an antibody or fragment thereof having CDR 1 sequence EYPSNFYA (SEQ ID NO:6), CDR2 sequence VSRDGLTT (SEQ ID NO:7); CDR3 sequence AIVITGVWNKVDVNSRSYHY (SEQ ID NO:8), IDS (SEQ ID NO:24), and an albumin targeting moiety comprising CDR1 sequence GSTFSSSS (SEQ ID NO:20), CDR2 sequence ITSGGST (SEQ ID NO:21), and CDR3 sequence NVAGRNWVPISRYSPGPY (SEQ ID NO:22);
4) IGF1R3H5-IDS-HSA (K573P) (SEQ ID NO: 35);
5) IGF1R3H5-IDS-R28 (SEQ ID NO: 36); and
6) IGF1R3H5-IDS-M79 (SEQ ID NO: 37).

The present invention also encompasses a composition comprising one or more than one of the compound as described herein. The composition may comprise a single compound as described above, or may be a mixture of compounds. Furthermore, in a composition comprising a mixture of compounds of the present invention, the compound may have the same specificity, or may differ in their specificities; for example, and without wishing to be limiting in any manner, the composition may comprise antibodies or fragments thereof specific to IGF1R (same or different epitope).

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but not limited to lyophilized or encapsulated), capsule or tablet form.

For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the compound of the present invention. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the compound of the present invention to the gastrointestinal tract of the subject. Thus, the composition may comprise encapsulation, time-release, or other suitable technologies for delivery of the compound of the present invention. It would be within the competency of a person of skill in the art to prepare suitable compositions comprising the present compounds.

The present invention further provides a method of transporting a molecule of interest across the blood-brain barrier. Such methods also encompass methods of treating a lysosomal storage disease (LSD), treating α-synucleinopathy, or both across the blood-brain barrier, comprising administering the compound according to the present invention or a composition according to the present invention to a subject in need thereof. This also includes use of the compound or of a composition of the present invention related to the treatment of LSD, treating α-synucleinopathy, or both in the brain in a subject in need thereof The method comprises administering the compounds as described herein to a subject; the antibody part or fragment thereof transmigrates the blood-brain barrier. The molecule may be any desired molecule, including the cargo molecules as previously described, related to the treatment of LSD, the treatment of α-synucleinopathy, or both; the molecule may be "linked" to the antibody or fragment thereof using any suitable method, including, but not limited to conjugation or expression in a fusion protein. The administration may be by any suitable method, for example parenteral administration, including but not limited to intravenous (iv), subcutaneous (sc), and intramuscular (im) administration. In this method, the antibody or fragment thereof of the present invention "ferries" the molecule of interest across the BBB to its brain target.

The invention also encompasses a method of quantifying an amount of a cargo molecule delivered across the BBB of a subject, wherein the cargo molecule is linked to one or more than one isolated or purified antibody or fragment thereof as described herein, the method comprising
  a) collecting cerebrospinal fluid (CSF) from the subject; and
  b) using targeted proteomics methods to quantify the amount of the cargo molecule linked to one or more than one antibody or fragment thereof in the CSF.

The cargo molecule may be any desired molecule, including the cargo molecules, as previously described; the isolated compound of the present invention transmigrates the blood-brain barrier; and the molecule may be "linked" to the antibody or fragment thereof using any suitable method, including, but not limited to conjugation or expression in a fusion protein, as previously described. In the above method, the CSF is collected from a subject using any suitable method known in the art. The amount of CSF required for the targeted proteomics method in step b) may be between about 1 to 10 pL; for example, the amount of CSF required may be about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 pL, or any amount there between, or any range defined by the amount just described. The compound of the present invention may have been administered to the subject prior to collection of the CSF. A suitable delay between administration and delivery of the antibody or fragment linked to the cargo molecule across the BBB may be required. The delay may be at least 30 minutes following administration of the antibody or fragment linked to the cargo molecule; for example and without wishing to be limiting in any manner, the delay may be at least 30 minutes, 1 hour, 1.5 hour, 2 hours, 2.5 hours, 3 hours, 3.5 hours, 4 hours, 4.5 hours, or 5 hours. The targeted proteomics methods used to quantify the amount of the one or more than one antibody or fragment thereof linked to the cargo molecule may be any suitable method known in the art. For example and without wishing to be limiting, the targeted proteomics method may be a mass spectrometry method, such as but not limited to multiple reaction monitoring using an isotopically labeled internal standard (MRM-ILIS; see for example (Haqqani et al., 2013)). MRM is advantageous in that it allows for rapid, sensitive, and specific quantification of unlabeled targeted analytes (for example, a compound as described herein) in a biological sample. The multiplexing capability of the assay may allow for quantification of both the antibody or fragment thereof and the cargo molecule.

The invention also encompasses nucleic acid vectors comprising a nucleotide sequence encoding a compound of the present invention, as well as cells comprising the nucleic acid vector, for expressing the compound of the present invention, and cells for expressing the compound of the present invention.

The present invention will be further illustrated in the following examples. However, it is to be understood that these examples are for illustrative purposes only and should not be used to limit the scope of the present invention in any manner.

EXAMPLE 1

Production, Purification and Characterization of Recombinant IGF1R3H5-IDS

A recombinant fusion protein comprising an IGF1R3H5 sdAb domain, an IDS domain and C-terminal affinity purification tags (shown in FIG. 1; see also amino acids SEQ ID NO:30) was prepared. The fusion protein comprised a 17 amino acid N-terminal signal peptide, the 127 amino acid IGF1R3H5 sdAb domain (SEQ ID NO:43), a 25 amino acid linker sequence, the 525 amino acid mature human IDS sequence (SEQ ID NO:24) and a 16 amino acid HIS-strep tag sequence. The protein is produced in a 10 L fermentation of the IGF1R3H5-IDS expressing *Yarrowia lipolytica* strain OXYY5632. *Yarrowia lipolytica* strain OXYY5632 co-expresses IGF1R3H5-IDS and *Bos Taurus* formylglycine generating enzyme (FGE) to produce catalytically active IDS. Furthermore, the strain is glycol-engineered to obtain glycoproteins with high levels of phosphorylated N-glycans. The fermentation and subsequent harvest step were performed, after which the clarified medium containing the target protein IGF1R3H5-IDS was subjected to different chromatography steps to yield the pure product. The purification protocol consisted of a Ni-IMAC capturing step to remove most of the contaminants, followed by an enzymatic treatment with Jack Bean α-mannosidase (JBMan) at pH 4.5 to uncap the shielded Man-6-P and further trim terminal α-linked mannose residues from the protein-linked N-glycans. A second Ni-IMAC step was included for JBMan removal. The final samples were formulated by diafiltration in 20 mM sodium phosphate+137 mM NaCl, pH 6.2. The same production and purification method is applied for all other compounds or other recombinant proteins referred to within the following examples. Only in the case of the IGF1R3H5-IDS-HSA (K573P) fusion construct, an extra polishing step needed to be developed to reach the same level of purity as for the other variants.

Purity Analysis.

Figure 2:
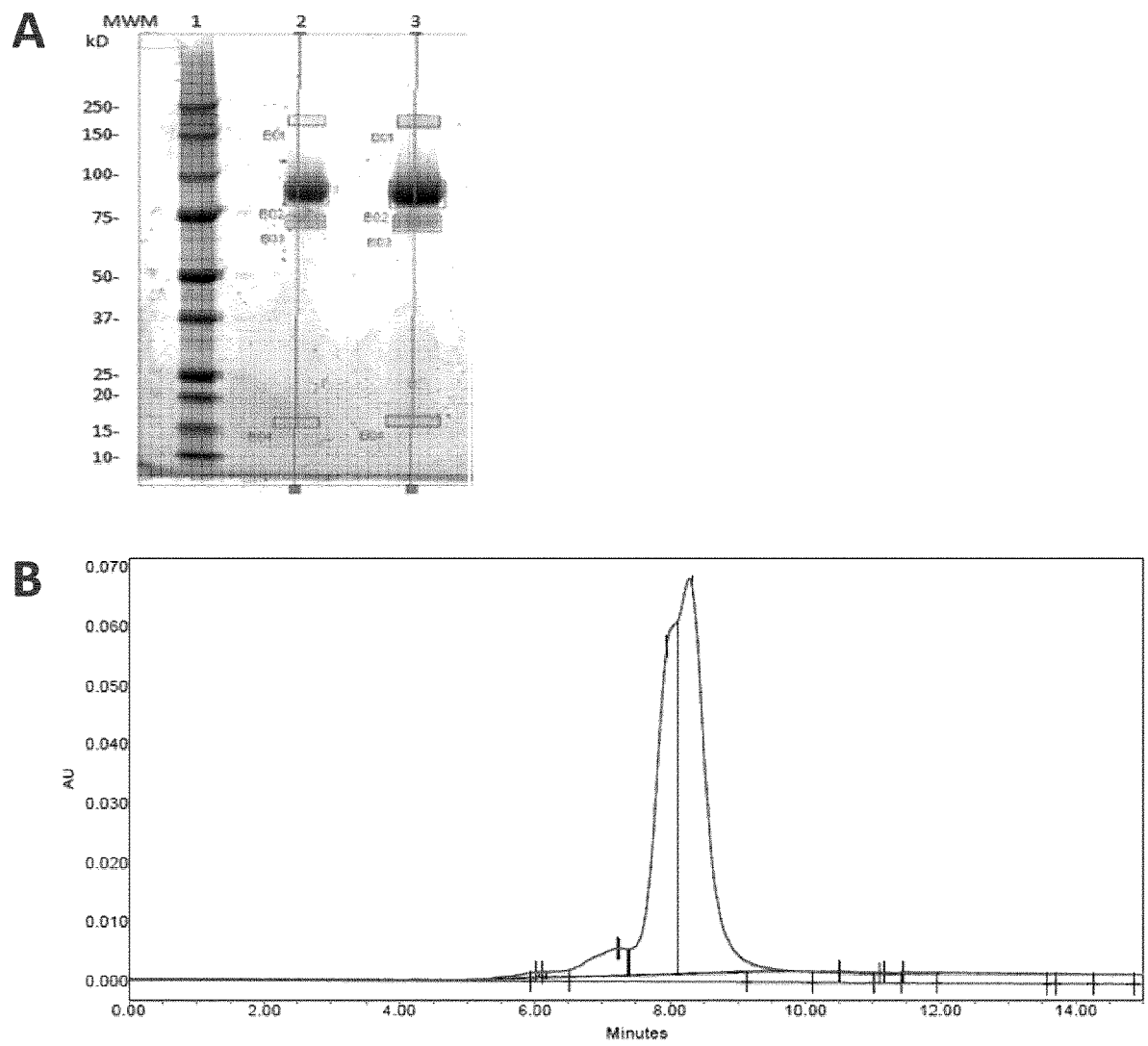
FIG. 2 shows (A) a coomassie-stained SDS-PAGE of IGF1R3H5-IDS. (B) shows an HPLC-SEC chromatogram of IGR1R3H5-IDS. The purity of the product is typically >90%.

SDS-PAGE analysis. A sample of purified IGF1R3H5-IDS compound was prepared with reducing agent, heat-denatured at 95° C. and loaded at a concentration of 1 μg and 2 μg on a NuPAGE Novex 4-12% Bis-Tris gel (1.5 mm thick, 15-well), run with MOPS-SDS running buffer. Following electrophoresis, the gel was stained for 1 hour in InstantBlue staining solution and de-stained with water until background decolorization. The gel was scanned using scanning software (Odyssey) (FIG. 2A). IGF1R3H5-IDS corresponds to a ~90 kDa band, when taking the presence of N-glycans into account. The obtained band pattern was consistent with the expectations.

HPLC-SEC analysis. A size exclusion chromatography method was used to measure aggregates and degradation products of IDS fusion proteins. All chromatograms of uncapped IGF1R3H5-IDS demonstrate a broad, asymmetric main peak due to the presence of a prominent species eluting earlier than the main apex and forming a shoulder, which is believed to be an N-glycan variant. The apex of the species eluting before the main peak is even more discernible in (FIG. 2B), which represents an HPLC-SEC purity analysis of two consecutive injections of undiluted IGF1R3H5-IDS.

Figure 3:
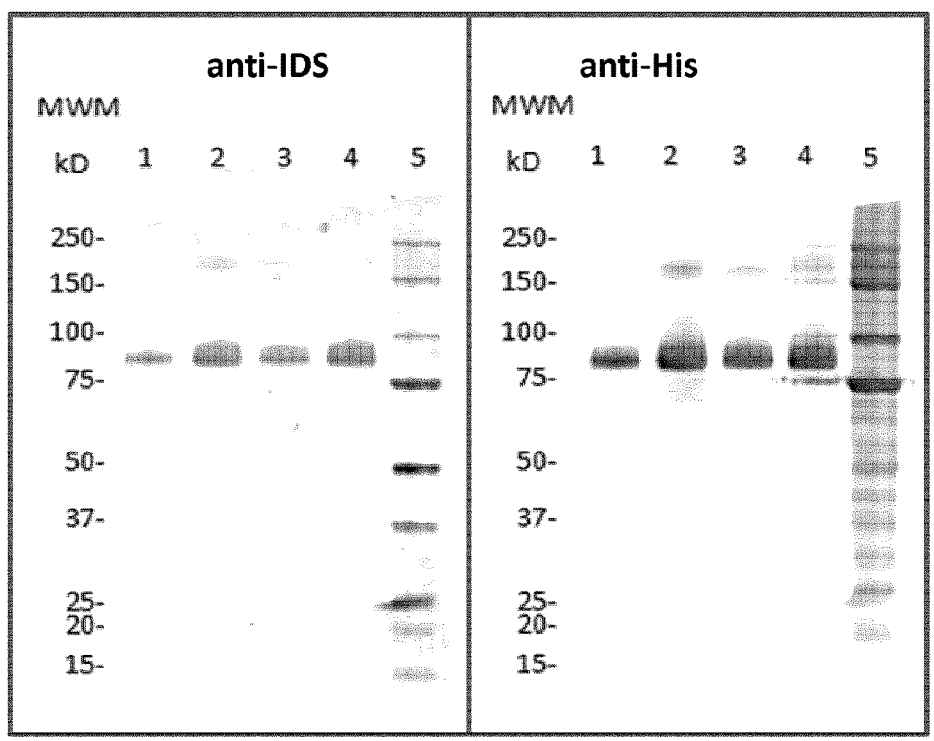
FIG. 3 shows (A) immunoblot analysis of IGF1R3H5-IDS using anti-IDS and anti-His. (B) Samples loaded are described in the table legend below.

Western blot analysis. Samples of purified uncapped IGF1R3H5-IDS (here referred as P454 and P453) were prepared with a reducing agent, heat-denatured at 95° C. and loaded at 100 and 500 ng on a NuPAGE Novex 4-12% Bis-Tris Gel (1.5-mm thick, 10-well), and run with MOPS-SDS running buffer. After electrophoresis, an overnight transfer with transfer buffer on a nitrocellulose membrane (~16 h; constant current 50 mA) was performed. Immuno-detection of IDS consisted of a 2 h-incubation with rabbit anti-elaprase polyclonal antibody (in-house batch OX010) and a subsequent 30 min-incubation with goat anti-rabbit IgG, IRdye (680 nm) conjugated antibody (Sigma). Immunodetection of the His-tag was performed in a similar manner, but with THE™ His Tag mouse monoclonal antibody (Genscript) and goat anti-mouse IgG, IRdye (800 nm) conjugated antibody. The membrane was then scanned using the Odyssey software. Immunodetection with anti-IDS antibody (FIG. 3A, left panel) shows a main band at ~90 kDa, corresponding to the full-length IGF1R3H5-IDS construct. Immunodetection with anti-His antibody (FIG. 3A, right panel) reveals a main band at ~90 kDa, confirming the integrity of the C-terminal end of IGF1R3H5-IDS. In addition to this band, an aggregate at ~200 kDa and the protein band at ~75 kDa (2 bands) can also be seen in lane 2 and 4, corresponding to the highest loaded concentration of the construct. The extra bands in lane 4 at 75, 100, 150 and 250 kDa are due to overflow of the marker to the adjacent lane.

N-glycan analysis. To evaluate the uncapping process and to analyze the N-glycan profile of uncapped IGF1R3H5-IDS, the N-glycans are released with PNGaseF, labeled with APTS and subsequently analyzed via capillary electrophoresis. From the obtained profile, the surface area of peaks representing relevant N-glycan structures was calculated to determine the peak ratios and thus the corresponding N-glycan distribution (FIG. 4). The N-glycan distribution of the uncapped IGF1R3H5-IDS gives a 48%/52% ratio of bi- and monophosphorylated N-glycans (FIG. 4: 2 bottom rows). The calculation, not taking the neutral N-glycans into account, allows us to conclude that no bi-phosphorylated N-glycans are lost (e.g. if a contaminating phosphatase or endoglycosidase activity would be present) during the uncapping and downstream purification process. During the JBMan treatment these structures are trimmed down to smaller mannose structures which are harder to detect with this electrophoresis method. Therefore, neutral N-glycans are only calculated for a capped sample.

Figure 5:
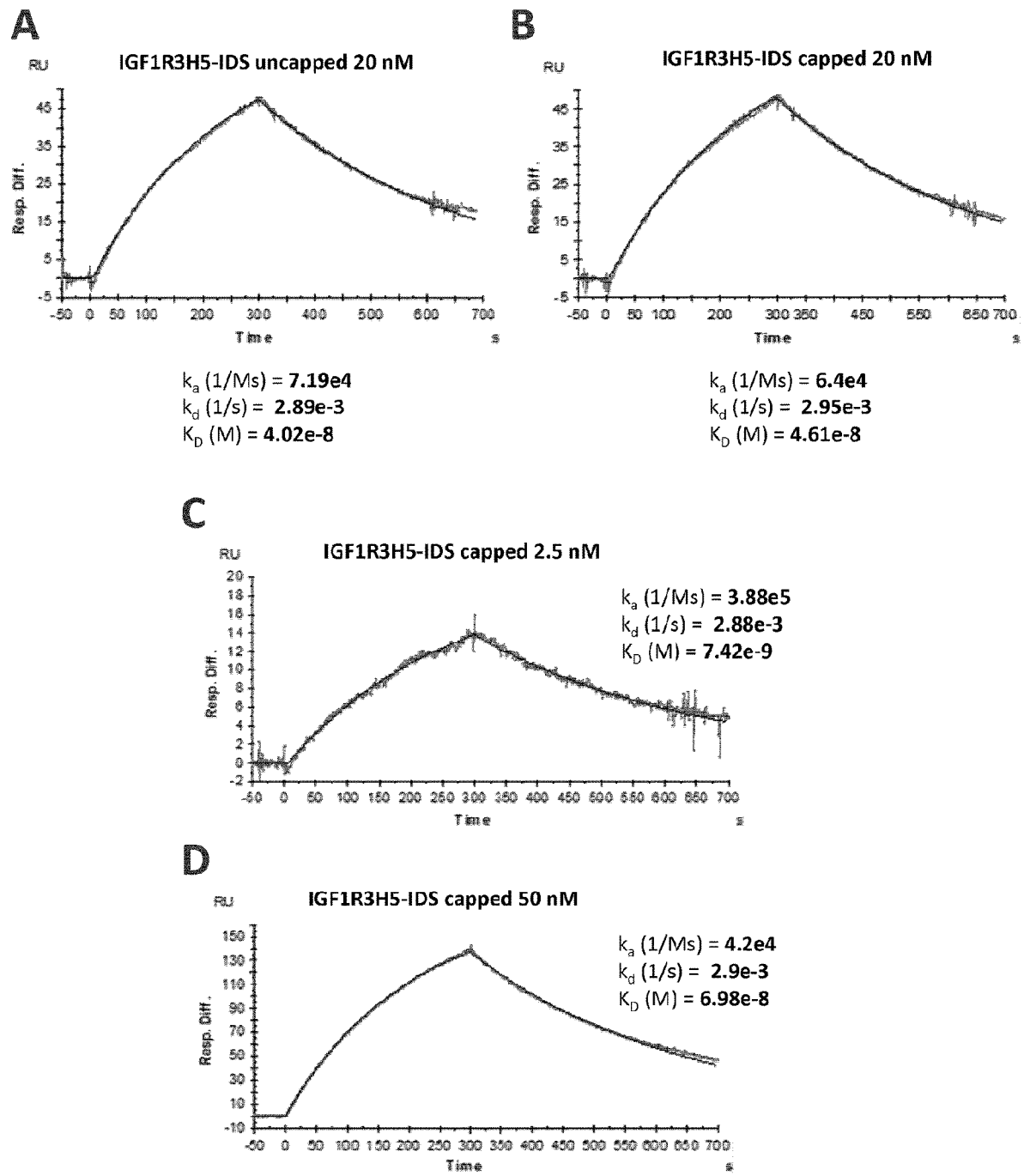
FIG. 5 shows the binding kinetics of (A) uncapped and (B, C and D) capped IGF1R3H5-IDS to human IGF1R using surface plasmon resonance. The capped and uncapped forms give essentially identical rate constants and affinities. The observed $K_D$ values are concentration dependent, indicating a matrix effect that reduces $K_D$ values at high concentrations.

SPR analysis. Surface Plasmon Resonance (SPR) analysis was performed to determine the affinity of the IGF1R3H5-IDS construct towards human IGF1R (hIGR1R). The SPR analysis was performed on a Biacore T200 (GE Healthcare) under the following conditions: hIGF1R was immobilized on a CM4 chip at high density (FC1-ethanoloamine blocked; FC3-2,500 RUs of hIGF1R). A variable concentration of the flowing molecule was used, with contact and dissociations times of 300 and 400 s, respectively. The assay was performed at 25° C. with a flow rate of 40 µL/min and the chip was regenerated in 10 mM glycine (pH 5.5). FIGS. 5A and 5B show that the uncapped and capped versions of IGF1R3H5-IDS (20 nM) exhibit rate constants and affinities that are essentially identical. Strong binding to immobilized h-IGF1R (on the CM4 chip) was observed for both capped and uncapped IGF1R3H5-IDS constructs. FIG. 5C shows that 2.5 nM IGF1R3H5-IDS exhibits binding characteristics that are similar to the parental VHH: at these low concentrations (2.5 nM), IGF1R3H5-IDS gave a $K_D$ of approximately 7 nM and on- and off-rates similar to the parental VHH IGF1R3H5 [$k_a$=3.34E+05 (1/Ms), $k_d$=2.51E−03 (1/s), $K_D$=7.50E−09 (M)]. However, at 50 nM (FIG. 5D), matrix effects (build-up of charge) reduced the on-rate of IGF1R3H5-IDS, consequently resulting in inaccurate affinity values ($K_D$ of ~70 nM). In summary, the IGF1R3H5-IDS construct retains its ability to bind to the target receptor IGF1R.

EXAMPLE 2

In Vitro BBB Transcytosis of IGF1R3H5-IDS and Similar Test Compounds

In vitro BBB transcytosis in rat brain endothelial cells. SV-ARBECs were seeded at 80,000 cells/membrane on rat-tail collagen-coated 0.83 cm$^2$ Falcon cell inserts, 1 µm pore size, in 1 mL SV-ARBEC feeding medium without phenol red. The model characterization is described in detail in Garberg et al. (2005). For cell growth and maintenance prior to the assays, the wells of a 12-well tissue culture plate (i.e., bottom chamber) contained 2 mL of 50:50 (v/v) mixtures of SV-ARBEC medium without phenol red and rat astrocyte-conditioned medium. The model was used when Pe[sucrose] was between 0.4 and 0.6 (×10$^{-3}$) cm/min. Transport experiments were performed exactly as described in Haqqani et al. (2013) by adding a mixture of the test compounds in equimolar concentrations to the top chamber and by collecting 100 µL aliquots (with subsequent replacement with 100 µL of transport buffer) from the bottom chamber at 90 min for simultaneous quantification of all test compounds using the multiplexed selected reaction monitoring (SRM) method. The samples are diluted in transport buffer (TB; 5 mM MgCl$_2$, 10 mM HEPES in Hanks' balanced salt solution (HBSS), pH 7.4) and added (1:1) to the top chamber containing SV-ARBEC media with 5% fetal bovine serum (FBS). For assays where samples were assessed by SRM, the bottom chamber contains TB. For assays where the samples were assessed for IDS activity, the bottom chamber contains sulfate-free transport buffer (SFTB; 5 mM MgCl$_2$, 10 mM HEPES in sulfate-free HBSS, pH 7.4). The apparent permeability coefficient $P_{app}$ was calculated as described previously (Artursson and Karlsson, 1991).

In vitro BBB transcytosis in human brain endothelial cells. A human BBB model was created using brain endothelial cells derived from amniotic fluid induced pluripotent stem cells (AF-iPSC-BEC). Except for the origin of the cell line, this model is essentially the same as the SV-ARVBEC model. Details pertaining to the production of AF-iPSC-BEC are found in CA2970173, to Ribecco-Lutkiewicz et al. (2018).

nanoLC/MS/MS. Pure VHH or VHH-Fc fusion proteins, in vitro BBB transport or body fluid samples containing these proteins, were reduced, alkylated, and trypsin digested using previously described protocol (Haqqani et al., 2008a, 2013). For isotopically labeled internal standard (ILIS)-based quantification, isotopically heavy versions of the peptides that contained heavy C-terminal K (+8 Da) were synthesized from a commercial source (New England Peptide LLC, Gardner, MA, USA) (Lin et al., 2013). Each protein was first analyzed by nanoLC-MS/MS [nanoAcquity UPLC (Waters, Milford, MA, USA) coupled to LTQ XL ETD MS (ThermoFisher, Waltham, MA, USA)] using data-dependent acquisition to identify all ionizable peptides, and the 3-5 most intense fragment ions were chosen. An initial SRM assay was developed to monitor these fragments at attomole amounts of the digest. Fragments that showed reproducible intensity ratios at low amounts (~100-300 amol; Pearson $r^2 \geq 0.95$) were considered stable and were chosen for the final SRM assay.

Figure 6:
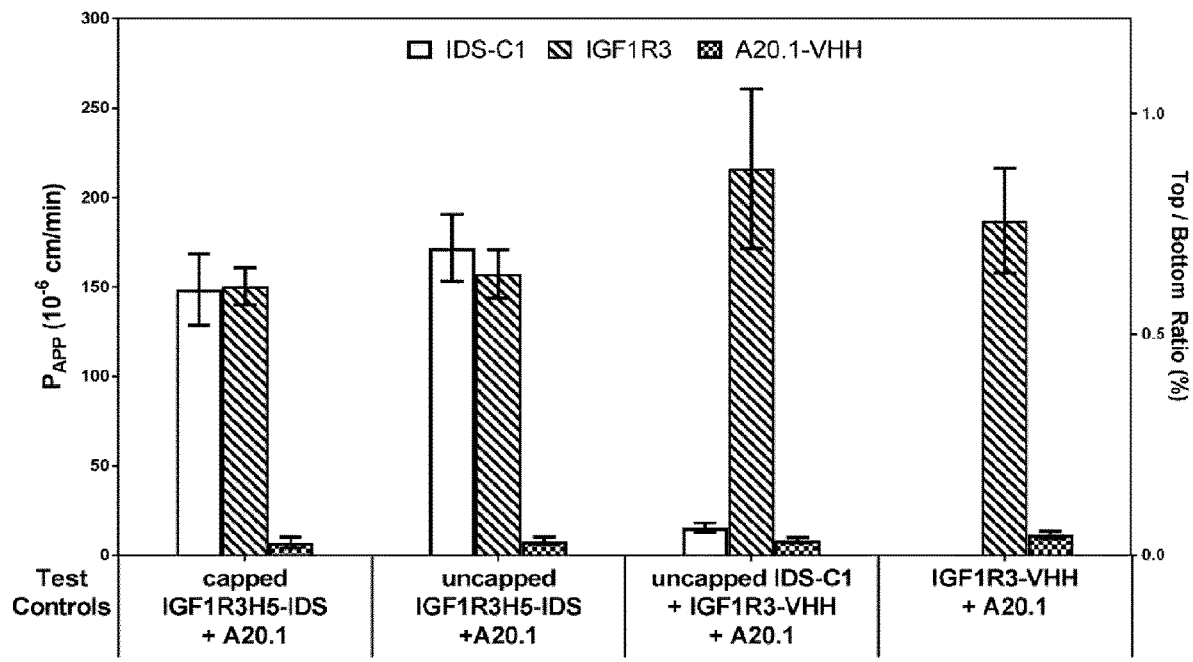
FIG. 6 shows that the in vitro BBB permeability ($P_{APP}$) of uncapped IDS-C1 (IDS) is comparable to the non-permeable negative control protein (A20.1). In contrast, the BBB carrier IGF1R3-VHH is highly permeable. The fusion proteins (capped and uncapped IGF1R3H5-IDS) exhibited permeability that is comparable to that of IGF1R3-VHH.
Figure 7:
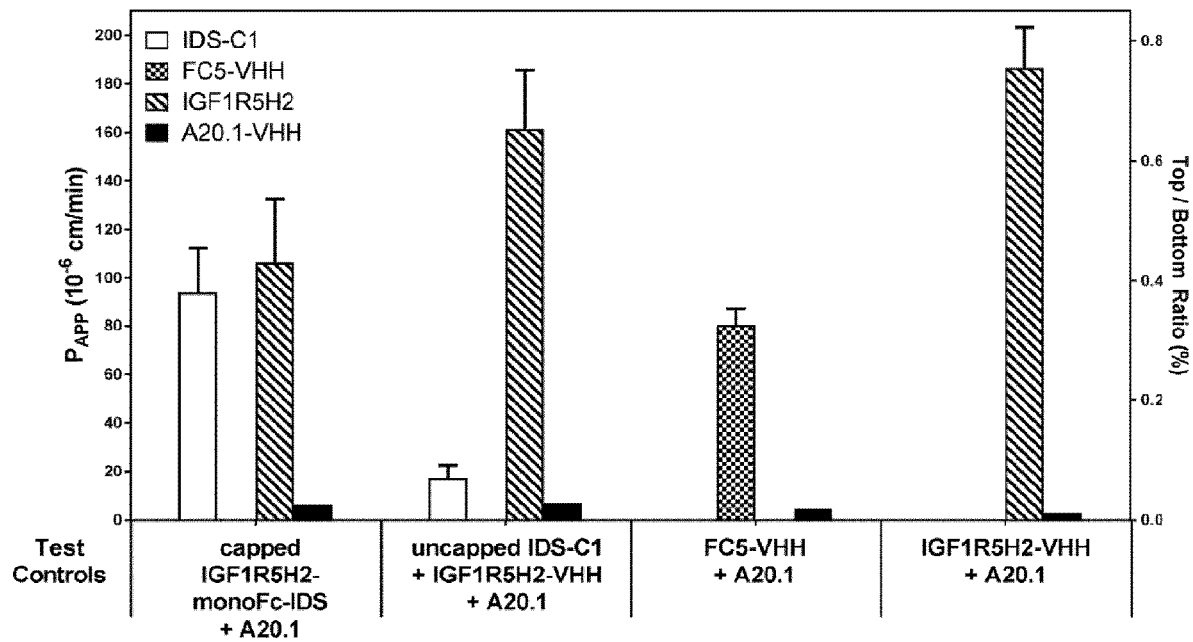
FIG. 7 shows that the construct consisting of an IGF1R5H2 carrier fused to monomeric Fc (monoFc) (Ying et al., 2012) and IDS exhibits good in vitro BBB permeability, exceeding that of the FC5-VHH.
Figure 8:
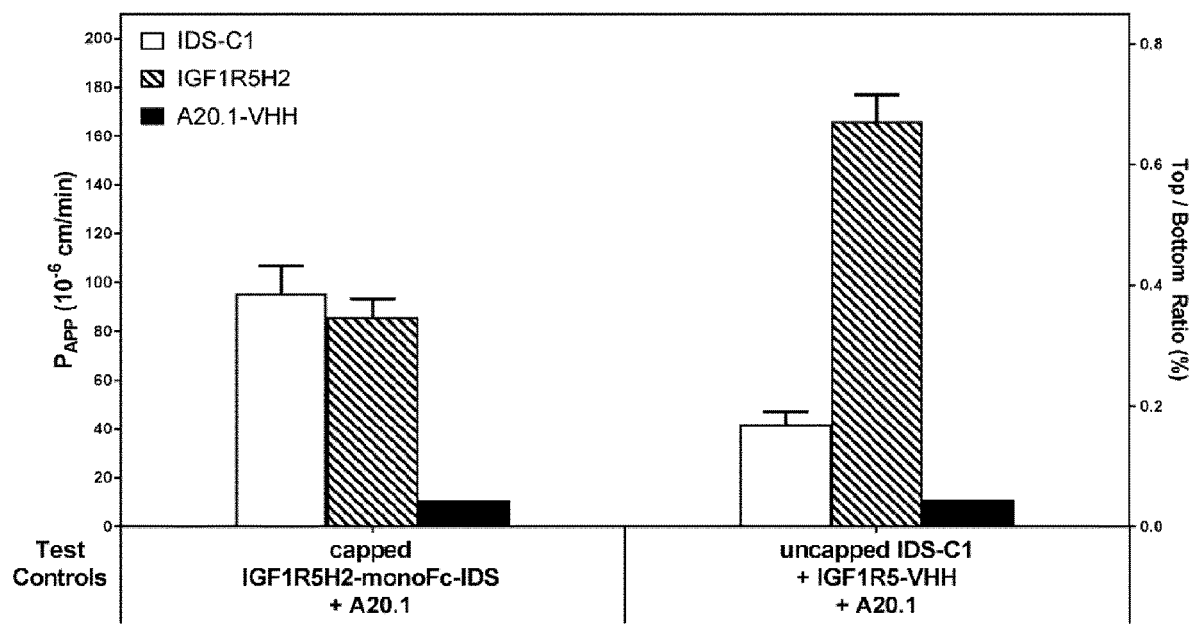
FIG. 8 shows that IGF1R5H2-monoFc-IDS exhibits permeability in an in vitro human BBB model that is comparable to the rat BBB model.
Figure 9:
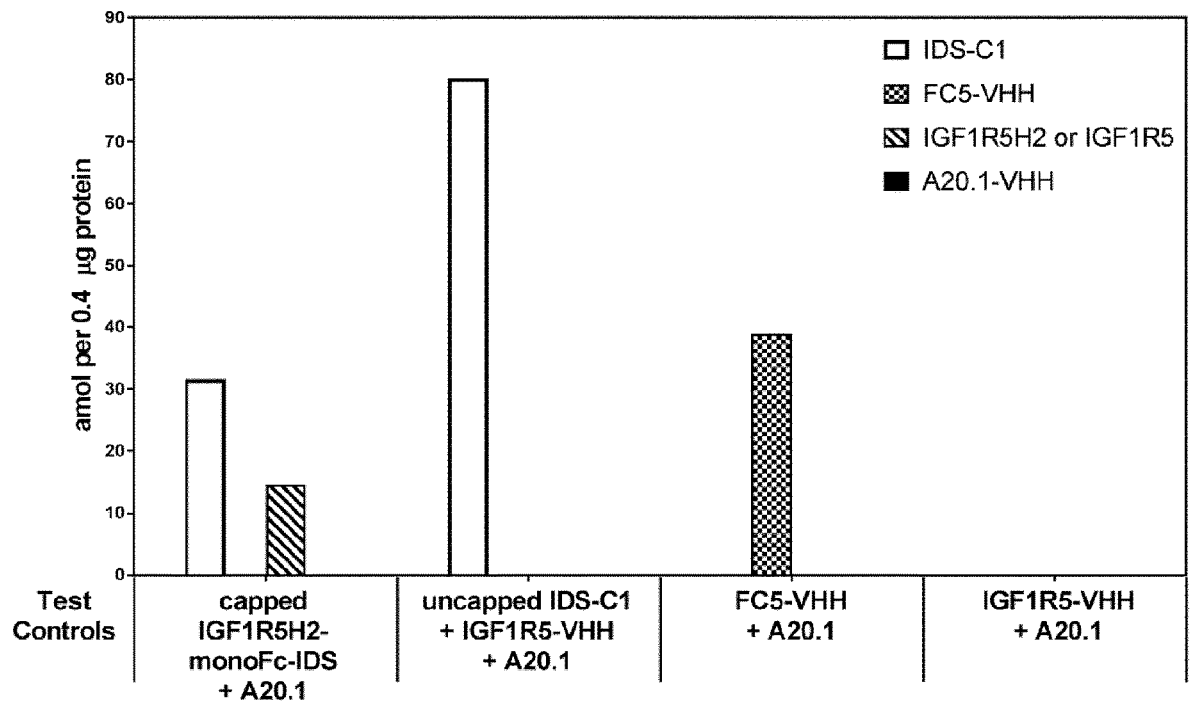
FIG. 9 shows that IGF1R5H2 reduces trapping of IDS in brain endothelial cells. The amounts of IGF1R5H2-monoFc-IDS were significantly lower compared to IDS-C1. Similarly, IGF1R5-VHH was not detected in the SV-ARBEC cells.
Figure 10:
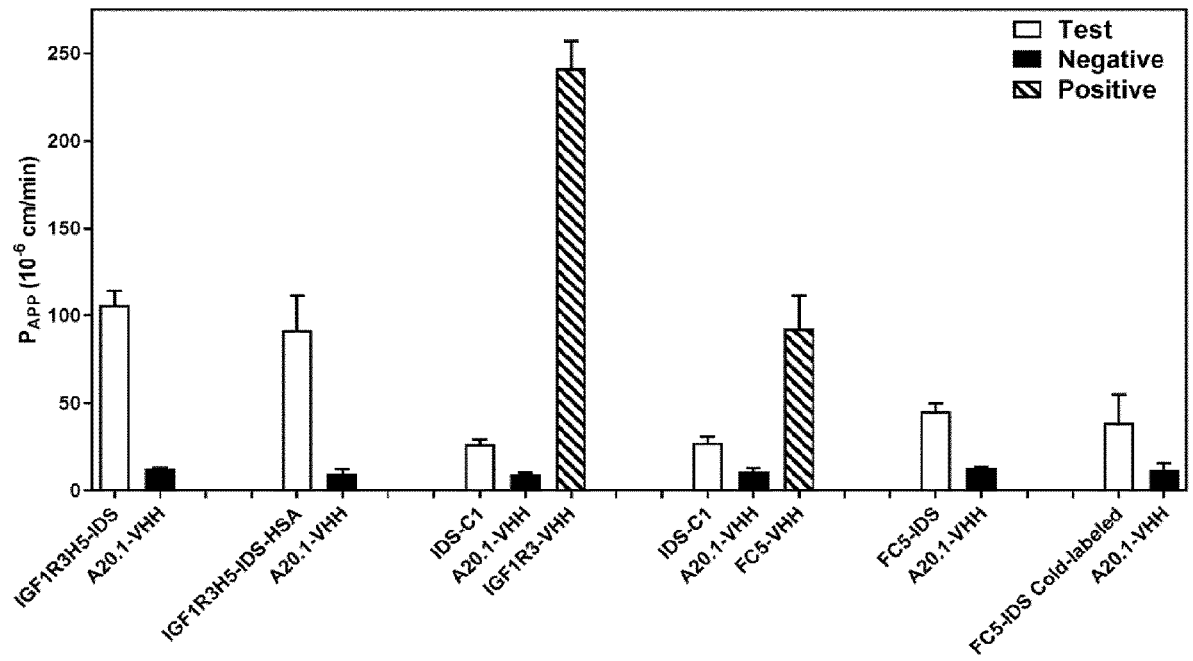
FIG. 10 shows IGF1R3H5-IDS-HSA exhibits in vitro BBB permeability that is comparable to IGF1R3H5-IDS.
Figure 11:
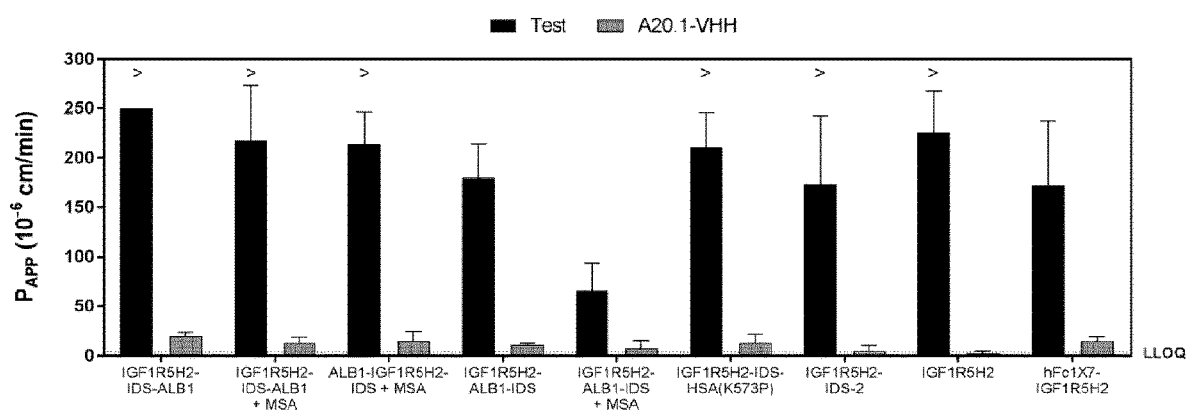
FIG. 11 shows that IGF1R5H2 significantly increase the in vitro BBB permeability of constructs containing, IDS and anti-albumin domains in rat SV-ARBEC cells. The figure also shows the effect of domain arrangement and mouse serum on IGF1R5H2-mediated BBB permeability. > indicates values exceeding the upper limit of quantitation were set to 250.
Figure 12:
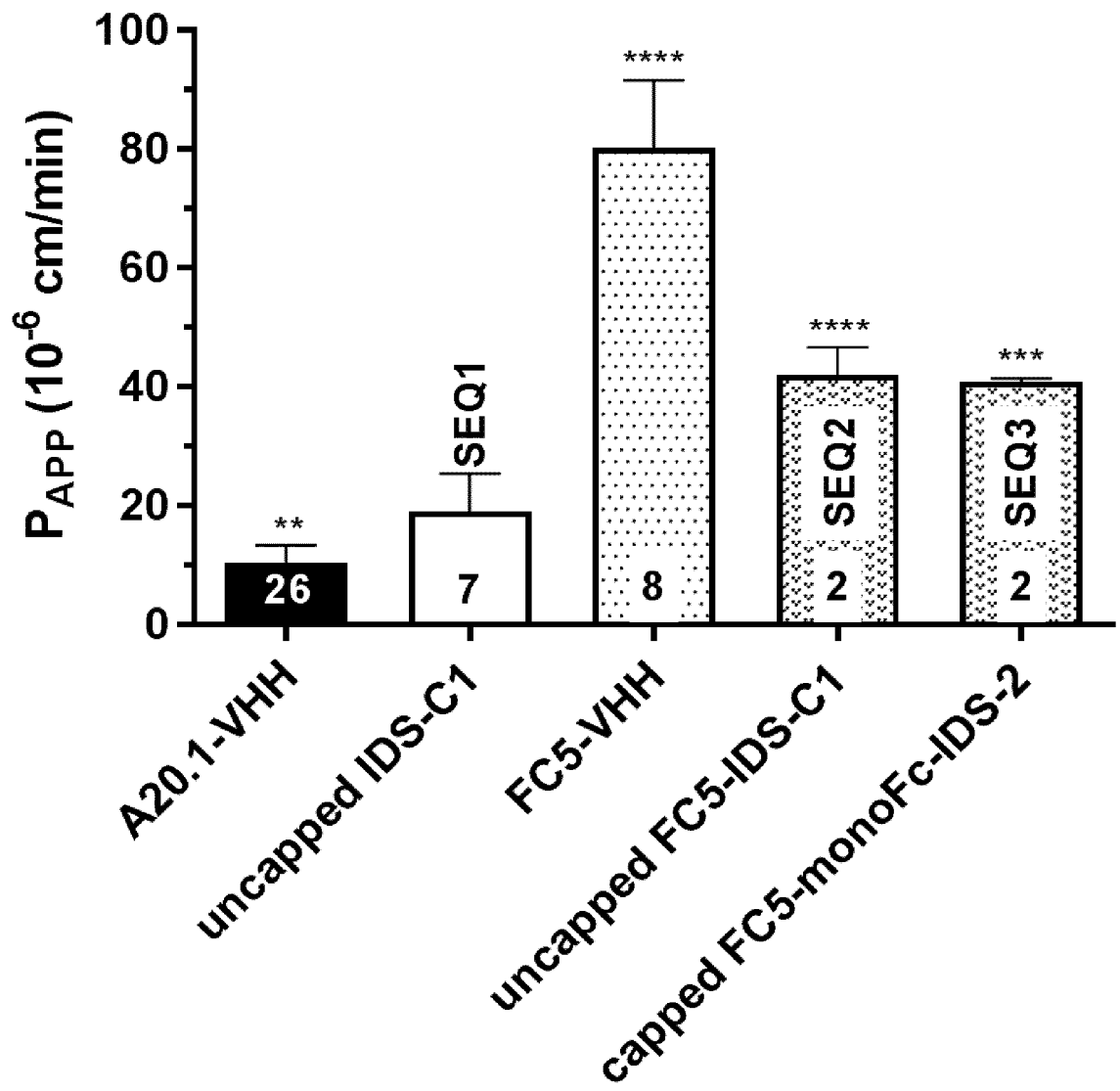
FIG. 12 shows that FC5 significantly increases in vitro BBB permeability of capped or uncapped IDS in rat SV-ARBEC cells.
Figure 13:
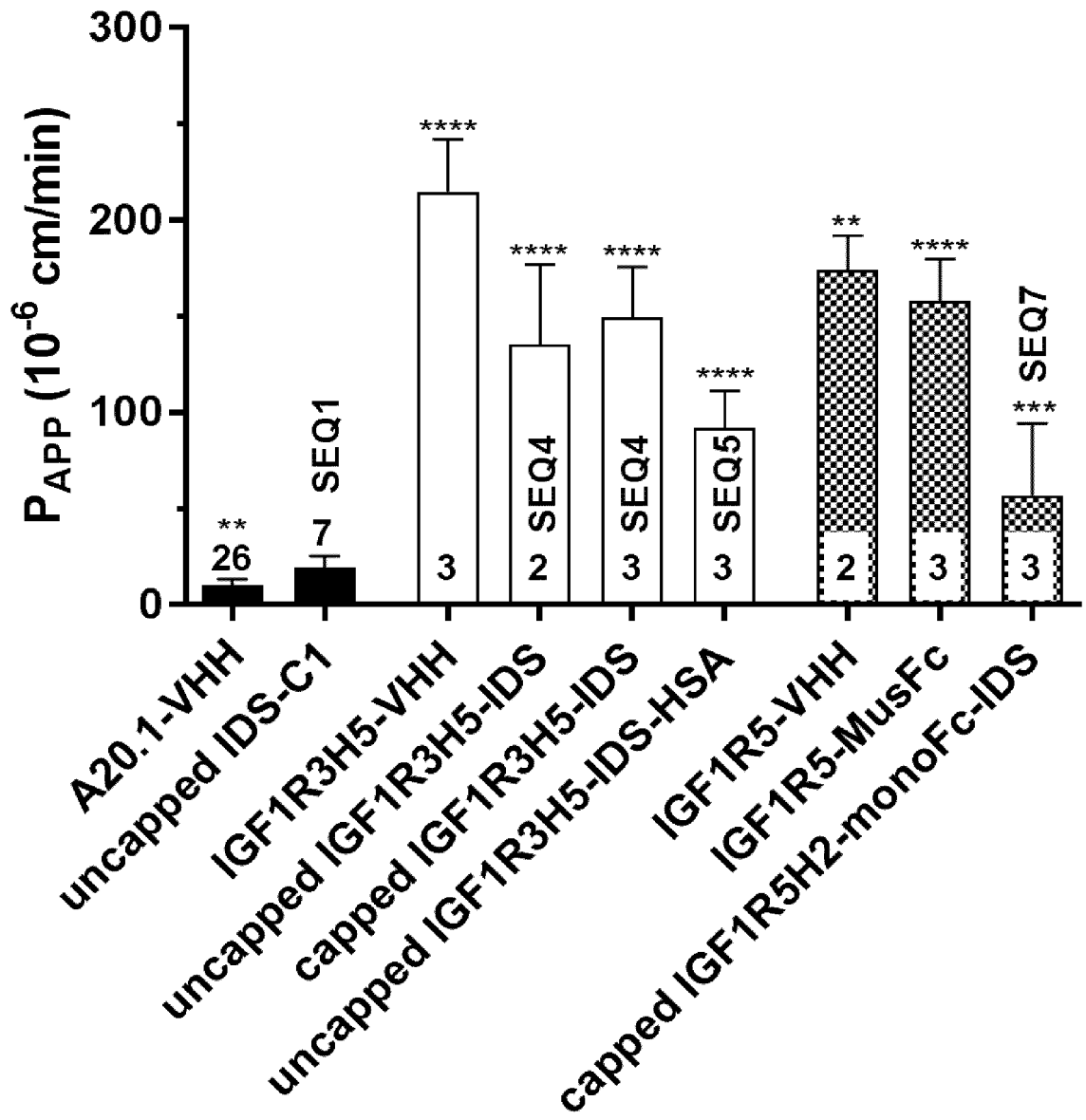
FIG. 13 shows that IGF1R3H5 and IGF1R5H2 significantly increase the in vitro BBB permeability of IDS and IDS-HSA in rat SV-ARBEC cells.
Figure 14:
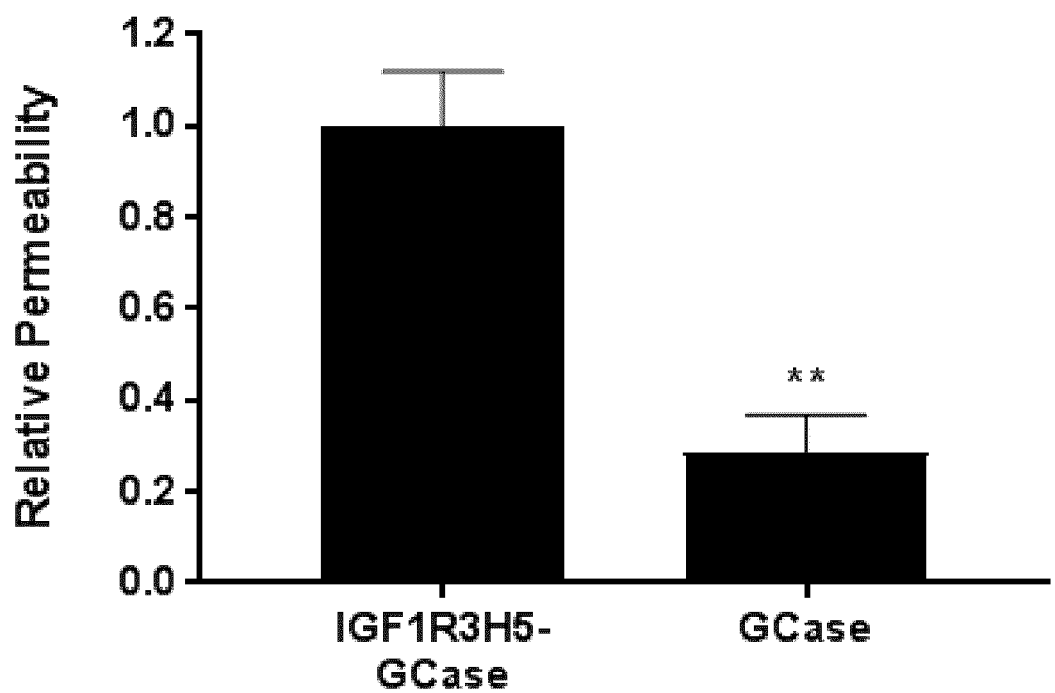
FIG. 14 shows that IGF1R3H5 increases the in vitro BBB permeability of GCase in rat SV-ARBEC cells.

FIG. 6 shows that permeability ($P_{APP}$) of uncapped IDS-C1 (which comprises a C-terminal HIS-Strep tag) was not different from the negative control (A20.1—a VHH that targets a bacterial toxin protein and is used here as a negative control for BBB crossing), whereas the permeability of the IGF1R3H5-IDS constructs was comparable to the positive control IGF1R3-VHH and far exceeded that of uncapped IDS-C1 and A20.1. The BBB transcytosing positive controls (IGF1R3-VHH) exhibited permeability consistent with historical values (IGF1R5-VHH, ~200; IGF1R3-VHH, ~250). FIG. 6 also shows no difference in the permeability of the capped and uncapped fusion proteins. Lastly, the permeability of these fusion proteins (~150) was sufficient to justify evaluation in an in vivo transport assay. In another demonstration, IGF1R5H2-monoFc-IDS (SEQ ID NO:65) enhanced the in vitro transcytosis of IDS across the rat BBB (FIG. 7): IGF1R5H2-monoFc-IDS was shown to exhibit a marked increase in permeability relative to the negative control (A20.1) and comparable to the VHH alone. Furthermore, this construct was capable of effecting transcytosis in a human BBB model, thereby confirming its cross-reactivity between rat and human endothelial cells (FIG. 8). Further analysis of the rat brain endothelial cells used in the assay depicted in FIG. 7 indicated that the uncapped IDS-C1 was taken up by the endothelial cells, but did not undergo transcytosis (FIG. 9). Furthermore, endothelial cell retention of the IGF1R5H2-monoFc-IDS construct was consistent with the positive control FC5-VHH. In another demonstration, permeability of FC5-IDS and IGF1R3H5-IDS-HSA (K573P) were compared to that of IGF1R3H5-IDS (FIG. 10). The figure shows that permeability of VHH alone (FC5 or IGF1R3) is markedly increased relative to the negative control (A20.1) and IDS-C1. Additionally, permeability of IDS was enhanced by fusion with FC5 or IGF1R3H5. Lastly, permeability of a fusion protein containing human serum albumin (IGFR13H5-IDS-HSA (K573P)) was virtually identical to the construct lacking HSA. FIG. 11 confirmed that IGF1R5H2 bearing constructs exhibit elevated BBB permeability, with IGF1R5H2-IDS-2 exhibiting permeability that is comparable to IGF1R5H2 VHH and hFc1X7-IGF1R5H2 (SEQ ID: 70). Furthermore, constructs containing ALB1 or HSA (K573P) were equally permeable. The effect of domain (IGF1R5H2, ALB1, IDS) arrangement was also assessed. While interpretation of the data is limited by the presence of values that exceeded the upper limit of quantitation, it is apparent that alterations in domain arrangement did not produce marked reductions in permeability. However, the presence of mouse serum albumin (MSA; 5 UM) in the upper chamber did reduce the permeability of the IGF1R5H2-ALB1-IDS construct. This indicates that binding of MSA by the anti-albumin domain (ALB1) reduced its availability for IGF1R-mediated transcytosis, an effect that would be expected to be observed in vivo. FIG. 12 summarizes the permeability of the FC5-containing constructs relative to the non-transcytosing negative control (A20.1) and IDS-C1. The figure shows that the permeability of uncapped IDS-C1 was greater than A20.1, but significantly lower than the transcytosing VHH FC5 and the FC5-IDS fusions. FIG. 13 summarizes the permeability of the constructs containing IGF1R-binding VHHs relative to the non-transcytosing negative control (A20.1) and IDS-C1. The figure shows that the permeability of IDS constructs containing IGF1R-binding VHHs was consistently and significantly greater than uncapped IDS-C1. FIG. 14 shows that the relative permeability of IGF1R3H5-GCase (SEQ ID NO:32) was significantly greater than GCase.

Figure 15:
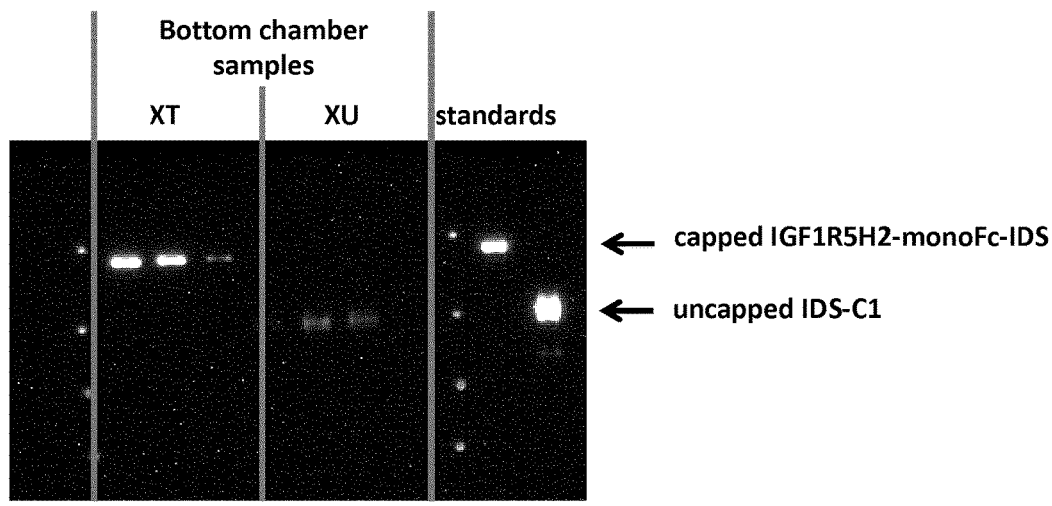
FIG. 15 shows that IGFR1R5H2-monoFc-IDS is not degraded following in vitro transcytosis in rat SV-ARBEC cells. (A) is an anti-IDS western blot showing the detection of IGF1R5H2-monoFc-IDS (XT) and IDS-C1 (XU) in the bottom chambers of the in vitro BBB assay, and (B) is a quantitation of the western blot in panel (A).
Figure 15:
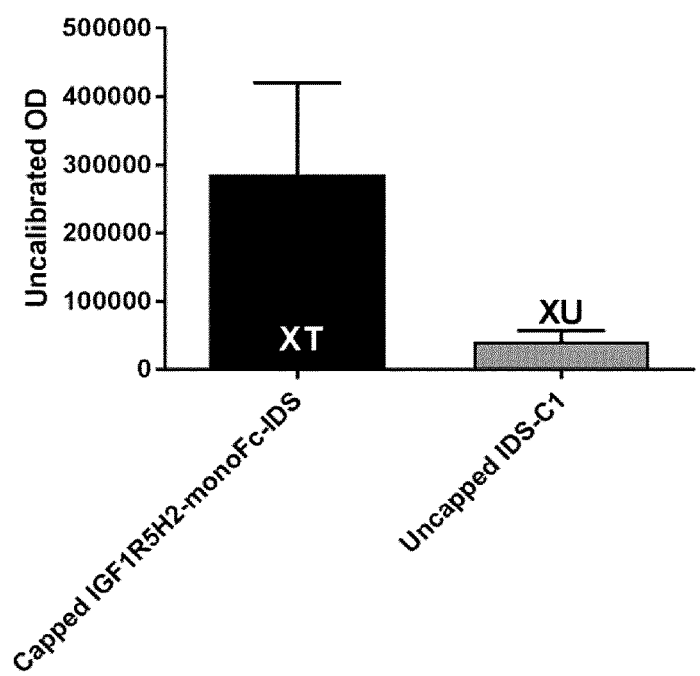

Western blot analysis of in vitro BBB transcytosis in rat brain endothelial cells. An assessment of transcytosis was attempted by evaluating protein levels using western blotting (anti-IDS) of SDS-PAGE gels. Prior to SDS-PAGE, the samples from bottom chamber (500 µL) were concentrated using Amicon Ultra spin columns (10 K cut-off). Immunoreactivity was quantified using FluorChem E analysis (FIG. 15). Analysis of the blot indicated that transport of IGF1R5H2-monoFc-IDS was significantly greater than IDS-C1 (FIG. 15), although the protein amount varies among replicates. Additionally, no evidence for degradation or protein cleavage of the samples was observed in either the bottom or top (not shown) chambers.

EXAMPLE 3

In Vivo PK/PD Analysis of IGF1R3H5-IDS and Similar Test Compounds in Rats and Non-Human Primates Biodistribution: CSF and brain collection. All animals were purchased from Charles River Laboratories International, Inc. (Wilmington, MA, USA). Animals were housed in groups of three in a 12 h light-dark cycle at a temperature of 24° C., a relative humidity of 50±5%, and were allowed free access to food and water. All animal procedures were approved by the NRC's Animal Care Committee and were in compliance with the Canadian Council of Animal Care guidelines. Male Wistar rats aged 8-10 weeks (weight range, 230-250 g) were used for sample collection. CSF and brain were collected to assess the biodistribution of the test sample. The animals were provided analgesia (sustained release buprenorphine, 1.2 mg/kg) before the first CSF collection. Rats were anaesthetized with 3% isoflurane and placed in a stereotaxic frame with the head rotated downward at a 45° angle. A midline incision was made beginning at the occipital crest and extending caudally about 2 cm on the back of the neck. The superficial neck muscles and underlying layers of muscle covering the cisterna magna were separated along the midline by blunt dissection. The neck muscles were retracted in order to expose the dura mater. A 27G butterfly needle with tubing attached to 1 ml syringe was inserted with the bevel of the needle faced up and the angle of insertion was parallel with the dura membrane. One hand was used to gently retract the syringe plunger and aspirate the CSF (~ 15-20 µL) while the other hand firmly held the needle in its original position. The CSF sample was ejected into a glass sample vial and the vial was immediately placed on dry ice; the frozen sample was subsequently transferred to a −80° C. freezer until further analysis. The wound was then closed and a blood sample was collected from the tail vein, according to Fluttert et al. (2000). The rat was then returned to its home cage and housed in the recovery room until the next CSF collection. For subsequent CSF and blood collections, the rat was anaesthetized and the sutures removed. The muscles covering the cisterna magna were gently separated and the dura mater exposed. CSF sampling was then performed as described above. Approximately 15-20 µL of CSF can be collected at each time point. For the terminal CSF collection, approximately 50-100 µL of CSF can be collected and blood is collected by heart puncture. Finally, euthanasia is performed by cervical dislocation under deep isoflurane anesthesia.

Brain homogenization and processing. Prior to MRM analysis the entire right hemisphere was weighed while frozen and the middle third was extracted and weighed (typically ~0.16 g). The remaining tissue was stored at −80° C. The brain tissue was then homogenized in 1.0 mL ice-cold homogenization buffer (50 mM Tris-HCl, pH 8, 150 mM NaCl, 1.0% sodium deoxycholate (Sigma), and 1× protease inhibitor cocktail (Sigma)) using a Wheaton Dounce homogenizer (10-12 strokes with a Glas-Col drill (model #099C K54) at 60% speed, at 4° C.) until pieces of tissue are no longer detectable. Samples were sonicated (Fisher, Model 300 Sonic Dismembrator) on ice with three 10 s bursts at 30%, and insoluble material was removed by centrifugation (20,000 g for 10 min at 4° C.). The supernatants were then transferred to new tubes on ice. Protein concentrations were then determined using the Bradford method with a standard curve based on bovine serum albumin (BSA Quick Start Standard; BioRad). A 5.0 µL aliquot of the brain extract was diluted 1:5 in 25 mM ammonium bicarbonate (ABC; Sigma), and a volume corresponding to 20 µg was transferred to a new tube. The 20 µg aliquot was made up to 12.5 µL with 25 mM ABC and 12.5 µL of 10% sodium deoxycholate (DOC; Sigma) was added to give a concentration of 5% DOC. The samples were then vortexed and briefly centrifuged prior to the addition of 2.5 µL freshly prepared 10× DL-dithiothreitol (DTT; Sigma) to provide a concentration of 5 mM DTT. The samples were vortexed and centrifuged briefly and then incubated at 95° C. for 10 minutes. The samples were then cooled, and briefly centrifuged prior to the addition of 2.75 µL 10× iodoacetamide (Sigma) for a concentration of 10 mM. The samples were vortexed and centrifuged prior to incubation at room temp for 30 minutes in the dark. The samples were then diluted to 125.0 µL with 25 mM ABC. A 2.0 µL (1.0 µg) aliquot of trypsin (Promega) was then added to each sample, which were then mixed gently and briefly centrifuged prior to incubation in a Multitherm Incubator/Chiller unit (model H5000) at 37° C. for 12 hours and at 4° C. thereafter. The samples were then stored at −80° C. until MRM analysis was conducted. Prior to MRM analysis, the DOC was precipitated by adding 15 µL AAF buffer (54% acetic acid, 150 mM ammonium acetate, 10% formic acid) to a 115 µL aliquot of the digested sample. The samples were then centrifuged at 50,400×g for 10 min at 4° C., and 60 µL of the supernatant was transferred to a fresh vial. MRM analysis was performed using 20 µL of the supernatant.

In selected animals, brain homogenates of the left hemisphere were subjected to a vessel depletion protocol to obtain brain parenchyma and brain vessel fractions. The tissues were homogenized as above and sequential filtration through 100 µm and 20 µm nylon Nitex mesh filters (pluriSelect, Leipzig, Germany) was performed to obtain the brain fractions. Concentrations of test substances were determined in the vessel-depleted parenchymal fractions and the vessel fractions using SRM as above.

Serum and CSF pharmacokinetics. At several post-injection timepoints, blood was collected, and serum was prepared to determine serum half-life. Blood samples were taken from the lateral tail vein at 5, 10, 15 and 30 min and 1, 2, 4, 6, 8, and 24 h post administration. Samples were centrifuged (15 min at 15,000 rpm; room temperature) and serum was stored at −80° C. until analysis. Serum half-life was determined by plotting serum concentration (in M) versus time and performing non-linear curve fitting using the one-phase and two-phase decay models. In both models, the plateau value was set to zero and the best fit (one-phase vs. two-phase) was determined by performing an F test on the sum of squares. Area under the curve (AUC) data was also calculated for serum using GraphPad Prism.

nanoLC/MS/MS. The protein levels of the test samples in ex vivo samples (serum, cerebrospinal fluid (CSF), and brain) were quantified using targeted nanoflow liquid chromatography tandem mass spectrometry (nanoLC MS/MS). Pure VHH or fusion proteins and body fluid samples containing these proteins are reduced, alkylated, and trypsin digested (Haqqani et al., 2008b, 2013). Typically, for isotopically labeled internal standard (ILIS)-based quantification, isotopically heavy versions of a peptide that contains heavy C-terminal K (+8 Da) is synthesized from a commercial source (New England Peptide LLC, Gardner, MA, USA). However, since no ILIS for the protein-of-interest are available, ILIS for an alternative protein (e.g., FC5 or hFc) is included as an indicator of sample-cleanup variability. Each protein is first analyzed by nanoLC-MS/MS [nanoAcquity UPLC (Waters, Milford, MA, USA) coupled to LTQ XL ETD MS (ThermoFisher, Waltham, MA, USA)] using data-dependent acquisition to identify all ionizable peptides, and the 3-5 of the most intense fragment ions are chosen. An initial selected reaction monitoring (SRM) assay is developed to monitor these fragments at attomole amounts of the digest. Fragments showing reproducible intensity ratios at low amounts (~100-300 amol; Pearson $r^2 \geq 0.95$) are considered stable and are chosen for the final SRM assay. Blood contamination of CSF samples is evaluated by in-reaction monitoring of rat albumin levels using a nanoLC-SRM method. Measurement of CSF protein concentration is used as a rapid quantitative and nonspecific method for identifying serum contaminated samples. Typical protein concentration of CSF is 0.2-0.4 mg/mL in rat. Protein concentrations >0.4 mg/ml are considered to be likely contaminated with blood. The albumin blood-CSF ratio is determined by multiple SRM analysis of CSF and the corresponding serum sample. Ratios less than 1500-fold are considered contaminated with blood and are excluded from further analyses.

Figure 16:
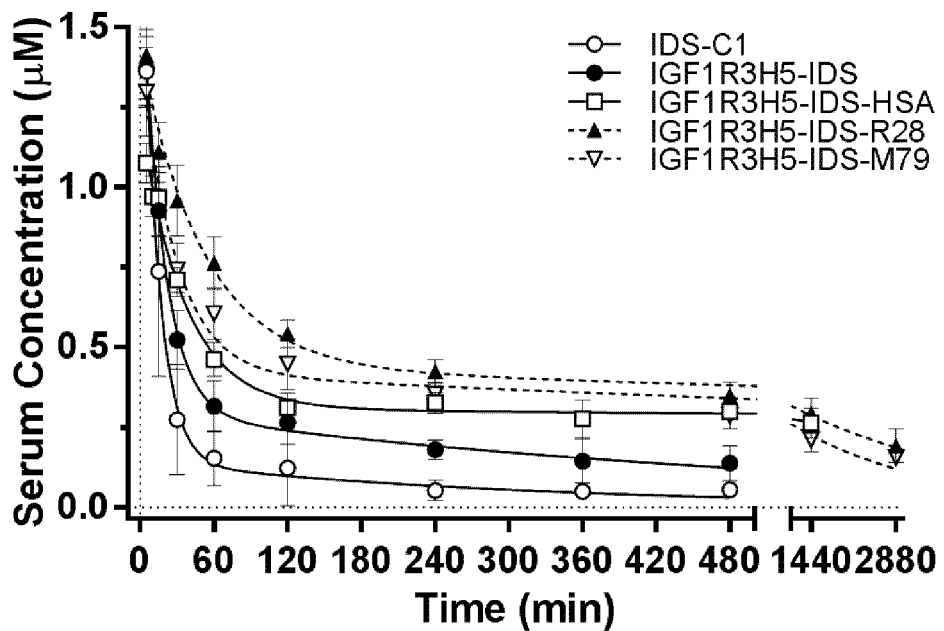
FIG. 16 shows protein concentrations of IDS-C1, IGF1R3H5-IDS, IGF1R3H5-IDS-HSA, IGF1R3H5-IDS-R28 and IGF1R3H5-IDS-M79 in rat serum following single bolus iv injections of equimolar doses of the test articles. (A) Levels were determined by MRM and (B) by IDS activity of IDS-C1 and IGF1R3H5-IDS only.
Figure 16:
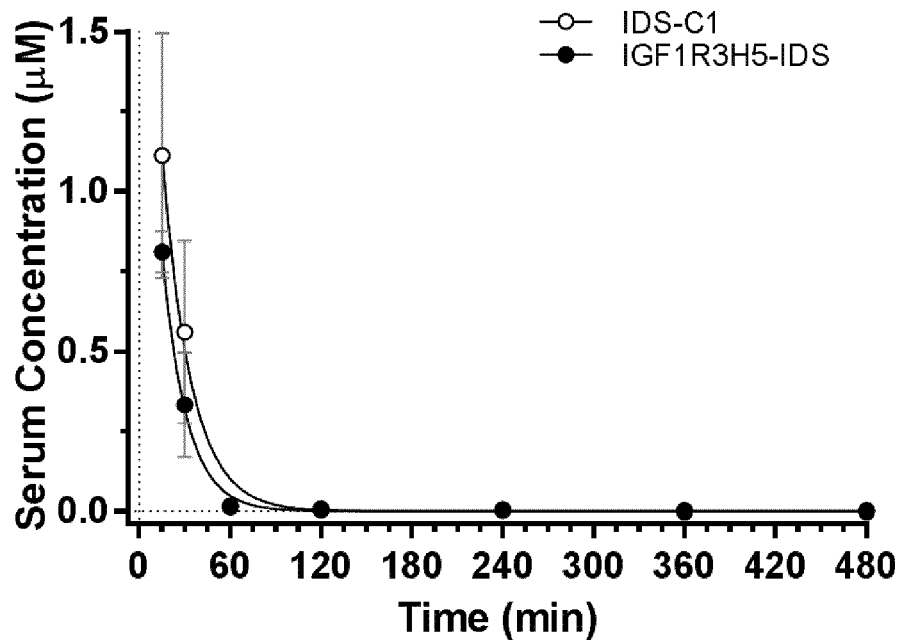

FIG. 16A shows protein concentrations of IDS-C1, IGF1R3H5-IDS, IGF1R3H5-IDS-HSA (K573P), IGF1R3H5-IDS-R28 and IGF1R3H5-IDS-M79 in rat serum following single bolus iv injections of equimolar doses of the test articles. The data indicate that both IDS-C1 and IGF1R3H5-IDS are rapidly cleared from the serum with kinetics (Alpha_hl and Beta_hl) that are appreciably different (FIG. 17). In comparison to IDS-C1, the serum PK of IGF1R3H5-IDS was unexpectedly extended, resulting in an 80% increase in the serum area under the curve (AUC). Analysis of serum IDS concentration based on IDS enzymatic activity confirmed that IDS-C1 and IGF1R3H5-IDS are quickly cleared from the serum (FIG. 16B). In comparison, the serum PK data shown in FIG. 17 indicate that the IGF1R3H5-IDS-HSA (K573P) construct had a greatly reduced serum clearance ($C_L$) rate (0.0705 mL/min/kg) compared to IGF1R3H5-IDS (0.516 mL/min/kg) and IDS-C1 (0.924 mL/min/kg). The PK analysis indicated that the test sample (IGF1R3H5-IDS-HSA) exhibited a much longer serum half-life ($\alpha t_{1/2}$=27.6 min, $\beta\beta t_{1/2}$=36.8 hr; FIGS. 16 and 17) than what was previously observed for IGF1R3H5-IDS and IDS-C1. Correspondingly, the elimination of IGF1R3H5-IDS-HSA (K573P) was ~8- to 14-fold (according to serum AUC values) slower than the constructs lacking HSA (FIG. 17). Similarly, the constructs containing albumin binding VHH domains (IGF1R3H5-IDS-M79 and IGF1R3H5-IDS-R28) exhibited reduced serum clearance and increased serum $t_{1/2}$ values. Unexpectedly, the serum clearance of IGF1R3H5-IDS-M79 and IGF1R3H5-IDS-R28 were less than that observed for IGF1R3H5-IDS-HSA (K573P). As a result, the serum $\alpha t_{1/2}$ values of IGF1R3H5-IDS-M79 and IGF1R3H5-IDS-R28 were 1.51- and 1.61-fold longer than for IGF1R3H5-IDS-HSA (K573P). Importantly, the anti-albumin containing constructs exhibited serum PK values that were consistent with the HSA containing construct. Thus, serum half-life extension was realized using two distinct strategies.

Figure 18:
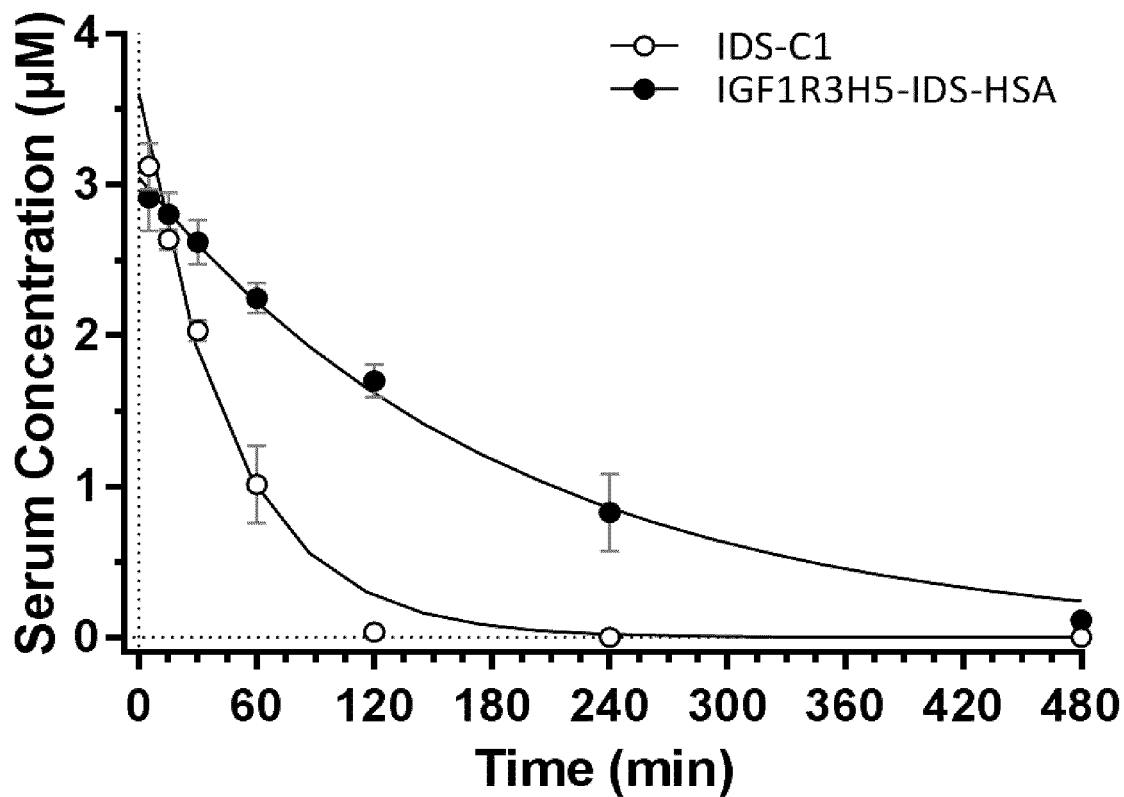
FIG. 18 shows protein concentrations of IDS-C1 and IGF1R3H5-IDS-HSA in cynomolgus monkey (*Macaca fascicularis*) serum following single bolus iv injections of equimolar doses of the test articles. Levels were determined by MRM.

FIG. 18 shows protein concentrations of IDS-C1 and IGF1R3H5-IDS-HSA (K573P) in cynomolgus monkey (*Macaca fascicularis*) serum following single bolus iv injections of equimolar doses of the test articles. Levels were determined by MRM. The data confirms that IDS-C1 is rapidly cleared from serum ($t_{1/2}$=32 min) in non-human primates. Additionally, a significant, 4-fold increase in serum $t_{1/2}$ is observed for the IGF1R3H5-IDS-HSA (K573P) construct ($t_{1/2}$=131 min).

Figure 19:
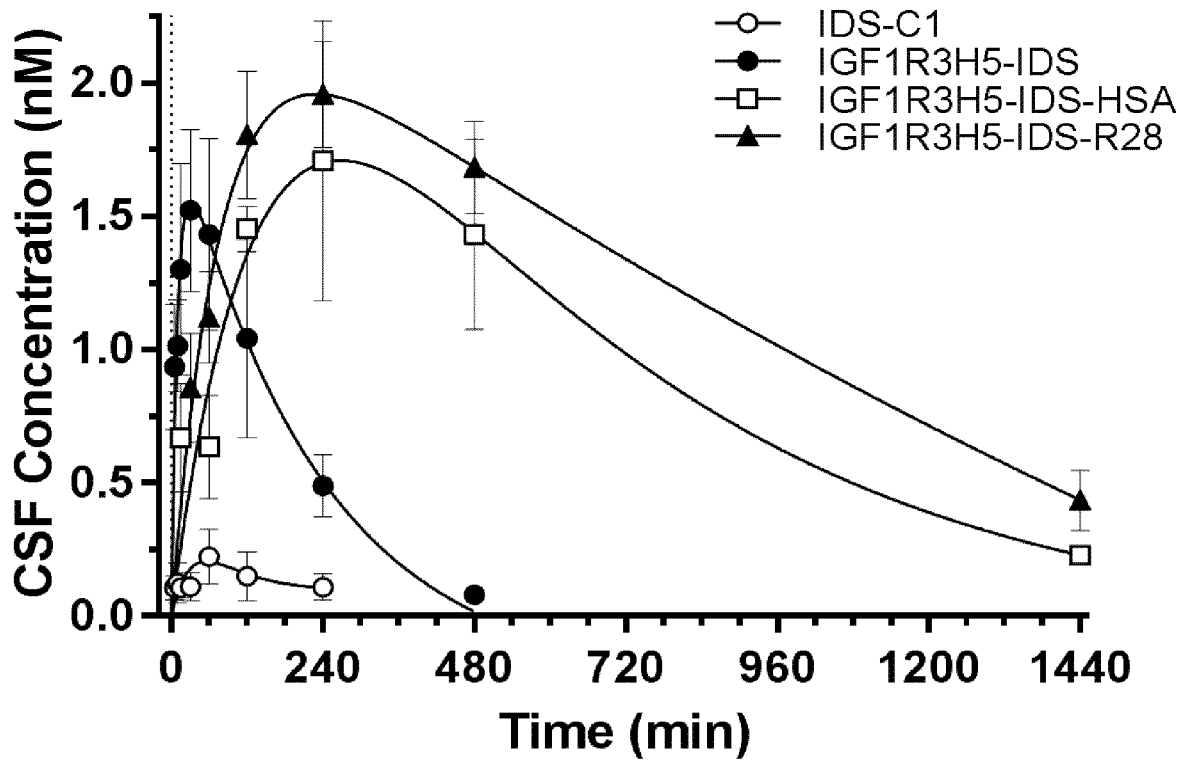
FIG. 19 shows protein concentrations of IDS-C1, IGF1R3H5-IDS, IGF1R3H5-IDS-HSA and IGF1R3H5-IDS-R28 in rat CSF following single bolus iv injections of equimolar doses of the test articles.

FIG. 19 compares protein concentrations of IDS-C1, IGF1R3H5-IDS, IGF1R3H5-IDS-HSA (K573P) and IGF1R3H5-IDS-R28 in rat CSF following single bolus iv injections of equimolar doses of the test articles. It can be seen that the peak CSF concentrations of IGF1R3H5-IDS, IGF1R3H5-IDS-HSA (K573P) and IGF1R3H5-IDS-R28 are very similar, which is likely the result of the similar dosing levels employed. This is in stark contrast to the minimal amounts of IDS-C1 that were detected in the CSF, thus confirming the capability of the IGF1R3H5 VHH to enable in vivo BBB transcytosis of IDS. Analysis of CSF levels of IGF1R3H5-IDS-HSA (K573P) and IGF1R3H5-IDS-R28 indicates that maximum peak levels were observed 4 hr post-administration, with detectable levels present 24 post-administration (FIG. 19). In comparison, peak CSF levels of IGF1R3H5-IDS were observed at 30-60 min post-administration and were virtually absent by 8 hr post-administration. In comparison to IGF1R3H5-IDS, IGF1R3H5-IDS-HSA (K573P) levels in CSF at 8 hr post-administration were comparable to the peak observed levels (FIG. 19). Importantly, the IGF1R3H5-IDS-HSA (K573P) and IGF1R3H5-IDS-R28 constructs exhibited distinctly prolonged CSF PK profiles, resulting in 42.4- and 52.4-fold increases, respectively, in the observed AUC compared to IDS-C1 (FIG. 20). Calculation of the AUC ratio (CSF/serum) indicated that the IGR1R3H5 containing constructs exhibited a similar degree of BBB transcytosis, with all constructs being improved by a factor of ~ 3-5 compared to IDS-C1. Furthermore, these data emphasize the dramatic effect of serum half-life prolongation on increasing brain delivery. Analysis of the IDS-R28 construct indicated that it exhibited an increased serum PK relative to IGF1R3H5-IDS and IDS-C1, with 2.6- and 5.3-fold increases in serum AUC, respectively. Surprisingly, the serum AUC of IGF1R3H5-IDS-R28 was 3.1-fold greater than IDS-R28. Considering the unexpected serum PK extension observed with the inclusion of IGF1R3H5 (FIG. 17, FIG. 20), it appears that IGF1R3H5 and R28 act through an unpredicted mechanism to synergistically extend the serum PK of IDS-C1.

Figure 21:
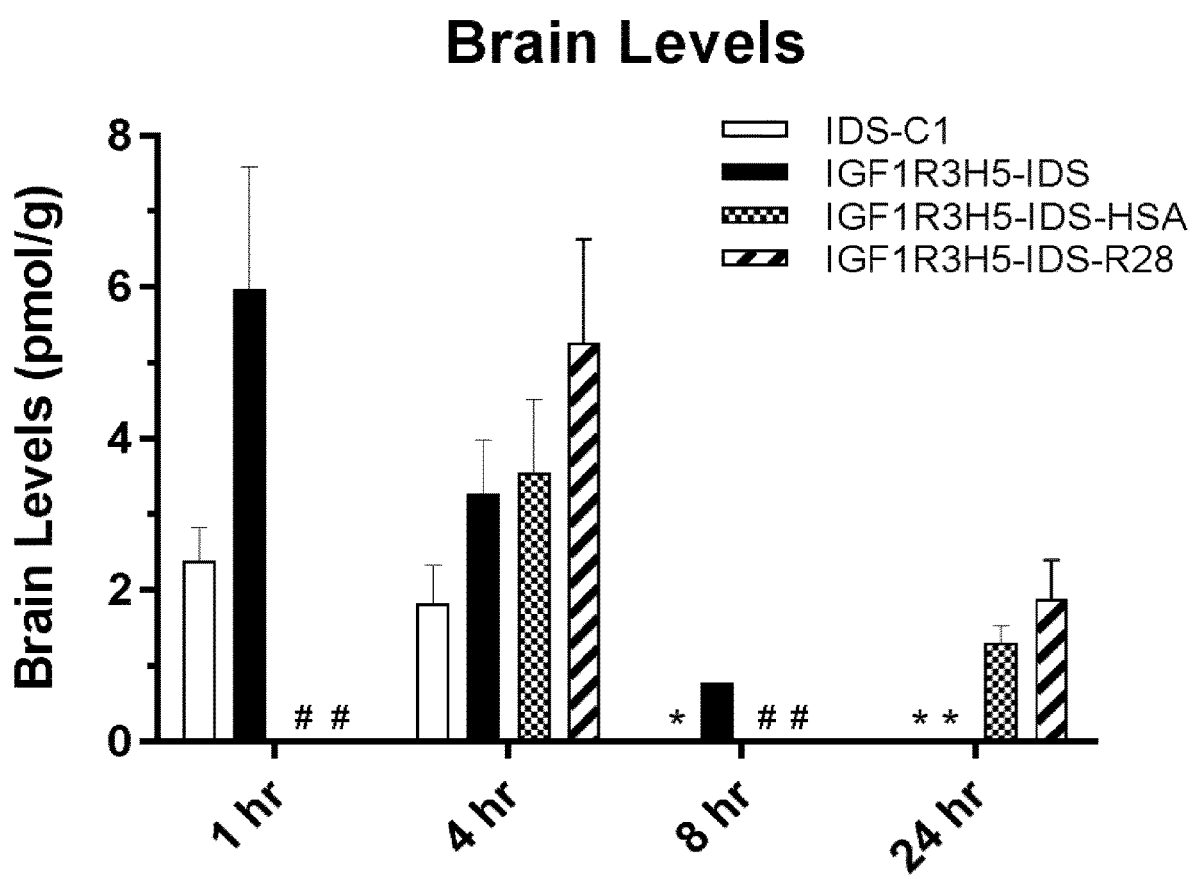
FIG. 21 shows protein concentrations of IDS-C1, IGF1R3H5-IDS, IGF1R3H5-IDS-HSA and IGF1R3H5-IDS-R28 in rat whole brain homogenates following single bolus iv injections of equimolar doses of the test articles. * not detected; # not determined.
Figure 22:
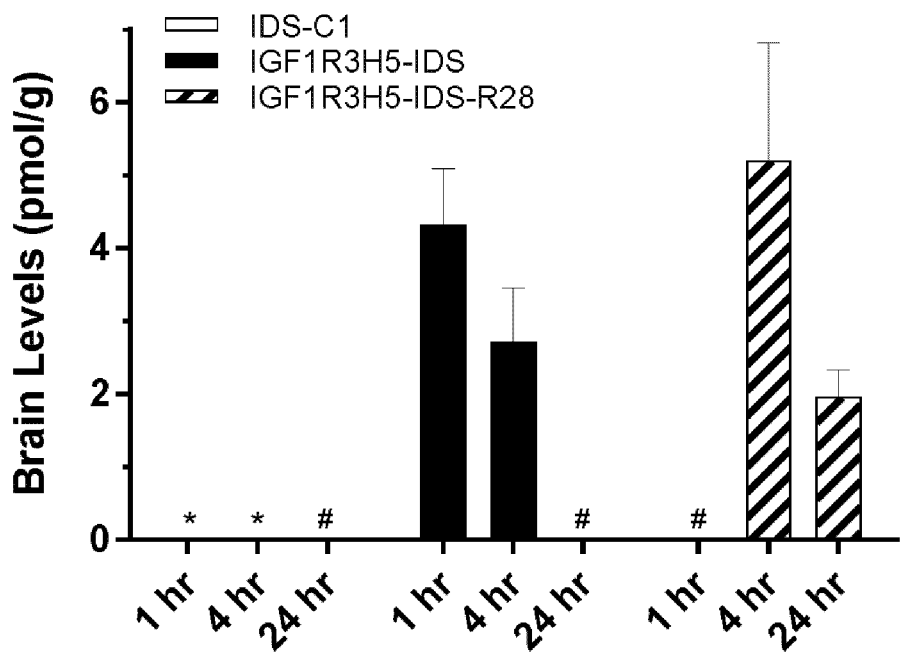
FIG. 22 shows protein concentrations of IDS-C1, IGF1R3H5-IDS and IGF1R3H5-IDS-R28 in rat brain parenchyma and vessels following single bolus iv injections of equimolar doses of the test articles. * not detected; # not determined.
Figure 22:
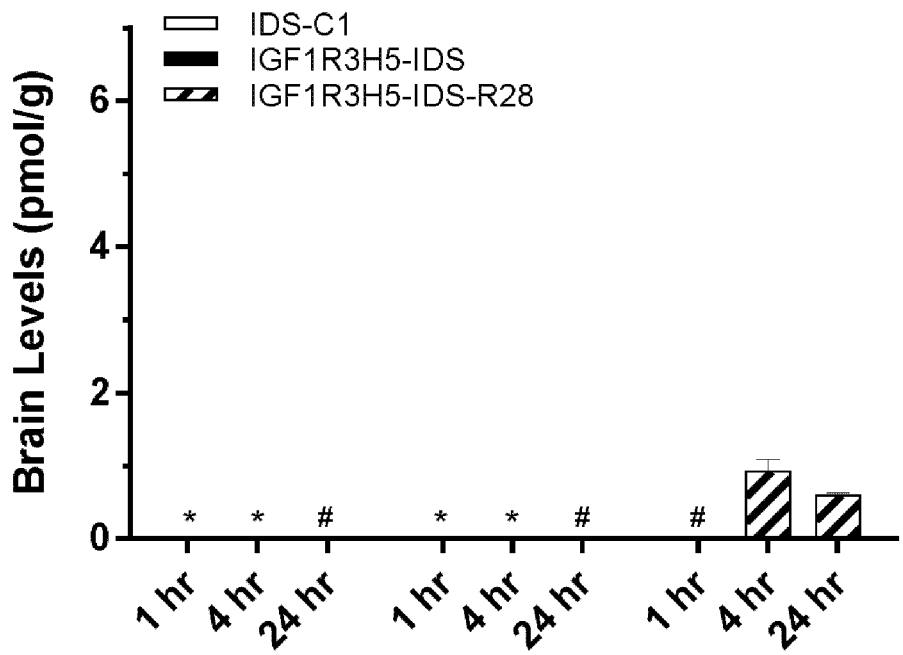
Figure 23:
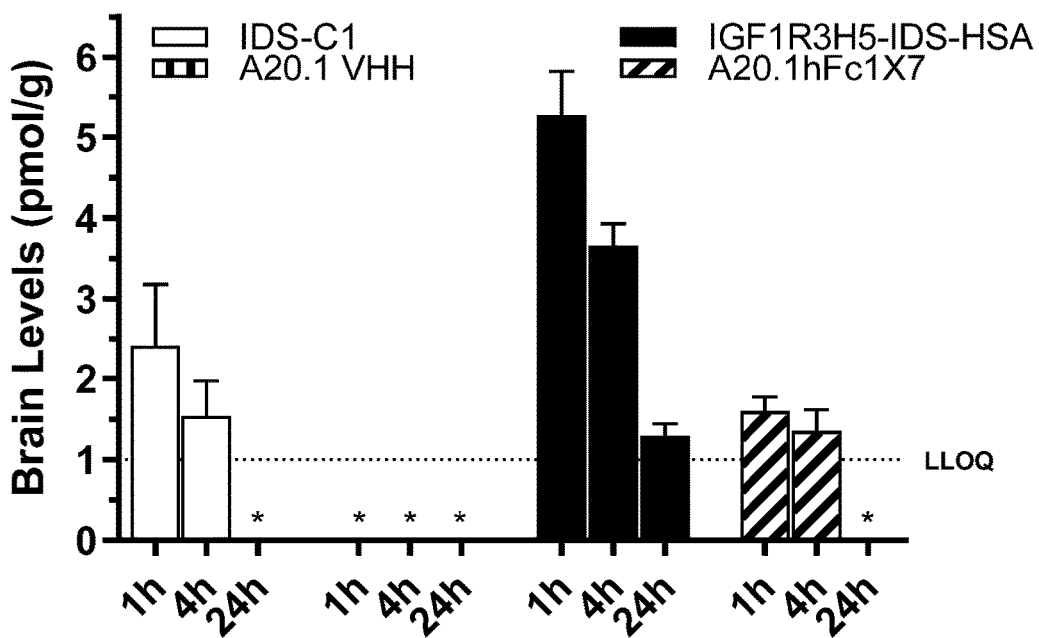
FIG. 23 shows protein concentrations of IDS-C1, A20.1 VHH, IGF1R3H5-IDS-HSA and A20.1hFc1X7 (SEQ ID NO:69) in (A) whole rat brain 1, 4 and 24 hours and (B) rat brain parenchyma and vessels 4 hours post-treatment following single bolus iv injections of equimolar doses of the test articles. * not detected.
Figure 23:
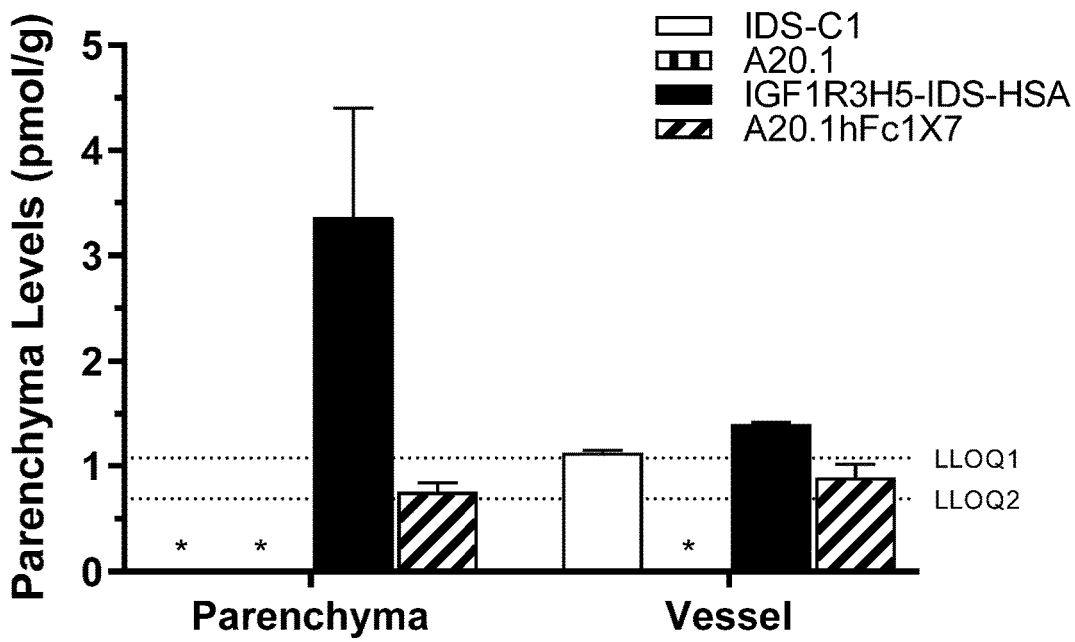

Whole brain levels of IDS-C1 (1, 4 & 8 hours), IGF1R3H5-IDS (1, 4, 8 & 24 hours), IGF1R3H5-IDS-HSA (K573P) (4 & 24 hours) and IGF1R3H5-IDS-R28 (4 & 24 hours only) were quantified and FIG. 21 shows the test sample levels in rat brain over a 24-hour period. Brain levels of IGF1R3H5-IDS were substantially greater than IDS-C1 at 1 and 4 hours, with IDS-C1 not detected at 8 hours. In comparison, detectable levels of IGF1R3H5-IDS-HSA (K573P) and IGF1R3H5-IDS-R28 were observed in the brain at 4 and 24 hours, indicating an increase in brain delivery that is commensurate with the observed CSF levels. This indicates that overall brain exposure was enhanced by the inclusion of HSA or R28. FIG. 22 shows an analysis of IDS-C1, IGF1R3H5-IDS and IGF1R3H5-IDS-R28 in brain parenchyma and brain vessels. FIG. 21 shows that IDS-C1 was detected in whole brain at 1 and 4 hours post-administration. However, IDS-C1 was below the detection limits in brain parenchyma and vessel samples from the same animals (FIG. 22). In contrast, IGF1R3H5-IDS was detected in whole brain (FIG. 21) and brain parenchyma at 1 and 4 hours. Furthermore, IGF1R3H5-IDS was not detected in the vessel fractions. In comparison, IGF1R3H5-IDS-R28 was detected in whole brain (FIG. 21) as well as in brain parenchyma and vessels (FIG. 22). Importantly, the IGF1R3H5-IDS and IGF1R3H5-IDS-R28 levels in brain parenchyma were much greater than in brain vessels. This indicates that retention of IGF1R3H5-IDS and IGF1R3H5-IDS-R28 in the vessel component is likely to be limited and that delivery to the parenchyma is achieved. An additional experiment was conducted using higher doses of the test articles. FIG. 23 shows protein concentrations of IDS-C1 and IGF1R3H5-IDS-HSA (K573P) in rat brain parenchyma and vessels following single bolus iv injections of equimolar doses of the test articles. FIG. 23A confirms that IDS-C1 is detectable in whole brain at 1 and 4 hours, but not at 24 hours. The figure also demonstrates IGF1R3H5-IDS-HSA (K573P) levels were much greater than IDS-C1 and the non-BBB crossing controls (A20.1 VHH and A20.1hFc1X7). FIG. 23B demonstrates that IDS-C1 and A20.1hFc1X7 are not detectable in brain parenchyma at 4 hours, while IDS-C1 is present at low levels in brain vessels at 4 hours. In stark contrast, the majority of IGF1R3H5-IDS-HSA was found in the brain parenchyma and was not observed to be trapped in brain vessels. Furthermore, the low level of brain vessel "trapping" in the in vivo studies is consistent with observations in the in vitro BBB models (FIG. 9).

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

SEQUENCES

| SEQ ID NO: | Sequence | Description |
|---|---|---|
| SEQ ID NO: 1 | GFKITHYTMG | CDR1 FC5 |
| SEQ ID NO: 2 | RITWGGX1X2TX3YSNSVKG, where $X_1$ is D or K, $X_2$ is N or D, and $X_3$ is F, I or L | CDR2 FC5 |
| SEQ ID NO: 3 | GSTSTAX4PLRVDY, where $X_4$ is T or K | CDR3 FC5 |
| SEQ ID NO: 4 | EVQLQASGGGLVQAGGSLRLSCAASGFKITHYTMGWFRQAP GKEREFVSRITWGGDNTFYSNSVKGRFTISRDNAKNTVYLQM NSLKPEDTADYYCAAGSTSTATPLRVDYWGKGTQVTV | FC5 VHH |
| SEQ ID NO: 5 | $X_1$VQLVESGGGLVQPGGSLRLSCAASGFKITHYTMGWX$_2$RQA PGKX$_3$X$_4$EX$_5$VSRITWGGDNTFYSNSVKGRFTISRDNSKNTX$_6$Y LQMNSLRAEDTAVYYCAAGSTSTATPLRVDYWGQGTLVTVSS, wherein $X_1$ = D or E, $X_2$ = F or V, $X_3$ = E or G, $X_4$ = R or L, $X_5$ = F or W, and $X_6$ = L or V | FC5 VHH - Humanized |
| SEQ ID NO: 6 | EYPSNFYA | CDR1 IGF1R3 |
| SEQ ID NO: 7 | VSRDGLTT | CDR2 IGF1R3 |
| SEQ ID NO: 8 | AIVITGVWNKVDVNSRSYHY | CDR3 IGF1R3 |
| SEQ ID NO: 9 | $X_1$VX$_2$LX$_3$ESGGGLVQX$_4$GGSLRLSCX$_5$ASEYPSNFYAMSWX$_6$R QAPGKX$_7$X$_8$EX$_9$VX$_{10}$GVSRDGLTTLYADSVKGRFTX$_{11}$SRDNX$_{12}$ KNTX$_{13}$X$_{14}$LQMNSX$_{15}$X$_{16}$AEDTAVYYCAIVITGVWNKVDVNSRS YHYWGQGTX$_{17}$VTVSS, wherein $X_1$ is E or Q; $X_2$ is K or Q; $X_3$ is V or E; $X_4$ is A or P; $X_5$ is V or A; $X_6$ is F or V; $X_7$ is E or G; $X_8$ is R or L; $X_9$ is F or W; $X_{10}$ is A or S; $X_{11}$ is M or I; $X_{12}$ is A or S; $X_{13}$ is V or L; $X_{14}$ is D or Y; $X_{15}$ is V or L; $X_{16}$ is K or R; and $X_{17}$ is Q or L | IGF1R3 VHH - Humanized |
| SEQ ID NO: 10 | EVQLVESGGGLVQPGGSLRLSCAASEYPSNFYAMSWFRQAP GKEREFVSGVSRDGLTTLYADSVKGRFTISRDNSKNTLYLQM NSLRAEDTAVYYCAIVITGVWNKVDVNSRSYHYWGQGTLVTV SS | IGF1R3H5 VHH |
| SEQ ID NO: 11 | GRTIDNYA | CDR1 IGF1R5 |
| SEQ ID NO: 12 | IDWGDGGX, where X is A or T | CDR2 IGF1R5 |
| SEQ ID NO: 13 | AMARQSRVNLDVARYDY | CDR3 IGF1R5 |

-continued

| SEQ ID NO: | Sequence | Description |
|---|---|---|
| SEQ ID NO: 14 | $X_1VX_2LX_3$ESGGGLVQ$X_4$GGSLRLSCAASGRTIDNYAMAW$X_5$RQ APGK$X_6X_7$E$X_8$V$X_9$TIDWGDGG$X_{10}$RYANSVKGRFTISRDN$X_{11}$K $X_{12}$T$X_{13}$YLQMN$X_{14}$L$X_{15}X_{16}$EDTAVY$X_{17}$CAMARQSRVNLDVAR YDYWGQGT$X_{18}$VTVSS, wherein $X_1$ is E or Q; $X_2$ is K or Q; $X_3$ is V or E; $X_4$ is A or P; $X_5$ is V or S; $X_6$ is D or G; $X_7$ is L or R; $X_8$ is F or W; $X_9$ is A or S; $X_{10}$ is A or T; $X_{11}$ is A or S; $X_{12}$ is G or N; $X_{13}$ is M or L; $X_{14}$ is N or R; $X_{15}$ is E or R; $X_{16}$ is P or A; $X_{17}$ is S or Y; and $X_{18}$ is Q or L | IGF1R5 VHH - Humanized |
| SEQ ID NO: 15 | QVQLVESGGGLVQPGGSLRLSCAASGRTIDNYAMAWVRQAP GKGLEWVATIDWGDGGTRYANSVKGRFTISRDNSKNTMYLQ MNSLRAEDTAVYYCAMARQSRVNLDVARYDYWGQGTLVTVS S | IGF1R5H2 VHH |
| SEQ ID NO: 16 | GRTFIAYA | CDR1 of R28 |
| SEQ ID NO: 17 | ITNFAGGTT | CDR2 of R28 |
| SEQ ID NO: 18 | AADRSAQTMRQVRPVLPY | CDR3 of R28 |
| SEQ ID NO: 19 | QVQLVESGGGLVQAGGSLRLSCVASGRTFIAYAMGWFRQAP GKEREFVAAITNFAGGTTYYADSVKGRFTISRDNAKTTVYLQM NSLKPEDTALYYCAADRSAQTMRQVRPVLPYWGQGTQVTVS S | R28 VHH |
| SEQ ID NO: 20 | GSTFSSSS | CDR1 of M79 |
| SEQ ID NO: 21 | ITSGGST | CDR2 of M79 |
| SEQ ID NO: 22 | NVAGRNWVPISRYSPGPY | CDR3 of M79 |
| SEQ ID NO: 23 | QVKLEESGGGLVQAGGSLKLSCAASGSTFSSSSVGWYRQAP GQQRELVAAITSGGSTNTADSVKGRFTMSRDNAKNTVYLQMR DLKPEDTAVYYCNVAGRNWVPISRYSPGPYWGQGTQVTVSS | M79 VHH |
| SEQ ID NO: 24 | SETQANSTTDALNVLLIIVDDLRPSLGCYGDKLVRSPNIDQLAS HSLLFQNAFAQQAVCAPSRVSFLTGRRPDTTRLYDFNSYWRV HAGNFSTIPQYFKENGYVTMSVGKVFHPGISSNHTDDSPYSW SFPPYHPSSEKYENTKTCRGPDGELHANLLCPVDVLDVPEGT LPDKQSTEQAIQLLEKMKTSASPFFLAVGYHKPHIPFRYPKEF QKLYPLENITLAPDPEVPDGLPPVAYNPWMDIRQREDVQALNI SVPYGPIPVDFQRKIRQSYFASVSYLDTQVGRLLSALDDLQLA NSTIIAFTSDHGWALGEHGEWAKYSNFDVATHVPLIFYVPGRT ASLPEAGEKLFPYLDPFDSASQLMEPGRQSMDLVELVSLFPTL AGLAGLQVPPRCPVPSFHVELCREGKNLLKHFRFRDLEEDPY LPGNPRELIAYSQYPRPSDIPQWNSDKPSLKDIKIMGYSIRTIDY RYTVWVGFNPDEFLANFSDIHAGELYFVDSDPLQDHNMYNDS QGGDLFQLLMP | IDS-C1 without C-terminal HIS-Strep tag |
| SEQ ID NO: 25 | SETQANSTTDALNVLLIIVDDLRPSLGCYGDKLVRSPNIDQLAS HSLLFQNAFAQQAVCAPSRVSFLTGRRPDTTRLYDFNSYWRV HAGNFSTIPQYFKENGYVTMSVGKVFHPGISSNHTDDSPYSW SFPPYHPSSEKYENTKTCRGPDGELHANLLCPVDVLDVPEGT LPDKQSTEQAIQLLEKMKTSASPFFLAVGYHKPHIPFRYPKEF QKLYPLENITLAPDPEVPDGLPPVAYNPWMDIRQREDVQALNI SVPYGPIPVDFQRKIRQSYFASVSYLDTQVGRLLSALDDLQLA NSTIIAFTSDHGWALGEHGEWAKYSNFDVATHVPLIFYVPGRT ASLPEAGEKLFPYLDPFDSASQLMEPGRQSMDLVELVSLFPTL AGLAGLQVPPRCPVPSFHVELCREGKNLLKHFRFRDLEEDPY LPGNPRELIAYSQYPRPSDIPQWNSDKPSLKDIKIMGYSIRTIDY RYTVWVGFNPDEFLANFSDIHAGELYFVDSDPLQDHNMYNDS QGGDLFQLLMPHHHHHHHWSHPQFEK | IDS-C1 |
| SEQ ID NO: 26 | ARPCIPKSFGYSSVVCVCNATYCDSFDPPTFPALGTFSRYEST RSGRRMELSMGPIQANHTGTGLLLTLQPEQKFQKVKGFGGA MTDAAALNILALSPPAQNLLLKSYFSEEGIGYNIIRVPMASCDF IRTYTYADTPDDFQLLNFSLPEEDTKLKIPLIHRALQAQRPVSL LASPWTSPTWLKTNGAVNGKGSLKGQPGDIYHQTWARYFVK FLDAYAEHKLQFWAVTAENEPSAGLLSGYPFQCLGFTPEHQR DFIARDLGPTLANSTHHNVRLLMLDDQRLLLPHWAKVVLTDPE | GCasemut1 without C-terminal HIS-Strep tag |

-continued

SEQUENCES

| SEQ ID NO: | Sequence | Description |
|---|---|---|
| | AAKYVHGIAVHWYLDFLAPANATLGETHRLFPNTMLFASEACV<br>GSKFWEQSVRLGSWDRGMQYSHSIITNLLYHVVGWTDWNLA<br>LNPEGGPNWVRNFVDSPIIVDITKDTFYKQPMFYHLGHFSKFIP<br>EGSQRVGLVASQKNDLDAVALMHPDGSAVVVLNRSSKDVPL<br>TIKDPAVGFLETISPGYSIHTYLWRRQ | |
| SEQ ID NO: 27 | ARPCIPKSFGYSSVVCVCNATYCDSFDPPTFPALGTFSRYEST<br>RSGRRMELSMGPIQANHTGTGLLLTLQPEQKFQKVKGFGGA<br>MTDAAALNILALSPPAQNLLLKSYFSEEGIGYNIIRVPMASCDF<br>IRTYTYADTPDDFQLLNFSLPEEDTKLKIPLIHRALQLAQRPVSL<br>LASPWTSPTWLKTNGAVNGKGSLKGQPGDIYHQTWARYFVK<br>FLDAYAEHKLQFWAVTAENEPSAGLLSGYPFQCLGFTPEHQR<br>DFIARDLGPTLANSTHHNVRLLMLDDQRLLLPHWAKVVLTDPE<br>AAKYVHGIAVHWYLDFLAPANATLGETHRLFPNTMLFASEACV<br>GSKFWEQSVRLGSWDRGMQYSHSIITNLLYHVVGWTDWNLA<br>LNPEGGPNWVRNFVDSPIIVDITKDTFYKQPMFYHLGHFSKFIP<br>EGSQRVGLVASQKNDLDAVALMHPDGSAVVVLNRSSKDVPL<br>TIKDPAVGFLETISPGYSIHTYLWRRQHHHHHH | GCasemut1 with c-term His tag |
| SEQ ID NO: 28 | DAHKSEVAHRFKDLGEENFKALVLIAFAQYLQQCPFEDHVKLV<br>NVTEFAKTCVADESAENCDKSLHTLFGDKLCTVATLRETYGE<br>MADCCAKQEPERNECFLQHKDDNPNLPRLVRPEVDVMCTAF<br>HDNEETFLKKYLYEIARRHPYFYAPELLFFAKRYKAAFTECCQ<br>AADKAACLLPKLDELRDEGKASSAKQRLKCASLQKFGERAFK<br>AWAVARLSQRFPKAEFAEVSKLVTDLTKVHTECCHGDLLECA<br>DDRADLAKYICENQDSISSKLKECCEKPLLEKSHCIAEVENDE<br>MPADLPSLAADFVESKDVCKNYAEAKDVFLGMFLYEYARRHP<br>DYSVVLLLRLAKTYETTLEKCCAAADPHECYAKVFDEFKPLVE<br>EPQNLIKQNCELFEQLGEYKFQNALLVRYTKKVPQVSTPTLVE<br>VSRNLGKVGSKCCKHPEAKRMPCAEDYLSVVLNQLCVLHEKT<br>PVSDRVTKCCTESLVNRRPCFSALEVDETYVPKEFNAETFTFH<br>ADICTLSEKERQIKKQTALVELVKHKPKATKEQLKAVMDDFAAF<br>VEKCCKADDKETCFAEEGPKLVAASQAALGL | HSA(K573P) |
| SEQ ID NO: 29 | EVQLQASGGGLVQAGGSLRLSCAASGFKITHYTMGWFRQAP<br>GKEREFVSRITWGGDNTFYSNSVKGRFTISRDNAKNTVYLQM<br>NSLKPEDTADYYCAAGSTSTATPLRVDYWGKGTQVTVSSGG<br>GGSSETQANSTTDALNVLLIIVDDLRPSLGCYGDKLVRSPNIDQ<br>LASHSLLFQNAFAQQAVCAPSRVSFLTGRRPDTTRLYDFNSY<br>WRVHAGNFSTIPQYFKENGYVTMSVGKVFHPGISSNHTDDSP<br>YSWSFPPYHPSSEKYENTKTCRGPDGELHANLLCPVDVLDVP<br>EGTLPDKQSTEQAIQLLEKMKTSASPFFLAVGYHKPHIPFRYP<br>KEFQKLYPLENITLAPDPEVPDGLPPVAYNPWMDIRQREDVQA<br>LNISVPYGPIPVDFQRKIRQSYFASVSYLDTQVGRLLSALDDLQ<br>LANSTIIAFTSDHGWALGEHGEWAKYSNFDVATHVPLIFYVPG<br>RTASLPEAGEKLFPYLDPFDSASQLMEPGRQSMDLVELVSLF<br>PTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTVWVGFNPDEFLANFSDIHAGELYFVDSDPLQDHNMY<br>NDSQGGDLFQLLMPHHHHHHHWSHPQFEK | FC5-IDS |
| SEQ ID NO: 30 | EVQLVESGGGLVQPGGSLRLSCAASEYPSNFYAMSWFRQAP<br>GKEREFVSGVSRDGLTTLYADSVKGRFTISRDNSKNTLYLQM<br>NSLRAEDTAVYYCAIVITGVWNKVDVNSRSYHYWGQGTLVTV<br>SSGGGGSGGGGSGGGGSGGGGSGGGGSSETQANSTTDAL<br>NVLLIIVDDLRPSLGCYGDKLVRSPNIDQLASHSLLFQNAFAQQ<br>AVCAPSRVSFLTGRRPDTTRLYDFNSYWRVHAGNFSTIPQYF<br>KENGYVTMSVGKVFHPGISSNHTDDSPYSWSFPPYHPSSEKY<br>ENTKTCRGPDGELHANLLCPVDVLDVPEGTLPDKQSTEQAIQL<br>LEKMKTSASPFFLAVGYHKPHIPFRYPKEFQKLYPLENITLAPD<br>PEVPDGLPPVAYNPWMDIRQREDVQALNISVPYGPIPVDFQR<br>KIRQSYFASVSYLDTQVGRLLSALDDLQLANSTIIAFTSDHGWA<br>LGEHGEWAKYSNFDVATHVPLIFYVPGRTASLPEAGEKLFPYL<br>DPFDSASQLMEPGRQSMDLVELVSLFPTLAGLAGLQVPPRCP<br>VPSFHVELCREGKNLLKHFRFRDLEEDPYLPGNPRELIAYSQY<br>PRPSDIPQWNSDKPSLKDIKIMGYSIRTIDYRYTVWVGFNPDEF<br>LANFSDIHAGELYFVDSDPLQDHNMYNDSQGGDLFQLLMPHH<br>HHHHHWSHPQFEK | IGF1R3H5-IDS |
| SEQ ID NO: 31 | QVQLVESGGGLVQPGGSLRLSCAASGRTIDNYAMAWVRQAP<br>GKGLEWVATIDWGDGGTRYANSVKGRFTISRDNSKNTMYLQ<br>MNSLRAEDTAVYYCAMARQSRVNLDVARYDYWGQGTLVTVS<br>SGGGGSGGGGSGGGGSGGGGSGGGGSSETQANSTTDALN<br>VLLIIVDDLRPSLGCYGDKLVRSPNIDQLASHSLLFQNAFAQQA<br>VCAPSRVSFLTGRRPDTTRLYDFNSYWRVHAGNFSTIPQYFK<br>ENGYVTMSVGKVFHPGISSNHTDDSPYSWSFPPYHPSSEKYE | IGF1R5H2-IDS |

SEQUENCES

| SEQ ID NO: | Sequence | Description |
|---|---|---|
| | NTKTCRGPDGELHANLLCPVDVLDVPEGTLPDKQSTEQAIQLL<br>EKMKTSASPFFLAVGYHKPHIPFRYPKEFQKLYPLENITLAPDP<br>EVPDGLPPVAYNPWMDIRQREDVQALNISVPYGPIPVDFQRKI<br>RQSYFASVSYLDTQVGRLLSALDDLQLANSTIIAFTSDHGWAL<br>GEHGEWAKYSNFDVATHVPLIFYVPGRTASLPEAGEKLFPYLD<br>PFDSASQLMEPGRQSMDLVELVSLFPTLAGLAGLQVPPRCPV<br>PSFHVELCREGKNLLKHFRFRDLEEDPYLPGNPRELIAYSQYP<br>RPSDIPQWNSDKPSLKDIKIMGYSIRTIDYRYTVWVGFNPDEFL<br>ANFSDIHAGELYFVDSDPLQDHNMYNDSQGGDLFQLLMPHHH<br>HHHHHWSHPQFEK | |
| SEQ ID NO: 32 | EVQLVESGGGLVQPGGSLRLSCAASEYPSNFYAMSWFRQAP<br>GKEREFVSGVSRDGLTTLYADSVKGRFTISRDNSKNTLYLQM<br>NSLRAEDTAVYYCAIVITGVWNKVDVNSRSYHYWGQGTLVTV<br>SSGGGGSGGGGSGGGGSGGGGSGGGGSARPCIPKSFGYSS<br>VVCVCNATYCDSFDPPTFPALGTFSRYESTRSGRRMELSMGP<br>IQANHTGTGLLLTLQPEQFKFQKVKGFGGAMTDAAALNILALSP<br>PAQNLLLKSYFSEEGIGYNIIRVPMASCDFSIRTYTYADTPDDF<br>QLLNFSLPEEDTKLKIPLIHRALQLAQRPVSLLASPWTSPTWLK<br>TNGAVNGKGSLKGQPGDIYHQTWARYFVKFLDAYAEHKLQF<br>WAVTAENEPSAGLLSGYPFQCLGFTPEHQRDFIARDLGPTLA<br>NSTHHNVRLLMLDDQRLLLPHWAKVVLTDPEAAKYVHGIAVH<br>WYLDFLAPANATLGETHRLFPNTMLFASEACVGSKFWEQSVR<br>LGSWDRGMQYSHSIITNLLYHVVGWTDWNLALNPEGGPNWV<br>RNFVDSPIIVDITKDTFYKQPMFYHLGHFSKFIPEGSQRVGLVA<br>SQKNDLDAVALMHPDGSAVVVVLNRSSKDVPLTIKDPAVGFLE<br>TISPGYSIHTYLWRRQHHHHHHH | IGF1R3H5-<br>GCaseMut1 |
| SEQ ID NO: 33 | SETQANSTTDALNVLLIIVDDLRPSLGCYGDKLVRSPNIDQLAS<br>HSLLFQNAFAQQAVCAPSRVSFLTGRRPDTTRLYDFNSYWRV<br>HAGNFSTIPQYFKENGYVTMSVGKVFHPGISSNHTDDSPYSW<br>SFPPYHPSSEKYENTKTCRGPDGELHANLLCPVDVLDVPEGT<br>LPDKQSTEQAIQLLEKMKTSASPFFLAVGYHKPHIPFRYPKEF<br>QKLYPLENITLAPDPEVPDGLPPVAYNPWMDIRQREDVQALNI<br>SVPYGPIPVDFQRKIRQSYFASVSYLDTQVGRLLSALDDLQLA<br>NSTIIAFTSDHGWALGEHGEWAKYSNFDVATHVPLIFYVPGRT<br>ASLPEAGEKLFPYLDPFDSASQLMEPGRQSMDLVELVSLFPTL<br>AGLAGLQVPPRCPVPSFHVELCREGKNLLKHFRFRDLEEDPY<br>LPGNPRELIAYSQYPRPSDIPQWNSDKPSLKDIKIMGYSIRTIDY<br>RYTVWVGFNPDEFLANFSDIHAGELYFVDSDPLQDHNMYNDS<br>QGGDLFQLLMPGGGGSGGGGSGGGGSGGGGSGGGGSQV<br>QLVESGGGLVQAGGSLRLSCVASGRTFIAYAMGWFRQAPGK<br>EREFVAAITNFAGGTTYYADSVKGRFTISRDNAKTTVYLQMNS<br>LKPEDTALYYCAADRSAQTMRQVRPVLPYWGQGTQVTVSHH<br>HHHHHH | IDS-R28 |
| SEQ ID NO: 34 | SETQANSTTDALNVLLIIVDDLRPSLGCYGDKLVRSPNIDQLAS<br>HSLLFQNAFAQQAVCAPSRVSFLTGRRPDTTRLYDFNSYWRV<br>HAGNFSTIPQYFKENGYVTMSVGKVFHPGISSNHTDDSPYSW<br>SFPPYHPSSEKYENTKTCRGPDGELHANLLCPVDVLDVPEGT<br>LPDKQSTEQAIQLLEKMKTSASPFFLAVGYHKPHIPFRYPKEF<br>QKLYPLENITLAPDPEVPDGLPPVAYNPWMDIRQREDVQALNI<br>SVPYGPIPVDFQRKIRQSYFASVSYLDTQVGRLLSALDDLQLA<br>NSTIIAFTSDHGWALGEHGEWAKYSNFDVATHVPLIFYVPGRT<br>ASLPEAGEKLFPYLDPFDSASQLMEPGRQSMDLVELVSLFPTL<br>AGLAGLQVPPRCPVPSFHVELCREGKNLLKHFRFRDLEEDPY<br>LPGNPRELIAYSQYPRPSDIPQWNSDKPSLKDIKIMGYSIRTIDY<br>RYTVWVGFNPDEFLANFSDIHAGELYFVDSDPLQDHNMYNDS<br>QGGDLFQLLMPGGGGSGGGGSGGGGSGGGGSGGGGSQVK<br>LEESGGGLVQAGGSLKLSCAASGSTFSSSSVGWYRQAPGQQ<br>RELVAAITSGGSTNTADSVKGRFTMSRDNAKNTVYLQMRDLK<br>PEDTAVYYCNVAGRNWVPISRYSPGPYWGQGTQVTVSSHH<br>HHHHH | IDS-M79 |
| SEQ ID NO: 35 | EVQLVESGGGLVQPGGSLRLSCAASEYPSNFYAMSWFRQAP<br>GKEREFVSGVSRDGLTTLYADSVKGRFTISRDNSKNTLYLQM<br>NSLRAEDTAVYYCAIVITGVWNKVDVNSRSYHYWGQGTLVTV<br>SSGGGGSGGGGSGGGGSGGGGSGGGGSSETQANSTTDAL<br>NVLLIIVDDLRPSLGCYGDKLVRSPNIDQLASHSLLFQNAFAQQ<br>AVCAPSRVSFLTGRRPDTTRLYDFNSYWRVHAGNFSTIPQYF<br>KENGYVTMSVGKVFHPGISSNHTDDSPYSWSFPPYHPSSEKY<br>ENTKTCRGPDGELHANLLCPVDVLDVPEGTLPDKQSTEQAIQL<br>LEKMKTSASPFFLAVGYHKPHIPFRYPKEFQKLYPLENITLAPD<br>PEVPDGLPPVAYNPWMDIRQREDVQALNISVPYGPIPVDFQR<br>KIRQSYFASVSYLDTQVGRLLSALDDLQLANSTIIAFTSDHGWA | IGF1R3H5-IDS-<br>HSA(K573P) |

| SEQ ID NO: | Sequence | Description |
|---|---|---|
| | LGEHGEWAKYSNFDVATHVPLIFYVPGRTASLPEAGEKLFPYL<br>DPFDSASQLMEPGRQSMDLVELVSLFPTLAGLAGLQVPPRCP<br>VPSFHVELCREGKNLLKHFRFRDLEEDPYLPGNPRELIAYSQY<br>PRPSDIPQWNSDKPSLKDIKIMGYSIRTIDYRYTVWVGFNPDEF<br>LANFSDIHAGELYFVDSDPLQDHNMYNDSQGGDLFQLLMPGG<br>GGSDAHKSEVAHRFKDLGEENFKALVLIAFAQYLQQCPFEDH<br>VKLVNEVTEFAKTCVADESAENCDKSLHTLFGDKLCTVATLRE<br>TYGEMADCCAKQEPERNECFLQHKDDNPNLPRLVRPEVDVM<br>CTAFHDNEETFLKKYLYEIARRHPYFYAPELLFFAKRYKAAFTE<br>CCQAADKAACLLPKLDELRDEGKASSAKQRLKCASLQKFGER<br>AFKAWAVARLSQRFPKAEFAEVSKLVTDLTKVHTECCHGDLL<br>ECADDRADLAKYICENQDSISSKLKECCEKPLLEKSHCIAEVEN<br>DEMPADLPSLAADFVESKDVCKNYAEAKDVFLGMFLYEYARR<br>HPDYSVVLLLRLAKTYETTLEKCCAAADPHECYAKVFDEFKPL<br>VEEPQNLIKQNCELFEQLGEYKFQNALLVRYTKKVPQVSTPTL<br>VEVSRNLGKVGSKCCKHPEAKRMPCAEDYLSVVLNQLCVLHE<br>KTPVSDRVTKCCTESLVNRRPCFSALEVDETYVPKEFNAETFT<br>FHADICTLSEKERQIKKQTALVELVKHKPKATKEQLKAVMDDF<br>AAFVEKCCKADDKETCFAEEGPKLVAASQAALGLHHHHHH | |
| SEQ ID NO: 36 | EVQLVESGGGLVQPGGSLRLSCAASEYPSNFYAMSWFRQAP<br>GKEREFVSGVSRDGLTTLYADSVKGRFTISRDNSKNTLYLQM<br>NSLRAEDTAVYYCAIVITGVWNKVDVNSRSYHYWGQGTLVTV<br>SSGGGGSGGGGSGGGGSGGGGSGGGGSSETQANSTTDAL<br>NVLLIIVDDLRPSLGCYGDKLVRSPNIDQLASHSLLFQNAFAQQ<br>AVCAPSRVSFLTGRRPDTTRLYDFNSYWRVHAGNFSTIPQYF<br>KENGYVTMSVGKVFHPGISSNHTDDSPYSWSFPPYHPSSEKY<br>ENTKTCRGPDGELHANLLCPVDVLDVPEGTLPDKQSTEQAIQL<br>LEKMKTSASPFFLAVGYHKPHIPFRYPKEFQKLYPLENITLAPD<br>PEVPDGLPPVAYNPWMDIRQREDVQALNISVPYGPIPVDFQR<br>KIRQSYFASVSYLDTQVGRLLSALDDLQLANSTIIAFTSDHGWA<br>LGEHGEWAKYSNFDVATHVPLIFYVPGRTASLPEAGEKLFPYL<br>DPFDSASQLMEPGRQSMDLVELVSLFPTLAGLAGLQVPPRCP<br>VPSFHVELCREGKNLLKHFRFRDLEEDPYLPGNPRELIAYSQY<br>PRPSDIPQWNSDKPSLKDIKIMGYSIRTIDYRYTVWVGFNPDEF<br>LANFSDIHAGELYFVDSDPLQDHNMYNDSQGGDLFQLLMPGG<br>GGSGGGGSGGGGSGGGGSGGGGSQVQLVESGGGLVQAGG<br>SLRLSCVASGRTFIAYAMGWFRQAPGKEREFVAAITNFAGGTT<br>YYADSVKGRFTISRDNAKTTVYLQMNSLKPEDTALYYCAADRS<br>AQTMRQVRPVLPYWGQGTQVTVSHHHHHHHH | IGF1R3H5-IDS-<br>R28 |
| SEQ ID NO: 37 | EVQLVESGGGLVQPGGSLRLSCAASEYPSNFYAMSWFRQAP<br>GKEREFVSGVSRDGLTTLYADSVKGRFTISRDNSKNTLYLQM<br>NSLRAEDTAVYYCAIVITGVWNKVDVNSRSYHYWGQGTLVTV<br>SSGGGGSGGGGSGGGGSGGGGSGGGGSSETQANSTTDAL<br>NVLLIIVDDLRPSLGCYGDKLVRSPNIDQLASHSLLFQNAFAQQ<br>AVCAPSRVSFLTGRRPDTTRLYDFNSYWRVHAGNFSTIPQYF<br>KENGYVTMSVGKVFHPGISSNHTDDSPYSWSFPPYHPSSEKY<br>ENTKTCRGPDGELHANLLCPVDVLDVPEGTLPDKQSTEQAIQL<br>LEKMKTSASPFFLAVGYHKPHIPFRYPKEFQKLYPLENITLAPD<br>PEVPDGLPPVAYNPWMDIRQREDVQALNISVPYGPIPVDFQR<br>KIRQSYFASVSYLDTQVGRLLSALDDLQLANSTIIAFTSDHGWA<br>LGEHGEWAKYSNFDVATHVPLIFYVPGRTASLPEAGEKLFPYL<br>DPFDSASQLMEPGRQSMDLVELVSLFPTLAGLAGLQVPPRCP<br>VPSFHVELCREGKNLLKHFRFRDLEEDPYLPGNPRELIAYSQY<br>PRPSDIPQWNSDKPSLKDIKIMGYSIRTIDYRYTVWVGFNPDEF<br>LANFSDIHAGELYFVDSDPLQDHNMYNDSQGGDLFQLLMPGG<br>GGSGGGGSGGGGSGGGGGGSQVKLEESGGGLVQAGG<br>SLKLSCAASGSTFSSSSVGWYRQAPGQQRELVAAITSGGSTN<br>TADSVKGRFTMSRDNAKNTVYLQMRDLKPEDTAVYYCNVAG<br>RNWVPISRYSPGPYWGQGTQVTVSSHHHHHHHH | IGF1R3H5-IDS-<br>M79 |
| SEQ ID NO: 38 | EVQLVESGGGLVQPGNSLRLSCAASGFTFSSFGMSWVRQAP<br>GKGLEWVSSISGSGSDTLYADSVKGRFTISRDNAKTTLYLQMN<br>SLRPEDTAVYYCTIGGSLSRSSQGTLVTVSS | Alb8 |
| SEQ ID NO: 39 | EVQLVESGGGLVQPGGSLRLSCAASEYPSNFYAMSWFRQAP<br>GKEREFVSGVSRDGLTTLYADSVKGRFTISRDNSKNTLYLQM<br>NSLRAEDTAVYYCAIVITGVWNKVDVNSRSYHYWGQGTLVTV<br>SSGGGGSGGGGSGGGGGGGSGGGGSSETQANSTTDAL<br>NVLLIIVDDLRPSLGCYGDKLVRSPNIDQLASHSLLFQNAFAQQ<br>AVCAPSRVSFLTGRRPDTTRLYDFNSYWRVHAGNFSTIPQYF<br>KENGYVTMSVGKVFHPGISSNHTDDSPYSWSFPPYHPSSEKY<br>ENTKTCRGPDGELHANLLCPVDVLDVPEGTLPDKQSTEQAIQL<br>LEKMKTSASPFFLAVGYHKPHIPFRYPKEFQKLYPLENITLAPD | IGF1R3H5-IDS-<br>Alb8 |

-continued

| SEQUENCES | | |
|---|---|---|
| SEQ ID NO: | Sequence | Description |
| | PEVPDGLPPVAYNPWMDIRQREDVQALNISVPYGPIPVDFQR KIRQSYFASVSYLDTQVGRLLSALDDLQLANSTIIAFTSDHGWA LGEHGEWAKYSNFDVATHVPLIFYVPGRTASLPEAGEKLFPYL DPFDSASQLMEPGRQSMDLVELVSLFPTLAGLAGLQVPPRCP VPSFHVELCREGKNLLKHFRFRDLEEDPYLPGNPRELIAYSQY PRPSDIPQWNSDKPSLKDIKIMGYSIRTIDYRYTVWVGFNPDEF LANFSDIHAGELYFVDSDPLQDHNMYNDSQGGDLFQLLMPGG GGSGGGGSGGGGSGGGGSGGGGSEVQLVESGGGLVQPGN SLRLSCAASGFTFSSFGMSWVRQAPGKGLEWVSSISGSGSD TLYADSVKGRFTISRDNAKTTLYLQMNSLRPEDTAVYYCTIGG SLSRSSQGTLVTVSSHHHHHHHH | |
| SEQ ID NO: 40 | AVQLVESGGGLVQPGNSLRLSCAASGFTFRSFGMSWVRQAP GKEPEWVSSISGSGSDTLYADSVKGRFTISRDNAKTTLYLQMN SLKPEDTAVYYCTIGGSLSRSSQGTQVTVSS | Alb1 |
| SEQ ID NO: 41 | QVQLVESGGGLVQPGGSLRLSCAASGRTIDNYAMAWVRQAP GKGLEWVATIDWGDGGTRYANSVKGRFTISRDNSKNTMYLQ MNSLRAEDTAVYYCAMARQSRVNLDVARYDYWGQGTLVTVS SGGGGSGGGGSGGGGSGGGGSGGGGSSETQANSTTDALN VLLIIVDDLRPSLGCYGDKLVRSPNIDQLASHSLLFQNAFAQQA VCAPSRVSFLTGRRPDTTRLYDFNSYWRVHAGNFSTIPQYFK ENGYVTMSVGKVFHPGISSNHTDDSPYSWSFPPYHPSSEKYE NTKTCRGPDGELHANLLCPVDVLDVPEGTLPDKQSTEQAIQLL EKMKTSASPFFLAVGYHKPHIPFRYPKEFQKLYPLENITLAPDP EVPDGLPPVAYNPWMDIRQREDVQALNISVPYGPIPVDFQRKI RQSYFASVSYLDTQVGRLLSALDDLQLANSTIIAFTSDHGWAL GEHGEWAKYSNFDVATHVPLIFYVPGRTASLPEAGEKLFPYLD PFDSASQLMEPGRQSMDLVELVSLFPTLAGLAGLQVPPRCPV PSFHVELCREGKNLLKHFRFRDLEEDPYLPGNPRELIAYSQYP RPSDIPQWNSDKPSLKDIKIMGYSIRTIDYRYTVWVGFNPDEFL ANFSDIHAGELYFVDSDPLQDHNMYNDSQGGDLFQLLMPGG GGSGGGGSGGGGSGGGGSGGGGSAVQLVESGGGLVQPGN SLRLSCAASGFTFRSFGMSWVRQAPGKEPEWVSSISGSGSD TLYADSVKGRFTISRDNAKTTLYLQMNSLKPEDTAVYYCTIGG SLSRSSQGTQVTVSSHHHHHHHHWSHPQFEK | IGF1R5H2-IDS-Alb1 |
| SEQ ID NO: 42 | QVQLVESGGGLVQPGGSLRLSCAASGRTIDNYAMAWVRQAP GKGLEWVATIDWGDGGTRYANSVKGRFTISRDNSKNTMYLQ MNSLRAEDTAVYYCAMARQSRVNLDVARYDYWGQGTLVTVS SGGGGSGGGGSGGGGSGGGGSGGGGSAVQLVESGGGLVQ PGNSLRLSCAASGFTFRSFGMSWVRQAPGKEPEWVSSISGS GSDTLYADSVKGRFTISRDNAKTTLYLQMNSLKPEDTAVYYCT IGGSLSRSSQGTQVTVSSGGGGSGGGGSGGGGSGGGGSGG GGSSETQANSTTDALNVLLIIVDDLRPSLGCYGDKLVRSPNIDQ LASHSLLFQNAFAQQAVCAPSRVSFLTGRRPDTTRLYDFNSY WRVHAGNFSTIPQYFKENGYVTMSVGKVFHPGISSNHTDDSP YSWSFPPYHPSSEKYENTKTCRGPDGELHANLLCPVDVLDVP EGTLPDKQSTEQAIQLLEKMKTSASPFFLAVGYHKPHIPFRYP KEFQKLYPLENITLAPDPEVPDGLPPVAYNPWMDIRQREDVQA LNISVPYGPIPVDFQRKIRQSYFASVSYLDTQVGRLLSALDDLQ LANSTIIAFTSDHGWALGEHGEWAKYSNFDVATHVPLIFYVPG RTASLPEAGEKLFPYLDPFDSASQLMEPGRQSMDLVELVSLF PTLAGLAGLQVPPRCPVPSFHVELCREGKNLLKHFRFRDLEE DPYLPGNPRELIAYSQYPRPSDIPQWNSDKPSLKDIKIMGYSIR TIDYRYTVWVGFNPDEFLANFSDIHAGELYFVDSDPLQDHNMY NDSQGGDLFQLLMPHHHHHHHHWSHPQFEK | IGF1R5H2-Alb1-IDS |
| SEQ ID NO: 43 | VQLVESGGGLVQPGNSLRLSCAASGFTFRSFGMSWVRQAPG KEPEWVSSISGSGSDTLYADSVKGRFTISRDNAKTTLYLQMNS LKPEDTAVYYCTIGGSLSRSSQGTQVTVSSGGGGSGGGGSG GGGSGGGGSGGGGSQVQLVESGGGLVQPGGSLRLSCAASG RTIDNYAMAWVRQAPGKGLEWVATIDWGDGGTRYANSVKGR FTISRDNSKNTMYLQMNSLRAEDTAVYYCAMARQSRVNLDVA RYDYWGQGTLVTVSSGGGGSGGGGSGGGGSGGGGSGGG GSSETQANSTTDALNVLLIIVDDLRPSLGCYGDKLVRSPNIDQL ASHSLLFQNAFAQQAVCAPSRVSFLTGRRPDTTRLYDFNSYW RVHAGNFSTIPQYFKENGYVTMSVGKVFHPGISSNHTDDSPY SWSFPPYHPSSEKYENTKTCRGPDGELHANLLCPVDVLDVPE GTLPDKQSTEQAIQLLEKMKTSASPFFLAVGYHKPHIPFRYPK EFQKLYPLENITLAPDPEVPDGLPPVAYNPWMDIRQREDVQAL NISVPYGPIPVDFQRKIRQSYFASVSYLDTQVGRLLSALDDLQL ANSTIIAFTSDHGWALGEHGEWAKYSNFDVATHVPLIFYVPGR TASLPEAGEKLFPYLDPFDSASQLMEPGRQSMDLVELVSLFPT LAGLAGLQVPPRCPVPSFHVELCREGKNLLKHFRFRDLEEDP | Alb1-IGF1R5H2-IDS |

| SEQ ID NO: | Sequence | Description |
|---|---|---|
| | YLPGNPRELIAYSQYPRPSDIPQWNSDKPSLKDIKIMGYSIRTID YRYTVWVGFNPDEFLANFSDIHAGELYFVDSDPLQDHNMYND SQGGDLFQLLMPHHHHHHHHWSHPQFEK QVQLVESGGGLVQPGGSLRLSCAASGRTIDNYAMAWVRQAP GKGLEWVATIDWGDGGTRYANSVKGRFTISRDNSKNTMYLQ MNSLRAEDTAVYYCAMARQSRVNLDVARYDYWGQGTLVTVS SGGGGSGGGGSGGGGSGGGGSGGGGSSETQANSTTDALN VLLIIVDDLRPSLGCYGDKLVRSPNIDQLASHSLLFQNAFAQQA VCAPSRVSFLTGRRPDTTRLYDFNSYWRVHAGNFSTIPQYFK | |
| SEQ ID NO: 44 | ENGYVTMSVGKVFHPGISSNHTDDSPYSWSFPPYHPSSEKYE NTKTCRGPDGELHANLLCPVDVLDVPEGTLPDKQSTEQAIQLL EKMKTSASPFFLAVGYHKPHIPFRYPKEFQKLYPLENITLAPDP EVPDGLPPVAYNPWMDIRQREDVQALNISVPYGIPVDFQRKI RQSYFASVSYLDTQVGRLLSALDDLQLANSTIIAFTSDHGWAL GEHGEWAKYSNFDVATHVPLIFYVPGRTASLPEAGEKLFPYLD PFDSASQLMEPGRQSMDLVELVSLFPTLAGLAGLQVPPRCPV PSFHVELCREGKNLLKHFRFRDLEEDPYLPGNPRELIAYSQYP RPSDIPQWNSDKPSLKDIKIMGYSIRTIDYRYTVWVGFNPDEFL ANFSDIHAGELYFVDSDPLQDHNMYNDSQGGDLFQLLMPGG GGSDAHKSEVAHRFKDLGEENFKALVLIAFAQYLQQCPFEDH VKLVNEVTEFAKTCVADESAENCDKSLHTLFGDKLCTVATLRE TYGEMADCCAKQEPERNECFLQHKDDNPNLPRLVRPEVDVM CTAFHDNEETFLKKYLYEIARRHPYFYAPELLFFAKRYKAAFTE CCQAADKAACLLPKLDELRDEGKASSAKQRLKCASLQKFGER APKAWAVARLSQRFPKAEFAEVSKLVTDLTKVHTECCHGDLL ECADDRADLAKYICENQDSISSKLKECCEKPLLEKSHCIAEVEN DEMPADLPSLAADFVESKDVCKNYAEAKDVFLGMFLYEYARR HPDYSVVLLLRLAKTYETTLEKCCAAADPHECYAKVFDEFKPL VEEPQNLIKQNCELFEQLGEYKFQNALLVRYTKKVPQVSTPTL VEVSRNLGKVGSKCCKHPEAKRMPCAEDYLSVVLNQLCVLHE KTPVSDRVTKCCTESLVNRRPCFSALEVDETYVPKEFNAETFT FHADICTLSEKERQIKKQTALVELVKHKPKATKEQLKAVMDDF AAFVEKCCKADDKETCFAEEGPKLVAASQAALGLHHHHHHW SHPQFEK | IGF1R5H2-IDS-HSA(K573P) |
| SEQ ID NO: 45 | GGPSVFLFPPKPKDTLMISRTPEVTCVVVDVSQEDPEVQFNW YVDGVEVHNAKTKPREEQFNSTYRVVSVLTVLHQDWLNGKEY KCKVSNKGLPSSIEKTISKAKGQPREPQVYTKPPSQEEMKNQ VSLSCLVKGFYPSDIAVEWESNGQPENNYKTTVPVLDSDGSF RLASYLTVDKSRWQEGNVFSCSVMHEALHNHYTQKSLSLSLG K | Monomeric Fc |
| SEQ ID NO: 46 | MKLSTILFTACATLAAAASETQANSTTDALNVLLIIVDDLRPSLG CYGDKLVRSPNIDQLASHSLLFQNAFAQQAVCAPSRVSFLTG RRPDTTRLYDFNSYWRVHAGNFSTIPQYFKENGYVTMSVGKV FHPGISSNHTDDSPYSWSFPPYHPSSEKYENTKTCRGPDGEL HANLLCPVDVLDVPEGTLPDKQSTEQAIQLLEKMKTSASPFFL AVGYHKPHIPFRYPKEFQKLYPLENITLAPDPEVPDGLPPVAYN PWMDIRQREDVQALNISVPYGIPVDFQRKIRQSYFASVSYLD TQVGRLLSALDDLQLANSTIIAFTSDHGWALGEHGEWAKYSNF DVATHVPLIFYVPGRTASLPEAGEKLFPYLDPFDSASQLMEPG RQSMDLVELVSLFPTLAGLAGLQVPPRCPVPSFHVELCREGK NLLKHFRFRDLEEDPYLPGNPRELIAYSQYPRPSDIPQWNSDK PSLKDIKIMGYSIRTIDYRYTVWVGFNPDEFLANFSDIHAGELYF VDSDPLQDHNMYNDSQGGDLFQLLMP | IDS-C1 yarrowia-specific signal peptide with signal peptide and without C-terminal HIS-Strep tag |
| SEQ ID NO: 47 | GGGGSDAHKSEVAHRFKDLGEENFKALVLIAFAQYLQQCPFE DHVKLVNEVTEFAKTCVADESAENCDKSLHTLFGDKLCTVATL RETYGEMADCCAKQEPERNECFLQHKDDNPNLPRLVRPEVD VMCTAFHDNEETFLKKYLYEIARRHPYFYAPELLFFAKRYKAAF TECCQAADKAACLLPKLDELRDEGKASSAKQRLKCASLQKFG ERAFKAWAVARLSQRFPKAEFAEVSKLVTDLTKVHTECCHGD LLECADDRADLAKYICENQDSISSKLKECCEKPLLEKSHCIAEV ENDEMPADLPSLAADFVESKDVCKNYAEAKDVFLGMFLYEYA RRHPDYSVVLLLRLAKTYETTLEKCCAAADPHECYAKVFDEFK PLVEEPQNLIKQNCELFEQLGEYKFQNALLVRYTKKVPQVSTP TLVEVSRNLGKVGSKCCKHPEAKRMPCAEDYLSVVLNQLCVL HEKTPVSDRVTKCCTESLVNRRPCFSALEVDETYVPKEFNAET FTFHADICTLSEKERQIKKQTALVELVKHKPKATKEQLKAVMDD FAAFVEKCCKADDKETCFAEEGPKLVAASQAALGL | HSA(K573P) with a linker |
| SEQ ID NO: 48 | MKLSTILFTACATLAAAAEVQLVESGGGLVQPGGSLRLSCAASE YPSNFYAMSWFRQAPGKEREFVSGVSRDGLTTLYADSVKGR FTISRDNSKNTLYLQMNSLRAEDTAVYYCAIVITGVWNKDVN | IGF1R3H5-IDS-HSA(K573P) with yarrowia- |

| SEQ ID NO: | Sequence | Description |
|---|---|---|
| | SRSYHYWGQGTLVTVSSGGGGSGGGGSGGGGSGGGGSGG<br>GGSSETQANSTTDALNVLLIIVDDLRPSLGCYGDKLVRSPNIDQ<br>LASHSLLFQNAFAQQAVCAPSRVSFLTGRRPDTTRLYDFNSY<br>WRVHAGNFSTIPQYFKENGYVTMSVGKVFHPGISSNHTDDSP<br>YSWSFPPYHPSSEKYENTKTCRGPDGELHANLLCPVDVLDVP<br>EGTLPDKQSTEQAIQLLEKMKTSASPFFLAVGYHKPHIPFRYP<br>KEFQKLYPLENITLAPDPEVPDGLPPVAYNPWMDIRQREDVQA<br>LNISVPYGPIPVDFQRKIRQSYFASVSYLDTQVGRLLSALDDLQ<br>LANSTIIAFTSDHGWALGEHGEWAKYSNFDVATHVPLIFYVPG<br>RTASLPEAGEKLFPYLDPFDSASQLMEPGRQSMDLVELVSLF<br>PTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTVWVGFNPDEFLANFSDIHAGELYFVDSDPLQDHNMY<br>NDSQGGDLFQLLMPGGGGSDAHKSEVAHRFKDLGEENFKAL<br>VLIAFAQYLQQCPFEDHVKLVNEVTEFAKTCVADESAENCDKS<br>LHTLFGDKLCTVATLRETYGEMADCCAKQEPERNECFLQHKD<br>DNPNLPRLVRPEVDVMCTAFHDNEETFLKKYLYEIARRHPYFY<br>APELLFFAKRYKAAFTECCQAADKAACLLPKLDELRDEGKASS<br>AKQRLKCASLQKFGERAFKAWAVARLSQRFPKAEFAEVSKLV<br>TDLTKVHTECCHGDLLECADDRADLAKYICENQDSISSKLKEC<br>CEKPLLEKSHCIAEVENDEMPADLPSLAADFVESKDVCKNYAE<br>AKDVFLGMFLYEYARRHPDYSVVLLLRLAKTYETTLEKCCAAA<br>DPHECYAKVFDEFKPLVEEPQNLIKQNCELFEQLGEYKFQNAL<br>LVRYTKKVPQVSTPTLVEVSRNLGKVGSKCCKHPEAKRMPCA<br>EDYLSVVLNQLCVLHEKTPVSDRVTKCCTESLVNRRPCFSALE<br>VDETYVPKEFNAETFTFHADICTLSEKERQIKKQTALVELVKHK<br>PKATKEQLKAVMDDFAAFVEKCCKADDKETCFAEEGPKLVAA<br>SQAALGLHHHHHHHH | specific signal peptide |
| SEQ ID NO: 49 | MKLSTILFTACATLAAAEVQLVESGGGLVQPGGSLRLSCAASE<br>YPSNFYAMSWFRQAPGKEREFVSGVSRDGLTTLYADSVKGR<br>FTISRDNSKNTLYLQMNSLRAEDTAVYYCAIVITGVWNKVDVN<br>SRSYHYWGQGTLVTVSSGGGGSGGGGSGGGGSGGGGSGG<br>GGSSETQANSTTDALNVLLIIVDDLRPSLGCYGDKLVRSPNIDQ<br>LASHSLLFQNAFAQQAVCAPSRVSFLTGRRPDTTRLYDFNSY<br>WRVHAGNFSTIPQYFKENGYVTMSVGKVFHPGISSNHTDDSP<br>YSWSFPPYHPSSEKYENTKTCRGPDGELHANLLCPVDVLDVP<br>EGTLPDKQSTEQAIQLLEKMKTSASPFFLAVGYHKPHIPFRYP<br>KEFQKLYPLENITLAPDPEVPDGLPPVAYNPWMDIRQREDVQA<br>LNISVPYGPIPVDFQRKIRQSYFASVSYLDTQVGRLLSALDDLQ<br>LANSTIIAFTSDHGWALGEHGEWAKYSNFDVATHVPLIFYVPG<br>RTASLPEAGEKLFPYLDPFDSASQLMEPGRQSMDLVELVSLF<br>PTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTVWVGFNPDEFLANFSDIHAGELYFVDSDPLQDHNMY<br>NDSQGGDLFQLLMPGGGGSGGGGSGGGGSGGGGSGGGGS<br>QVQLVESGGGLVQAGGSLRLSCVASGRTFIAYAMGWFRQAP<br>GKEREFVAAITNFAGGTTYYADSVKGRFTISRDNAKTTVYLQM<br>NSLKPEDTALYYCAADRSAQTMRQVRPVLPYWGQGTQVTVS<br>HHHHHHHH | IGF1R3H5-IDS-R28 with yarrowia-specific signal peptide |
| SEQ ID NO: 50 | MKLSTILFTACATLAAAEVQLVESGGGLVQPGGSLRLSCAASE<br>YPSNFYAMSWFRQAPGKEREFVSGVSRDGLTTLYADSVKGR<br>FTISRDNSKNTLYLQMNSLRAEDTAVYYCAIVITGVWNKVDVN<br>SRSYHYWGQGTLVTVSSGGGGSGGGGSGGGGSGGGGSGG<br>GGSSETQANSTTDALNVLLIIVDDLRPSLGCYGDKLVRSPNIDQ<br>LASHSLLFQNAFAQQAVCAPSRVSFLTGRRPDTTRLYDFNSY<br>WRVHAGNFSTIPQYFKENGYVTMSVGKVFHPGISSNHTDDSP<br>YSWSFPPYHPSSEKYENTKTCRGPDGELHANLLCPVDVLDVP<br>EGTLPDKQSTEQAIQLLEKMKTSASPFFLAVGYHKPHIPFRYP<br>KEFQKLYPLENITLAPDPEVPDGLPPVAYNPWMDIRQREDVQA<br>LNISVPYGPIPVDFQRKIRQSYFASVSYLDTQVGRLLSALDDLQ<br>LANSTIIAFTSDHGWALGEHGEWAKYSNFDVATHVPLIFYVPG<br>RTASLPEAGEKLFPYLDPFDSASQLMEPGRQSMDLVELVSLF<br>PTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTVWVGFNPDEFLANFSDIHAGELYFVDSDPLQDHNMY<br>NDSQGGDLFQLLMPGGGGSGGGGSGGGGSGGGGSGGGGS<br>QVKLEESGGGLVQAGGSLKLSCAASGSTFSSSSVGWYRQAP<br>GQQRELVAAITSGGSTNTADSVKGRFTMSRDNAKNTVYLQMR<br>DLKPEDTAVYYCGVAGRNWVPISRYSPGPYWGQGTQVTVSS<br>HHHHHHHH | IGF1R3H5-IDS-M79 with yarrowia-specific signal peptide |
| SEQ ID NO: 51 | MKLSTILFTACATLAAAASETQANSTTDALNVLLIIVDDLRPSLG<br>CYGDKLVRSPNIDQLASHSLLFQNAFAQQAVCAPSRVSFLTG | IDS-C1 with yarrowia- |

| SEQ ID NO: | Sequence | Description |
|---|---|---|
| | RRPDTTRLYDFNSYWRVHAGNFSTIPQYFKENGYVTMSVGKV<br>FHPGISSNHTDDSPYSWSFPPYHPSSEKYENTKTCRGPDGEL<br>HANLLCPVDVLDVPEGTLPDKQSTEQAIQLLEKMKTSASPFFL<br>AVGYHKPHIPFRYPKEFQKLYPLENITLAPDPEVPDGLPPVAYN<br>PWMDIRQREDVQALNISVPYGPIPVDFQRKIRQSYFASVSYLD<br>TQVGRLLSALDDLQLANSTIIAFTSDHGWALGEHGEWAKYSNF<br>DVATHVPLIFYVPGRTASLPEAGEKLFPYLDPFDSASQLMEPG<br>RQSMDLVELVSLFPTLAGLAGLQVPPRCPVPSFHVELCREGK<br>NLLKHFRFRDLEEDPYLPGNPRELIAYSQYPRPSDIPQWNSDK<br>PSLKDIKIMGYSIRTIDYRYTVWVGFNPDEFLANFSDIHAGELYF<br>VDSDPLQDHNMYNDSQGGDLFQLLMPHHHHHHHHWSHPQF<br>EK | specific signal peptide |
| SEQ ID NO: 52 | MKLSTILFTACATLAAAEVQLQASGGGLVQAGGSLRLSCAASG<br>FKITHYTMGWFRQAPGKEREFVSRITWGGDNTFYSNSVKGRF<br>TISRDNAKNTVYLQMNSLKPEDTADYYCAAGSTSTATPLRVDY<br>WGKGTQVTVSSGGGGSSETQANSTTDALNVLLIIVDDLRPSLG<br>CYGDKLVRSPNIDQLASHSLLFQNAFAQQAVCAPSRVSFLTG<br>RRPDTTRLYDFNSYWRVHAGNFSTIPQYFKENGYVTMSVGKV<br>FHPGISSNHTDDSPYSWSFPPYHPSSEKYENTKTCRGPDGEL<br>HANLLCPVDVLDVPEGTLPDKQSTEQAIQLLEKMKTSASPFFL<br>AVGYHKPHIPFRYPKEFQKLYPLENITLAPDPEVPDGLPPVAYN<br>PWMDIRQREDVQALNISVPYGPIPVDFQRKIRQSYFASVSYLD<br>TQVGRLLSALDDLQLANSTIIAFTSDHGWALGEHGEWAKYSNF<br>DVATHVPLIFYVPGRTASLPEAGEKLFPYLDPFDSASQLMEPG<br>RQSMDLVELVSLFPTLAGLAGLQVPPRCPVPSFHVELCREGK<br>NLLKHFRFRDLEEDPYLPGNPRELIAYSQYPRPSDIPQWNSDK<br>PSLKDIKIMGYSIRTIDYRYTVWVGFNPDEFLANFSDIHAGELYF<br>VDSDPLQDHNMYNDSQGGDLFQLLMPHHHHHHHHWSHPQF<br>EK | FC5-IDS with yarrowia-specific signal peptide |
| SEQ ID NO: 53 | MKLSTILFTACATLAAAEVQLVESGGGLVQPGGSLRLSCAASE<br>YPSNFYAMSWFRQAPGKEREFVSGVSRDGLTTLYADSVKGR<br>FTISRDNSKNTLYLQMNSLRAEDTAVYYCAIVITGVWNKVDVN<br>SRSYHYWGQGTLVTVSSGGGGSGGGGSGGGGSGGGGSGG<br>GGSSETQANSTTDALNVLLIIVDDLRPSLGCYGDKLVRSPNIDQ<br>LASHSLLFQNAFAQQAVCAPSRVSFLTGRRPDTTRLYDFNSY<br>WRVHAGNFSTIPQYFKENGYVTMSVGKVFHPGISSNHTDDSP<br>YSWSFPPYHPSSEKYENTKTCRGPDGELHANLLCPVDVLDVP<br>EGTLPDKQSTEQAIQLLEKMKTSASPFFLAVGYHKPHIPFRYP<br>KEFQKLYPLENITLAPDPEVPDGLPPVAYNPWMDIRQREDVQA<br>LNISVPYGPIPVDFQRKIRQSYFASVSYLDTQVGRLLSALDDLQ<br>LANSTIIAFTSDHGWALGEHGEWAKYSNFDVATHVPLIFYVPG<br>RTASLPEAGEKLFPYLDPFDSASQLMEPGRQSMDLVELVSLF<br>PTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTVWVGFNPDEFLANFSDIHAGELYFVDSDPLQDHNMY<br>NDSQGGDLFQLLMPHHHHHHHHWSHPQFEK | IGF1R3H5-IDS with yarrowia-specific signal peptide |
| SEQ ID NO: 54 | MKLSTILFTACATLAAAQVQLVESGGGLVQPGGSLRLSCAASG<br>RTIDNYAMAWVRQAPGKGLEWVATIDWGDGGTRYANSVKGR<br>FTISRDNSKNTMYLQMNSLRAEDTAVYYCAMARQSRVNLDVA<br>RYDYWGQGTLVTVSSGGGGSGGGGGGGSGGGGSGGG<br>GSSETQANSTTDALNVLLIIVDDLRPSLGCYGDKLVRSPNIDQL<br>ASHSLLFQNAFAQQAVCAPSRVSFLTGRRPDTTRLYDFNSYW<br>RVHAGNFSTIPQYFKENGYVTMSVGKVFHPGISSNHTDDSPY<br>SWSFPPYHPSSEKYENTKTCRGPDGELHANLLCPVDVLDVPE<br>GTLPDKQSTEQAIQLLEKMKTSASPFFLAVGYHKPHIPFRYPK<br>EFQKLYPLENITLAPDPEVPDGLPPVAYNPWMDIRQREDVQAL<br>NISVPYGPIPVDFQRKIRQSYFASVSYLDTQVGRLLSALDDLQL<br>ANSTIIAFTSDHGWALGEHGEWAKYSNFDVATHVPLIFYVPGR<br>TASLPEAGEKLFPYLDPFDSASQLMEPGRQSMDLVELVSLFPT<br>_AGLAGLQVPPRCPVPSFHVELCREGKNLLKHFRFRDLEEDP<br>YLPGNPRELIAYSQYPRPSDIPQWNSDKPSLKDIKIMGYSIRTID<br>YRYTVWVGFNPDEFLANFSDIHAGELYFVDSDPLQDHNMYND<br>SQGGDLFQLLMPHHHHHHHHWSHPQFEK | IGF1R5H2-IDS with yarrowia-specific signal peptide |
| SEQ ID NO: 55 | MKLSTILFTACATLAAAEVQLVESGGGLVQPGGSLRLSCAASE<br>YPSNFYAMSWFRQAPGKEREFVSGVSRDGLTTLYADSVKGR<br>FTISRDNSKNTLYLQMNSLRAEDTAVYYCAIVITGVWNKVDVN<br>SRSYHYWGQGTLVTVSSGGGGSGGGGSGGGGSGGGGSGG<br>GGSARPCIPKSFGYSSVVCVCNATYCDSFDPPTFPALGTFSR<br>YESTRSGRRMELSMGPIQANHTGTGLLLTLQPEQKFQKVKGF<br>GGAMTDAAALNILALSPPAQNLLLKSYFSEEGIGYNIIRVPMAS<br>CDFSIRTYTYADTPDDFQLLNFSLPEEDTKLKIPLIHRALQAQR<br>PVSLLASPWTSPTWLKTNGAVNGKGSLKGQPGDIYHQTWAR | IGF1R3H5-GCaseMut1 with yarrowia-specific signal peptide |

| SEQ ID NO: | Sequence | Description |
|---|---|---|
| | YFVKFLDAYAEHKLQFWAVTAENEPSAGLLSGYPFQCLGFTP<br>EHQRDFIARDLGPTLANSTHHNVRLLMLDDQRLLLPHWAKVVL<br>TDPEAAKYVHGIAVHWYLDFLAPANATLGETHRLFPNTMLFAS<br>EACVGSKFWEQSVRLGSWDRGMQYSHSIITNLLYHVVGWTD<br>WNLALNPEGGPNWVRNFVDSPIIVDITKDTFYKQPMFYHLGHF<br>SKFIPEGSQRVGLVASQKNDLDAVALMHPDGSAVVVVLNRSS<br>KDVPLTIKDPAVGFLETISPGYSIHTYLWRRQHHHHHHHH | |
| SEQ ID NO: 56 | MKLSTILFTACATLAAAEVQLVESGGGLVQPGGSLRLSCAASE<br>YPSNFYAMSWFRQAPGKEREFVSGVSRDGLTTLYADSVKGR<br>FTISRDNSKNTLYLQMNSLRAEDTAVYYCAIVITGVWNKVDVN<br>SRSYHYWGQGTLVTVSSGGGGSGGGGSGGGGSGGGGSGGG<br>GGSSETQANSTTDALNVLLIIVDDLRPSLGCYGDKLVRSPNIDQ<br>LASHSLLFQNAFAQQAVCAPSRVSFLTGRRPDTTRLYDFNSY<br>WRVHAGNFSTIPQYFKENGYVTMSVGKVFHPGISSNHTDDSP<br>YSWSFPPYHPSSEKYENTKTCRGPDGELHANLLCPVDVLDVP<br>EGTLPDKQSTEQAIQLLEKMKTSASPFFLAVGYHKPHIPFRYP<br>KEFQKLYPLENITLAPDPEVPDGLPPVAYNPWMDIRQREDVQA<br>LNISVPYGPIPVDFQRKIRQSYFASVSYLDTQVGRLLSALDDLQ<br>LANSTIIAFTSDHGWALGEHGEWAKYSNFDVATHVPLIFYVPG<br>RTASLPEAGEKLFPYLDPFDSASQLMEPGRQSMDLVELVSLF<br>PTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTVWVGFNPDEFLANFSDIHAGELYFVDSDPLQDHNMY<br>NDSQGGDLFQLLMPGGGSGGGGSGGGGSGGGGSGGGGS<br>EVQLVESGGGLVQPGNSLRLSCAASGFTFSSFGMSWVRQAP<br>GKGLEWVSSISGSGSDTLYADSVKGRFTISRDNAKTTLYLQMN<br>SLRPEDTAVYYCTIGGSLSRSSQGTLVTVSSHHHHHHHH | IGF1R3H5-IDS-Alb8 with yarrowia-specific signal peptide |
| SEQ ID NO: 57 | MKLSTILFTACATLAAAQVQLVESGGGLVQPGGSLRLSCAASG<br>RTIDNYAMAWVRQAPGKGLEWVATIDWGDGGTRYANSVKGR<br>FTISRDNSKNTMYLQMNSLRAEDTAVYYCAMARQSRVNLDVA<br>RYDYWGQGTLVTVSSGGGGSGGGGSGGGGSGGGGSGGG<br>GSSETQANSTTDALNVLLIIVDDLRPSLGCYGDKLVRSPNIDQL<br>ASHSLLFQNAFAQQAVCAPSRVSFLTGRRPDTTRLYDFNSYW<br>RVHAGNFSTIPQYFKENGYVTMSVGKVFHPGISSNHTDDSPY<br>SWSFPPYHPSSEKYENTKTCRGPDGELHANLLCPVDVLDVPE<br>GTLPDKQSTEQAIQLLEKMKTSASPFFLAVGYHKPHIPFRYPK<br>EFQKLYPLENITLAPDPEVPDGLPPVAYNPWMDIRQREDVQAL<br>NISVPYGPIPVDFQRKIRQSYFASVSYLDTQVGRLLSALDDLQL<br>ANSTIIAFTSDHGWALGEHGEWAKYSNFDVATHVPLIFYVPGR<br>TASLPEAGEKLFPYLDPFDSASQLMEPGRQSMDLVELVSLFPT<br>LAGLAGLQVPPRCPVPSFHVELCREGKNLLKHFRFRDLEEDP<br>YLPGNPRELIAYSQYPRPSDIPQWNSDKPSLKDIKIMGYSIRTID<br>YRYTVWVGFNPDEFLANFSDIHAGELYFVDSDPLQDHNMYND<br>SQGGDLFQLLMPGGGSGGGGSGGGGSGGGGSGGGGSAV<br>QLVESGGGLVQPGNSLRLSCAASGFTFRSFGMSWVRQAPGK<br>EPEWVSSISGSGSDTLYADSVKGRFTISRDNAKTTLYLQMNSL<br>KPEDTAVYYCTIGGSLSRSSQGTQVTVSSHHHHHHHHWSHP<br>QFEK | IGF1R5H2-IDS-Alb1 with yarrowia-specific signal peptide |
| SEQ ID NO: 58 | MKLSTILFTACATLAAAQVQLVESGGGLVQPGGSLRLSCAASG<br>RTIDNYAMAWVRQAPGKGLEWVATIDWGDGGTRYANSVKGR<br>FTISRDNSKNTMYLQMNSLRAEDTAVYYCAMARQSRVNLDVA<br>RYDYWGQGTLVTVSSGGGGSGGGGGGGGSGGGGSGGG<br>GSAVQLVESGGGLVQPGNSLRLSCAASGFTFRSFGMSWVRQ<br>APGKEPEWVSSISGSGSDTLYADSVKGRFTISRDNAKTTLYLQ<br>MNSLKPEDTAVYYCTIGGSLSRSSQGTQVTVSSGGGGSGGG<br>GSGGGGSGGGGSGGGGSSETQANSTTDALNVLLIIVDDLRPS<br>LGCYGDKLVRSPNIDQLASHSLLFQNAFAQQAVCAPSRVSFLT<br>GRRPDTTRLYDFNSYWRVHAGNFSTIPQYFKENGYVTMSVGK<br>VFHPGISSNHTDDSPYSWSFPPYHPSSEKYENTKTCRGPDGE<br>LHANLLCPVDVLDVPEGTLPDKQSTEQAIQLLEKMKTSASPFF<br>LAVGYHKPHIPFRYPKEFQKLYPLENITLAPDPEVPDGLPPVAY<br>NPWMDIRQREDVQALNISVPYGPIPVDFQRKIRQSYFASVSYL<br>DTQVGRLLSALDDLQLANSTIIAFTSDHGWALGEHGEWAKYS<br>NFDVATHVPLIFYVPGRTASLPEAGEKLFPYLDPFDSASQLME<br>PGRQSMDLVELVSLFPTLAGLAGLQVPPRCPVPSFHVELCRE<br>GKNLLKHFRFRDLEEDPYLPGNPRELIAYSQYPRPSDIPQWNS<br>DKPSLKDIKIMGYSIRTIDYRYTVWVGFNPDEFLANFSDIHAGE<br>LYFVDSDPLQDHNMYNDSQGGDLFQLLMPHHHHHHHHWSH<br>PQFEK | IGF1R5H2-Alb1-IDS with yarrowia-specific signal peptide |
| SEQ ID NO: 59 | MKLSTILFTACATLAAAAVQLVESGGGLVQPGNSLRLSCAASG<br>FTFRSFGMSWVRQAPGKEPEWVSSISGSGSDTLYADSVKGR | Alb1-IGF1R5H2-IDS |

-continued

| SEQ ID NO: | Sequence | Description |
|---|---|---|
| | FTISRDNAKTTLYLQMNSLKPEDTAVYYCTIGGSLSRSSQGTQ<br>VTVSSGGGGSGGGGSGGGGSGGGGSGGGGSQVQLVESGG<br>GLVQPGGSLRLSCAASGRTIDNYAMAWVRQAPGKGLEWVATI<br>DWGDGGTRYANSVKGRFTISRDNSKNTMYLQMNSLRAEDTA<br>VYYCAMARQSRVNLDVARYDYWGQGTLVTVSSGGGGSGGG<br>GSGGGGSGGGGSGGGGSSETQANSTTDALNVLLIIVDDLRPS<br>LGCYGDKLVRSPNIDQLASHSLLFQNAFAQQAVCAPSRVSFLT<br>GRRPDTTRLYDFNSYWRVHAGNFSTIPQYFKENGYVTMSVGK<br>VFHPGISSNHTDDSPYSWSFPPYHPSSEKYENTKTQRGPDGE<br>LHANLLCPVDVLDVPEGTLPDKQSTEQAIQLLEKMKTSASPFF<br>LAVGYHKPHIPFRYPKEFQKLYPLENITLAPDPEVPDGLPPVAY<br>NPWMDIRQREDVQALNISVPYGPIPVDFQRKIRQSYFASVSYL<br>DTQVGRLLSALDDLQLANSTIIAFTSDHGWALGEHGEWAKYS<br>NFDVATHVPLIFYVPGRTASLPEAGEKLFPYLDPFDSASQLME<br>PGRQSMDLVELVSLFPTLAGLAGLQVPPRCPVPSFHVELCRE<br>GKNLLKHFRFRDLEEDPYLPGNPRELIAYSQYPRPSDIPQWNS<br>DKPSLKDIKIMGYSIRTIDYRYTVWVGFNPDEFLANFSDIHAGE<br>LYFVDSDPLQDHNMYNDSQGGDLFQLLMPHHHHHHHWSH<br>PQFEK | with yarrowia-<br>specific signal<br>peptide |
| SEQ ID NO: 60 | MKLSTILFTACATLAAAQVQLVESGGGLVQPGGSLRLSCAASG<br>RTIDNYAMAWVRQAPGKGLEWVATIDWGDGGTRYANSVKGR<br>FTISRDNSKNT MYLQMNSLRAEDTAVYYCAMARQSRVNLDVA<br>RYDYWGQGTLVTVSSGGGGSGGGGSGGGGSGGGGSGGG<br>GSSETQANSTTDALNVLLIIVDDLRPSLGCYGDKLVRSPNIDQL<br>ASHSLLFQNAFAQQAVCAPSRVSFLTGRRPDTTRLYDFNSYW<br>RVHAGNFSTIPQYFKENGYVTMSVGKVFHPGISSNHTDDSPY<br>SWSFPPYHPSSEKYENTKTCRGPDGELHANLLCPVDVLDVPE<br>GTLPDKQSTEQAIQLLEKMKTSASPFFLAVGYHKPHIPFRYPK<br>EFQKLYPLENITLAPDPEVPDGLPPVAYNPWMDIRQREDVQAL<br>NISVPYGPIPVDFQRKIRQSYFASVSYLDTQVGRLLSALDDLQL<br>ANSTIIAFTSDHGWALGEHGEWAKYSNFDVATHVPLIFYVPGR<br>TASLPEAGEKLFPYLDPFDSASQLMEPGRQSMDLVELVSLFPT<br>LAGLAGLQVPPRCPVPSFHVELCREGKNLLKHFRFRDLEEDP<br>YLPGNPRELIAYSQYPRPSDIPQWNSDKPSLKDIKIMGYSIRTID<br>YRYTVWVGFNPDEFLANFSDIHAGELYFVDSDPLQDHNMYND<br>SQGGDLFQLLMPGGGGSDAHKSEVAHRFKDLGEENFKALVLI<br>AFAQYLQQCPFEDHVKLVNEVTEFAKTCVADESAENCDKSLH<br>TLFGDKLCTVATLRETYGEMADCCAKQEPERNECFLQHKDDN<br>PNLPRLVRPEVDVMCTAFHDNEETFLKKYLYEIARRHPYFYAP<br>ELLFFAKRYKAAFTECCQAADKAACLLPKLDELRDEGKASSAK<br>QRLKCASLQKFGERAFKAWAVARLSQRFPKAEFAEVSKLVTD<br>LTKVHTECCHGDLLECADDRADLAKYICENQDSISSKLKECCE<br>KPLLEKSHCIAEVENDEMPADLPSLAADFVESKDVCKNYAEAK<br>DVFLGMFLYEYARRHPDYSVVLLLRLAKTYETTLEKCCAAADP<br>HECYAKVFDEFKPLVEEPQNLIKQNCELFEQLGEYKFQNALLV<br>RYTKKVPQVSTPTLVEVSRNLGKVGSKCCKHPEAKRMPCAED<br>YLSVVLNQLCVLHEKTPVSDRVTKCCTESLVNRRPCFSALEVD<br>ETYVPKEFNAETFTFHADICTLSEKERQIKKQTALVELVKHKPK<br>ATKEQLKAVMDDFAAFVEKCCKADDKETCFAEEGPKLVAASQ<br>AALGLHHHHHHWSHPQFEK | IGF1R5H2-IDS-<br>HSA(K573P)<br>with yarrowia-<br>specific signal<br>peptide |
| SEQ ID NO: 61 | MKLSTILFTACATLAAASETQANSTTDALNVLLIIVDDLRPSLGC<br>YGDKLVRSPNIDQLASHSLLFQNAFAQQAVCAPSRVSFLTGR<br>RPDTTRLYDFNSYWRVHAGNFSTIPQYFKENGYVTMSVGKVF<br>HPGISSNHTDDSPYSWSFPPYHPSSEKYENTKTCRGPDGELH<br>ANLLCPVDVLDVPEGTLPDKQSTEQAIQLLEKMKTSASPFFLA<br>VGYHKPHIPFRYPKEFQKLYPLENITLAPDPEVPDGLPPVAYNP<br>WMDIRQREDVQALNISVPYGPIPVDFQRKIRQSYFASVSYLDT<br>QVGRLLSALDDLQLANSTIIAFTSDHGWALGEHGEWAKYSNF<br>DVATHVPLIFYVPGRTASLPEAGEKLFPYLDPFDSASQLMEPG<br>RQSMDLVELVSLFPTLAGLAGLQVPPRCPVPSFHVELCREGK<br>NLLKHFRFRDLEEDPYLPGNPRELIAYSQYPRPSDIPQWNSDK<br>PSLKDIKIMGYSIRTIDYRYTVWVGFNPDEFLANFSDIHAGELYF<br>VDSDPLQDHNMYNDSQGGDLFQLLMPGGGGSGGGGSGGG<br>GSGGGGSGGGGSQVQLVESGGGLVQAGGSLRLSCVASGRT<br>FIAYAMGWFRQAPGKEREFVAAITNFAGGTTYYADSVKGRFTI<br>SRDNAKTTVYLQMNSLKPEDTALYYCAADRSAQTMRQVRPVL<br>PYWGQGTQVTVSSHHHHHH | CIDS-R28 with<br>yarrowia-<br>specific signal<br>peptide |
| SEQ ID NO: 62 | MKLSTILFTACATLAAASETQANSTTDALNVLLIIVDDLRPSLGC<br>YGDKLVRSPNIDQLASHSLLFQNAFAQQAVCAPSRVSFLTGR<br>RPDTTRLYDFNSYWRVHAGNFSTIPQYFKENGYVTMSVGKVF<br>HPGISSNHTDDSPYSWSFPPYHPSSEKYENTKTCRGPDGELH<br>ANLLCPVDVLDVPEGTLPDKQSTEQAIQLLEKMKTSASPFFLA | CIDS-M79 with<br>yarrowia-<br>specific signal<br>peptide |

SEQUENCES

| SEQ ID NO: | Sequence | Description |
| --- | --- | --- |
| | VGYHKPHIPFRYPKEFQKLYPLENITLAPDPEVPDGLPPVAYNP<br>WMDIRQREDVQALNISVPYGPIPVDFQRKIRQSYFASVSYLDT<br>QVGRLLSALDDLQLANSTIIAFTSDHGWALGEHGEWAKYSNF<br>DVATHVPLIFYVPGRTASLPEAGEKLFPYLDPFDSASQLMEPG<br>RQSMDLVELVSLFPTLAGLAGLQVPPRCPVPSFHVELCREGK<br>NLLKHFRFRDLEEDPYLPGNPRELIAYSQYPRPSDIPQWNSDK<br>PSLKDIKIMGYSIRTIDYRYTWWVGFNPDEFLANFSDIHAGELYF<br>VDSDPLQDHNMYNDSQGGDLFQLLMPGGGGGGGGSGGG<br>GSGGGGSGGGGSQVKLEESGGGLVQAGGSLKLSCAASGST<br>FSSSSVGWYRQAPGQQRELVAAITSGGSTNTADSVKGRFTM<br>SRDNAKNTVYLQMRDLKPEDTAVYYCNVAGRNWVPISRYSP<br>GPYWGQGTQVTVSSHHHHHHHH | |
| SEQ ID NO: 63 | SSESKYGPPCPSCPAPEFLGGPSVFLFPPKPKDTLMISRTPEV<br>TCVVVDVSQEDPEVQFNWYVDGVEVHNAKTKPREEQFNSTY<br>RVVSVLTVLHQDWLNGKEYKCKVSNKGLPSSIEKTISKAKGQP<br>REPQVYTKPPSQEEMTKNQVSLSCLVKGFYPSDIAVEWESNG<br>QPENNYKTTVPVLDSDGSFRLASYLTVDKSRWQEGNVFSCSV<br>MHEALHNHYTQKSLSLSLGK | monoFc |
| SEQ ID NO: 64 | MKLSTILFTACATLAAAQVQLVESGGGLVQPGGSLRLSCAASG<br>RTIDNYAMAWVRQAPGKGLEWVATIDWGDGGTRYANSVKGR<br>FTISRDNSKNTMYLQMNSLRAEDTAVYYCAMARQSRVNLDVA<br>RYDYWGQGTLVTVSSESKYGPPCPSCPAPEFLGGPSVFLFPP<br>KPKDTLMISRTPEVTCVVVDVSQEDPEVQFNWYVDGVEVHNA<br>KTKPREEQFNSTYRVVSVLTVLHQDWLNGKEYKCKVSNKGLP<br>SSIEKTISKAKGQPREPQVYTKPPSQEEMTKNQVSLSCLVKGF<br>YPSDIAVEWESNGQPENNYKTTVPVLDSDGSFRLASYLTVDK<br>SRWQEGNVFSCSVMHEALHNHYTQKSLSLSLGKGGGGSGG<br>GGSGGGGSGGGGSGGGGSSETQANSTTDALNVLLIIVDDLRP<br>SLGCYGDKLVRSPNIDQLASHSLLFQNAFAQQAVCAPSRVSFL<br>TGRRPDTTRLYDFNSYWRVHAGNFSTIPQYFKENGYVTMSVG<br>KVFHPGISSNHTDDSPYSWSFPPYHPSSEKYENTKTCRGPDG<br>ELHANLLCPVDVLDVPEGTLPDKQSTEQAIQLLEKMKTSASPF<br>FLAVGYHKPHIPFRYPKEFQKLYPLENITLAPDPEVPDGLPPVA<br>YNPWMDIRQREDVQALNISVPYGPIPVDFQRKIRQSYFASVSY<br>LDTQVGRLLSALDDLQLANSTIIAFTSDHGWALGEHGEWAKYS<br>NFDVATHVPLIFYVPGRTASLPEAGEKLFPYLDPFDSASQLME<br>PGRQSMDLVELVSLFPTLAGLAGLQVPPRCPVPSFHVELCRE<br>GKNLLKHFRFRDLEEDPYLPGNPRELIAYSQYPRPSDIPQWNS<br>DKPSLKDIKIMGYSIRTIDYRYTWWVGFNPDEFLANFSDIHAGE<br>LYFVDSDPLQDHNMYNDSQGGDLFQLLMP | IGF1R5H2-monoFc-IDS with yarrowia-specific signal peptide |
| SEQ ID NO: 65 | QVQLVESGGGLVQPGGSLRLSCAASGRTIDNYAMAWVRQAP<br>GKGLEWVATIDWGDGGTRYANSVKGRFTISRDNSKNTMYLQ<br>MNSLRAEDTAVYYCAMARQSRVNLDVARYDYWGQGTLVTVS<br>SESKYGPPCPSCPAPEFLGGPSVFLFPPKPKDTLMISRTPEVT<br>CVVVDVSQEDPEVQFNWYVDGVEVHNAKTKPREEQFNSTYR<br>VVSVLTVLHQDWLNGKEYKCKVSNKGLPSSIEKTISKAKGQPR<br>EPQVYTKPPSQEEMTKNQVSLSCLVKGFYPSDIAVEWESNGQ<br>PENNYKTTVPVLDSDGSFRLASYLTVDKSRWQEGNVFSCSVM<br>HEALHNHYTQKSLSLSLGKGGGGSGGGGSGGGGSGGGGSG<br>GGGSSETQANSTTDALNVLLIIVDDLRPSLGCYGDKLVRSPNID<br>QLASHSLLFQNAFAQQAVCAPSRVSFLTGRRPDTTRLYDFNS<br>YWRVHAGNFSTIPQYFKENGYVTMSVGKVFHPGISSNHTDDS<br>PYSWSFPPYHPSSEKYENTKTCRGPDGELHANLLCPVDVLDV<br>PEGTLPDKQSTEQAIQLLEKMKTSASPFFLAVGYHKPHIPFRY<br>PKEFQKLYPLENITLAPDPEVPDGLPPVAYNPWMDIRQREDVQ<br>ALNISVPYGPIPVDFQRKIRQSYFASVSYLDTQVGRLLSALDDL<br>QLANSTIIAFTSDHGWALGEHGEWAKYSNFDVATHVPLIFYVP<br>GRTASLPEAGEKLFPYLDPFDSASQLMEPGRQSMDLVELVSL<br>FPTLAGLAGLQVPPRCPVPSFHVELCREGKNLLKHFRFRDLEE<br>DPYLPGNPRELIAYSQYPRPSDIPQWNSDKPSLKDIKIMGYSIR<br>TIDYRYTWWVGFNPDEFLANFSDIHAGELYFVDSDPLQDHNMY<br>NDSQGGDLFQLLMPHHHHHH | IGF1R5H2-monoFc-IDS - with purification tag |
| SEQ ID NO: 66 | TDALNVLLIIVDDLRPSLGCYGDKLVRSPNIDQLASHSLLFQNA<br>FAQQAVCAPSRVSFLTGRRPDTTRLYDFNSYWRVHAGNFSTI<br>PQYFKENGYVTMSVGKVFHPGISSNHTDDSPYSWSFPPYHPS<br>SEKYENTKTCRGPDGELHANLLCPVDVLDVPEGTLPDKQSTE<br>QAIQLLEKMKTSASPFFLAVGYHKPHIPFRYPKEFQKLYPLENI<br>TLAPDPEVPDGLPPVAYNPWMDIRQREDVQALNISVPYGPIPV<br>DFQRKIRQSYFASVSYLDTQVGRLLSALDDLQLANSTIIAFTSD<br>HGWALGEHGEWAKYSNFDVATHVPLIFYVPGRTASLPEAGEK<br>LFPYLDPFDSASQLMEPGRQSMDLVELVSLFPTLAGLAGLQVP | human IDS - no signal/pro sequence |

| SEQ ID NO: | Sequence | Description |
|---|---|---|
| | PRCPVPSFHVELCREGKNLLKHFRFRDLEEDPYLPGNPRELIA<br>YSQYPRPSDIPQWNSDKPSLKDIKIMGYSIRTIDYRYTVWVGF<br>NPDEFLANFSDIHAGELYFVDSDPLQDHNMYNDSQGGDLFQL<br>LMP | |
| SEQ ID NO: 67 | DAHKSEVAHRFKDLGEENFKALVLIAFAQYLQQCPFEDHVKLV<br>NEVTEFAKTCVADESAENCDKSLHTLFGDKLCTVATLRETYGE<br>MADCCAKQEPERNECFLQHKDDNPNLPRLVRPEVDVMCTAF<br>HDNEETFLKKYLYEIARRHPYFYAPELLFFAKRYKAAFTECCQ<br>AADKAACLLPKLDELRDEGKASSAKQRLKCASLQKFGERAFK<br>AWAVARLSQRFPKAEFAEVSKLVTDLTKVHTECCHGDLLECA<br>DDRADLAKYICENQDSISSKLKECCEKPLLEKSHCIAEVENDE<br>MPADLPSLAADFVESKDVCKNYAEAKDVFLGMFLYEYARRHP<br>DYSVVLLLRLAKTYETTLEKCCAAADPHECYAKVFDEFKPLVE<br>EPQNLIKQNCELFEQLGEYKFQNALLVRYTKKVPQVSTPTLVE<br>VSRNLGKVGSKCCKHPEAKRMPCAEDYLSVVLNQLCVLHEKT<br>PVSDRVTKCCTESLVNRRPCFSALEVDETYVPKEFNAETFTFH<br>ADICTLSEKERQIKKQTALVELVKHKPKATKEQLKAVMDDFAAF<br>VEKCCKADDKETCFAEEGKKLVAASQAALGL | human albumin<br>(ALB) - no<br>signal/pro<br>sequence |
| SEQ ID NO: 68 | ARPCIPKSFGYSSVVCVCNATYCDSFDPPTFPALGTFSRYEST<br>RSGRRMELSMGPIQANHTGTGLLLTLQPEQKFQKVKGFGGA<br>MTDAAALNILALSPPAQNLLLKSYFSEEGIGYNIIRVPMASCDFS<br>IRTYTYADTPDDFQLHNFSLPEEDTKLKIPLIHRALQLAQRPVSL<br>LASPWTSPTWLKTNGAVNGKGSLKGQPGDIYHQTWARYFVK<br>FLDAYAEHKLQFWAVTAENEPSAGLLSGYPFQCLGFTPEHQR<br>DFIARDLGPTLANSTHHNVRLLMLDDQRLLLPHWAKVVLTDPE<br>AAKYVHGIAVHWYLDFLAPAKATLGETHRLFPNTMLFASEACV<br>GSKFWEQSVRLGSWDRGMQYSHSIITNLLYHVVGWTDWNLA<br>LNPEGGPNWVRNFVDSPIIVDITKDTFYKQPMFYHLGHFSKFIP<br>EGSQRVGLVASQKNDLDAVALMHPDGSAVVVVLNRSSKDVPL<br>TIKDPAVGFLETISPGYSIHTYLWRRQ | human GCase<br>(GBA) - no<br>signal sequence |
| SEQ ID: 69 | QVQLVESGGGLAQAGGSLRLSCAASGRTFSMDPMAWFRQP<br>PGKEREFVAAGSSTGRTTYYADSVKGRFTISRDNAKNTVYLQ<br>MNSLKPEDTAVYYCAAAPYGANWYRDEYAYWGQGTQVTVSS<br>AEPKSSDKTHTCPPCPAPELLGGPSVFLFPPKPKDTLMISRTP<br>EVTCVVVDVSHEGPEVKFNWYVDGVEVHNAKTKPREEQYNS<br>TYRVVSVLTVLHQDWLNGKEYKCKVSNKALPAPIEKTISKAKG<br>QPREPQVYTLPPSRDELTKNQVSLTCLVKGFYPSDIAVEWES<br>NGQPENNYKTTPPVLDSDGSFFLYSKLTVDKSRWQQGNVFS<br>CSVMHEALHNHYTQKSLSLSPG | A20.1hFc1X7 |
| SEQ ID: 70 | AEPKSSDKTHTCPPCPAPELLGGPSVFLFPPKPKDTLMISRTP<br>EVTCVVVDVSHEGPEVKFNWYVDGVEVHNAKTKPREEQYNS<br>TYRVVSVLTVLHQDWLNGKEYKCKVSNKALPAPIEKTISKAKG<br>QPREPQVYTLPPSRDELTKNQVSLTCLVKGFYPSDIAVEWES<br>NGQPENNYKTTPPVLDSDGSFFLYSKLTVDKSRWQQGNVFS<br>CSVMHEALHNHYTQKSLSLSPGGGGSGGGGSQVQLVESGG<br>GLVQPGGSLRLSCAASGRTIDNYAMAWVRQAPGKGLEWVATI<br>DWGDGGTRYANSVKGRFTISRDNSKNTMYLQMNSLRAEDTA<br>VYYCAMARQSRVNLDVARYDYWGQGTLVTVSS | hFc1X7-<br>IGF1R5H2 |

REFERENCES

All patents, patent applications and publications referred to herein and throughout the application are hereby incorporated by reference.

1. Arbabi Ghahroudi, M., Desmyter, A., Wyns, L., Hamers, R., and Muyldermans, S. (1997). Selection and identification of single domain antibody fragments from camel heavy-chain antibodies. FEBS Lett. 414:521-526.
2. Artursson, P., and Karlsson, J. (1991). Correlation between oral drug absorption in humans and apparent drug permeability coefficients in human intestinal epithelial (Caco-2) cells. Biochem. Biophys. Res. Commun. 175:880-5.
3. Balestrino, R., and Schapira, A. H. V (2018). Glucocerebrosidase and Parkinson Disease: Molecular, Clinical, and Therapeutic Implications. Neuroscientist 1073858417748875.
4. Bell, A., Wang, Z. J., Arbabi-Ghahroudi, M., Chang, T. A., Durocher, Y., Trojahn, U., et al. (2010). Differential tumor-targeting abilities of three single-domain antibody formats. Cancer Lett. 289:81-90.
5. Chothia, C., and Lesk, A. M. (1987). Canonical structures for the hypervariable regions of immunoglobulins. J. Mol. Biol. 196:901-917.
6. Davies, J., and Riechmann, L. (1996). Affinity improvement of single antibody VH domains: residues in all three hypervariable regions affect antigen binding. Immunotechnology 2:169-79.
7. Dumoulin, M., Conrath, K., Meirhaeghe, A. Van, Meersman, F., Heremans, K., Frenken, L. G. J., et al. (2002). Single-domain antibody fragments with high conformational stability. Protein Sci. 11:500-15.

8. Eisenberg, D., Schwarz, E., Komaromy, M., and Wall, R. (1984). Analysis of membrane and surface protein sequences with the hydrophobic moment plot. J. Mol. Biol. 179:125-42.
9. Fluttert, M., Dalm, S., and Oitzl, M. S. (2000). A refined method for sequential blood sampling by tail incision in rats. Lab. Anim. 34:372-8.
10. Garberg, P., Ball, M., Borg, N., Cecchelli, R., Fenart, L., Hurst, R. D., et al. (2005). In vitro models for the blood-brain barrier. Toxicol. In Vitro 19:299-334.
11. Gottesman, M. M., and Pastan, I. (1993). Biochemistry of Multidrug Resistance Mediated by the Multidrug Transporter. Annu. Rev. Biochem. 62:385-427.
12. Hamers-Casterman, C., Atarhouch, T., Muyldermans, S., Robinson, G., Hammers, C., Songa, E. B., et al. (1993). Naturally occurring antibodies devoid of light chains. Nature 363:446-448.
13. Haqqani, A. S., Caram-Salas, N., Ding, W., Brunette, E., Delaney, C. E., Baumann, E., et al. (2013). Multiplexed evaluation of serum and CSF pharmacokinetics of brain-targeting single-domain antibodies using a NanoLC-SRM-ILIS method. Mol. Pharm. 10:1542-56.
14. Haqqani, A. S., Kelly, J. F., and Stanimirovic, D. B. (2008a). Quantitative protein profiling by mass spectrometry using isotope-coded affinity tags. Methods Mol. Biol. 439:225-240.
15. Haqqani, A. S., Kelly, J. F., and Stanimirovic, D. B. (2008b). Quantitative protein profiling by mass spectrometry using label-free proteomics. Methods Mol. Biol. 439:241-256.
16. Hussack, G., Arbabi-Ghahroudi, M., Faassen, H. Van, Songer, J. G., Ng, K. K. S., Mackenzie, R., et al. (2011a). Neutralization of Clostridium difficile toxin A with single-domain antibodies targeting the cell receptor binding domain. J. Biol. Chem. 286:8961-8976.
17. Hussack, G., Hirama, T., Ding, W., Mackenzie, R., and Tanha, J. (2011b). Engineered single-domain antibodies with high protease resistance and thermal stability. PLOS One 6: e28218.
18. Iqbal, U., Trojahn, U., Albaghdadi, H., Zhang, J., O'Connor-McCourt, M., Stanimirovic, D., et al. (2010). Kinetic analysis of novel mono- and multivalent VHH-fragments and their application for molecular imaging of brain tumours. Br. J. Pharmacol. 160:1016-28.
19. Jespers, L., Schon, O., Famm, K., and Winter, G. (2004). Aggregation-resistant domain antibodies selected on phage by heat denaturation. Nat. Biotechnol. 22:1161-1165.
20. Kabat, E. A., and Wu, T. T. (1991). Identical V region amino acid sequences and segments of sequences in antibodies of different specificities. Relative contributions of VH and VL genes, minigenes, and complementarity-determining regions to binding of antibody-combining sites. J. Immunol. 147:1709-1719.
21. Kim, D. Y., Kandalaft, H., Ding, W., Ryan, S., Faassen, H. Van, Hirama, T., et al. (2012). Disulfide linkage engineering for improving biophysical properties of human $V_H$ domains. Protein Eng. Des. Sel. 25:581-589.
22. Kruif, J. De, and Logtenberg, T. (1996). Leucine zipper dimerized bivalent and bispecific scFv antibodies from a semi-synthetic antibody phage display library. J. Biol. Chem. 271:7630-7634.
23. Li, S., Zheng, W., KuoLee, R., Hirama, T., Henry, M., Makvandi-Nejad, S., et al. (2009). Pentabody-mediated antigen delivery induces antigen-specific mucosal immune response. Mol. Immunol. 46:1718-1726.
24. Lin, D., Alborn, W. E., Slebos, R. J. C., and Liebler, D. C. (2013). Comparison of protein immunoprecipitation-multiple reaction monitoring with ELISA for assay of biomarker candidates in plasma. J. Proteome Res. 12:5996-6003.
25. Merritt, E. A., and Hol, W. G. (1995). AB5 toxins. Curr. Opin. Struct. Biol. 5:165-171.
26. Mitsui, J., Matsukawa, T., Sasaki, H., Yabe, I., Matsushima, M., Dürr, A., et al. (2015). Variants associated with Gaucher disease in multiple system atrophy. Ann. Clin. Transl. Neurol. 2:417-26.
27. Nicaise, M., Valerio-Lepiniec, M., Minard, P., and Desmadril, M. (2004). Affinity transfer by CDR grafting on a nonimmunoglobulin scaffold. Protein Sci. 13:1882-1891.
28. Nielsen, U. B., Adams, G. P., Weiner, L. M., and Marks, J. D. (2000). Targeting of bivalent anti-ErbB2 diabody antibody fragments to tumor cells is independent of the intrinsic antibody affinity. Cancer Res. 60:6434-6440.
29. Nuttall, S. D., Krishnan, U. V, Doughty, L., Pearson, K., Ryan, M. T., Hoogenraad, N.J., et al. (2003). Isolation and characterization of an IgNAR variable domain specific for the human mitochondrial translocase receptor Tom70. Eur. J. Biochem. 270:3543-3554.
30. Pardridge, W. M. (1995). Transport of small molecules through the blood-brain barrier: biology and methodology. Adv. Drug Deliv. Rev. 15:5-36.
31. Puschmann, A., Bhidayasiri, R., and Weiner, W. J. (2012). Synucleinopathies from bench to bedside. Parkinsonism Relat. Disord. 18 Suppl 1: S24-7.
32. Ribecco-Lutkiewicz, M., Sodja, C., Haukenfrers, J., Haqqani, A. S., Ly, D., Zachar, P., et al. (2018). A novel human induced pluripotent stem cell blood-brain barrier model: Applicability to study antibody-triggered receptor-mediated transcytosis. Sci. Rep. 8:1873.
33. Ridgway, J. B. B., Presta, L. G., and Carter, P. (1996). 'Knobs-into-holes' engineering of antibody C H 3 domains for heavy chain heterodimerization. Protein Eng. 9:617-621.
34. Samuels, B. L., Mick, R., Vogelzang, N. J., Williams, S. F., Schilsky, R. L., Safa, A. R., et al. (1993). Modulation of vinblastine resistance with cyclosporine: A phase I study. Clin. Pharmacol. Ther. 54:421-429.
35. To, R., Hirama, T., Arbabi-Ghahroudi, M., Mackenzie, R., Wang, P., Xu, P., et al. (2005). Isolation of monomeric human VHs by a phage selection. J. Biol. Chem. 280: 41395-41403.
36. Watanabe, T., Tsuge, H., Oh-Hara, T., Naito, M., Tsuruo, T., Gigante, M., et al. (1995). Comparative study on reversal efficacy of SDZ PSC 833, cyclosporin A and verapamil on multidrug resistance in vitro and in vivo. Acta Oncol. 34:235-41.
37. Ying, T., Chen, W., Gong, R., Feng, Y., and Dimitrov, D. S. (2012). Soluble monomeric IgG1 Fc. J. Biol. Chem. 287:19399-408.
38. Yun, S. P., Kim, D., Kim, S., Kim, S., Karuppagounder, S. S., Kwon, S. H., et al. (2018). α-Synuclein accumulation and GBA deficiency due to L444P GBA mutation contributes to MPTP-induced parkinsonism. Mol. Neurodegener. 13:1.
39. Zhang, J., Li, Q., Nguyen, T. D., Tremblay, T. L., Stone, E., To, R., et al. (2004a). A pentavalent single-domain antibody approach to tumor antigen discovery and the development of novel proteomics reagents. J. Mol. Biol. 341:161-169.
40. Zhang, J., Tanha, J., Hirama, T., Khieu, N. H., To, R., Tong-Sevinc, H., et al. (2004b). Pentamerization of single-domain antibodies from phage libraries: A novel strategy for the rapid generation of high-avidity antibody reagents. J. Mol. Biol. 335:49-56.
41. Zhu, X., Wang, L., Liu, R., Flutter, B., Li, S., Ding, J., et al. (2010). COMBODY: One-domain antibody multimer with improved avidity. Immunol. Cell Biol. 88:667-675.
42. Zunke, F., Moise, A. C., Belur, N. R., Gelyana, E., Stojkovska, I., Dzaferbegovic, H., et al. (2017). Reversible Conformational Conversion of α-Synuclein into Toxic Assemblies by Glucosylceramide. Neuron 97:92-107.e10.
43. European Patent No. 519596
44. European Patent No. 626390
45. U.S. Pat. No. 5,693,761
46. U.S. Pat. No. 5,766,886
47. U.S. Pat. No. 5,821,123
48. U.S. Pat. No. 5,859,205
49. U.S. Pat. No. 5,869,619
50. U.S. Pat. No. 6,054,297
51. U.S. Pat. No. 6,180,370
52. WO 02/057445
53. WO 2011/127580
54. WO 95/04069
55. WO/2004/076670
56. WO2003/046560
57. WO2015/131257

The invention claimed is:

1. A fusion protein comprising
   an antibody or a fragment thereof, operable to transmigrate the blood-brain barrier (BBB), that selectively binds IGF1R,
   a therapeutic polypeptide for the treatment of a lysosomal storage disease (LSD), and
   a serum half-life extending element selected from the group consisting of a human serum albumin and an albumin targeting moiety,
   wherein the antibody or fragment thereof comprises
      a complementarity determining region (CDR) 1 sequence EYPSNFYA (SEQ ID NO:6); CDR2 sequence VSRDGLTT (SEQ ID NO:7); and CDR3 sequence AIVITGVWNKVDVNSRSYHY (SEQ ID NO:8); or
      a complementarity determining region (CDR) 1 sequence GRTIDNYA (SEQ ID NO:11); CDR2 sequence IDWGDGGX, where X is A or T (SEQ ID NO: 12); and CDR3 sequence AMARQSRVNLDVARYDY (SEQ ID NO: 13).

2. The fusion protein of claim 1, wherein the antibody or fragment thereof comprises an amino acid sequence selected from the group consisting of:
   $X_1VX_2LX_3ESGGGLVQX_4GGSLRLSCX_5ASEYPS$-$NFYAMSWX_6RQAPGKX_7X_8EX_9VX_{10}GVSRD$-$GLTTLYADSVKGRFTX_{11}SRDNX_{12}KNTX_{13}X_{14}L$-$QMNSX_{15}X_{16}AEDTA VYYCAIVITGVWNKVDVN$-$SRSYHYWG$-$QGTX_{17}VTVSS$ (SEQ ID NO:9), wherein $X_1$ is E or Q; $X_2$ is K or Q; $X_3$ is V or E; $X_4$ is A or P; $X_5$ is V or A; $X_6$ is F or V; $X_7$ is E or G; $X_8$ is R or L; $X_9$ is F or W; $X_{10}$ is A or S; $X_{11}$ is M or I; $X_{12}$ is A or S; $X_{13}$ is V or L; $X_{14}$ is D or Y; $X_{15}$ is V or L; $X_{16}$ is K or R; and $X_{17}$ is Q or L; and
   $X_1VX_2LX_3ESGGGLVQX_4GGSLRLSCAASGRTI$-$DNYAMAWX_5RQAPGKX_6X_7EX$: V $X_9TIDWGDGGX_{10}RYANSVKGRFTIS$-$RDNX_{11}KX_{12}TX_{13}YLQMNX_{14}LX_{15}X_{16}EDTAV$ $YX_{17}CAMARQSRVNLDVARYDYWGQGTX_{18}VTVSS$ (SEQ ID NO: 14), wherein $X_1$ is E or Q; $X_2$ is K or Q; $X_3$ is V or E; $X_4$ is A or P; $X_5$ is V or S; $X_6$ is D or G; $X_7$ is L or R; $X_8$ is F or W; $X_9$ is A or S; $X_{10}$ is A or T; $X_{11}$ is A or S; $X_{12}$ is G or N; $X_{13}$ is M or L; $X_{14}$ is N or R; $X_{15}$ is E or R; $X_{16}$ is P or A; $X_{17}$ is S or Y; and $X_{18}$ is Q or L.

3. The fusion protein of claim 1, wherein the antibody or fragment thereof is a single chain Fab (scFab), a single chain Fv (scFv), or a single domain antibody (sdAb).

4. The fusion protein of claim 1, wherein the therapeutic polypeptide is selected from the group consisting of a Type I sulfatase, a glucosidase, and a glucocerebrosidase.

5. The fusion protein of claim 1, wherein the therapeutic polypeptide is an iduronate-2-sulfatase (IDS) or an acid-beta-glucosidase (GCase).

6. The fusion protein of claim 5, wherein the therapeutic polypeptide is iduronate-2-sulfatase (IDS) (SEQ ID NO:24), acid-beta-glucosidase (GCase) (SEQ ID NO: 68), or acid-beta-glucosidase mut1 (GCase-mut1) (SEQ ID NO:26).

7. The fusion protein of claim 1, wherein the antibody or fragment thereof is linked to the therapeutic polypeptide.

8. The fusion protein of claim 7, wherein said antibody or fragment thereof is linked to the therapeutic polypeptide with a linker sequence.

9. The fusion protein of claim 8, wherein said linker sequence, in any one of SEQ ID NO: 30, 31, 32, 33, 34, 35, 36, 37, 39, 41, 42, 43, 44, 47, 48, 49, 50, 52, 53, 54, 55, 56, 57, 58, 59, 60, 61, 62, 64, 65, or 70, is $(GGGGS)_n$, wherein $n \geq 1$.

10. The fusion protein of claim 1, wherein said fusion protein is glycosylated.

11. The fusion protein of claim 1, wherein the therapeutic polypeptide related to the treatment of an LSD is a glycosylated polypeptide with one or more N-glycans.

12. The fusion protein of claim 11, wherein the one or more N-glycans of said glycosylated polypeptide contain one or more mannose 6-phosphate residues.

13. The fusion protein of claim 11, wherein said glycosylated polypeptide contains monophosphorylated N-glycans, bi-phosphorylated N-glycans or a combination thereof.

14. The fusion protein of claim 1, wherein said serum half-life extending element is human serum albumin (HSA) of SEQ ID NO:67, human serum albumin K573P (HSA (K573P)) of SEQ ID NO:28, or an albumin targeting moiety.

15. The fusion protein of claim 14, wherein said albumin targeting moiety is an antibody or a fragment thereof capable of targeting albumin.

16. The fusion protein of claim 15, wherein said fusion protein is:
   1) A fusion protein comprising:
      an antibody or fragment thereof having CDR 1 sequence EYPSNFYA (SEQ ID NO: 6), CDR2 sequence VSRDGLTT (SEQ ID NO:7), CDR3 sequence AIVITGVWNKVDVNSRSYHY (SEQ ID NO:8),
      IDS (SEQ ID NO: 24); and
      human serum albumin (HSA) (SEQ ID NO:67) or human serum albumin K573P (HSA (K573P)) (SEQ ID NO:28);
   2) A fusion protein comprising:
      an antibody or fragment thereof having CDR 1 sequence EYPSNFYA (SEQ ID NO: 6), CDR2 sequence VSRDGLTT (SEQ ID NO:7), a CDR3 sequence AIVITGVWNKVDVNSRSYHY (SEQ ID NO:8),
      IDS (SEQ ID NO:24), and
      a CDR1 sequence GRTFIAYA (SEQ ID NO:16), CDR2 sequence ITNFAGGTT (SEQ ID NO:17), and CDR3 sequence AADRSAQTMRQVRPVLPY (SEQ ID NO: 18);
   3) A fusion protein comprising:
      an antibody or fragment thereof having CDR 1 sequence EYPSNFYA (SEQ ID NO: 6), CDR2 sequence VSRDGLTT (SEQ ID NO:7); CDR3 sequence AIVITGVWNKVDVNSRSYHY (SEQ ID NO:8),
      IDS (SEQ ID NO:24), and
      a CDR1 sequence GSTFSSSS (SEQ ID NO:20), CDR2 sequence ITSGGST (SEQ ID NO:21), and CDR3 sequence NVAGRNWVPISRYSPGPY (SEQ ID NO: 22);
   4) IGF1R3H5-IDS-HSA (K573P) (SEQ ID NO:35);
   5) IGF1R3H5-IDS-R28 (SEQ ID NO:36); or
   6) IGF1R3H5-IDS-M79 (SEQ ID NO:37).

17. The fusion protein of claim 14, wherein said albumin targeting moiety is a single domain antibody (sdAb) comprising:
   a CDR1 sequence GRTFIAYA (SEQ ID NO:16), CDR2 sequence ITNFAGGTT (SEQ ID NO: 17), and CDR3 sequence AADRSAQTMRQVRPVLPY (SEQ ID NO:18);
   a CDR1 sequence GSTFSSSS (SEQ ID NO:20), CDR2 sequence ITSGGST (SEQ ID NO: 21), and CDR3 sequence NVAGRNWPISRYSPGPY (SEQ ID NO:22);

an amino acid sequence (SEQ ID NO: 19)
QVQLVESGGGLVQAGGSLRLSCVASGRTFIAYAMGWFRQAPGKEREFVA

AITNFAGGTTYYADSVKGRFTISRDNAKTTVYLQMNSLKPEDTALYYCA

ADRSAQTMRQVRPVLPYWGQGTQVTVSS;

or an amino acid sequence (SEQ ID NO: 23)
QVKLEESGGGLVQAGGSLKLSCAASGSTFSSSSVGWYRQAPGQQRELVA

AITSGGSTNTADSVKGRFTMSRDNAKNTVYLQMRDLKPEDTAVYYCNVA

GRNWVPISRYSPGPYWGQGTQVTVSS.

18. A composition comprising the fusion protein of claim 1 and a pharmaceutically acceptable diluent, carrier, or excipient.

19. A method of delivering a therapeutic polypeptide related to the treatment of an LSD across the BBB, comprising administering to a subject the fusion protein according to claim 1.

20. The method of claim 19, wherein said administering is intravenous (iv), subcutaneous (sc), or intramuscular (im).

21. The method of claim 19, wherein said LSD is a sphingolipidosis, a mucopolysaccharidosis, a glycoproteinosis, an oligosaccharidosis, a glycogenosis, a lipidosis, or a neuronal ceroid lipofuscinosis.

22. The method of claim 19, wherein said LSD is Hunter syndrome.

23. The method of claim 19, wherein said LSD is Gaucher's disease.

\* \* \* \* \*

SEQUENCE LISTING

```
<160> NUMBER OF SEQ ID NOS: 70

<210> SEQ ID NO 1
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 1

Gly Phe Lys Ile Thr His Tyr Thr Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<221> NAME/KEY: VARIANT
<222> LOCATION: (7)..(7)
<223> OTHER INFORMATION: Xaa can be D or K
<220> FEATURE:
<221> NAME/KEY: VARIANT
<222> LOCATION: (8)..(8)
<223> OTHER INFORMATION: Xaa can be N or D
<220> FEATURE:
<221> NAME/KEY: VARIANT
<222> LOCATION: (10)..(10)
<223> OTHER INFORMATION: Xaa can be F, I or L

<400> SEQUENCE: 2

Arg Ile Thr Trp Gly Gly Xaa Xaa Thr Xaa Tyr Ser Asn Ser Val Lys
1               5                   10                  15
Gly

<210> SEQ ID NO 3
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<221> NAME/KEY: VARIANT
<222> LOCATION: (7)..(7)
<223> OTHER INFORMATION: Xaa can be T or K

<400> SEQUENCE: 3
```

```
Gly Ser Thr Ser Thr Ala Xaa Pro Leu Arg Val Asp Tyr
1               5                   10
```

<210> SEQ ID NO 4
<211> LENGTH: 120
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 4

```
Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val
        115                 120
```

<210> SEQ ID NO 5
<211> LENGTH: 122
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<221> NAME/KEY: VARIANT
<222> LOCATION: (1)..(1)
<223> OTHER INFORMATION: Xaa can be D or E
<220> FEATURE:
<221> NAME/KEY: VARIANT
<222> LOCATION: (37)..(37)
<223> OTHER INFORMATION: Xaa can be F or V
<220> FEATURE:
<221> NAME/KEY: VARIANT
<222> LOCATION: (44)..(44)
<223> OTHER INFORMATION: Xaa can be E or G
<220> FEATURE:
<221> NAME/KEY: VARIANT
<222> LOCATION: (45)..(45)
<223> OTHER INFORMATION: Xaa can be R or L
<220> FEATURE:
<221> NAME/KEY: VARIANT
<222> LOCATION: (47)..(47)
<223> OTHER INFORMATION: Xaa can be F or W
<220> FEATURE:
<221> NAME/KEY: VARIANT
<222> LOCATION: (79)..(79)
<223> OTHER INFORMATION: Xaa can be L or V

<400> SEQUENCE: 5

```
Xaa Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
```

```
                    20                  25                  30
Thr Met Gly Trp Xaa Arg Gln Ala Pro Gly Lys Xaa Xaa Glu Xaa Val
                35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
                100                 105                 110

Gly Gln Gly Thr Leu Val Thr Val Ser Ser
                115                 120

<210> SEQ ID NO 6
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 6

Glu Tyr Pro Ser Asn Phe Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Amino Acid

<400> SEQUENCE: 7

Val Ser Arg Asp Gly Leu Thr Thr
1               5

<210> SEQ ID NO 8
<211> LENGTH: 20
<212> TYPE: PRT
<213> ORGANISM: Artificial Sequence
<220> FEATURE:
<223> OTHER INFORMATION: Amino Acid

<400> SEQUENCE: 8

Ala Ile Val Ile Thr Gly Val Trp Asn Lys Val Asp Val Asn Ser Arg
1               5                   10                  15

Ser Tyr His Tyr
            20

<210> SEQ ID NO 9
<211> LENGTH: 127
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<221> NAME/KEY: VARIANT
<222> LOCATION: (1)..(1)
<223> OTHER INFORMATION: Xaa can be E or Q
<220> FEATURE:
<221> NAME/KEY: VARIANT
```

```
<222> LOCATION: (3)..(3)
<223> OTHER INFORMATION: Xaa can be K or Q
<220> FEATURE:
<221> NAME/KEY: VARIANT
<222> LOCATION: (5)..(5)
<223> OTHER INFORMATION: Xaa can be V or E
<220> FEATURE:
<221> NAME/KEY: VARIANT
<222> LOCATION: (14)..(14)
<223> OTHER INFORMATION: Xaa can be A or P
<220> FEATURE:
<221> NAME/KEY: VARIANT
<222> LOCATION: (23)..(23)
<223> OTHER INFORMATION: Xaa can be V or A
<220> FEATURE:
<221> NAME/KEY: VARIANT
<222> LOCATION: (37)..(37)
<223> OTHER INFORMATION: Xaa can be F or V
<220> FEATURE:
<221> NAME/KEY: VARIANT
<222> LOCATION: (44)..(44)
<223> OTHER INFORMATION: Xaa can be E or G
<220> FEATURE:
<221> NAME/KEY: VARIANT
<222> LOCATION: (45)..(45)
<223> OTHER INFORMATION: Xaa can be R or L
<220> FEATURE:
<221> NAME/KEY: VARIANT
<222> LOCATION: (47)..(47)
<223> OTHER INFORMATION: Xaa can be F or W
<220> FEATURE:
<221> NAME/KEY: VARIANT
<222> LOCATION: (49)..(49)
<223> OTHER INFORMATION: Xaa can be A or S
<220> FEATURE:
<221> NAME/KEY: VARIANT
<222> LOCATION: (70)..(70)
<223> OTHER INFORMATION: Xaa can be M or I
<220> FEATURE:
<221> NAME/KEY: VARIANT
<222> LOCATION: (75)..(75)
<223> OTHER INFORMATION: Xaa can be A or S
<220> FEATURE:
<221> NAME/KEY: VARIANT
<222> LOCATION: (79)..(79)
<223> OTHER INFORMATION: Xaa can be V or L
<220> FEATURE:
<221> NAME/KEY: VARIANT
<222> LOCATION: (80)..(80)
<223> OTHER INFORMATION: Xaa can be D or Y
<220> FEATURE:
<221> NAME/KEY: VARIANT
<222> LOCATION: (86)..(86)
<223> OTHER INFORMATION: Xaa can be V or L
<220> FEATURE:
<221> NAME/KEY: VARIANT
<222> LOCATION: (87)..(87)
<223> OTHER INFORMATION: Xaa can be K or R
<220> FEATURE:
<221> NAME/KEY: VARIANT
<222> LOCATION: (122)..(122)
<223> OTHER INFORMATION: Xaa can be Q or L

<400> SEQUENCE: 9

Xaa Val Xaa Leu Xaa Glu Ser Gly Gly Gly Leu Val Gln Xaa Gly Gly
 1               5                  10                  15

Ser Leu Arg Leu Ser Cys Xaa Ala Ser Glu Tyr Pro Ser Asn Phe Tyr
                20                  25                  30

Ala Met Ser Trp Xaa Arg Gln Ala Pro Gly Lys Xaa Xaa Glu Xaa Val
            35                  40                  45

Xaa Gly Val Ser Arg Asp Gly Leu Thr Thr Leu Tyr Ala Asp Ser Val
    50                  55                  60

Lys Gly Arg Phe Thr Xaa Ser Arg Asp Asn Xaa Lys Asn Thr Xaa Xaa
65                  70                  75                  80
```

Leu Gln Met Asn Ser Xaa Xaa Ala Glu Asp Thr Ala Val Tyr Tyr Cys
                    85                  90                  95

Ala Ile Val Ile Thr Gly Val Trp Asn Lys Val Asp Val Asn Ser Arg
                100                 105                 110

Ser Tyr His Tyr Trp Gly Gln Gly Thr Xaa Val Thr Val Ser Ser
            115                 120                 125

<210> SEQ ID NO 10
<211> LENGTH: 127
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Pro Ser Asn Phe Tyr
                20                  25                  30

Ala Met Ser Trp Phe Arg Gln Ala Pro Gly Lys Glu Arg Glu Phe Val
            35                  40                  45

Ser Gly Val Ser Arg Asp Gly Leu Thr Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Val Ile Thr Gly Val Trp Asn Lys Val Asp Val Asn Ser Arg
                100                 105                 110

Ser Tyr His Tyr Trp Gly Gln Gly Thr Leu Val Thr Val Ser Ser
            115                 120                 125

<210> SEQ ID NO 11
<211> LENGTH: 8
<212> TYPE: PRT
<213> ORGANISM: Artificial Sequence
<220> FEATURE:
<223> OTHER INFORMATION: Amino Acid

<400> SEQUENCE: 11

Gly Arg Thr Ile Asp Asn Tyr Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<221> NAME/KEY: VARIANT
<222> LOCATION: (8)..(8)
<223> OTHER INFORMATION: Xaa can be A or T

<400> SEQUENCE: 12

Ile Asp Trp Gly Asp Gly Gly Xaa
1               5

```
<210> SEQ ID NO 13
<211> LENGTH: 17
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 13

Ala Met Ala Arg Gln Ser Arg Val Asn Leu Asp Val Ala Arg Tyr Asp
1               5                   10                  15

Tyr

<210> SEQ ID NO 14
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<221> NAME/KEY: VARIANT
<222> LOCATION: (1)..(1)
<223> OTHER INFORMATION: Xaa can be E or Q
<220> FEATURE:
<221> NAME/KEY: VARIANT
<222> LOCATION: (3)..(3)
<223> OTHER INFORMATION: Xaa can be K or Q
<220> FEATURE:
<221> NAME/KEY: VARIANT
<222> LOCATION: (5)..(5)
<223> OTHER INFORMATION: Xaa can be V or E
<220> FEATURE:
<221> NAME/KEY: VARIANT
<222> LOCATION: (14)..(14)
<223> OTHER INFORMATION: Xaa can be A or P
<220> FEATURE:
<221> NAME/KEY: VARIANT
<222> LOCATION: (37)..(37)
<223> OTHER INFORMATION: Xaa can be V or S
<220> FEATURE:
<221> NAME/KEY: VARIANT
<222> LOCATION: (44)..(44)
<223> OTHER INFORMATION: Xaa can be D or G
<220> FEATURE:
<221> NAME/KEY: VARIANT
<222> LOCATION: (45)..(45)
<223> OTHER INFORMATION: Xaa can be L or R
<220> FEATURE:
<221> NAME/KEY: VARIANT
<222> LOCATION: (47)..(47)
<223> OTHER INFORMATION: Xaa can be F or W
<220> FEATURE:
<221> NAME/KEY: VARIANT
<222> LOCATION: (49)..(49)
<223> OTHER INFORMATION: Xaa can be A or S
<220> FEATURE:
<221> NAME/KEY: VARIANT
<222> LOCATION: (58)..(58)
<223> OTHER INFORMATION: Xaa can be A or T
<220> FEATURE:
<221> NAME/KEY: VARIANT
<222> LOCATION: (75)..(75)
<223> OTHER INFORMATION: Xaa can be A or S
<220> FEATURE:
<221> NAME/KEY: VARIANT
<222> LOCATION: (77)..(77)
<223> OTHER INFORMATION: Xaa can be G or N
<220> FEATURE:
<221> NAME/KEY: VARIANT
<222> LOCATION: (79)..(79)
<223> OTHER INFORMATION: Xaa can be M or L
<220> FEATURE:
<221> NAME/KEY: VARIANT
```

```
<222> LOCATION: (85)..(85)
<223> OTHER INFORMATION: Xaa can be N or R
<220> FEATURE:
<221> NAME/KEY: VARIANT
<222> LOCATION: (87)..(87)
<223> OTHER INFORMATION: Xaa can be E or R
<220> FEATURE:
<221> NAME/KEY: VARIANT
<222> LOCATION: (88)..(88)
<223> OTHER INFORMATION: Xaa can be P or A
<220> FEATURE:
<221> NAME/KEY: VARIANT
<222> LOCATION: (95)..(95)
<223> OTHER INFORMATION: Xaa can be S or Y
<220> FEATURE:
<221> NAME/KEY: VARIANT
<222> LOCATION: (119)..(119)
<223> OTHER INFORMATION: Xaa can be Q or L

<400> SEQUENCE: 14

Xaa Val Xaa Leu Xaa Glu Ser Gly Gly Gly Leu Val Gln Xaa Gly Gly
1               5                   10                  15

Ser Leu Arg Leu Ser Cys Ala Ala Ser Gly Arg Thr Ile Asp Asn Tyr
            20                  25                  30

Ala Met Ala Trp Xaa Arg Gln Ala Pro Gly Lys Xaa Xaa Glu Xaa Val
        35                  40                  45

Xaa Thr Ile Asp Trp Gly Asp Gly Xaa Arg Tyr Ala Asn Ser Val
    50                  55                  60

Lys Gly Arg Phe Thr Ile Ser Arg Asp Asn Xaa Lys Xaa Thr Xaa Tyr
65                  70                  75                  80

Leu Gln Met Asn Xaa Leu Xaa Xaa Glu Asp Thr Ala Val Tyr Xaa Cys
                85                  90                  95

Ala Met Ala Arg Gln Ser Arg Val Asn Leu Asp Val Ala Arg Tyr Asp
            100                 105                 110

Tyr Trp Gly Gln Gly Thr Xaa Val Thr Val Ser Ser
        115                 120

<210> SEQ ID NO 15
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Gly Thr Arg Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Ser
```

```
<210> SEQ ID NO 16
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 16

Gly Arg Thr Phe Ile Ala Tyr Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 17

Ile Thr Asn Phe Ala Gly Gly Thr Thr
1               5

<210> SEQ ID NO 18
<211> LENGTH: 18
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 18

Ala Ala Asp Arg Ser Ala Gln Thr Met Arg Gln Val Arg Pro Val Leu
1               5                   10                  15

Pro Tyr

<210> SEQ ID NO 19
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 19

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ile Ala Tyr
            20                  25                  30

Ala Met Gly Trp Phe Arg Gln Ala Pro Gly Lys Glu Arg Glu Phe Val
        35                  40                  45

Ala Ala Ile Thr Asn Phe Ala Gly Gly Thr Thr Tyr Tyr Ala Asp Ser
    50                  55                  60

Val Lys Gly Arg Phe Thr Ile Ser Arg Asp Asn Ala Lys Thr Thr Val
65                  70                  75                  80

Tyr Leu Gln Met Asn Ser Leu Lys Pro Glu Asp Thr Ala Leu Tyr Tyr
                85                  90                  95
```

```
Cys Ala Ala Asp Arg Ser Ala Gln Thr Met Arg Gln Val Arg Pro Val
                100                 105                 110

Leu Pro Tyr Trp Gly Gln Gly Thr Gln Val Thr Val Ser Ser
            115                 120                 125

<210> SEQ ID NO 20
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 20

Gly Ser Thr Phe Ser Ser Ser Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 21

Ile Thr Ser Gly Gly Ser Thr
1               5

<210> SEQ ID NO 22
<211> LENGTH: 18
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 22

Asn Val Ala Gly Arg Asn Trp Val Pro Ile Ser Arg Tyr Ser Pro Gly
1               5                   10                  15

Pro Tyr

<210> SEQ ID NO 23
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 23

Gln Val Lys Leu Glu Glu Ser Gly Gly Leu Val Gln Ala Gly Gly
1               5                   10                  15

Ser Leu Lys Leu Ser Cys Ala Ala Ser Gly Ser Thr Phe Ser Ser Ser
                20                  25                  30

Ser Val Gly Trp Tyr Arg Gln Ala Pro Gly Gln Gln Arg Glu Leu Val
            35                  40                  45

Ala Ala Ile Thr Ser Gly Gly Ser Thr Asn Thr Ala Asp Ser Val Lys
        50                  55                  60

Gly Arg Phe Thr Met Ser Arg Asp Asn Ala Lys Asn Thr Val Tyr Leu
65                  70                  75                  80
```

-continued

Gln Met Arg Asp Leu Lys Pro Glu Asp Thr Ala Val Tyr Tyr Cys Asn
                85                  90                  95

Val Ala Gly Arg Asn Trp Val Pro Ile Ser Arg Tyr Ser Pro Gly Pro
            100                 105                 110

Tyr Trp Gly Gln Gly Thr Gln Val Thr Val Ser Ser
        115                 120

<210> SEQ ID NO 24
<211> LENGTH: 525
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 24

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

```
Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
        340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525

<210> SEQ ID NO 25
<211> LENGTH: 541
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 25

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
            85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
```

```
              130                 135                 140
Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
                195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
                275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
                355                 360                 365

Gly Arg Gln Ser Met Asp Leu Val Glu Leu Val Ser Leu Phe Pro Thr
                370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
                435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro His His His
                515                 520                 525

His His His His His Trp Ser His Pro Gln Phe Glu Lys
530                 535                 540

<210> SEQ ID NO 26
```

```
<211> LENGTH: 497
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 26

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

Leu Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Asn Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365
```

```
Thr Asn Leu Leu Tyr His Val Val Gly Trp Thr Asp Trp Asn Leu Ala
    370                 375                 380
Leu Asn Pro Glu Gly Gly Pro Asn Trp Val Arg Asn Phe Val Asp Ser
385                 390                 395                 400
Pro Ile Ile Val Asp Ile Thr Lys Asp Thr Phe Tyr Lys Gln Pro Met
                405                 410                 415
Phe Tyr His Leu Gly His Phe Ser Lys Phe Ile Pro Glu Gly Ser Gln
            420                 425                 430
Arg Val Gly Leu Val Ala Ser Gln Lys Asn Asp Leu Asp Ala Val Ala
                435                 440                 445
Leu Met His Pro Asp Gly Ser Ala Val Val Val Leu Asn Arg Ser
450                 455                 460
Ser Lys Asp Val Pro Leu Thr Ile Lys Asp Pro Ala Val Gly Phe Leu
465                 470                 475                 480
Glu Thr Ile Ser Pro Gly Tyr Ser Ile His Thr Tyr Leu Trp Arg Arg
                485                 490                 495
Gln

<210> SEQ ID NO 27
<211> LENGTH: 505
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 27

Ala Arg Pro Cys Ile Pro Lys Ser Phe Gly Tyr Ser Ser Val Val Cys
1               5                   10                  15
Val Cys Asn Ala Thr Tyr Cys Asp Ser Phe Asp Pro Pro Thr Phe Pro
                20                  25                  30
Ala Leu Gly Thr Phe Ser Arg Tyr Glu Ser Thr Arg Ser Gly Arg Arg
            35                  40                  45
Met Glu Leu Ser Met Gly Pro Ile Gln Ala Asn His Thr Gly Thr Gly
        50                  55                  60
Leu Leu Leu Thr Leu Gln Pro Glu Gln Lys Phe Gln Lys Val Lys Gly
65                  70                  75                  80
Phe Gly Gly Ala Met Thr Asp Ala Ala Ala Leu Asn Ile Leu Ala Leu
                85                  90                  95
Ser Pro Pro Ala Gln Asn Leu Leu Leu Lys Ser Tyr Phe Ser Glu Glu
                100                 105                 110
Gly Ile Gly Tyr Asn Ile Ile Arg Val Pro Met Ala Ser Cys Asp Phe
            115                 120                 125
Ser Ile Arg Thr Tyr Thr Tyr Ala Asp Thr Pro Asp Asp Phe Gln Leu
        130                 135                 140
Leu Asn Phe Ser Leu Pro Glu Glu Asp Thr Lys Leu Lys Ile Pro Leu
145                 150                 155                 160
Ile His Arg Ala Leu Gln Leu Ala Gln Arg Pro Val Ser Leu Leu Ala
                165                 170                 175
Ser Pro Trp Thr Ser Pro Thr Trp Leu Lys Thr Asn Gly Ala Val Asn
                180                 185                 190
Gly Lys Gly Ser Leu Lys Gly Gln Pro Gly Asp Ile Tyr His Gln Thr
            195                 200                 205
Trp Ala Arg Tyr Phe Val Lys Phe Leu Asp Ala Tyr Ala Glu His Lys
        210                 215                 220
```

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Asn Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln His His His His His His His
            500                 505

<210> SEQ ID NO 28
<211> LENGTH: 585
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 28

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

-continued

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr

-continued

```
                485                 490                 495
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
            565                 570                 575

Ala Ala Ser Gln Ala Ala Leu Gly Leu
            580                 585

<210> SEQ ID NO 29
<211> LENGTH: 668
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 29

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser Gly Gly Gly Gly Ser Ser
            115                 120                 125

Glu Thr Gln Ala Asn Ser Thr Thr Asp Ala Leu Asn Val Leu Leu Ile
130                 135                 140

Ile Val Asp Asp Leu Arg Pro Ser Leu Gly Cys Tyr Gly Asp Lys Leu
145                 150                 155                 160

Val Arg Ser Pro Asn Ile Asp Gln Leu Ala Ser His Ser Leu Leu Phe
            165                 170                 175

Gln Asn Ala Phe Ala Gln Gln Ala Val Cys Ala Pro Ser Arg Val Ser
            180                 185                 190

Phe Leu Thr Gly Arg Arg Pro Asp Thr Thr Arg Leu Tyr Asp Phe Asn
        195                 200                 205

Ser Tyr Trp Arg Val His Ala Gly Asn Phe Ser Thr Ile Pro Gln Tyr
    210                 215                 220

Phe Lys Glu Asn Gly Tyr Val Thr Met Ser Val Gly Lys Val Phe His
225                 230                 235                 240
```

-continued

```
Pro Gly Ile Ser Ser Asn His Thr Asp Asp Ser Pro Tyr Ser Trp Ser
            245                 250                 255

Phe Pro Pro Tyr His Pro Ser Ser Glu Lys Tyr Glu Asn Thr Lys Thr
        260                 265                 270

Cys Arg Gly Pro Asp Gly Glu Leu His Ala Asn Leu Leu Cys Pro Val
    275                 280                 285

Asp Val Leu Asp Val Pro Glu Gly Thr Leu Pro Asp Lys Gln Ser Thr
290                 295                 300

Glu Gln Ala Ile Gln Leu Leu Glu Lys Met Lys Thr Ser Ala Ser Pro
305                 310                 315                 320

Phe Phe Leu Ala Val Gly Tyr His Lys Pro His Ile Pro Phe Arg Tyr
                325                 330                 335

Pro Lys Glu Phe Gln Lys Leu Tyr Pro Leu Glu Asn Ile Thr Leu Ala
            340                 345                 350

Pro Asp Pro Glu Val Pro Asp Gly Leu Pro Pro Val Ala Tyr Asn Pro
        355                 360                 365

Trp Met Asp Ile Arg Gln Arg Glu Asp Val Gln Ala Leu Asn Ile Ser
    370                 375                 380

Val Pro Tyr Gly Pro Ile Pro Val Asp Phe Gln Arg Lys Ile Arg Gln
385                 390                 395                 400

Ser Tyr Phe Ala Ser Val Ser Tyr Leu Asp Thr Gln Val Gly Arg Leu
                405                 410                 415

Leu Ser Ala Leu Asp Asp Leu Gln Leu Ala Asn Ser Thr Ile Ile Ala
            420                 425                 430

Phe Thr Ser Asp His Gly Trp Ala Leu Gly Glu His Gly Glu Trp Ala
        435                 440                 445

Lys Tyr Ser Asn Phe Asp Val Ala Thr His Val Pro Leu Ile Phe Tyr
    450                 455                 460

Val Pro Gly Arg Thr Ala Ser Leu Pro Glu Ala Gly Glu Lys Leu Phe
465                 470                 475                 480

Pro Tyr Leu Asp Pro Phe Asp Ser Ala Ser Gln Leu Met Glu Pro Gly
                485                 490                 495

Arg Gln Ser Met Asp Leu Val Glu Leu Val Ser Leu Phe Pro Thr Leu
            500                 505                 510

Ala Gly Leu Ala Gly Leu Gln Val Pro Pro Arg Cys Pro Val Pro Ser
        515                 520                 525

Phe His Val Glu Leu Cys Arg Glu Gly Lys Asn Leu Leu Lys His Phe
    530                 535                 540

Arg Phe Arg Asp Leu Glu Glu Asp Pro Tyr Leu Pro Gly Asn Pro Arg
545                 550                 555                 560

Glu Leu Ile Ala Tyr Ser Gln Tyr Pro Arg Pro Ser Asp Ile Pro Gln
                565                 570                 575

Trp Asn Ser Asp Lys Pro Ser Leu Lys Asp Ile Lys Ile Met Gly Tyr
            580                 585                 590

Ser Ile Arg Thr Ile Asp Tyr Arg Tyr Thr Val Trp Val Gly Phe Asn
        595                 600                 605

Pro Asp Glu Phe Leu Ala Asn Phe Ser Asp Ile His Ala Gly Glu Leu
    610                 615                 620

Tyr Phe Val Asp Ser Asp Pro Leu Gln Asp His Asn Met Tyr Asn Asp
625                 630                 635                 640

Ser Gln Gly Gly Asp Leu Phe Gln Leu Leu Met Pro His His His
                645                 650                 655

His His His His Trp Ser His Pro Gln Phe Glu Lys
```

<210> SEQ ID NO 30
<211> LENGTH: 693
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Pro Ser Asn Phe Tyr
            20                  25                  30

Ala Met Ser Trp Phe Arg Gln Ala Pro Gly Lys Glu Arg Glu Phe Val
        35                  40                  45

Ser Gly Val Ser Arg Asp Gly Leu Thr Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Leu Val Thr Val Ser Ser Gly
        115                 120                 125

Gly Gly Gly Ser Gly Gly Gly Ser Gly Gly Gly Ser Gly
    130                 135                 140

Gly Gly Ser Gly Gly Gly Ser Ser Glu Thr Gln Ala Asn Ser Thr
145                 150                 155                 160

Thr Asp Ala Leu Asn Val Leu Leu Ile Ile Val Asp Asp Leu Arg Pro
                165                 170                 175

Ser Leu Gly Cys Tyr Gly Asp Lys Leu Val Arg Ser Pro Asn Ile Asp
            180                 185                 190

Gln Leu Ala Ser His Ser Leu Leu Phe Gln Asn Ala Phe Ala Gln Gln
        195                 200                 205

Ala Val Cys Ala Pro Ser Arg Val Ser Phe Leu Thr Gly Arg Arg Pro
    210                 215                 220

Asp Thr Thr Arg Leu Tyr Asp Phe Asn Ser Tyr Trp Arg Val His Ala
225                 230                 235                 240

Gly Asn Phe Ser Thr Ile Pro Gln Tyr Phe Lys Glu Asn Gly Tyr Val
                245                 250                 255

Thr Met Ser Val Gly Lys Val Phe His Pro Gly Ile Ser Ser Asn His
            260                 265                 270

Thr Asp Asp Ser Pro Tyr Ser Trp Ser Phe Pro Pro Tyr His Pro Ser
        275                 280                 285

Ser Glu Lys Tyr Glu Asn Thr Lys Thr Cys Arg Gly Pro Asp Gly Glu
    290                 295                 300

Leu His Ala Asn Leu Leu Cys Pro Val Asp Val Leu Asp Val Pro Glu
305                 310                 315                 320

Gly Thr Leu Pro Asp Lys Gln Ser Thr Glu Gln Ala Ile Gln Leu Leu
                325                 330                 335
```

Glu Lys Met Lys Thr Ser Ala Ser Pro Phe Leu Ala Val Gly Tyr
                340                 345                 350

His Lys Pro His Ile Pro Phe Arg Tyr Pro Lys Glu Phe Gln Lys Leu
            355                 360                 365

Tyr Pro Leu Glu Asn Ile Thr Leu Ala Pro Asp Pro Glu Val Pro Asp
        370                 375                 380

Gly Leu Pro Pro Val Ala Tyr Asn Pro Trp Met Asp Ile Arg Gln Arg
385                 390                 395                 400

Glu Asp Val Gln Ala Leu Asn Ile Ser Val Pro Tyr Gly Pro Ile Pro
                405                 410                 415

Val Asp Phe Gln Arg Lys Ile Arg Gln Ser Tyr Phe Ala Ser Val Ser
            420                 425                 430

Tyr Leu Asp Thr Gln Val Gly Arg Leu Leu Ser Ala Leu Asp Asp Leu
        435                 440                 445

Gln Leu Ala Asn Ser Thr Ile Ile Ala Phe Thr Ser Asp His Gly Trp
    450                 455                 460

Ala Leu Gly Glu His Gly Glu Trp Ala Lys Tyr Ser Asn Phe Asp Val
465                 470                 475                 480

Ala Thr His Val Pro Leu Ile Phe Tyr Val Pro Gly Arg Thr Ala Ser
                485                 490                 495

Leu Pro Glu Ala Gly Glu Lys Leu Phe Pro Tyr Leu Asp Pro Phe Asp
            500                 505                 510

Ser Ala Ser Gln Leu Met Glu Pro Gly Arg Gln Ser Met Asp Leu Val
        515                 520                 525

Glu Leu Val Ser Leu Phe Pro Thr Leu Ala Gly Leu Ala Gly Leu Gln
    530                 535                 540

Val Pro Pro Arg Cys Pro Val Pro Ser Phe His Val Glu Leu Cys Arg
545                 550                 555                 560

Glu Gly Lys Asn Leu Leu Lys His Phe Arg Phe Arg Asp Leu Glu Glu
                565                 570                 575

Asp Pro Tyr Leu Pro Gly Asn Pro Arg Glu Leu Ile Ala Tyr Ser Gln
            580                 585                 590

Tyr Pro Arg Pro Ser Asp Ile Pro Gln Trp Asn Ser Asp Lys Pro Ser
        595                 600                 605

Leu Lys Asp Ile Lys Ile Met Gly Tyr Ser Ile Arg Thr Ile Asp Tyr
    610                 615                 620

Arg Tyr Thr Val Trp Val Gly Phe Asn Pro Asp Glu Phe Leu Ala Asn
625                 630                 635                 640

Phe Ser Asp Ile His Ala Gly Glu Leu Tyr Phe Val Asp Ser Asp Pro
                645                 650                 655

Leu Gln Asp His Asn Met Tyr Asn Asp Ser Gln Gly Gly Asp Leu Phe
            660                 665                 670

Gln Leu Leu Met Pro His His His His His His Trp Ser His
        675                 680                 685

Pro Gln Phe Glu Lys
    690

<210> SEQ ID NO 31
<211> LENGTH: 690
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:

<223> OTHER INFORMATION: Homo Sapiens

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Thr Arg Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Ser Glu Thr Gln Ala Asn Ser Thr Thr Asp Ala
145                 150                 155                 160

Leu Asn Val Leu Leu Ile Ile Val Asp Asp Leu Arg Pro Ser Leu Gly
                165                 170                 175

Cys Tyr Gly Asp Lys Leu Val Arg Ser Pro Asn Ile Asp Gln Leu Ala
            180                 185                 190

Ser His Ser Leu Leu Phe Gln Asn Ala Phe Ala Gln Ala Val Cys
        195                 200                 205

Ala Pro Ser Arg Val Ser Phe Leu Thr Gly Arg Arg Pro Asp Thr Thr
    210                 215                 220

Arg Leu Tyr Asp Phe Asn Ser Tyr Trp Arg Val His Ala Gly Asn Phe
225                 230                 235                 240

Ser Thr Ile Pro Gln Tyr Phe Lys Glu Asn Gly Tyr Val Thr Met Ser
                245                 250                 255

Val Gly Lys Val Phe His Pro Gly Ile Ser Ser Asn His Thr Asp Asp
            260                 265                 270

Ser Pro Tyr Ser Trp Ser Phe Pro Pro Tyr His Pro Ser Ser Glu Lys
        275                 280                 285

Tyr Glu Asn Thr Lys Thr Cys Arg Gly Pro Asp Gly Glu Leu His Ala
    290                 295                 300

Asn Leu Leu Cys Pro Val Asp Val Leu Asp Val Pro Glu Gly Thr Leu
305                 310                 315                 320

Pro Asp Lys Gln Ser Thr Glu Gln Ala Ile Gln Leu Leu Glu Lys Met
                325                 330                 335

Lys Thr Ser Ala Ser Pro Phe Phe Leu Ala Val Gly Tyr His Lys Pro
            340                 345                 350

His Ile Pro Phe Arg Tyr Pro Lys Glu Phe Gln Lys Leu Tyr Pro Leu
        355                 360                 365

Glu Asn Ile Thr Leu Ala Pro Asp Pro Glu Val Pro Asp Gly Leu Pro
    370                 375                 380

Pro Val Ala Tyr Asn Pro Trp Met Asp Ile Arg Gln Arg Glu Asp Val
385                 390                 395                 400

Gln Ala Leu Asn Ile Ser Val Pro Tyr Gly Pro Ile Pro Val Asp Phe
                405                 410                 415

Gln Arg Lys Ile Arg Gln Ser Tyr Phe Ala Ser Val Ser Tyr Leu Asp
            420                 425                 430

Thr Gln Val Gly Arg Leu Leu Ser Ala Leu Asp Asp Leu Gln Leu Ala
        435                 440                 445

Asn Ser Thr Ile Ile Ala Phe Thr Ser Asp His Gly Trp Ala Leu Gly
    450                 455                 460

Glu His Gly Glu Trp Ala Lys Tyr Ser Asn Phe Asp Val Ala Thr His
465                 470                 475                 480

Val Pro Leu Ile Phe Tyr Val Pro Gly Arg Thr Ala Ser Leu Pro Glu
                485                 490                 495

Ala Gly Glu Lys Leu Phe Pro Tyr Leu Asp Pro Phe Asp Ser Ala Ser
            500                 505                 510

Gln Leu Met Glu Pro Gly Arg Gln Ser Met Asp Leu Val Glu Leu Val
        515                 520                 525

Ser Leu Phe Pro Thr Leu Ala Gly Leu Ala Gly Leu Gln Val Pro Pro
    530                 535                 540

Arg Cys Pro Val Pro Ser Phe His Val Glu Leu Cys Arg Glu Gly Lys
545                 550                 555                 560

Asn Leu Leu Lys His Phe Arg Phe Arg Asp Leu Glu Glu Asp Pro Tyr
                565                 570                 575

Leu Pro Gly Asn Pro Arg Glu Leu Ile Ala Tyr Ser Gln Tyr Pro Arg
            580                 585                 590

Pro Ser Asp Ile Pro Gln Trp Asn Ser Asp Lys Pro Ser Leu Lys Asp
        595                 600                 605

Ile Lys Ile Met Gly Tyr Ser Ile Arg Thr Ile Asp Tyr Arg Tyr Thr
    610                 615                 620

Val Trp Val Gly Phe Asn Pro Asp Glu Phe Leu Ala Asn Phe Ser Asp
625                 630                 635                 640

Ile His Ala Gly Glu Leu Tyr Phe Val Asp Ser Asp Pro Leu Gln Asp
                645                 650                 655

His Asn Met Tyr Asn Asp Ser Gln Gly Gly Asp Leu Phe Gln Leu Leu
            660                 665                 670

Met Pro His His His His His His His Trp Ser His Pro Gln Phe
        675                 680                 685

Glu Lys
    690

<210> SEQ ID NO 32
<211> LENGTH: 657
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Pro Ser Asn Phe Tyr
            20                  25                  30

Ala Met Ser Trp Phe Arg Gln Ala Pro Gly Lys Glu Arg Glu Phe Val
        35                  40                  45

```
Ser Gly Val Ser Arg Asp Gly Leu Thr Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Leu Val Thr Val Ser Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Ala Arg Pro Cys Ile Pro Lys Ser
145                 150                 155                 160

Phe Gly Tyr Ser Ser Val Val Cys Val Cys Asn Ala Thr Tyr Cys Asp
                165                 170                 175

Ser Phe Asp Pro Pro Thr Phe Pro Ala Leu Gly Thr Phe Ser Arg Tyr
            180                 185                 190

Glu Ser Thr Arg Ser Gly Arg Arg Met Glu Leu Ser Met Gly Pro Ile
        195                 200                 205

Gln Ala Asn His Thr Gly Thr Gly Leu Leu Leu Thr Leu Gln Pro Glu
    210                 215                 220

Gln Lys Phe Gln Lys Val Lys Gly Phe Gly Gly Ala Met Thr Asp Ala
225                 230                 235                 240

Ala Ala Leu Asn Ile Leu Ala Leu Ser Pro Pro Ala Gln Asn Leu Leu
                245                 250                 255

Leu Lys Ser Tyr Phe Ser Glu Glu Gly Ile Gly Tyr Asn Ile Ile Arg
            260                 265                 270

Val Pro Met Ala Ser Cys Asp Phe Ser Ile Arg Thr Tyr Thr Tyr Ala
        275                 280                 285

Asp Thr Pro Asp Asp Phe Gln Leu Leu Asn Phe Ser Leu Pro Glu Glu
    290                 295                 300

Asp Thr Lys Leu Lys Ile Pro Leu Ile His Arg Ala Leu Gln Leu Ala
305                 310                 315                 320

Gln Arg Pro Val Ser Leu Leu Ala Ser Pro Trp Thr Ser Pro Thr Trp
                325                 330                 335

Leu Lys Thr Asn Gly Ala Val Asn Gly Lys Gly Ser Leu Lys Gly Gln
            340                 345                 350

Pro Gly Asp Ile Tyr His Gln Thr Trp Ala Arg Tyr Phe Val Lys Phe
        355                 360                 365

Leu Asp Ala Tyr Ala Glu His Lys Leu Gln Phe Trp Ala Val Thr Ala
    370                 375                 380

Glu Asn Glu Pro Ser Ala Gly Leu Leu Ser Gly Tyr Pro Phe Gln Cys
385                 390                 395                 400

Leu Gly Phe Thr Pro Glu His Gln Arg Asp Phe Ile Ala Arg Asp Leu
                405                 410                 415

Gly Pro Thr Leu Ala Asn Ser Thr His His Asn Val Arg Leu Leu Met
            420                 425                 430

Leu Asp Asp Gln Arg Leu Leu Leu Pro His Trp Ala Lys Val Val Leu
        435                 440                 445

Thr Asp Pro Glu Ala Ala Lys Tyr Val His Gly Ile Ala Val His Trp
    450                 455                 460
```

```
Tyr Leu Asp Phe Leu Ala Pro Ala Asn Ala Thr Leu Gly Glu Thr His
465                 470                 475                 480

Arg Leu Phe Pro Asn Thr Met Leu Phe Ala Ser Glu Ala Cys Val Gly
            485                 490                 495

Ser Lys Phe Trp Glu Gln Ser Val Arg Leu Gly Ser Trp Asp Arg Gly
        500                 505                 510

Met Gln Tyr Ser His Ser Ile Ile Thr Asn Leu Leu Tyr His Val Val
            515                 520                 525

Gly Trp Thr Asp Trp Asn Leu Ala Leu Asn Pro Glu Gly Gly Pro Asn
        530                 535                 540

Trp Val Arg Asn Phe Val Asp Ser Pro Ile Ile Val Asp Ile Thr Lys
545                 550                 555                 560

Asp Thr Phe Tyr Lys Gln Pro Met Phe Tyr His Leu Gly His Phe Ser
                565                 570                 575

Lys Phe Ile Pro Glu Gly Ser Gln Arg Val Gly Leu Val Ala Ser Gln
            580                 585                 590

Lys Asn Asp Leu Asp Ala Val Ala Leu Met His Pro Asp Gly Ser Ala
        595                 600                 605

Val Val Val Val Leu Asn Arg Ser Ser Lys Asp Val Pro Leu Thr Ile
610                 615                 620

Lys Asp Pro Ala Val Gly Phe Leu Glu Thr Ile Ser Pro Gly Tyr Ser
625                 630                 635                 640

Ile His Thr Tyr Leu Trp Arg Arg Gln His His His His His His His
                645                 650                 655

His

<210> SEQ ID NO 33
<211> LENGTH: 683
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 33

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140
```

```
Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
            515                 520                 525

Gly Ser Gly Gly Gly Gly Ser Gly Gly Gly Gly Ser Gly Gly Gly Gly
        530                 535                 540

Ser Gly Gly Gly Gly Ser Gln Val Gln Leu Val Glu Ser Gly Gly Gly
545                 550                 555                 560

Leu Val Gln Ala Gly Gly Ser Leu Arg Leu Ser Cys Val Ala Ser Gly
```

```
                      565                 570                 575
Arg Thr Phe Ile Ala Tyr Ala Met Gly Trp Phe Arg Gln Ala Pro Gly
                580                 585                 590

Lys Glu Arg Glu Phe Val Ala Ala Ile Thr Asn Phe Ala Gly Gly Thr
            595                 600                 605

Thr Tyr Tyr Ala Asp Ser Val Lys Gly Arg Phe Thr Ile Ser Arg Asp
        610                 615                 620

Asn Ala Lys Thr Thr Val Tyr Leu Gln Met Asn Ser Leu Lys Pro Glu
625                 630                 635                 640

Asp Thr Ala Leu Tyr Tyr Cys Ala Ala Asp Arg Ser Ala Gln Thr Met
                645                 650                 655

Arg Gln Val Arg Pro Val Leu Pro Tyr Trp Gly Gln Gly Thr Gln Val
                660                 665                 670

Thr Val Ser His His His His His His His
            675                 680

<210> SEQ ID NO 34
<211> LENGTH: 682
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 34

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220
```

```
Ala Pro Asp Pro Glu Val Pro Asp Gly Leu Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
            290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
            450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
            515                 520                 525

Gly Ser Gly Gly Gly Gly Ser Gly Gly Gly Gly Ser Gly Gly Gly Gly
530                 535                 540

Ser Gly Gly Gly Gly Ser Gln Val Lys Leu Glu Glu Ser Gly Gly Gly
545                 550                 555                 560

Leu Val Gln Ala Gly Gly Ser Leu Lys Leu Ser Cys Ala Ala Ser Gly
            565                 570                 575

Ser Thr Phe Ser Ser Ser Val Gly Trp Tyr Arg Gln Ala Pro Gly
            580                 585                 590

Gln Gln Arg Glu Leu Val Ala Ala Ile Thr Ser Gly Gly Ser Thr Asn
            595                 600                 605

Thr Ala Asp Ser Val Lys Gly Arg Phe Thr Met Ser Arg Asp Asn Ala
            610                 615                 620

Lys Asn Thr Val Tyr Leu Gln Met Arg Asp Leu Lys Pro Glu Asp Thr
625                 630                 635                 640

Ala Val Tyr Tyr Cys Asn Val Ala Gly Arg Asn Trp Val Pro Ile Ser
```

```
                        645                 650                 655
Arg Tyr Ser Pro Gly Pro Tyr Trp Gly Gln Gly Thr Gln Val Thr Val
                660                 665                 670

Ser Ser His His His His His His His
            675                 680

<210> SEQ ID NO 35
<211> LENGTH: 1275
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Pro Ser Asn Phe Tyr
            20                  25                  30

Ala Met Ser Trp Phe Arg Gln Ala Pro Gly Lys Glu Arg Glu Phe Val
        35                  40                  45

Ser Gly Val Ser Arg Asp Gly Leu Thr Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Leu Val Thr Val Ser Ser Gly
        115                 120                 125

Gly Gly Gly Ser Gly Gly Gly Ser Gly Gly Gly Gly Ser Gly Gly
    130                 135                 140

Gly Gly Ser Gly Gly Gly Ser Ser Glu Thr Gln Ala Asn Ser Thr
145                 150                 155                 160

Thr Asp Ala Leu Asn Val Leu Ile Ile Val Asp Asp Leu Arg Pro
                165                 170                 175

Ser Leu Gly Cys Tyr Gly Asp Lys Leu Val Arg Ser Pro Asn Ile Asp
            180                 185                 190

Gln Leu Ala Ser His Ser Leu Leu Phe Gln Asn Ala Phe Ala Gln Gln
        195                 200                 205

Ala Val Cys Ala Pro Ser Arg Val Ser Phe Leu Thr Gly Arg Arg Pro
    210                 215                 220

Asp Thr Thr Arg Leu Tyr Asp Phe Asn Ser Tyr Trp Arg Val His Ala
225                 230                 235                 240

Gly Asn Phe Ser Thr Ile Pro Gln Tyr Phe Lys Glu Asn Gly Tyr Val
                245                 250                 255

Thr Met Ser Val Gly Lys Val Phe His Pro Gly Ile Ser Ser Asn His
            260                 265                 270

Thr Asp Asp Ser Pro Tyr Ser Trp Ser Phe Pro Tyr His Pro Ser
        275                 280                 285

Ser Glu Lys Tyr Glu Asn Thr Lys Thr Cys Arg Gly Pro Asp Gly Glu
    290                 295                 300
```

```
Leu His Ala Asn Leu Leu Cys Pro Val Asp Val Leu Asp Val Pro Glu
305                 310                 315                 320

Gly Thr Leu Pro Asp Lys Gln Ser Thr Glu Gln Ala Ile Gln Leu Leu
                325                 330                 335

Glu Lys Met Lys Thr Ser Ala Ser Pro Phe Phe Leu Ala Val Gly Tyr
                340                 345                 350

His Lys Pro His Ile Pro Phe Arg Tyr Pro Lys Glu Phe Gln Lys Leu
                355                 360                 365

Tyr Pro Leu Glu Asn Ile Thr Leu Ala Pro Asp Pro Glu Val Pro Asp
    370                 375                 380

Gly Leu Pro Pro Val Ala Tyr Asn Pro Trp Met Asp Ile Arg Gln Arg
385                 390                 395                 400

Glu Asp Val Gln Ala Leu Asn Ile Ser Val Pro Tyr Gly Pro Ile Pro
                405                 410                 415

Val Asp Phe Gln Arg Lys Ile Arg Gln Ser Tyr Phe Ala Ser Val Ser
                420                 425                 430

Tyr Leu Asp Thr Gln Val Gly Arg Leu Leu Ser Ala Leu Asp Asp Leu
                435                 440                 445

Gln Leu Ala Asn Ser Thr Ile Ile Ala Phe Thr Ser Asp His Gly Trp
450                 455                 460

Ala Leu Gly Glu His Gly Glu Trp Ala Lys Tyr Ser Asn Phe Asp Val
465                 470                 475                 480

Ala Thr His Val Pro Leu Ile Phe Tyr Val Pro Gly Arg Thr Ala Ser
                485                 490                 495

Leu Pro Glu Ala Gly Glu Lys Leu Phe Pro Tyr Leu Asp Pro Phe Asp
                500                 505                 510

Ser Ala Ser Gln Leu Met Glu Pro Gly Arg Gln Ser Met Asp Leu Val
                515                 520                 525

Glu Leu Val Ser Leu Phe Pro Thr Leu Ala Gly Leu Ala Gly Leu Gln
                530                 535                 540

Val Pro Pro Arg Cys Pro Val Pro Ser Phe His Val Glu Leu Cys Arg
545                 550                 555                 560

Glu Gly Lys Asn Leu Leu Lys His Phe Arg Phe Arg Asp Leu Glu Glu
                565                 570                 575

Asp Pro Tyr Leu Pro Gly Asn Pro Arg Glu Leu Ile Ala Tyr Ser Gln
                580                 585                 590

Tyr Pro Arg Pro Ser Asp Ile Pro Gln Trp Asn Ser Asp Lys Pro Ser
                595                 600                 605

Leu Lys Asp Ile Lys Ile Met Gly Tyr Ser Ile Arg Thr Ile Asp Tyr
        610                 615                 620

Arg Tyr Thr Val Trp Val Gly Phe Asn Pro Asp Glu Phe Leu Ala Asn
625                 630                 635                 640

Phe Ser Asp Ile His Ala Gly Glu Leu Tyr Phe Val Asp Ser Asp Pro
                645                 650                 655

Leu Gln Asp His Asn Met Tyr Asn Asp Ser Gln Gly Gly Asp Leu Phe
                660                 665                 670

Gln Leu Leu Met Pro Gly Gly Gly Ser Asp Ala His Lys Ser Glu
                675                 680                 685

Val Ala His Arg Phe Lys Asp Leu Gly Glu Glu Asn Phe Lys Ala Leu
                690                 695                 700

Val Leu Ile Ala Phe Ala Gln Tyr Leu Gln Gln Cys Pro Phe Glu Asp
705                 710                 715                 720

His Val Lys Leu Val Asn Glu Val Thr Glu Phe Ala Lys Thr Cys Val
```

-continued

```
                725                 730                 735
Ala Asp Glu Ser Ala Glu Asn Cys Asp Lys Ser Leu His Thr Leu Phe
                740                 745                 750
Gly Asp Lys Leu Cys Thr Val Ala Thr Leu Arg Glu Thr Tyr Gly Glu
                755                 760                 765
Met Ala Asp Cys Cys Ala Lys Gln Glu Pro Glu Arg Asn Glu Cys Phe
        770                 775                 780
Leu Gln His Lys Asp Asp Asn Pro Asn Leu Pro Arg Leu Val Arg Pro
785                 790                 795                 800
Glu Val Asp Val Met Cys Thr Ala Phe His Asp Asn Glu Glu Thr Phe
                805                 810                 815
Leu Lys Lys Tyr Leu Tyr Glu Ile Ala Arg Arg His Pro Tyr Phe Tyr
                820                 825                 830
Ala Pro Glu Leu Leu Phe Phe Ala Lys Arg Tyr Lys Ala Ala Phe Thr
                835                 840                 845
Glu Cys Cys Gln Ala Ala Asp Lys Ala Ala Cys Leu Leu Pro Lys Leu
                850                 855                 860
Asp Glu Leu Arg Asp Glu Gly Lys Ala Ser Ser Ala Lys Gln Arg Leu
865                 870                 875                 880
Lys Cys Ala Ser Leu Gln Lys Phe Gly Glu Arg Ala Phe Lys Ala Trp
                885                 890                 895
Ala Val Ala Arg Leu Ser Gln Arg Phe Pro Lys Ala Glu Phe Ala Glu
                900                 905                 910
Val Ser Lys Leu Val Thr Asp Leu Thr Lys Val His Thr Glu Cys Cys
                915                 920                 925
His Gly Asp Leu Leu Glu Cys Ala Asp Asp Arg Ala Asp Leu Ala Lys
        930                 935                 940
Tyr Ile Cys Glu Asn Gln Asp Ser Ile Ser Ser Lys Leu Lys Glu Cys
945                 950                 955                 960
Cys Glu Lys Pro Leu Leu Glu Lys Ser His Cys Ile Ala Glu Val Glu
                965                 970                 975
Asn Asp Glu Met Pro Ala Asp Leu Pro Ser Leu Ala Ala Asp Phe Val
            980                 985                 990
Glu Ser Lys Asp Val Cys Lys Asn Tyr Ala Glu Ala Lys Asp Val Phe
            995                 1000                1005
Leu Gly Met Phe Leu Tyr Glu Tyr Ala Arg Arg His Pro Asp Tyr
        1010                1015                1020
Ser Val Val Leu Leu Leu Arg Leu Ala Lys Thr Tyr Glu Thr Thr
        1025                1030                1035
Leu Glu Lys Cys Cys Ala Ala Ala Asp Pro His Glu Cys Tyr Ala
        1040                1045                1050
Lys Val Phe Asp Glu Phe Lys Pro Leu Val Glu Glu Pro Gln Asn
        1055                1060                1065
Leu Ile Lys Gln Asn Cys Glu Leu Phe Glu Gln Leu Gly Glu Tyr
        1070                1075                1080
Lys Phe Gln Asn Ala Leu Leu Val Arg Tyr Thr Lys Lys Val Pro
        1085                1090                1095
Gln Val Ser Thr Pro Thr Leu Val Glu Val Ser Arg Asn Leu Gly
        1100                1105                1110
Lys Val Gly Ser Lys Cys Cys Lys His Pro Glu Ala Lys Arg Met
        1115                1120                1125
Pro Cys Ala Glu Asp Tyr Leu Ser Val Val Leu Asn Gln Leu Cys
        1130                1135                1140
```

```
Val Leu His Glu Lys Thr Pro Val Ser Asp Arg Val Thr Lys Cys
    1145                1150                1155

Cys Thr Glu Ser Leu Val Asn Arg Arg Pro Cys Phe Ser Ala Leu
    1160                1165                1170

Glu Val Asp Glu Thr Tyr Val Pro Lys Glu Phe Asn Ala Glu Thr
    1175                1180                1185

Phe Thr Phe His Ala Asp Ile Cys Thr Leu Ser Glu Lys Glu Arg
    1190                1195                1200

Gln Ile Lys Lys Gln Thr Ala Leu Val Glu Leu Val Lys His Lys
    1205                1210                1215

Pro Lys Ala Thr Lys Glu Gln Leu Lys Ala Val Met Asp Asp Phe
    1220                1225                1230

Ala Ala Phe Val Glu Lys Cys Cys Lys Ala Asp Asp Lys Glu Thr
    1235                1240                1245

Cys Phe Ala Glu Glu Gly Pro Lys Leu Val Ala Ala Ser Gln Ala
    1250                1255                1260

Ala Leu Gly Leu His His His His His His His
    1265                1270                1275
```

<210> SEQ ID NO 36
<211> LENGTH: 835
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 36

```
Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Pro Ser Asn Phe Tyr
            20                  25                  30

Ala Met Ser Trp Phe Arg Gln Ala Pro Gly Lys Glu Arg Glu Phe Val
        35                  40                  45

Ser Gly Val Ser Arg Asp Gly Leu Thr Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Leu Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Ser Glu Thr Gln Ala Asn Ser Thr
145                 150                 155                 160

Thr Asp Ala Leu Asn Val Leu Leu Ile Ile Val Asp Asp Leu Arg Pro
                165                 170                 175

Ser Leu Gly Cys Tyr Gly Asp Lys Leu Val Arg Ser Pro Asn Ile Asp
            180                 185                 190

Gln Leu Ala Ser His Ser Leu Leu Phe Gln Asn Ala Phe Ala Gln Gln
```

```
            195                 200                 205
Ala Val Cys Ala Pro Ser Arg Val Ser Phe Leu Thr Gly Arg Arg Pro
210                 215                 220

Asp Thr Thr Arg Leu Tyr Asp Phe Asn Ser Tyr Trp Arg Val His Ala
225                 230                 235                 240

Gly Asn Phe Ser Thr Ile Pro Gln Tyr Phe Lys Glu Asn Gly Tyr Val
            245                 250                 255

Thr Met Ser Val Gly Lys Val Phe His Pro Gly Ile Ser Ser Asn His
            260                 265                 270

Thr Asp Asp Ser Pro Tyr Ser Trp Ser Phe Pro Tyr His Pro Ser
            275                 280                 285

Ser Glu Lys Tyr Glu Asn Thr Lys Thr Cys Arg Gly Pro Asp Gly Glu
290                 295                 300

Leu His Ala Asn Leu Leu Cys Pro Val Asp Val Leu Asp Val Pro Glu
305                 310                 315                 320

Gly Thr Leu Pro Asp Lys Gln Ser Thr Glu Gln Ala Ile Gln Leu Leu
                325                 330                 335

Glu Lys Met Lys Thr Ser Ala Ser Pro Phe Phe Leu Ala Val Gly Tyr
            340                 345                 350

His Lys Pro His Ile Pro Phe Arg Tyr Pro Lys Glu Phe Gln Lys Leu
            355                 360                 365

Tyr Pro Leu Glu Asn Ile Thr Leu Ala Pro Asp Pro Glu Val Pro Asp
370                 375                 380

Gly Leu Pro Pro Val Ala Tyr Asn Pro Trp Met Asp Ile Arg Gln Arg
385                 390                 395                 400

Glu Asp Val Gln Ala Leu Asn Ile Ser Val Pro Tyr Gly Pro Ile Pro
                405                 410                 415

Val Asp Phe Gln Arg Lys Ile Arg Gln Ser Tyr Phe Ala Ser Val Ser
                420                 425                 430

Tyr Leu Asp Thr Gln Val Gly Arg Leu Leu Ser Ala Leu Asp Asp Leu
            435                 440                 445

Gln Leu Ala Asn Ser Thr Ile Ile Ala Phe Thr Ser Asp His Gly Trp
450                 455                 460

Ala Leu Gly Glu His Gly Glu Trp Ala Lys Tyr Ser Asn Phe Asp Val
465                 470                 475                 480

Ala Thr His Val Pro Leu Ile Phe Tyr Val Pro Gly Arg Thr Ala Ser
                485                 490                 495

Leu Pro Glu Ala Gly Glu Lys Leu Phe Pro Tyr Leu Asp Pro Phe Asp
                500                 505                 510

Ser Ala Ser Gln Leu Met Glu Pro Gly Arg Gln Ser Met Asp Leu Val
            515                 520                 525

Glu Leu Val Ser Leu Phe Pro Thr Leu Ala Gly Leu Ala Gly Leu Gln
            530                 535                 540

Val Pro Pro Arg Cys Pro Val Pro Ser Phe His Val Glu Leu Cys Arg
545                 550                 555                 560

Glu Gly Lys Asn Leu Leu Lys His Phe Arg Phe Arg Asp Leu Glu Glu
                565                 570                 575

Asp Pro Tyr Leu Pro Gly Asn Pro Arg Glu Leu Ile Ala Tyr Ser Gln
            580                 585                 590

Tyr Pro Arg Pro Ser Asp Ile Pro Gln Trp Asn Ser Asp Lys Pro Ser
            595                 600                 605

Leu Lys Asp Ile Lys Ile Met Gly Tyr Ser Ile Arg Thr Ile Asp Tyr
            610                 615                 620
```

-continued

```
Arg Tyr Thr Val Trp Val Gly Phe Asn Pro Asp Glu Phe Leu Ala Asn
625                 630                 635                 640

Phe Ser Asp Ile His Ala Gly Glu Leu Tyr Phe Val Asp Ser Asp Pro
            645                 650                 655

Leu Gln Asp His Asn Met Tyr Asn Asp Ser Gln Gly Gly Asp Leu Phe
        660                 665                 670

Gln Leu Leu Met Pro Gly Gly Gly Ser Gly Gly Gly Gly Ser Gly
            675                 680                 685

Gly Gly Gly Ser Gly Gly Gly Ser Gly Gly Gly Ser Gln Val
        690                 695                 700

Gln Leu Val Glu Ser Gly Gly Gly Leu Val Gln Ala Gly Gly Ser Leu
705                 710                 715                 720

Arg Leu Ser Cys Val Ala Ser Gly Arg Thr Phe Ile Ala Tyr Ala Met
                725                 730                 735

Gly Trp Phe Arg Gln Ala Pro Gly Lys Glu Arg Glu Phe Val Ala Ala
            740                 745                 750

Ile Thr Asn Phe Ala Gly Gly Thr Thr Tyr Tyr Ala Asp Ser Val Lys
        755                 760                 765

Gly Arg Phe Thr Ile Ser Arg Asp Asn Ala Lys Thr Thr Val Tyr Leu
770                 775                 780

Gln Met Asn Ser Leu Lys Pro Glu Asp Thr Ala Leu Tyr Tyr Cys Ala
785                 790                 795                 800

Ala Asp Arg Ser Ala Gln Thr Met Arg Gln Val Arg Pro Val Leu Pro
                805                 810                 815

Tyr Trp Gly Gln Gly Thr Gln Val Thr Val Ser His His His His
            820                 825                 830

His His His
        835

<210> SEQ ID NO 37
<211> LENGTH: 834
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Pro Ser Asn Phe Tyr
            20                  25                  30

Ala Met Ser Trp Phe Arg Gln Ala Pro Gly Lys Glu Arg Glu Phe Val
        35                  40                  45

Ser Gly Val Ser Arg Asp Gly Leu Thr Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Leu Val Thr Val Ser Ser Gly
```

-continued

```
            115                 120                 125
Gly Gly Gly Ser Gly Gly Gly Ser Gly Gly Gly Ser Gly Gly
        130                 135                 140

Gly Gly Ser Gly Gly Gly Ser Ser Glu Thr Gln Ala Asn Ser Thr
145                 150                 155                 160

Thr Asp Ala Leu Asn Val Leu Leu Ile Ile Val Asp Asp Leu Arg Pro
                165                 170                 175

Ser Leu Gly Cys Tyr Gly Asp Lys Leu Val Arg Ser Pro Asn Ile Asp
                180                 185                 190

Gln Leu Ala Ser His Ser Leu Leu Phe Gln Asn Ala Phe Ala Gln Gln
                195                 200                 205

Ala Val Cys Ala Pro Ser Arg Val Ser Phe Leu Thr Gly Arg Arg Pro
            210                 215                 220

Asp Thr Thr Arg Leu Tyr Asp Phe Asn Ser Tyr Trp Arg Val His Ala
225                 230                 235                 240

Gly Asn Phe Ser Thr Ile Pro Gln Tyr Phe Lys Glu Asn Gly Tyr Val
                245                 250                 255

Thr Met Ser Val Gly Lys Val Phe His Pro Gly Ile Ser Ser Asn His
                260                 265                 270

Thr Asp Asp Ser Pro Tyr Ser Trp Ser Phe Pro Pro Tyr His Pro Ser
                275                 280                 285

Ser Glu Lys Tyr Glu Asn Thr Lys Thr Cys Arg Gly Pro Asp Gly Glu
            290                 295                 300

Leu His Ala Asn Leu Leu Cys Pro Val Asp Val Leu Asp Val Pro Glu
305                 310                 315                 320

Gly Thr Leu Pro Asp Lys Gln Ser Thr Glu Gln Ala Ile Gln Leu Leu
                325                 330                 335

Glu Lys Met Lys Thr Ser Ala Ser Pro Phe Phe Leu Ala Val Gly Tyr
                340                 345                 350

His Lys Pro His Ile Pro Phe Arg Tyr Pro Lys Glu Phe Gln Lys Leu
                355                 360                 365

Tyr Pro Leu Glu Asn Ile Thr Leu Ala Pro Asp Pro Glu Val Pro Asp
            370                 375                 380

Gly Leu Pro Pro Val Ala Tyr Asn Pro Trp Met Asp Ile Arg Gln Arg
385                 390                 395                 400

Glu Asp Val Gln Ala Leu Asn Ile Ser Val Pro Tyr Gly Pro Ile Pro
                405                 410                 415

Val Asp Phe Gln Arg Lys Ile Arg Gln Ser Tyr Phe Ala Ser Val Ser
                420                 425                 430

Tyr Leu Asp Thr Gln Val Gly Arg Leu Leu Ser Ala Leu Asp Asp Leu
            435                 440                 445

Gln Leu Ala Asn Ser Thr Ile Ile Ala Phe Thr Ser Asp His Gly Trp
            450                 455                 460

Ala Leu Gly Glu His Gly Glu Trp Ala Lys Tyr Ser Asn Phe Asp Val
465                 470                 475                 480

Ala Thr His Val Pro Leu Ile Phe Tyr Val Pro Gly Arg Thr Ala Ser
                485                 490                 495

Leu Pro Glu Ala Gly Lys Leu Phe Pro Tyr Leu Asp Pro Phe Asp
            500                 505                 510

Ser Ala Ser Gln Leu Met Glu Pro Gly Arg Gln Ser Met Asp Leu Val
            515                 520                 525

Glu Leu Val Ser Leu Phe Pro Thr Leu Ala Gly Leu Ala Gly Leu Gln
            530                 535                 540
```

Val Pro Pro Arg Cys Pro Val Pro Ser Phe His Val Glu Leu Cys Arg
545                 550                 555                 560

Glu Gly Lys Asn Leu Leu Lys His Phe Arg Phe Arg Asp Leu Glu Glu
                565                 570                 575

Asp Pro Tyr Leu Pro Gly Asn Pro Arg Glu Leu Ile Ala Tyr Ser Gln
            580                 585                 590

Tyr Pro Arg Pro Ser Asp Ile Pro Gln Trp Asn Ser Asp Lys Pro Ser
                595                 600                 605

Leu Lys Asp Ile Lys Ile Met Gly Tyr Ser Ile Arg Thr Ile Asp Tyr
            610                 615                 620

Arg Tyr Thr Val Trp Val Gly Phe Asn Pro Asp Glu Phe Leu Ala Asn
625                 630                 635                 640

Phe Ser Asp Ile His Ala Gly Glu Leu Tyr Phe Val Asp Ser Asp Pro
                645                 650                 655

Leu Gln Asp His Asn Met Tyr Asn Asp Ser Gln Gly Gly Asp Leu Phe
                660                 665                 670

Gln Leu Leu Met Pro Gly Gly Gly Ser Gly Gly Gly Gly Ser Gly
            675                 680                 685

Gly Gly Gly Ser Gly Gly Gly Ser Gly Gly Gly Ser Gln Val
690                 695                 700

Lys Leu Glu Glu Ser Gly Gly Gly Leu Val Gln Ala Gly Gly Ser Leu
705                 710                 715                 720

Lys Leu Ser Cys Ala Ala Ser Gly Ser Thr Phe Ser Ser Ser Val
                725                 730                 735

Gly Trp Tyr Arg Gln Ala Pro Gly Gln Gln Arg Glu Leu Val Ala Ala
                740                 745                 750

Ile Thr Ser Gly Gly Ser Thr Asn Thr Ala Asp Ser Val Lys Gly Arg
                755                 760                 765

Phe Thr Met Ser Arg Asp Asn Ala Lys Asn Thr Val Tyr Leu Gln Met
                770                 775                 780

Arg Asp Leu Lys Pro Glu Asp Thr Ala Val Tyr Tyr Cys Asn Val Ala
785                 790                 795                 800

Gly Arg Asn Trp Val Pro Ile Ser Arg Tyr Ser Pro Gly Pro Tyr Trp
                805                 810                 815

Gly Gln Gly Thr Gln Val Thr Val Ser Ser His His His His His His
                820                 825                 830

His His

<210> SEQ ID NO 38
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 38

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val

```
                    50                  55                  60
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                    85                  90                  95

Thr Ile Gly Gly Ser Leu Ser Arg Ser Ser Gln Gly Thr Leu Val Thr
                100                 105                 110

Val Ser Ser
        115

<210> SEQ ID NO 39
<211> LENGTH: 825
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 39

Glu Val Gln Leu Val Glu Ser Gly Gly Gly Leu Val Gln Pro Gly Gly
 1               5                  10                  15

Ser Leu Arg Leu Ser Cys Ala Ala Ser Glu Tyr Pro Ser Asn Phe Tyr
                20                  25                  30

Ala Met Ser Trp Phe Arg Gln Ala Pro Gly Lys Glu Arg Glu Phe Val
            35                  40                  45

Ser Gly Val Ser Arg Asp Gly Leu Thr Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Leu Val Thr Val Ser Ser Gly
        115                 120                 125

Gly Gly Ser Gly Gly Gly Gly Ser Gly Gly Gly Gly Ser Gly Gly
    130                 135                 140

Gly Gly Ser Gly Gly Gly Ser Ser Glu Thr Gln Ala Asn Ser Thr
145                 150                 155                 160

Thr Asp Ala Leu Asn Val Leu Leu Ile Ile Val Asp Asp Leu Arg Pro
                165                 170                 175

Ser Leu Gly Cys Tyr Gly Asp Lys Leu Val Arg Ser Pro Asn Ile Asp
            180                 185                 190

Gln Leu Ala Ser His Ser Leu Leu Phe Gln Asn Ala Phe Ala Gln Gln
        195                 200                 205

Ala Val Cys Ala Pro Ser Arg Val Ser Phe Leu Thr Gly Arg Arg Pro
    210                 215                 220

Asp Thr Thr Arg Leu Tyr Asp Phe Asn Ser Tyr Trp Arg Val His Ala
225                 230                 235                 240

Gly Asn Phe Ser Thr Ile Pro Gln Tyr Phe Lys Glu Asn Gly Tyr Val
                245                 250                 255

Thr Met Ser Val Gly Lys Val Phe His Pro Gly Ile Ser Ser Asn His
            260                 265                 270
```

```
Thr Asp Asp Ser Pro Tyr Ser Trp Ser Phe Pro Tyr His Pro Ser
            275                 280                 285

Ser Glu Lys Tyr Glu Asn Thr Lys Thr Cys Arg Gly Pro Asp Gly Glu
290                 295                 300

Leu His Ala Asn Leu Leu Cys Pro Val Asp Val Leu Asp Val Pro Glu
305                 310                 315                 320

Gly Thr Leu Pro Asp Lys Gln Ser Thr Glu Gln Ala Ile Gln Leu Leu
                    325                 330                 335

Glu Lys Met Lys Thr Ser Ala Ser Pro Phe Phe Leu Ala Val Gly Tyr
                340                 345                 350

His Lys Pro His Ile Pro Phe Arg Tyr Pro Lys Glu Phe Gln Lys Leu
            355                 360                 365

Tyr Pro Leu Glu Asn Ile Thr Leu Ala Pro Asp Pro Glu Val Pro Asp
370                 375                 380

Gly Leu Pro Pro Val Ala Tyr Asn Pro Trp Met Asp Ile Arg Gln Arg
385                 390                 395                 400

Glu Asp Val Gln Ala Leu Asn Ile Ser Val Pro Tyr Gly Pro Ile Pro
                405                 410                 415

Val Asp Phe Gln Arg Lys Ile Arg Gln Ser Tyr Phe Ala Ser Val Ser
            420                 425                 430

Tyr Leu Asp Thr Gln Val Gly Arg Leu Leu Ser Ala Leu Asp Asp Leu
            435                 440                 445

Gln Leu Ala Asn Ser Thr Ile Ile Ala Phe Thr Ser Asp His Gly Trp
            450                 455                 460

Ala Leu Gly Glu His Gly Glu Trp Ala Lys Tyr Ser Asn Phe Asp Val
465                 470                 475                 480

Ala Thr His Val Pro Leu Ile Phe Tyr Val Pro Gly Arg Thr Ala Ser
                485                 490                 495

Leu Pro Glu Ala Gly Glu Lys Leu Phe Pro Tyr Leu Asp Pro Phe Asp
                500                 505                 510

Ser Ala Ser Gln Leu Met Glu Pro Gly Arg Gln Ser Met Asp Leu Val
            515                 520                 525

Glu Leu Val Ser Leu Phe Pro Thr Leu Ala Gly Leu Ala Gly Leu Gln
530                 535                 540

Val Pro Pro Arg Cys Pro Val Pro Ser Phe His Val Glu Leu Cys Arg
545                 550                 555                 560

Glu Gly Lys Asn Leu Leu Lys His Phe Arg Phe Arg Asp Leu Glu Glu
                565                 570                 575

Asp Pro Tyr Leu Pro Gly Asn Pro Arg Glu Leu Ile Ala Tyr Ser Gln
                580                 585                 590

Tyr Pro Arg Pro Ser Asp Ile Pro Gln Trp Asn Ser Asp Lys Pro Ser
            595                 600                 605

Leu Lys Asp Ile Lys Ile Met Gly Tyr Ser Ile Arg Thr Ile Asp Tyr
610                 615                 620

Arg Tyr Thr Val Trp Val Gly Phe Asn Pro Asp Glu Phe Leu Ala Asn
625                 630                 635                 640

Phe Ser Asp Ile His Ala Gly Glu Leu Tyr Phe Val Asp Ser Asp Pro
                645                 650                 655

Leu Gln Asp His Asn Met Tyr Asn Asp Ser Gln Gly Gly Asp Leu Phe
                660                 665                 670

Gln Leu Leu Met Pro Gly Gly Gly Ser Gly Gly Gly Ser Gly
            675                 680                 685

Gly Gly Gly Ser Gly Gly Gly Gly Ser Gly Gly Gly Gly Ser Glu Val
```

```
                690             695             700
Gln Leu Val Glu Ser Gly Gly Leu Val Gln Pro Gly Asn Ser Leu
705             710             715             720

Arg Leu Ser Cys Ala Ala Ser Gly Phe Thr Phe Ser Ser Phe Gly Met
            725             730             735

Ser Trp Val Arg Gln Ala Pro Gly Lys Gly Leu Glu Trp Val Ser Ser
            740             745             750

Ile Ser Gly Ser Gly Ser Asp Thr Leu Tyr Ala Asp Ser Val Lys Gly
            755             760             765

Arg Phe Thr Ile Ser Arg Asp Asn Ala Lys Thr Thr Leu Tyr Leu Gln
            770             775             780

Met Asn Ser Leu Arg Pro Glu Asp Thr Ala Val Tyr Tyr Cys Thr Ile
785             790             795             800

Gly Gly Ser Leu Ser Arg Ser Ser Gln Gly Thr Leu Val Thr Val Ser
            805             810             815

Ser His His His His His His His
            820             825
```

<210> SEQ ID NO 40
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 40

```
Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115
```

<210> SEQ ID NO 41
<211> LENGTH: 830
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 41

```
Gln Val Gln Leu Val Glu Ser Gly Gly Gly Leu Val Gln Pro Gly Gly
1               5                   10                  15
```

Ser Leu Arg Leu Ser Cys Ala Ala Ser Gly Arg Thr Ile Asp Asn Tyr
        20                  25                  30

Ala Met Ala Trp Val Arg Gln Ala Pro Gly Lys Gly Leu Glu Trp Val
            35                  40                  45

Ala Thr Ile Asp Trp Gly Asp Gly Thr Arg Tyr Ala Asn Ser Val
     50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Gly Gly Gly Gly
         115                 120                 125

Ser Gly Gly Gly Gly Ser Gly Gly Gly Ser Gly Gly Gly Gly Ser
     130                 135                 140

Gly Gly Gly Gly Ser Ser Glu Thr Gln Ala Asn Ser Thr Thr Asp Ala
145                 150                 155                 160

Leu Asn Val Leu Leu Ile Ile Val Asp Asp Leu Arg Pro Ser Leu Gly
                165                 170                 175

Cys Tyr Gly Asp Lys Leu Val Arg Ser Pro Asn Ile Asp Gln Leu Ala
            180                 185                 190

Ser His Ser Leu Leu Phe Gln Asn Ala Phe Ala Gln Ala Val Cys
     195                 200                 205

Ala Pro Ser Arg Val Ser Phe Leu Thr Gly Arg Arg Pro Asp Thr Thr
210                 215                 220

Arg Leu Tyr Asp Phe Asn Ser Tyr Trp Arg Val His Ala Gly Asn Phe
225                 230                 235                 240

Ser Thr Ile Pro Gln Tyr Phe Lys Glu Asn Gly Tyr Val Thr Met Ser
                245                 250                 255

Val Gly Lys Val Phe His Pro Gly Ile Ser Ser Asn His Thr Asp Asp
            260                 265                 270

Ser Pro Tyr Ser Trp Ser Phe Pro Pro Tyr His Pro Ser Ser Glu Lys
     275                 280                 285

Tyr Glu Asn Thr Lys Thr Cys Arg Gly Pro Asp Gly Glu Leu His Ala
290                 295                 300

Asn Leu Leu Cys Pro Val Asp Val Leu Asp Val Pro Glu Gly Thr Leu
305                 310                 315                 320

Pro Asp Lys Gln Ser Thr Glu Gln Ala Ile Gln Leu Leu Glu Lys Met
                325                 330                 335

Lys Thr Ser Ala Ser Pro Phe Phe Leu Ala Val Gly Tyr His Lys Pro
            340                 345                 350

His Ile Pro Phe Arg Tyr Pro Lys Glu Phe Gln Lys Leu Tyr Pro Leu
     355                 360                 365

Glu Asn Ile Thr Leu Ala Pro Asp Pro Glu Val Pro Asp Gly Leu Pro
370                 375                 380

Pro Val Ala Tyr Asn Pro Trp Met Asp Ile Arg Gln Arg Glu Asp Val
385                 390                 395                 400

Gln Ala Leu Asn Ile Ser Val Pro Tyr Gly Pro Ile Pro Val Asp Phe
                405                 410                 415

Gln Arg Lys Ile Arg Gln Ser Tyr Phe Ala Ser Val Ser Tyr Leu Asp
            420                 425                 430

Thr Gln Val Gly Arg Leu Leu Ser Ala Leu Asp Asp Leu Gln Leu Ala

```
                435                 440                 445
Asn Ser Thr Ile Ile Ala Phe Thr Ser Asp His Gly Trp Ala Leu Gly
            450                 455                 460
Glu His Gly Glu Trp Ala Lys Tyr Ser Asn Phe Asp Val Ala Thr His
465                 470                 475                 480
Val Pro Leu Ile Phe Tyr Val Pro Gly Arg Thr Ala Ser Leu Pro Glu
                485                 490                 495
Ala Gly Glu Lys Leu Phe Pro Tyr Leu Asp Pro Phe Asp Ser Ala Ser
            500                 505                 510
Gln Leu Met Glu Pro Gly Arg Gln Ser Met Asp Leu Val Glu Leu Val
        515                 520                 525
Ser Leu Phe Pro Thr Leu Ala Gly Leu Ala Gly Leu Gln Val Pro Pro
    530                 535                 540
Arg Cys Pro Val Pro Ser Phe His Val Glu Leu Cys Arg Glu Gly Lys
545                 550                 555                 560
Asn Leu Leu Lys His Phe Arg Phe Arg Asp Leu Glu Glu Asp Pro Tyr
                565                 570                 575
Leu Pro Gly Asn Pro Arg Glu Leu Ile Ala Tyr Ser Gln Tyr Pro Arg
            580                 585                 590
Pro Ser Asp Ile Pro Gln Trp Asn Ser Asp Lys Pro Ser Leu Lys Asp
        595                 600                 605
Ile Lys Ile Met Gly Tyr Ser Ile Arg Thr Ile Asp Tyr Arg Tyr Thr
    610                 615                 620
Val Trp Val Gly Phe Asn Pro Asp Glu Phe Leu Ala Asn Phe Ser Asp
625                 630                 635                 640
Ile His Ala Gly Glu Leu Tyr Phe Val Asp Ser Asp Pro Leu Gln Asp
                645                 650                 655
His Asn Met Tyr Asn Asp Ser Gln Gly Gly Asp Leu Phe Gln Leu Leu
            660                 665                 670
Met Pro Gly Gly Gly Ser Gly Gly Gly Ser Gly Gly Gly Gly
        675                 680                 685
Ser Gly Gly Gly Gly Ser Gly Gly Gly Ser Ala Val Gln Leu Val
    690                 695                 700
Glu Ser Gly Gly Gly Leu Val Gln Pro Gly Asn Ser Leu Arg Leu Ser
705                 710                 715                 720
Cys Ala Ala Ser Gly Phe Thr Phe Arg Ser Phe Gly Met Ser Trp Val
                725                 730                 735
Arg Gln Ala Pro Gly Lys Glu Pro Glu Trp Val Ser Ser Ile Ser Gly
            740                 745                 750
Ser Gly Ser Asp Thr Leu Tyr Ala Asp Ser Val Lys Gly Arg Phe Thr
        755                 760                 765
Ile Ser Arg Asp Asn Ala Lys Thr Thr Leu Tyr Leu Gln Met Asn Ser
    770                 775                 780
Leu Lys Pro Glu Asp Thr Ala Val Tyr Tyr Cys Thr Ile Gly Gly Ser
785                 790                 795                 800
Leu Ser Arg Ser Ser Gln Gly Thr Gln Val Thr Val Ser Ser His His
                805                 810                 815
His His His His Trp Ser His Pro Gln Phe Glu Lys
            820                 825                 830

<210> SEQ ID NO 42
<211> LENGTH: 830
<212> TYPE: PRT
<213> ORGANISM: Artificial Sequence
```

<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 42

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Thr Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Ala Val Gln Leu Val Glu Ser Gly Gly Gly Leu
145                 150                 155                 160

Val Gln Pro Gly Asn Ser Leu Arg Leu Ser Cys Ala Ala Ser Gly Phe
                165                 170                 175

Thr Phe Arg Ser Phe Gly Met Ser Trp Val Arg Gln Ala Pro Gly Lys
            180                 185                 190

Glu Pro Glu Trp Val Ser Ser Ile Ser Gly Ser Gly Ser Asp Thr Leu
        195                 200                 205

Tyr Ala Asp Ser Val Lys Gly Arg Phe Thr Ile Ser Arg Asp Asn Ala
    210                 215                 220

Lys Thr Thr Leu Tyr Leu Gln Met Asn Ser Leu Lys Pro Glu Asp Thr
225                 230                 235                 240

Ala Val Tyr Tyr Cys Thr Ile Gly Gly Ser Leu Ser Arg Ser Ser Gln
                245                 250                 255

Gly Thr Gln Val Thr Val Ser Ser Gly Gly Gly Gly Ser Gly Gly Gly
            260                 265                 270

Gly Ser Gly Gly Gly Gly Ser Gly Gly Gly Gly Ser Gly Gly Gly Gly
        275                 280                 285

Ser Ser Glu Thr Gln Ala Asn Ser Thr Thr Asp Ala Leu Asn Val Leu
    290                 295                 300

Leu Ile Ile Val Asp Asp Leu Arg Pro Ser Leu Gly Cys Tyr Gly Asp
305                 310                 315                 320

Lys Leu Val Arg Ser Pro Asn Ile Asp Gln Leu Ala Ser His Ser Leu
                325                 330                 335

Leu Phe Gln Asn Ala Phe Ala Gln Gln Ala Val Cys Ala Pro Ser Arg
            340                 345                 350

Val Ser Phe Leu Thr Gly Arg Arg Pro Asp Thr Thr Arg Leu Tyr Asp
        355                 360                 365

Phe Asn Ser Tyr Trp Arg Val His Ala Gly Asn Phe Ser Thr Ile Pro
```

-continued

```
                370                 375                 380
Gln Tyr Phe Lys Glu Asn Gly Tyr Val Thr Met Ser Val Gly Lys Val
385                 390                 395                 400

Phe His Pro Gly Ile Ser Ser Asn His Thr Asp Asp Ser Pro Tyr Ser
                405                 410                 415

Trp Ser Phe Pro Pro Tyr His Pro Ser Ser Glu Lys Tyr Glu Asn Thr
                420                 425                 430

Lys Thr Cys Arg Gly Pro Asp Gly Glu Leu His Ala Asn Leu Leu Cys
                435                 440                 445

Pro Val Asp Val Leu Asp Val Pro Glu Gly Thr Leu Pro Asp Lys Gln
                450                 455                 460

Ser Thr Glu Gln Ala Ile Gln Leu Leu Glu Lys Met Lys Thr Ser Ala
465                 470                 475                 480

Ser Pro Phe Phe Leu Ala Val Gly Tyr His Lys Pro His Ile Pro Phe
                485                 490                 495

Arg Tyr Pro Lys Glu Phe Gln Lys Leu Tyr Pro Leu Glu Asn Ile Thr
                500                 505                 510

Leu Ala Pro Asp Pro Glu Val Pro Asp Gly Leu Pro Pro Val Ala Tyr
                515                 520                 525

Asn Pro Trp Met Asp Ile Arg Gln Arg Glu Asp Val Gln Ala Leu Asn
                530                 535                 540

Ile Ser Val Pro Tyr Gly Pro Ile Pro Val Asp Phe Gln Arg Lys Ile
545                 550                 555                 560

Arg Gln Ser Tyr Phe Ala Ser Val Ser Tyr Leu Asp Thr Gln Val Gly
                565                 570                 575

Arg Leu Leu Ser Ala Leu Asp Asp Leu Gln Leu Ala Asn Ser Thr Ile
                580                 585                 590

Ile Ala Phe Thr Ser Asp His Gly Trp Ala Leu Gly Glu His Gly Glu
                595                 600                 605

Trp Ala Lys Tyr Ser Asn Phe Asp Val Ala Thr His Val Pro Leu Ile
                610                 615                 620

Phe Tyr Val Pro Gly Arg Thr Ala Ser Leu Pro Glu Ala Gly Glu Lys
625                 630                 635                 640

Leu Phe Pro Tyr Leu Asp Pro Phe Asp Ser Ala Ser Gln Leu Met Glu
                645                 650                 655

Pro Gly Arg Gln Ser Met Asp Leu Val Glu Leu Val Ser Leu Phe Pro
                660                 665                 670

Thr Leu Ala Gly Leu Ala Gly Leu Gln Val Pro Pro Arg Cys Pro Val
                675                 680                 685

Pro Ser Phe His Val Glu Leu Cys Arg Glu Gly Lys Asn Leu Leu Lys
                690                 695                 700

His Phe Arg Phe Arg Asp Leu Glu Glu Asp Pro Tyr Leu Pro Gly Asn
705                 710                 715                 720

Pro Arg Glu Leu Ile Ala Tyr Ser Gln Tyr Pro Arg Pro Ser Asp Ile
                725                 730                 735

Pro Gln Trp Asn Ser Asp Lys Pro Ser Leu Lys Asp Ile Lys Ile Met
                740                 745                 750

Gly Tyr Ser Ile Arg Thr Ile Asp Tyr Arg Tyr Thr Val Trp Val Gly
                755                 760                 765

Phe Asn Pro Asp Glu Phe Leu Ala Asn Phe Ser Asp Ile His Ala Gly
                770                 775                 780

Glu Leu Tyr Phe Val Asp Ser Asp Pro Leu Gln Asp His Asn Met Tyr
785                 790                 795                 800
```

Asn Asp Ser Gln Gly Gly Asp Leu Phe Gln Leu Leu Met Pro His His
                805                 810                 815

His His His His His His Trp Ser His Pro Gln Phe Glu Lys
            820                 825                 830

<210> SEQ ID NO 43
<211> LENGTH: 829
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 43

Val Gln Leu Val Glu Ser Gly Gly Gly Leu Val Gln Pro Gly Asn Ser
1               5                   10                  15

Leu Arg Leu Ser Cys Ala Ala Ser Gly Phe Thr Phe Arg Ser Phe Gly
            20                  25                  30

Met Ser Trp Val Arg Gln Ala Pro Gly Lys Glu Pro Glu Trp Val Ser
        35                  40                  45

Ser Ile Ser Gly Ser Gly Ser Asp Thr Leu Tyr Ala Asp Ser Val Lys
    50                  55                  60

Gly Arg Phe Thr Ile Ser Arg Asp Asn Ala Lys Thr Thr Leu Tyr Leu
65                  70                  75                  80

Gln Met Asn Ser Leu Lys Pro Glu Asp Thr Ala Val Tyr Tyr Cys Thr
                85                  90                  95

Ile Gly Gly Ser Leu Ser Arg Ser Ser Gln Gly Thr Gln Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Gly Gly Gly Ser Gln Val Gln Leu Val
    130                 135                 140

Glu Ser Gly Gly Gly Leu Val Gln Pro Gly Gly Ser Leu Arg Leu Ser
145                 150                 155                 160

Cys Ala Ala Ser Gly Arg Thr Ile Asp Asn Tyr Ala Met Ala Trp Val
                165                 170                 175

Arg Gln Ala Pro Gly Lys Gly Leu Glu Trp Val Ala Thr Ile Asp Trp
            180                 185                 190

Gly Asp Gly Gly Thr Arg Tyr Ala Asn Ser Val Lys Gly Arg Phe Thr
        195                 200                 205

Ile Ser Arg Asp Asn Ser Lys Asn Thr Met Tyr Leu Gln Met Asn Ser
    210                 215                 220

Leu Arg Ala Glu Asp Thr Ala Val Tyr Tyr Cys Ala Met Ala Arg Gln
225                 230                 235                 240

Ser Arg Val Asn Leu Asp Val Ala Arg Tyr Asp Tyr Trp Gly Gln Gly
                245                 250                 255

Thr Leu Val Thr Val Ser Ser Gly Gly Gly Gly Ser Gly Gly Gly Gly
            260                 265                 270

Ser Gly Gly Gly Gly Ser Gly Gly Gly Gly Ser Gly Gly Gly Gly Ser
        275                 280                 285

Ser Glu Thr Gln Ala Asn Ser Thr Thr Asp Ala Leu Asn Val Leu Leu
    290                 295                 300

Ile Ile Val Asp Asp Leu Arg Pro Ser Leu Gly Cys Tyr Gly Asp Lys

```
            305                 310                 315                 320
Leu Val Arg Ser Pro Asn Ile Asp Gln Leu Ala Ser His Ser Leu Leu
                325                 330                 335
Phe Gln Asn Ala Phe Ala Gln Ala Val Cys Ala Pro Ser Arg Val
            340                 345                 350
Ser Phe Leu Thr Gly Arg Arg Pro Asp Thr Thr Arg Leu Tyr Asp Phe
                355                 360                 365
Asn Ser Tyr Trp Arg Val His Ala Gly Asn Phe Ser Thr Ile Pro Gln
        370                 375                 380
Tyr Phe Lys Glu Asn Gly Tyr Val Thr Met Ser Val Gly Lys Val Phe
385                 390                 395                 400
His Pro Gly Ile Ser Ser Asn His Thr Asp Asp Ser Pro Tyr Ser Trp
                405                 410                 415
Ser Phe Pro Pro Tyr His Pro Ser Ser Glu Lys Tyr Glu Asn Thr Lys
                420                 425                 430
Thr Cys Arg Gly Pro Asp Gly Glu Leu His Ala Asn Leu Leu Cys Pro
            435                 440                 445
Val Asp Val Leu Asp Val Pro Glu Gly Thr Leu Pro Asp Lys Gln Ser
        450                 455                 460
Thr Glu Gln Ala Ile Gln Leu Leu Glu Lys Met Lys Thr Ser Ala Ser
465                 470                 475                 480
Pro Phe Phe Leu Ala Val Gly Tyr His Lys Pro His Ile Pro Phe Arg
                485                 490                 495
Tyr Pro Lys Glu Phe Gln Lys Leu Tyr Pro Leu Glu Asn Ile Thr Leu
            500                 505                 510
Ala Pro Asp Pro Glu Val Pro Asp Gly Leu Pro Pro Val Ala Tyr Asn
        515                 520                 525
Pro Trp Met Asp Ile Arg Gln Arg Glu Asp Val Gln Ala Leu Asn Ile
        530                 535                 540
Ser Val Pro Tyr Gly Pro Ile Pro Val Asp Phe Gln Arg Lys Ile Arg
545                 550                 555                 560
Gln Ser Tyr Phe Ala Ser Val Ser Tyr Leu Asp Thr Gln Val Gly Arg
                565                 570                 575
Leu Leu Ser Ala Leu Asp Asp Leu Gln Leu Ala Asn Ser Thr Ile Ile
                580                 585                 590
Ala Phe Thr Ser Asp His Gly Trp Ala Leu Gly Glu His Gly Glu Trp
            595                 600                 605
Ala Lys Tyr Ser Asn Phe Asp Val Ala Thr His Val Pro Leu Ile Phe
        610                 615                 620
Tyr Val Pro Gly Arg Thr Ala Ser Leu Pro Glu Ala Gly Glu Lys Leu
625                 630                 635                 640
Phe Pro Tyr Leu Asp Pro Phe Asp Ser Ala Ser Gln Leu Met Glu Pro
                645                 650                 655
Gly Arg Gln Ser Met Asp Leu Val Glu Leu Val Ser Leu Phe Pro Thr
            660                 665                 670
Leu Ala Gly Leu Ala Gly Leu Gln Val Pro Pro Arg Cys Pro Val Pro
        675                 680                 685
Ser Phe His Val Glu Leu Cys Arg Glu Gly Lys Asn Leu Leu Lys His
        690                 695                 700
Phe Arg Phe Arg Asp Leu Glu Glu Asp Pro Tyr Leu Pro Gly Asn Pro
705                 710                 715                 720
Arg Glu Leu Ile Ala Tyr Ser Gln Tyr Pro Arg Pro Ser Asp Ile Pro
                725                 730                 735
```

-continued

```
Gln Trp Asn Ser Asp Lys Pro Ser Leu Lys Asp Ile Lys Ile Met Gly
                740                 745                 750

Tyr Ser Ile Arg Thr Ile Asp Tyr Arg Tyr Thr Val Trp Val Gly Phe
            755                 760                 765

Asn Pro Asp Glu Phe Leu Ala Asn Phe Ser Asp Ile His Ala Gly Glu
        770                 775                 780

Leu Tyr Phe Val Asp Ser Asp Pro Leu Gln Asp His Asn Met Tyr Asn
785                 790                 795                 800

Asp Ser Gln Gly Gly Asp Leu Phe Gln Leu Leu Met Pro His His His
                805                 810                 815

His His His His His Trp Ser His Pro Gln Phe Glu Lys
            820                 825

<210> SEQ ID NO 44
<211> LENGTH: 1278
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 44

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Thr Arg Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Ser Glu Thr Gln Ala Asn Ser Thr Thr Asp Ala
145                 150                 155                 160

Leu Asn Val Leu Leu Ile Ile Val Asp Asp Leu Arg Pro Ser Leu Gly
                165                 170                 175

Cys Tyr Gly Asp Lys Leu Val Arg Ser Pro Asn Ile Asp Gln Leu Ala
            180                 185                 190

Ser His Ser Leu Leu Phe Gln Asn Ala Phe Ala Gln Ala Val Cys
    195                 200                 205

Ala Pro Ser Arg Val Ser Phe Leu Thr Gly Arg Arg Pro Asp Thr Thr
        210                 215                 220

Arg Leu Tyr Asp Phe Asn Ser Tyr Trp Arg Val His Ala Gly Asn Phe
225                 230                 235                 240

Ser Thr Ile Pro Gln Tyr Phe Lys Glu Asn Gly Tyr Val Thr Met Ser
```

-continued

```
                245                 250                 255
Val Gly Lys Val Phe His Pro Gly Ile Ser Ser Asn His Thr Asp Asp
            260                 265                 270
Ser Pro Tyr Ser Trp Ser Phe Pro Tyr His Pro Ser Ser Glu Lys
        275                 280                 285
Tyr Glu Asn Thr Lys Thr Cys Arg Gly Pro Asp Gly Glu Leu His Ala
        290                 295                 300
Asn Leu Leu Cys Pro Val Asp Val Leu Asp Val Pro Glu Gly Thr Leu
305                 310                 315                 320
Pro Asp Lys Gln Ser Thr Glu Gln Ala Ile Gln Leu Leu Glu Lys Met
                325                 330                 335
Lys Thr Ser Ala Ser Pro Phe Phe Leu Ala Val Gly Tyr His Lys Pro
                340                 345                 350
His Ile Pro Phe Arg Tyr Pro Lys Glu Phe Gln Lys Leu Tyr Pro Leu
                355                 360                 365
Glu Asn Ile Thr Leu Ala Pro Asp Pro Glu Val Pro Asp Gly Leu Pro
            370                 375                 380
Pro Val Ala Tyr Asn Pro Trp Met Asp Ile Arg Gln Arg Glu Asp Val
385                 390                 395                 400
Gln Ala Leu Asn Ile Ser Val Pro Tyr Gly Pro Ile Pro Val Asp Phe
                405                 410                 415
Gln Arg Lys Ile Arg Gln Ser Tyr Phe Ala Ser Val Ser Tyr Leu Asp
            420                 425                 430
Thr Gln Val Gly Arg Leu Leu Ser Ala Leu Asp Asp Leu Gln Leu Ala
            435                 440                 445
Asn Ser Thr Ile Ile Ala Phe Thr Ser Asp His Gly Trp Ala Leu Gly
        450                 455                 460
Glu His Gly Glu Trp Ala Lys Tyr Ser Asn Phe Asp Val Ala Thr His
465                 470                 475                 480
Val Pro Leu Ile Phe Tyr Val Pro Gly Arg Thr Ala Ser Leu Pro Glu
                485                 490                 495
Ala Gly Glu Lys Leu Phe Pro Tyr Leu Asp Pro Phe Asp Ser Ala Ser
            500                 505                 510
Gln Leu Met Glu Pro Gly Arg Gln Ser Met Asp Leu Val Glu Leu Val
        515                 520                 525
Ser Leu Phe Pro Thr Leu Ala Gly Leu Ala Gly Leu Gln Val Pro Pro
            530                 535                 540
Arg Cys Pro Val Pro Ser Phe His Val Glu Leu Cys Arg Glu Gly Lys
545                 550                 555                 560
Asn Leu Leu Lys His Phe Arg Phe Arg Asp Leu Glu Glu Asp Pro Tyr
                565                 570                 575
Leu Pro Gly Asn Pro Arg Glu Leu Ile Ala Tyr Ser Gln Tyr Pro Arg
            580                 585                 590
Pro Ser Asp Ile Pro Gln Trp Asn Ser Asp Lys Pro Ser Leu Lys Asp
            595                 600                 605
Ile Lys Ile Met Gly Tyr Ser Ile Arg Thr Ile Asp Tyr Arg Tyr Thr
610                 615                 620
Val Trp Val Gly Phe Asn Pro Asp Glu Phe Leu Ala Asn Phe Ser Asp
625                 630                 635                 640
Ile His Ala Gly Glu Leu Tyr Phe Val Asp Ser Asp Pro Leu Gln Asp
                645                 650                 655
His Asn Met Tyr Asn Asp Ser Gln Gly Gly Asp Leu Phe Gln Leu Leu
                660                 665                 670
```

-continued

```
Met Pro Gly Gly Gly Ser Asp Ala His Lys Ser Glu Val Ala His
            675                 680                 685

Arg Phe Lys Asp Leu Gly Glu Glu Asn Phe Lys Ala Leu Val Leu Ile
690                 695                 700

Ala Phe Ala Gln Tyr Leu Gln Gln Cys Pro Phe Glu Asp His Val Lys
705                 710                 715                 720

Leu Val Asn Glu Val Thr Glu Phe Ala Lys Thr Cys Val Ala Asp Glu
                725                 730                 735

Ser Ala Glu Asn Cys Asp Lys Ser Leu His Thr Leu Phe Gly Asp Lys
            740                 745                 750

Leu Cys Thr Val Ala Thr Leu Arg Glu Thr Tyr Gly Glu Met Ala Asp
            755                 760                 765

Cys Cys Ala Lys Gln Glu Pro Glu Arg Asn Glu Cys Phe Leu Gln His
            770                 775                 780

Lys Asp Asp Asn Pro Asn Leu Pro Arg Leu Val Arg Pro Glu Val Asp
785                 790                 795                 800

Val Met Cys Thr Ala Phe His Asp Asn Glu Glu Thr Phe Leu Lys Lys
                805                 810                 815

Tyr Leu Tyr Glu Ile Ala Arg Arg His Pro Tyr Phe Tyr Ala Pro Glu
            820                 825                 830

Leu Leu Phe Phe Ala Lys Arg Tyr Lys Ala Ala Phe Thr Glu Cys Cys
            835                 840                 845

Gln Ala Ala Asp Lys Ala Ala Cys Leu Leu Pro Lys Leu Asp Glu Leu
850                 855                 860

Arg Asp Glu Gly Lys Ala Ser Ser Ala Lys Gln Arg Leu Lys Cys Ala
865                 870                 875                 880

Ser Leu Gln Lys Phe Gly Glu Arg Ala Phe Lys Ala Trp Ala Val Ala
                885                 890                 895

Arg Leu Ser Gln Arg Phe Pro Lys Ala Glu Phe Ala Glu Val Ser Lys
            900                 905                 910

Leu Val Thr Asp Leu Thr Lys Val His Thr Glu Cys Cys His Gly Asp
            915                 920                 925

Leu Leu Glu Cys Ala Asp Asp Arg Ala Asp Leu Ala Lys Tyr Ile Cys
930                 935                 940

Glu Asn Gln Asp Ser Ile Ser Ser Lys Leu Lys Glu Cys Cys Glu Lys
945                 950                 955                 960

Pro Leu Leu Glu Lys Ser His Cys Ile Ala Glu Val Glu Asn Asp Glu
                965                 970                 975

Met Pro Ala Asp Leu Pro Ser Leu Ala Ala Asp Phe Val Glu Ser Lys
            980                 985                 990

Asp Val Cys Lys Asn Tyr Ala Glu Ala Lys Asp Val Phe Leu Gly Met
            995                 1000                1005

Phe Leu Tyr Glu Tyr Ala Arg Arg His Pro Asp Tyr Ser Val Val
    1010                1015                1020

Leu Leu Leu Arg Leu Ala Lys Thr Tyr Glu Thr Thr Leu Glu Lys
    1025                1030                1035

Cys Cys Ala Ala Ala Asp Pro His Glu Cys Tyr Ala Lys Val Phe
    1040                1045                1050

Asp Glu Phe Lys Pro Leu Val Glu Glu Pro Gln Asn Leu Ile Lys
    1055                1060                1065

Gln Asn Cys Glu Leu Phe Glu Gln Leu Gly Glu Tyr Lys Phe Gln
    1070                1075                1080
```

```
Asn Ala Leu Leu Val Arg Tyr Thr Lys Lys Val Pro Gln Val Ser
    1085                1090                1095

Thr Pro Thr Leu Val Glu Val Ser Arg Asn Leu Gly Lys Val Gly
    1100                1105                1110

Ser Lys Cys Cys Lys His Pro Glu Ala Lys Arg Met Pro Cys Ala
    1115                1120                1125

Glu Asp Tyr Leu Ser Val Val Leu Asn Gln Leu Cys Val Leu His
    1130                1135                1140

Glu Lys Thr Pro Val Ser Asp Arg Val Thr Lys Cys Cys Thr Glu
    1145                1150                1155

Ser Leu Val Asn Arg Arg Pro Cys Phe Ser Ala Leu Glu Val Asp
    1160                1165                1170

Glu Thr Tyr Val Pro Lys Glu Phe Asn Ala Glu Thr Phe Thr Phe
    1175                1180                1185

His Ala Asp Ile Cys Thr Leu Ser Glu Lys Glu Arg Gln Ile Lys
    1190                1195                1200

Lys Gln Thr Ala Leu Val Glu Leu Val Lys His Lys Pro Lys Ala
    1205                1210                1215

Thr Lys Glu Gln Leu Lys Ala Val Met Asp Asp Phe Ala Ala Phe
    1220                1225                1230

Val Glu Lys Cys Cys Lys Ala Asp Asp Lys Glu Thr Cys Phe Ala
    1235                1240                1245

Glu Glu Gly Pro Lys Leu Val Ala Ala Ser Gln Ala Ala Leu Gly
    1250                1255                1260

Leu His His His His His His Trp Ser His Pro Gln Phe Glu Lys
    1265                1270                1275

<210> SEQ ID NO 45
<211> LENGTH: 212
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 45

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

Gln Glu Asp Pro Glu Val Gln Phe Asn Trp Tyr Val Asp Gly Val Glu
        35                  40                  45

Val His Asn Ala Lys Thr Lys Pro Arg Glu Glu Gln Phe Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Gly Leu Pro Ser Ser
                85                  90                  95

Ile Glu Lys Thr Ile Ser Lys Ala Lys Gly Gln Pro Arg Glu Pro Gln
            100                 105                 110

Val Tyr Thr Lys Pro Pro Ser Gln Glu Glu Met Thr Lys Asn Gln Val
        115                 120                 125

Ser Leu Ser Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Val
```

```
                145                 150                 155                 160
Pro Val Leu Asp Ser Asp Gly Ser Phe Arg Leu Ala Ser Tyr Leu Thr
                    165                 170                 175

Val Asp Lys Ser Arg Trp Gln Glu Gly Asn Val Phe Ser Cys Ser Val
                    180                 185                 190

Met His Glu Ala Leu His Asn His Tyr Thr Gln Lys Ser Leu Ser Leu
                    195                 200                 205

Ser Leu Gly Lys
            210

<210> SEQ ID NO 46
<211> LENGTH: 543
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens
<220> FEATURE:
<223> OTHER INFORMATION: Yarrowia Lipolytica

<400> SEQUENCE: 46

Met Lys Leu Ser Thr Ile Leu Phe Thr Ala Cys Ala Thr Leu Ala Ala
1               5                   10                  15

Ala Ala Ser Glu Thr Gln Ala Asn Ser Thr Thr Asp Ala Leu Asn Val
                20                  25                  30

Leu Leu Ile Ile Val Asp Asp Leu Arg Pro Ser Leu Gly Cys Tyr Gly
            35                  40                  45

Asp Lys Leu Val Arg Ser Pro Asn Ile Asp Gln Leu Ala Ser His Ser
        50                  55                  60

Leu Leu Phe Gln Asn Ala Phe Ala Gln Ala Val Cys Ala Pro Ser
65                  70                  75                  80

Arg Val Ser Phe Leu Thr Gly Arg Arg Pro Asp Thr Thr Arg Leu Tyr
                85                  90                  95

Asp Phe Asn Ser Tyr Trp Arg Val His Ala Gly Asn Phe Ser Thr Ile
                100                 105                 110

Pro Gln Tyr Phe Lys Glu Asn Gly Tyr Val Thr Met Ser Val Gly Lys
                115                 120                 125

Val Phe His Pro Gly Ile Ser Ser Asn His Thr Asp Asp Ser Pro Tyr
            130                 135                 140

Ser Trp Ser Phe Pro Pro Tyr His Pro Ser Ser Glu Lys Tyr Glu Asn
145                 150                 155                 160

Thr Lys Thr Cys Arg Gly Pro Asp Gly Glu Leu His Ala Asn Leu Leu
                165                 170                 175

Cys Pro Val Asp Val Leu Asp Val Pro Glu Gly Thr Leu Pro Asp Lys
                180                 185                 190

Gln Ser Thr Glu Gln Ala Ile Gln Leu Leu Glu Lys Met Lys Thr Ser
                195                 200                 205

Ala Ser Pro Phe Phe Leu Ala Val Gly Tyr His Lys Pro His Ile Pro
            210                 215                 220

Phe Arg Tyr Pro Lys Glu Phe Gln Lys Leu Tyr Pro Leu Glu Asn Ile
225                 230                 235                 240

Thr Leu Ala Pro Asp Pro Glu Val Pro Asp Gly Leu Pro Pro Val Ala
                245                 250                 255

Tyr Asn Pro Trp Met Asp Ile Arg Gln Arg Glu Asp Val Gln Ala Leu
                260                 265                 270
```

```
Asn Ile Ser Val Pro Tyr Gly Pro Ile Pro Val Asp Phe Gln Arg Lys
            275                 280                 285

Ile Arg Gln Ser Tyr Phe Ala Ser Val Ser Tyr Leu Asp Thr Gln Val
    290                 295                 300

Gly Arg Leu Leu Ser Ala Leu Asp Asp Leu Gln Leu Ala Asn Ser Thr
305                 310                 315                 320

Ile Ile Ala Phe Thr Ser Asp His Gly Trp Ala Leu Gly Glu His Gly
                325                 330                 335

Glu Trp Ala Lys Tyr Ser Asn Phe Asp Val Ala Thr His Val Pro Leu
            340                 345                 350

Ile Phe Tyr Val Pro Gly Arg Thr Ala Ser Leu Pro Glu Ala Gly Glu
        355                 360                 365

Lys Leu Phe Pro Tyr Leu Asp Pro Phe Asp Ser Ala Ser Gln Leu Met
    370                 375                 380

Glu Pro Gly Arg Gln Ser Met Asp Leu Val Glu Leu Val Ser Leu Phe
385                 390                 395                 400

Pro Thr Leu Ala Gly Leu Ala Gly Leu Gln Val Pro Pro Arg Cys Pro
                405                 410                 415

Val Pro Ser Phe His Val Glu Leu Cys Arg Glu Gly Lys Asn Leu Leu
            420                 425                 430

Lys His Phe Arg Phe Arg Asp Leu Glu Glu Asp Pro Tyr Leu Pro Gly
        435                 440                 445

Asn Pro Arg Glu Leu Ile Ala Tyr Ser Gln Tyr Pro Arg Pro Ser Asp
    450                 455                 460

Ile Pro Gln Trp Asn Ser Asp Lys Pro Ser Leu Lys Asp Ile Lys Ile
465                 470                 475                 480

Met Gly Tyr Ser Ile Arg Thr Ile Asp Tyr Arg Tyr Thr Val Trp Val
                485                 490                 495

Gly Phe Asn Pro Asp Glu Phe Leu Ala Asn Phe Ser Asp Ile His Ala
            500                 505                 510

Gly Glu Leu Tyr Phe Val Asp Ser Asp Pro Leu Gln Asp His Asn Met
        515                 520                 525

Tyr Asn Asp Ser Gln Gly Gly Asp Leu Phe Gln Leu Leu Met Pro
    530                 535                 540

<210> SEQ ID NO 47
<211> LENGTH: 590
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 47

Gly Gly Gly Gly Ser Asp Ala His Lys Ser Glu Val Ala His Arg Phe
1               5                   10                  15

Lys Asp Leu Gly Glu Glu Asn Phe Lys Ala Leu Val Leu Ile Ala Phe
            20                  25                  30

Ala Gln Tyr Leu Gln Gln Cys Pro Phe Glu Asp His Val Lys Leu Val
        35                  40                  45

Asn Glu Val Thr Glu Phe Ala Lys Thr Cys Val Ala Asp Glu Ser Ala
    50                  55                  60

Glu Asn Cys Asp Lys Ser Leu His Thr Leu Phe Gly Asp Lys Leu Cys
65                  70                  75                  80

Thr Val Ala Thr Leu Arg Glu Thr Tyr Gly Glu Met Ala Asp Cys Cys
```

```
                              85                  90                  95
Ala Lys Gln Glu Pro Glu Arg Asn Glu Cys Phe Leu Gln His Lys Asp
            100                 105                 110

Asp Asn Pro Asn Leu Pro Arg Leu Val Arg Pro Glu Val Asp Val Met
            115                 120                 125

Cys Thr Ala Phe His Asp Asn Glu Glu Thr Phe Leu Lys Lys Tyr Leu
130                 135                 140

Tyr Glu Ile Ala Arg Arg His Pro Tyr Phe Tyr Ala Pro Glu Leu Leu
145                 150                 155                 160

Phe Phe Ala Lys Arg Tyr Lys Ala Ala Phe Thr Glu Cys Cys Gln Ala
            165                 170                 175

Ala Asp Lys Ala Ala Cys Leu Leu Pro Lys Leu Asp Glu Leu Arg Asp
            180                 185                 190

Glu Gly Lys Ala Ser Ser Ala Lys Gln Arg Leu Lys Cys Ala Ser Leu
            195                 200                 205

Gln Lys Phe Gly Glu Arg Ala Phe Lys Ala Trp Ala Val Ala Arg Leu
            210                 215                 220

Ser Gln Arg Phe Pro Lys Ala Glu Phe Ala Glu Val Ser Lys Leu Val
225                 230                 235                 240

Thr Asp Leu Thr Lys Val His Thr Glu Cys Cys His Gly Asp Leu Leu
            245                 250                 255

Glu Cys Ala Asp Asp Arg Ala Asp Leu Ala Lys Tyr Ile Cys Glu Asn
            260                 265                 270

Gln Asp Ser Ile Ser Ser Lys Leu Lys Glu Cys Cys Glu Lys Pro Leu
            275                 280                 285

Leu Glu Lys Ser His Cys Ile Ala Glu Val Glu Asn Asp Glu Met Pro
            290                 295                 300

Ala Asp Leu Pro Ser Leu Ala Ala Asp Phe Val Glu Ser Lys Asp Val
305                 310                 315                 320

Cys Lys Asn Tyr Ala Glu Ala Lys Asp Val Phe Leu Gly Met Phe Leu
            325                 330                 335

Tyr Glu Tyr Ala Arg Arg His Pro Asp Tyr Ser Val Val Leu Leu Leu
            340                 345                 350

Arg Leu Ala Lys Thr Tyr Glu Thr Thr Leu Glu Lys Cys Cys Ala Ala
            355                 360                 365

Ala Asp Pro His Glu Cys Tyr Ala Lys Val Phe Asp Glu Phe Lys Pro
            370                 375                 380

Leu Val Glu Glu Pro Gln Asn Leu Ile Lys Gln Asn Cys Glu Leu Phe
385                 390                 395                 400

Glu Gln Leu Gly Glu Tyr Lys Phe Gln Asn Ala Leu Leu Val Arg Tyr
            405                 410                 415

Thr Lys Lys Val Pro Gln Val Ser Thr Pro Thr Leu Val Glu Val Ser
            420                 425                 430

Arg Asn Leu Gly Lys Val Gly Ser Lys Cys Cys Lys His Pro Glu Ala
            435                 440                 445

Lys Arg Met Pro Cys Ala Glu Asp Tyr Leu Ser Val Val Leu Asn Gln
            450                 455                 460

Leu Cys Val Leu His Glu Lys Thr Pro Val Ser Asp Arg Val Thr Lys
465                 470                 475                 480

Cys Cys Thr Glu Ser Leu Val Asn Arg Arg Pro Cys Phe Ser Ala Leu
            485                 490                 495

Glu Val Asp Glu Thr Tyr Val Pro Lys Glu Phe Asn Ala Glu Thr Phe
            500                 505                 510
```

```
Thr Phe His Ala Asp Ile Cys Thr Leu Ser Glu Lys Glu Arg Gln Ile
            515                 520                 525

Lys Lys Gln Thr Ala Leu Val Glu Leu Val Lys His Lys Pro Lys Ala
        530                 535                 540

Thr Lys Glu Gln Leu Lys Ala Val Met Asp Asp Phe Ala Ala Phe Val
545                 550                 555                 560

Glu Lys Cys Cys Lys Ala Asp Asp Lys Glu Thr Cys Phe Ala Glu Glu
                565                 570                 575

Gly Pro Lys Leu Val Ala Ala Ser Gln Ala Ala Leu Gly Leu
            580                 585                 590

<210> SEQ ID NO 48
<211> LENGTH: 1292
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 48

Met Lys Leu Ser Thr Ile Leu Phe Thr Ala Cys Ala Thr Leu Ala Ala
1               5                   10                  15

Ala Glu Val Gln Leu Val Glu Ser Gly Gly Gly Leu Val Gln Pro Gly
            20                  25                  30

Gly Ser Leu Arg Leu Ser Cys Ala Ala Ser Glu Tyr Pro Ser Asn Phe
        35                  40                  45

Tyr Ala Met Ser Trp Phe Arg Gln Ala Pro Gly Lys Glu Arg Glu Phe
    50                  55                  60

Val Ser Gly Val Ser Arg Asp Gly Leu Thr Thr Leu Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Ile Val Ile Thr Gly Val Trp Asn Lys Val Asp Val Asn Ser
        115                 120                 125

Arg Ser Tyr His Tyr Trp Gly Gln Gly Thr Leu Val Thr Val Ser Ser
    130                 135                 140

Gly Gly Gly Gly Ser Gly Gly Gly Ser Gly Gly Gly Gly Ser Gly
145                 150                 155                 160

Gly Gly Gly Ser Gly Gly Gly Ser Ser Glu Thr Gln Ala Asn Ser
                165                 170                 175

Thr Thr Asp Ala Leu Asn Val Leu Leu Ile Ile Val Asp Asp Leu Arg
            180                 185                 190

Pro Ser Leu Gly Cys Tyr Gly Asp Lys Leu Val Arg Ser Pro Asn Ile
        195                 200                 205

Asp Gln Leu Ala Ser His Ser Leu Leu Phe Gln Asn Ala Phe Ala Gln
    210                 215                 220

Gln Ala Val Cys Ala Pro Ser Arg Val Ser Phe Leu Thr Gly Arg Arg
225                 230                 235                 240

Pro Asp Thr Thr Arg Leu Tyr Asp Phe Asn Ser Tyr Trp Arg Val His
                245                 250                 255
```

```
Ala Gly Asn Phe Ser Thr Ile Pro Gln Tyr Phe Lys Glu Asn Gly Tyr
            260                 265                 270

Val Thr Met Ser Val Gly Lys Val Phe His Pro Gly Ile Ser Ser Asn
        275                 280                 285

His Thr Asp Asp Ser Pro Tyr Ser Trp Ser Phe Pro Pro Tyr His Pro
    290                 295                 300

Ser Ser Glu Lys Tyr Glu Asn Thr Lys Thr Cys Arg Gly Pro Asp Gly
305                 310                 315                 320

Glu Leu His Ala Asn Leu Leu Cys Pro Val Asp Val Leu Asp Val Pro
                325                 330                 335

Glu Gly Thr Leu Pro Asp Lys Gln Ser Thr Glu Gln Ala Ile Gln Leu
            340                 345                 350

Leu Glu Lys Met Lys Thr Ser Ala Ser Pro Phe Phe Leu Ala Val Gly
        355                 360                 365

Tyr His Lys Pro His Ile Pro Phe Arg Tyr Pro Lys Glu Phe Gln Lys
    370                 375                 380

Leu Tyr Pro Leu Glu Asn Ile Thr Leu Ala Pro Asp Pro Glu Val Pro
385                 390                 395                 400

Asp Gly Leu Pro Pro Val Ala Tyr Asn Pro Trp Met Asp Ile Arg Gln
                405                 410                 415

Arg Glu Asp Val Gln Ala Leu Asn Ile Ser Val Pro Tyr Gly Pro Ile
            420                 425                 430

Pro Val Asp Phe Gln Arg Lys Ile Arg Gln Ser Tyr Phe Ala Ser Val
        435                 440                 445

Ser Tyr Leu Asp Thr Gln Val Gly Arg Leu Leu Ser Ala Leu Asp Asp
    450                 455                 460

Leu Gln Leu Ala Asn Ser Thr Ile Ile Ala Phe Thr Ser Asp His Gly
465                 470                 475                 480

Trp Ala Leu Gly Glu His Gly Glu Trp Ala Lys Tyr Ser Asn Phe Asp
                485                 490                 495

Val Ala Thr His Val Pro Leu Ile Phe Tyr Val Pro Gly Arg Thr Ala
            500                 505                 510

Ser Leu Pro Glu Ala Gly Glu Lys Leu Phe Pro Tyr Leu Asp Pro Phe
        515                 520                 525

Asp Ser Ala Ser Gln Leu Met Glu Pro Gly Arg Gln Ser Met Asp Leu
    530                 535                 540

Val Glu Leu Val Ser Leu Phe Pro Thr Leu Ala Gly Leu Ala Gly Leu
545                 550                 555                 560

Gln Val Pro Pro Arg Cys Pro Val Pro Ser Phe His Val Glu Leu Cys
                565                 570                 575

Arg Glu Gly Lys Asn Leu Leu Lys His Phe Arg Phe Arg Asp Leu Glu
            580                 585                 590

Glu Asp Pro Tyr Leu Pro Gly Asn Pro Arg Glu Leu Ile Ala Tyr Ser
        595                 600                 605

Gln Tyr Pro Arg Pro Ser Asp Ile Pro Gln Trp Asn Ser Asp Lys Pro
    610                 615                 620

Ser Leu Lys Asp Ile Lys Ile Met Gly Tyr Ser Ile Arg Thr Ile Asp
625                 630                 635                 640

Tyr Arg Tyr Thr Val Trp Val Gly Phe Asn Pro Asp Glu Phe Leu Ala
                645                 650                 655

Asn Phe Ser Asp Ile His Ala Gly Glu Leu Tyr Phe Val Asp Ser Asp
            660                 665                 670
```

-continued

```
Pro Leu Gln Asp His Asn Met Tyr Asn Asp Ser Gln Gly Gly Asp Leu
            675                 680                 685
Phe Gln Leu Leu Met Pro Gly Gly Gly Ser Asp Ala His Lys Ser
    690                 695                 700
Glu Val Ala His Arg Phe Lys Asp Leu Gly Glu Glu Asn Phe Lys Ala
705                 710                 715                 720
Leu Val Leu Ile Ala Phe Ala Gln Tyr Leu Gln Gln Cys Pro Phe Glu
                725                 730                 735
Asp His Val Lys Leu Val Asn Glu Val Thr Glu Phe Ala Lys Thr Cys
            740                 745                 750
Val Ala Asp Glu Ser Ala Glu Asn Cys Asp Lys Ser Leu His Thr Leu
        755                 760                 765
Phe Gly Asp Lys Leu Cys Thr Val Ala Thr Leu Arg Glu Thr Tyr Gly
    770                 775                 780
Glu Met Ala Asp Cys Cys Ala Lys Gln Glu Pro Glu Arg Asn Glu Cys
785                 790                 795                 800
Phe Leu Gln His Lys Asp Asp Asn Pro Asn Leu Pro Arg Leu Val Arg
                805                 810                 815
Pro Glu Val Asp Val Met Cys Thr Ala Phe His Asp Asn Glu Glu Thr
            820                 825                 830
Phe Leu Lys Lys Tyr Leu Tyr Glu Ile Ala Arg Arg His Pro Tyr Phe
        835                 840                 845
Tyr Ala Pro Glu Leu Leu Phe Phe Ala Lys Arg Tyr Lys Ala Ala Phe
    850                 855                 860
Thr Glu Cys Cys Gln Ala Ala Asp Lys Ala Ala Cys Leu Leu Pro Lys
865                 870                 875                 880
Leu Asp Glu Leu Arg Asp Glu Gly Lys Ala Ser Ser Ala Lys Gln Arg
                885                 890                 895
Leu Lys Cys Ala Ser Leu Gln Lys Phe Gly Glu Arg Ala Phe Lys Ala
            900                 905                 910
Trp Ala Val Ala Arg Leu Ser Gln Arg Phe Pro Lys Ala Glu Phe Ala
        915                 920                 925
Glu Val Ser Lys Leu Val Thr Asp Leu Thr Lys Val His Thr Glu Cys
    930                 935                 940
Cys His Gly Asp Leu Leu Glu Cys Ala Asp Asp Arg Ala Asp Leu Ala
945                 950                 955                 960
Lys Tyr Ile Cys Glu Asn Gln Asp Ser Ile Ser Ser Lys Leu Lys Glu
                965                 970                 975
Cys Cys Glu Lys Pro Leu Leu Glu Lys Ser His Cys Ile Ala Glu Val
            980                 985                 990
Glu Asn Asp Glu Met Pro Ala Asp Leu Pro Ser Leu Ala Ala Asp Phe
        995                 1000                1005
Val Glu Ser Lys Asp Val Cys Lys Asn Tyr Ala Glu Ala Lys Asp
    1010                1015                1020
Val Phe Leu Gly Met Phe Leu Tyr Glu Tyr Ala Arg Arg His Pro
    1025                1030                1035
Asp Tyr Ser Val Val Leu Leu Arg Leu Ala Lys Thr Tyr Glu
    1040                1045                1050
Thr Thr Leu Glu Lys Cys Cys Ala Ala Ala Asp Pro His Glu Cys
    1055                1060                1065
Tyr Ala Lys Val Phe Asp Glu Phe Lys Pro Leu Val Glu Glu Pro
    1070                1075                1080
Gln Asn Leu Ile Lys Gln Asn Cys Glu Leu Phe Glu Gln Leu Gly
```

-continued

```
                 1085                1090                1095

Glu Tyr Lys Phe Gln Asn Ala Leu Leu Val Arg Tyr Thr Lys Lys
            1100                1105                1110

Val Pro Gln Val Ser Thr Pro Thr Leu Val Glu Val Ser Arg Asn
        1115                1120                1125

Leu Gly Lys Val Gly Ser Lys Cys Cys Lys His Pro Glu Ala Lys
    1130                1135                1140

Arg Met Pro Cys Ala Glu Asp Tyr Leu Ser Val Val Leu Asn Gln
1145                1150                1155

Leu Cys Val Leu His Glu Lys Thr Pro Val Ser Asp Arg Val Thr
    1160                1165                1170

Lys Cys Cys Thr Glu Ser Leu Val Asn Arg Arg Pro Cys Phe Ser
        1175                1180                1185

Ala Leu Glu Val Asp Glu Thr Tyr Val Pro Lys Glu Phe Asn Ala
    1190                1195                1200

Glu Thr Phe Thr Phe His Ala Asp Ile Cys Thr Leu Ser Glu Lys
        1205                1210                1215

Glu Arg Gln Ile Lys Lys Gln Thr Ala Leu Val Glu Leu Val Lys
    1220                1225                1230

His Lys Pro Lys Ala Thr Lys Glu Gln Leu Lys Ala Val Met Asp
    1235                1240                1245

Asp Phe Ala Ala Phe Val Glu Lys Cys Cys Lys Ala Asp Asp Lys
    1250                1255                1260

Glu Thr Cys Phe Ala Glu Glu Gly Pro Lys Leu Val Ala Ala Ser
    1265                1270                1275

Gln Ala Ala Leu Gly Leu His His His His His His
    1280                1285                1290

<210> SEQ ID NO 49
<211> LENGTH: 852
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 49

Met Lys Leu Ser Thr Ile Leu Phe Thr Ala Cys Ala Thr Leu Ala Ala
1               5                   10                  15

Ala Glu Val Gln Leu Val Glu Ser Gly Gly Gly Leu Val Gln Pro Gly
            20                  25                  30

Gly Ser Leu Arg Leu Ser Cys Ala Ala Ser Glu Tyr Pro Ser Asn Phe
        35                  40                  45

Tyr Ala Met Ser Trp Phe Arg Gln Ala Pro Gly Lys Glu Arg Glu Phe
    50                  55                  60

Val Ser Gly Val Ser Arg Asp Gly Leu Thr Thr Leu Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Ile Val Ile Thr Gly Val Trp Asn Lys Val Asp Val Asn Ser
```

```
              115                 120                 125
Arg Ser Tyr His Tyr Trp Gly Gln Gly Thr Leu Val Thr Val Ser Ser
130                 135                 140
Gly Gly Gly Gly Ser Gly Gly Gly Ser Gly Gly Gly Ser Gly
145                 150                 155                 160
Gly Gly Gly Ser Gly Gly Gly Ser Ser Glu Thr Gln Ala Asn Ser
                    165                 170                 175
Thr Thr Asp Ala Leu Asn Val Leu Leu Ile Ile Val Asp Asp Leu Arg
            180                 185                 190
Pro Ser Leu Gly Cys Tyr Gly Asp Lys Leu Val Arg Ser Pro Asn Ile
            195                 200                 205
Asp Gln Leu Ala Ser His Ser Leu Leu Phe Gln Asn Ala Phe Ala Gln
            210                 215                 220
Gln Ala Val Cys Ala Pro Ser Arg Val Ser Phe Leu Thr Gly Arg Arg
225                 230                 235                 240
Pro Asp Thr Thr Arg Leu Tyr Asp Phe Asn Ser Tyr Trp Arg Val His
                    245                 250                 255
Ala Gly Asn Phe Ser Thr Ile Pro Gln Tyr Phe Lys Glu Asn Gly Tyr
                260                 265                 270
Val Thr Met Ser Val Gly Lys Val Phe His Pro Gly Ile Ser Ser Asn
            275                 280                 285
His Thr Asp Asp Ser Pro Tyr Ser Trp Ser Phe Pro Pro Tyr His Pro
            290                 295                 300
Ser Ser Glu Lys Tyr Glu Asn Thr Lys Thr Cys Arg Gly Pro Asp Gly
305                 310                 315                 320
Glu Leu His Ala Asn Leu Leu Cys Pro Val Asp Val Leu Asp Val Pro
                    325                 330                 335
Glu Gly Thr Leu Pro Asp Lys Gln Ser Thr Glu Gln Ala Ile Gln Leu
                340                 345                 350
Leu Glu Lys Met Lys Thr Ser Ala Ser Pro Phe Phe Leu Ala Val Gly
            355                 360                 365
Tyr His Lys Pro His Ile Pro Phe Arg Tyr Pro Lys Glu Phe Gln Lys
            370                 375                 380
Leu Tyr Pro Leu Glu Asn Ile Thr Leu Ala Pro Asp Pro Glu Val Pro
385                 390                 395                 400
Asp Gly Leu Pro Pro Val Ala Tyr Asn Pro Trp Met Asp Ile Arg Gln
                    405                 410                 415
Arg Glu Asp Val Gln Ala Leu Asn Ile Ser Val Pro Tyr Gly Pro Ile
                420                 425                 430
Pro Val Asp Phe Gln Arg Lys Ile Arg Gln Ser Tyr Phe Ala Ser Val
            435                 440                 445
Ser Tyr Leu Asp Thr Gln Val Gly Arg Leu Leu Ser Ala Leu Asp Asp
            450                 455                 460
Leu Gln Leu Ala Asn Ser Thr Ile Ile Ala Phe Thr Ser Asp His Gly
465                 470                 475                 480
Trp Ala Leu Gly Glu His Gly Glu Trp Ala Lys Tyr Ser Asn Phe Asp
                    485                 490                 495
Val Ala Thr His Val Pro Leu Ile Phe Tyr Val Pro Gly Arg Thr Ala
                500                 505                 510
Ser Leu Pro Glu Ala Gly Glu Lys Leu Phe Pro Tyr Leu Asp Pro Phe
            515                 520                 525
Asp Ser Ala Ser Gln Leu Met Glu Pro Gly Arg Gln Ser Met Asp Leu
            530                 535                 540
```

Val Glu Leu Val Ser Leu Phe Pro Thr Leu Ala Gly Leu Ala Gly Leu
545                 550                 555                 560

Gln Val Pro Pro Arg Cys Pro Val Pro Ser Phe His Val Glu Leu Cys
            565                 570                 575

Arg Glu Gly Lys Asn Leu Leu Lys His Phe Arg Phe Arg Asp Leu Glu
            580                 585                 590

Glu Asp Pro Tyr Leu Pro Gly Asn Pro Arg Glu Leu Ile Ala Tyr Ser
            595                 600                 605

Gln Tyr Pro Arg Pro Ser Asp Ile Pro Gln Trp Asn Ser Asp Lys Pro
            610                 615                 620

Ser Leu Lys Asp Ile Lys Ile Met Gly Tyr Ser Ile Arg Thr Ile Asp
625                 630                 635                 640

Tyr Arg Tyr Thr Val Trp Val Gly Phe Asn Pro Asp Glu Phe Leu Ala
                645                 650                 655

Asn Phe Ser Asp Ile His Ala Gly Glu Leu Tyr Phe Val Asp Ser Asp
            660                 665                 670

Pro Leu Gln Asp His Asn Met Tyr Asn Asp Ser Gln Gly Gly Asp Leu
            675                 680                 685

Phe Gln Leu Leu Met Pro Gly Gly Gly Ser Gly Gly Gly Ser
690                 695                 700

Gly Gly Gly Gly Ser Gly Gly Gly Ser Gly Gly Gly Ser Gln
705                 710                 715                 720

Val Gln Leu Val Glu Ser Gly Gly Leu Val Gln Ala Gly Ser
            725                 730                 735

Leu Arg Leu Ser Cys Val Ala Ser Gly Arg Thr Phe Ile Ala Tyr Ala
                740                 745                 750

Met Gly Trp Phe Arg Gln Ala Pro Gly Lys Glu Arg Glu Phe Val Ala
                755                 760                 765

Ala Ile Thr Asn Phe Ala Gly Gly Thr Thr Tyr Tyr Ala Asp Ser Val
770                 775                 780

Lys Gly Arg Phe Thr Ile Ser Arg Asp Asn Ala Lys Thr Thr Val Tyr
785                 790                 795                 800

Leu Gln Met Asn Ser Leu Lys Pro Glu Asp Thr Ala Leu Tyr Tyr Cys
            805                 810                 815

Ala Ala Asp Arg Ser Ala Gln Thr Met Arg Gln Val Arg Pro Val Leu
            820                 825                 830

Pro Tyr Trp Gly Gln Gly Thr Gln Val Thr Val Ser His His His His
            835                 840                 845

His His His His
    850

<210> SEQ ID NO 50
<211> LENGTH: 851
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 50

Met Lys Leu Ser Thr Ile Leu Phe Thr Ala Cys Ala Thr Leu Ala Ala
1               5                   10                  15

```
Ala Glu Val Gln Leu Val Glu Ser Gly Gly Leu Val Gln Pro Gly
            20                  25                  30

Gly Ser Leu Arg Leu Ser Cys Ala Ala Ser Glu Tyr Pro Ser Asn Phe
        35                  40                  45

Tyr Ala Met Ser Trp Phe Arg Gln Ala Pro Gly Lys Glu Arg Glu Phe
50                  55                  60

Val Ser Gly Val Ser Arg Asp Gly Leu Thr Thr Leu Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Ile Val Ile Thr Gly Val Trp Asn Lys Val Asp Val Asn Ser
        115                 120                 125

Arg Ser Tyr His Tyr Trp Gly Gln Gly Thr Leu Val Thr Val Ser Ser
130                 135                 140

Gly Gly Gly Gly Ser Gly Gly Gly Ser Gly Gly Gly Gly Ser Gly
145                 150                 155                 160

Gly Gly Gly Ser Gly Gly Gly Ser Ser Glu Thr Gln Ala Asn Ser
                165                 170                 175

Thr Thr Asp Ala Leu Asn Val Leu Leu Ile Ile Val Asp Asp Leu Arg
            180                 185                 190

Pro Ser Leu Gly Cys Tyr Gly Asp Lys Leu Val Arg Ser Pro Asn Ile
        195                 200                 205

Asp Gln Leu Ala Ser His Ser Leu Leu Phe Gln Asn Ala Phe Ala Gln
210                 215                 220

Gln Ala Val Cys Ala Pro Ser Arg Val Ser Phe Leu Thr Gly Arg Arg
225                 230                 235                 240

Pro Asp Thr Thr Arg Leu Tyr Asp Phe Asn Ser Tyr Trp Arg Val His
                245                 250                 255

Ala Gly Asn Phe Ser Thr Ile Pro Gln Tyr Phe Lys Glu Asn Gly Tyr
            260                 265                 270

Val Thr Met Ser Val Gly Lys Val Phe His Pro Gly Ile Ser Ser Asn
        275                 280                 285

His Thr Asp Asp Ser Pro Tyr Ser Trp Ser Phe Pro Pro Tyr His Pro
290                 295                 300

Ser Ser Glu Lys Tyr Glu Asn Thr Lys Thr Cys Arg Gly Pro Asp Gly
305                 310                 315                 320

Glu Leu His Ala Asn Leu Leu Cys Pro Val Asp Val Leu Asp Val Pro
                325                 330                 335

Glu Gly Thr Leu Pro Asp Lys Gln Ser Thr Glu Gln Ala Ile Gln Leu
            340                 345                 350

Leu Glu Lys Met Lys Thr Ser Ala Ser Pro Phe Phe Leu Ala Val Gly
        355                 360                 365

Tyr His Lys Pro His Ile Pro Phe Arg Tyr Pro Lys Glu Phe Gln Lys
370                 375                 380

Leu Tyr Pro Leu Glu Asn Ile Thr Leu Ala Pro Asp Pro Glu Val Pro
385                 390                 395                 400

Asp Gly Leu Pro Pro Val Ala Tyr Asn Pro Trp Met Asp Ile Arg Gln
                405                 410                 415

Arg Glu Asp Val Gln Ala Leu Asn Ile Ser Val Pro Tyr Gly Pro Ile
            420                 425                 430
```

```
Pro Val Asp Phe Gln Arg Lys Ile Arg Gln Ser Tyr Phe Ala Ser Val
        435                 440                 445

Ser Tyr Leu Asp Thr Gln Val Gly Arg Leu Leu Ser Ala Leu Asp Asp
    450                 455                 460

Leu Gln Leu Ala Asn Ser Thr Ile Ile Ala Phe Thr Ser Asp His Gly
465                 470                 475                 480

Trp Ala Leu Gly Glu His Gly Glu Trp Ala Lys Tyr Ser Asn Phe Asp
                485                 490                 495

Val Ala Thr His Val Pro Leu Ile Phe Tyr Val Pro Gly Arg Thr Ala
            500                 505                 510

Ser Leu Pro Glu Ala Gly Glu Lys Leu Phe Pro Tyr Leu Asp Pro Phe
    515                 520                 525

Asp Ser Ala Ser Gln Leu Met Glu Pro Gly Arg Gln Ser Met Asp Leu
    530                 535                 540

Val Glu Leu Val Ser Leu Phe Pro Thr Leu Ala Gly Leu Ala Gly Leu
545                 550                 555                 560

Gln Val Pro Pro Arg Cys Pro Val Pro Ser Phe His Val Glu Leu Cys
                565                 570                 575

Arg Glu Gly Lys Asn Leu Leu Lys His Phe Arg Phe Arg Asp Leu Glu
            580                 585                 590

Glu Asp Pro Tyr Leu Pro Gly Asn Pro Arg Glu Leu Ile Ala Tyr Ser
    595                 600                 605

Gln Tyr Pro Arg Pro Ser Asp Ile Pro Gln Trp Asn Ser Asp Lys Pro
    610                 615                 620

Ser Leu Lys Asp Ile Lys Ile Met Gly Tyr Ser Ile Arg Thr Ile Asp
625                 630                 635                 640

Tyr Arg Tyr Thr Val Trp Val Gly Phe Asn Pro Asp Glu Phe Leu Ala
                645                 650                 655

Asn Phe Ser Asp Ile His Ala Gly Glu Leu Tyr Phe Val Asp Ser Asp
            660                 665                 670

Pro Leu Gln Asp His Asn Met Tyr Asn Asp Ser Gln Gly Gly Asp Leu
    675                 680                 685

Phe Gln Leu Leu Met Pro Gly Gly Gly Ser Gly Gly Gly Ser
    690                 695                 700

Gly Gly Gly Gly Ser Gly Gly Gly Ser Gly Gly Gly Ser Gln
705                 710                 715                 720

Val Lys Leu Glu Glu Ser Gly Gly Leu Val Gln Ala Gly Ser
                725                 730                 735

Leu Lys Leu Ser Cys Ala Ala Ser Gly Ser Thr Phe Ser Ser Ser
                740                 745                 750

Val Gly Trp Tyr Arg Gln Ala Pro Gly Gln Gln Arg Glu Leu Val Ala
    755                 760                 765

Ala Ile Thr Ser Gly Gly Ser Thr Asn Thr Ala Asp Ser Val Lys Gly
    770                 775                 780

Arg Phe Thr Met Ser Arg Asp Asn Ala Lys Thr Val Tyr Leu Gln
785                 790                 795                 800

Met Arg Asp Leu Lys Pro Glu Asp Thr Ala Val Tyr Tyr Cys Asn Val
                805                 810                 815

Ala Gly Arg Asn Trp Val Pro Ile Ser Arg Tyr Ser Pro Gly Pro Tyr
            820                 825                 830

Trp Gly Gln Gly Thr Gln Val Thr Val Ser Ser His His His His
    835                 840                 845

His His His
```

<210> SEQ ID NO 51
<211> LENGTH: 559
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens
<220> FEATURE:
<223> OTHER INFORMATION: Yarrowia Lipolytica

<400> SEQUENCE: 51

```
Met Lys Leu Ser Thr Ile Leu Phe Thr Ala Cys Ala Thr Leu Ala Ala
1               5                   10                  15

Ala Ala Ser Glu Thr Gln Ala Asn Ser Thr Thr Asp Ala Leu Asn Val
            20                  25                  30

Leu Leu Ile Ile Val Asp Asp Leu Arg Pro Ser Leu Gly Cys Tyr Gly
        35                  40                  45

Asp Lys Leu Val Arg Ser Pro Asn Ile Asp Gln Leu Ala Ser His Ser
    50                  55                  60

Leu Leu Phe Gln Asn Ala Phe Ala Gln Ala Val Cys Ala Pro Ser
65                  70                  75                  80

Arg Val Ser Phe Leu Thr Gly Arg Arg Pro Asp Thr Thr Arg Leu Tyr
                85                  90                  95

Asp Phe Asn Ser Tyr Trp Arg Val His Ala Gly Asn Phe Ser Thr Ile
            100                 105                 110

Pro Gln Tyr Phe Lys Glu Asn Gly Tyr Val Thr Met Ser Val Gly Lys
        115                 120                 125

Val Phe His Pro Gly Ile Ser Ser Asn His Thr Asp Asp Ser Pro Tyr
    130                 135                 140

Ser Trp Ser Phe Pro Pro Tyr His Pro Ser Ser Glu Lys Tyr Glu Asn
145                 150                 155                 160

Thr Lys Thr Cys Arg Gly Pro Asp Gly Glu Leu His Ala Asn Leu Leu
                165                 170                 175

Cys Pro Val Asp Val Leu Asp Val Pro Glu Gly Thr Leu Pro Asp Lys
            180                 185                 190

Gln Ser Thr Glu Gln Ala Ile Gln Leu Leu Glu Lys Met Lys Thr Ser
        195                 200                 205

Ala Ser Pro Phe Phe Leu Ala Val Gly Tyr His Lys Pro His Ile Pro
    210                 215                 220

Phe Arg Tyr Pro Lys Glu Phe Gln Lys Leu Tyr Pro Leu Glu Asn Ile
225                 230                 235                 240

Thr Leu Ala Pro Asp Pro Glu Val Pro Asp Gly Leu Pro Pro Val Ala
                245                 250                 255

Tyr Asn Pro Trp Met Asp Ile Arg Gln Arg Glu Asp Val Gln Ala Leu
            260                 265                 270

Asn Ile Ser Val Pro Tyr Gly Pro Ile Pro Val Asp Phe Gln Arg Lys
        275                 280                 285

Ile Arg Gln Ser Tyr Phe Ala Ser Val Ser Tyr Leu Asp Thr Gln Val
    290                 295                 300

Gly Arg Leu Leu Ser Ala Leu Asp Asp Leu Gln Leu Ala Asn Ser Thr
305                 310                 315                 320

Ile Ile Ala Phe Thr Ser Asp His Gly Trp Ala Leu Gly Glu His Gly
                325                 330                 335
```

```
Glu Trp Ala Lys Tyr Ser Asn Phe Asp Val Ala Thr His Val Pro Leu
            340                 345                 350

Ile Phe Tyr Val Pro Gly Arg Thr Ala Ser Leu Pro Glu Ala Gly Glu
        355                 360                 365

Lys Leu Phe Pro Tyr Leu Asp Pro Phe Asp Ser Ala Ser Gln Leu Met
    370                 375                 380

Glu Pro Gly Arg Gln Ser Met Asp Leu Val Glu Leu Val Ser Leu Phe
385                 390                 395                 400

Pro Thr Leu Ala Gly Leu Ala Gly Leu Gln Val Pro Pro Arg Cys Pro
                405                 410                 415

Val Pro Ser Phe His Val Glu Leu Cys Arg Glu Gly Lys Asn Leu Leu
            420                 425                 430

Lys His Phe Arg Phe Arg Asp Leu Glu Glu Asp Pro Tyr Leu Pro Gly
        435                 440                 445

Asn Pro Arg Glu Leu Ile Ala Tyr Ser Gln Tyr Pro Arg Pro Ser Asp
    450                 455                 460

Ile Pro Gln Trp Asn Ser Asp Lys Pro Ser Leu Lys Asp Ile Lys Ile
465                 470                 475                 480

Met Gly Tyr Ser Ile Arg Thr Ile Asp Tyr Arg Tyr Thr Val Trp Val
                485                 490                 495

Gly Phe Asn Pro Asp Glu Phe Leu Ala Asn Phe Ser Asp Ile His Ala
            500                 505                 510

Gly Glu Leu Tyr Phe Val Asp Ser Asp Pro Leu Gln Asp His Asn Met
        515                 520                 525

Tyr Asn Asp Ser Gln Gly Gly Asp Leu Phe Gln Leu Leu Met Pro His
    530                 535                 540

His His His His His His Trp Ser His Pro Gln Phe Glu Lys
545                 550                 555

<210> SEQ ID NO 52
<211> LENGTH: 685
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 52

Met Lys Leu Ser Thr Ile Leu Phe Thr Ala Cys Ala Thr Leu Ala Ala
1               5                   10                  15

Ala Glu Val Gln Leu Gln Ala Ser Gly Gly Gly Leu Val Gln Ala Gly
            20                  25                  30

Gly Ser Leu Arg Leu Ser Cys Ala Ala Ser Gly Phe Lys Ile Thr His
        35                  40                  45

Tyr Thr Met Gly Trp Phe Arg Gln Ala Pro Gly Lys Glu Arg Glu Phe
    50                  55                  60

Val Ser Arg Ile Thr Trp Gly Gly Asp Asn Thr Phe Tyr Ser Asn Ser
65                  70                  75                  80

Val Lys Gly Arg Phe Thr Ile Ser Arg Asp Asn Ala Lys Asn Thr Val
                85                  90                  95

Tyr Leu Gln Met Asn Ser Leu Lys Pro Glu Asp Thr Ala Asp Tyr Tyr
            100                 105                 110
```

-continued

Cys Ala Ala Gly Ser Thr Ser Thr Ala Thr Pro Leu Arg Val Asp Tyr
        115                 120                 125

Trp Gly Lys Gly Thr Gln Val Thr Val Ser Ser Gly Gly Gly Gly Ser
        130                 135                 140

Ser Glu Thr Gln Ala Asn Ser Thr Thr Asp Ala Leu Asn Val Leu Leu
145                 150                 155                 160

Ile Ile Val Asp Asp Leu Arg Pro Ser Leu Gly Cys Tyr Gly Asp Lys
                165                 170                 175

Leu Val Arg Ser Pro Asn Ile Asp Gln Leu Ala Ser His Ser Leu Leu
            180                 185                 190

Phe Gln Asn Ala Phe Ala Gln Gln Ala Val Cys Ala Pro Ser Arg Val
        195                 200                 205

Ser Phe Leu Thr Gly Arg Arg Pro Asp Thr Thr Arg Leu Tyr Asp Phe
    210                 215                 220

Asn Ser Tyr Trp Arg Val His Ala Gly Asn Phe Ser Thr Ile Pro Gln
225                 230                 235                 240

Tyr Phe Lys Glu Asn Gly Tyr Val Thr Met Ser Val Gly Lys Val Phe
                245                 250                 255

His Pro Gly Ile Ser Ser Asn His Thr Asp Asp Ser Pro Tyr Ser Trp
            260                 265                 270

Ser Phe Pro Pro Tyr His Pro Ser Ser Glu Lys Tyr Glu Asn Thr Lys
        275                 280                 285

Thr Cys Arg Gly Pro Asp Gly Glu Leu His Ala Asn Leu Leu Cys Pro
    290                 295                 300

Val Asp Val Leu Asp Val Pro Glu Gly Thr Leu Pro Asp Lys Gln Ser
305                 310                 315                 320

Thr Glu Gln Ala Ile Gln Leu Leu Glu Lys Met Lys Thr Ser Ala Ser
                325                 330                 335

Pro Phe Phe Leu Ala Val Gly Tyr His Lys Pro His Ile Pro Phe Arg
            340                 345                 350

Tyr Pro Lys Glu Phe Gln Lys Leu Tyr Pro Leu Glu Asn Ile Thr Leu
        355                 360                 365

Ala Pro Asp Pro Glu Val Pro Asp Gly Leu Pro Pro Val Ala Tyr Asn
    370                 375                 380

Pro Trp Met Asp Ile Arg Gln Arg Glu Asp Val Gln Ala Leu Asn Ile
385                 390                 395                 400

Ser Val Pro Tyr Gly Pro Ile Pro Val Asp Phe Gln Arg Lys Ile Arg
                405                 410                 415

Gln Ser Tyr Phe Ala Ser Val Ser Tyr Leu Asp Thr Gln Val Gly Arg
            420                 425                 430

Leu Leu Ser Ala Leu Asp Asp Leu Gln Leu Ala Asn Ser Thr Ile Ile
        435                 440                 445

Ala Phe Thr Ser Asp His Gly Trp Ala Leu Gly Glu His Gly Glu Trp
    450                 455                 460

Ala Lys Tyr Ser Asn Phe Asp Val Ala Thr His Val Pro Leu Ile Phe
465                 470                 475                 480

Tyr Val Pro Gly Arg Thr Ala Ser Leu Pro Glu Ala Gly Glu Lys Leu
                485                 490                 495

Phe Pro Tyr Leu Asp Pro Phe Asp Ser Ala Ser Gln Leu Met Glu Pro
            500                 505                 510

Gly Arg Gln Ser Met Asp Leu Val Glu Leu Val Ser Leu Phe Pro Thr
        515                 520                 525

Leu Ala Gly Leu Ala Gly Leu Gln Val Pro Pro Arg Cys Pro Val Pro

-continued

```
            530             535             540
Ser Phe His Val Glu Leu Cys Arg Glu Gly Lys Asn Leu Leu Lys His
545                 550                 555                 560

Phe Arg Phe Arg Asp Leu Glu Glu Asp Pro Tyr Leu Pro Gly Asn Pro
                565                 570                 575

Arg Glu Leu Ile Ala Tyr Ser Gln Tyr Pro Arg Pro Ser Asp Ile Pro
                580                 585                 590

Gln Trp Asn Ser Asp Lys Pro Ser Leu Lys Asp Ile Lys Ile Met Gly
                595                 600                 605

Tyr Ser Ile Arg Thr Ile Asp Tyr Arg Tyr Thr Val Trp Val Gly Phe
                610                 615                 620

Asn Pro Asp Glu Phe Leu Ala Asn Phe Ser Asp Ile His Ala Gly Glu
625                 630                 635                 640

Leu Tyr Phe Val Asp Ser Asp Pro Leu Gln Asp His Asn Met Tyr Asn
                645                 650                 655

Asp Ser Gln Gly Gly Asp Leu Phe Gln Leu Leu Met Pro His His His
                660                 665                 670

His His His His His Trp Ser His Pro Gln Phe Glu Lys
                675                 680                 685

<210> SEQ ID NO 53
<211> LENGTH: 710
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 53

Met Lys Leu Ser Thr Ile Leu Phe Thr Ala Cys Ala Thr Leu Ala Ala
1               5                   10                  15

Ala Glu Val Gln Leu Val Glu Ser Gly Gly Gly Leu Val Gln Pro Gly
                20                  25                  30

Gly Ser Leu Arg Leu Ser Cys Ala Ala Ser Glu Tyr Pro Ser Asn Phe
                35                  40                  45

Tyr Ala Met Ser Trp Phe Arg Gln Ala Pro Gly Lys Glu Arg Glu Phe
                50                  55                  60

Val Ser Gly Val Ser Arg Asp Gly Leu Thr Thr Leu Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
                100                 105                 110

Cys Ala Ile Val Ile Thr Gly Val Trp Asn Lys Val Asp Val Asn Ser
                115                 120                 125

Arg Ser Tyr His Tyr Trp Gly Gln Gly Thr Leu Val Thr Val Ser Ser
                130                 135                 140

Gly Gly Gly Gly Ser Gly Gly Gly Gly Ser Gly Gly Gly Gly Ser Gly
145                 150                 155                 160

Gly Gly Ser Gly Gly Gly Ser Ser Glu Thr Gln Ala Asn Ser
                165                 170                 175

Thr Thr Asp Ala Leu Asn Val Leu Leu Ile Ile Val Asp Asp Leu Arg
```

```
            180                 185                 190
Pro Ser Leu Gly Cys Tyr Gly Asp Lys Leu Val Arg Ser Pro Asn Ile
            195                 200                 205

Asp Gln Leu Ala Ser His Ser Leu Leu Phe Gln Asn Ala Phe Ala Gln
    210                 215                 220

Gln Ala Val Cys Ala Pro Ser Arg Val Ser Phe Leu Thr Gly Arg Arg
225                 230                 235                 240

Pro Asp Thr Thr Arg Leu Tyr Asp Phe Asn Ser Tyr Trp Arg Val His
                245                 250                 255

Ala Gly Asn Phe Ser Thr Ile Pro Gln Tyr Phe Lys Glu Asn Gly Tyr
            260                 265                 270

Val Thr Met Ser Val Gly Lys Val Phe His Pro Gly Ile Ser Ser Asn
        275                 280                 285

His Thr Asp Asp Ser Pro Tyr Ser Trp Ser Phe Pro Pro Tyr His Pro
    290                 295                 300

Ser Ser Glu Lys Tyr Glu Asn Thr Lys Thr Cys Arg Gly Pro Asp Gly
305                 310                 315                 320

Glu Leu His Ala Asn Leu Leu Cys Pro Val Asp Val Leu Asp Val Pro
                325                 330                 335

Glu Gly Thr Leu Pro Asp Lys Gln Ser Thr Glu Gln Ala Ile Gln Leu
            340                 345                 350

Leu Glu Lys Met Lys Thr Ser Ala Ser Pro Phe Phe Leu Ala Val Gly
        355                 360                 365

Tyr His Lys Pro His Ile Pro Phe Arg Tyr Pro Lys Glu Phe Gln Lys
    370                 375                 380

Leu Tyr Pro Leu Glu Asn Ile Thr Leu Ala Pro Asp Pro Glu Val Pro
385                 390                 395                 400

Asp Gly Leu Pro Pro Val Ala Tyr Asn Pro Trp Met Asp Ile Arg Gln
                405                 410                 415

Arg Glu Asp Val Gln Ala Leu Asn Ile Ser Val Pro Tyr Gly Pro Ile
            420                 425                 430

Pro Val Asp Phe Gln Arg Lys Ile Arg Gln Ser Tyr Phe Ala Ser Val
        435                 440                 445

Ser Tyr Leu Asp Thr Gln Val Gly Arg Leu Leu Ser Ala Leu Asp Asp
    450                 455                 460

Leu Gln Leu Ala Asn Ser Thr Ile Ile Ala Phe Thr Ser Asp His Gly
465                 470                 475                 480

Trp Ala Leu Gly Glu His Gly Glu Trp Ala Lys Tyr Ser Asn Phe Asp
                485                 490                 495

Val Ala Thr His Val Pro Leu Ile Phe Tyr Val Pro Gly Arg Thr Ala
            500                 505                 510

Ser Leu Pro Glu Ala Gly Glu Lys Leu Phe Pro Tyr Leu Asp Pro Phe
        515                 520                 525

Asp Ser Ala Ser Gln Leu Met Glu Pro Gly Arg Gln Ser Met Asp Leu
    530                 535                 540

Val Glu Leu Val Ser Leu Phe Pro Thr Leu Ala Gly Leu Ala Gly Leu
545                 550                 555                 560

Gln Val Pro Pro Arg Cys Pro Val Pro Ser Phe His Val Glu Leu Cys
                565                 570                 575

Arg Glu Gly Lys Asn Leu Leu Lys His Phe Arg Phe Arg Asp Leu Glu
            580                 585                 590

Glu Asp Pro Tyr Leu Pro Gly Asn Pro Arg Glu Leu Ile Ala Tyr Ser
        595                 600                 605
```

-continued

Gln Tyr Pro Arg Pro Ser Asp Ile Pro Gln Trp Asn Ser Asp Lys Pro
610                 615                 620

Ser Leu Lys Asp Ile Lys Ile Met Gly Tyr Ser Ile Arg Thr Ile Asp
625                 630                 635                 640

Tyr Arg Tyr Thr Val Trp Val Gly Phe Asn Pro Asp Glu Phe Leu Ala
            645                 650                 655

Asn Phe Ser Asp Ile His Ala Gly Glu Leu Tyr Phe Val Asp Ser Asp
            660                 665                 670

Pro Leu Gln Asp His Asn Met Tyr Asn Asp Ser Gln Gly Gly Asp Leu
        675                 680                 685

Phe Gln Leu Leu Met Pro His His His His His His His Trp Ser
690                 695                 700

His Pro Gln Phe Glu Lys
705                 710

<210> SEQ ID NO 54
<211> LENGTH: 707
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 54

Met Lys Leu Ser Thr Ile Leu Phe Thr Ala Cys Ala Thr Leu Ala Ala
1               5                   10                  15

Ala Gln Val Gln Leu Val Glu Ser Gly Gly Gly Leu Val Gln Pro Gly
            20                  25                  30

Gly Ser Leu Arg Leu Ser Cys Ala Ala Ser Gly Arg Thr Ile Asp Asn
        35                  40                  45

Tyr Ala Met Ala Trp Val Arg Gln Ala Pro Gly Lys Gly Leu Glu Trp
    50                  55                  60

Val Ala Thr Ile Asp Trp Gly Asp Gly Gly Thr Arg Tyr Ala Asn Ser
65                  70                  75                  80

Val Lys Gly Arg Phe Thr Ile Ser Arg Asp Asn Ser Lys Asn Thr Met
                85                  90                  95

Tyr Leu Gln Met Asn Ser Leu Arg Ala Glu Asp Thr Ala Val Tyr Tyr
            100                 105                 110

Cys Ala Met Ala Arg Gln Ser Arg Val Asn Leu Asp Val Ala Arg Tyr
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gly Gly Gly Ser Ser Glu Thr Gln Ala Asn Ser Thr Thr Asp
                165                 170                 175

Ala Leu Asn Val Leu Leu Ile Ile Val Asp Asp Leu Arg Pro Ser Leu
            180                 185                 190

Gly Cys Tyr Gly Asp Lys Leu Val Arg Ser Pro Asn Ile Asp Gln Leu
        195                 200                 205

Ala Ser His Ser Leu Leu Phe Gln Asn Ala Phe Ala Gln Gln Ala Val
    210                 215                 220

```
Cys Ala Pro Ser Arg Val Ser Phe Leu Thr Gly Arg Pro Asp Thr
225                 230                 235                 240

Thr Arg Leu Tyr Asp Phe Asn Ser Tyr Trp Arg Val His Ala Gly Asn
            245                 250                 255

Phe Ser Thr Ile Pro Gln Tyr Phe Lys Glu Asn Gly Tyr Val Thr Met
                260                 265                 270

Ser Val Gly Lys Val Phe His Pro Gly Ile Ser Ser Asn His Thr Asp
            275                 280                 285

Asp Ser Pro Tyr Ser Trp Ser Phe Pro Tyr His Pro Ser Ser Glu
    290                 295                 300

Lys Tyr Glu Asn Thr Lys Thr Cys Arg Gly Pro Asp Gly Glu Leu His
305                 310                 315                 320

Ala Asn Leu Leu Cys Pro Val Asp Val Leu Asp Val Pro Glu Gly Thr
                325                 330                 335

Leu Pro Asp Lys Gln Ser Thr Glu Gln Ala Ile Gln Leu Leu Glu Lys
            340                 345                 350

Met Lys Thr Ser Ala Ser Pro Phe Leu Ala Val Gly Tyr His Lys
    355                 360                 365

Pro His Ile Pro Phe Arg Tyr Pro Lys Glu Phe Gln Lys Leu Tyr Pro
370                 375                 380

Leu Glu Asn Ile Thr Leu Ala Pro Asp Pro Glu Val Pro Asp Gly Leu
385                 390                 395                 400

Pro Pro Val Ala Tyr Asn Pro Trp Met Asp Ile Arg Gln Arg Glu Asp
                405                 410                 415

Val Gln Ala Leu Asn Ile Ser Val Pro Tyr Gly Pro Ile Pro Val Asp
                420                 425                 430

Phe Gln Arg Lys Ile Arg Gln Ser Tyr Phe Ala Ser Val Ser Tyr Leu
            435                 440                 445

Asp Thr Gln Val Gly Arg Leu Leu Ser Ala Leu Asp Asp Leu Gln Leu
    450                 455                 460

Ala Asn Ser Thr Ile Ile Ala Phe Thr Ser Asp His Gly Trp Ala Leu
465                 470                 475                 480

Gly Glu His Gly Glu Trp Ala Lys Tyr Ser Asn Phe Asp Val Ala Thr
                485                 490                 495

His Val Pro Leu Ile Phe Tyr Val Pro Gly Arg Thr Ala Ser Leu Pro
                500                 505                 510

Glu Ala Gly Glu Lys Leu Phe Pro Tyr Leu Asp Pro Phe Asp Ser Ala
            515                 520                 525

Ser Gln Leu Met Glu Pro Gly Arg Gln Ser Met Asp Leu Val Glu Leu
    530                 535                 540

Val Ser Leu Phe Pro Thr Leu Ala Gly Leu Ala Gly Leu Gln Val Pro
545                 550                 555                 560

Pro Arg Cys Pro Val Pro Ser Phe His Val Glu Leu Cys Arg Glu Gly
                565                 570                 575

Lys Asn Leu Leu Lys His Phe Arg Phe Arg Asp Leu Glu Glu Asp Pro
                580                 585                 590

Tyr Leu Pro Gly Asn Pro Arg Glu Leu Ile Ala Tyr Ser Gln Tyr Pro
            595                 600                 605

Arg Pro Ser Asp Ile Pro Gln Trp Asn Ser Asp Lys Pro Ser Leu Lys
    610                 615                 620

Asp Ile Lys Ile Met Gly Tyr Ser Ile Arg Thr Ile Asp Tyr Arg Tyr
625                 630                 635                 640
```

-continued

```
Thr Val Trp Val Gly Phe Asn Pro Asp Glu Phe Leu Ala Asn Phe Ser
                645                 650                 655

Asp Ile His Ala Gly Glu Leu Tyr Phe Val Asp Ser Asp Pro Leu Gln
            660                 665                 670

Asp His Asn Met Tyr Asn Asp Ser Gln Gly Gly Asp Leu Phe Gln Leu
        675                 680                 685

Leu Met Pro His His His His His His His Trp Ser His Pro Gln
690                 695                 700

Phe Glu Lys
705

<210> SEQ ID NO 55
<211> LENGTH: 674
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 55

Met Lys Leu Ser Thr Ile Leu Phe Thr Ala Cys Ala Thr Leu Ala Ala
1               5                   10                  15

Ala Glu Val Gln Leu Val Glu Ser Gly Gly Gly Leu Val Gln Pro Gly
            20                  25                  30

Gly Ser Leu Arg Leu Ser Cys Ala Ala Ser Glu Tyr Pro Ser Asn Phe
        35                  40                  45

Tyr Ala Met Ser Trp Phe Arg Gln Ala Pro Gly Lys Glu Arg Glu Phe
    50                  55                  60

Val Ser Gly Val Ser Arg Asp Gly Leu Thr Thr Leu Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Ile Val Ile Thr Gly Val Trp Asn Lys Val Asp Val Asn Ser
        115                 120                 125

Arg Ser Tyr His Tyr Trp Gly Gln Gly Thr Leu Val Thr Val Ser Ser
    130                 135                 140

Gly Gly Gly Gly Ser Gly Gly Gly Ser Gly Gly Gly Gly Ser Gly
145                 150                 155                 160

Gly Gly Gly Ser Gly Gly Gly Ser Ala Arg Pro Cys Ile Pro Lys
                165                 170                 175

Ser Phe Gly Tyr Ser Ser Val Val Cys Val Cys Asn Ala Thr Tyr Cys
            180                 185                 190

Asp Ser Phe Asp Pro Pro Thr Phe Pro Ala Leu Gly Thr Phe Ser Arg
        195                 200                 205

Tyr Glu Ser Thr Arg Ser Gly Arg Arg Met Glu Leu Ser Met Gly Pro
    210                 215                 220

Ile Gln Ala Asn His Thr Gly Thr Gly Leu Leu Leu Thr Leu Gln Pro
225                 230                 235                 240

Glu Gln Lys Phe Gln Lys Val Lys Gly Phe Gly Gly Ala Met Thr Asp
                245                 250                 255
```

```
Ala Ala Ala Leu Asn Ile Leu Ala Leu Ser Pro Pro Ala Gln Asn Leu
            260                 265                 270

Leu Leu Lys Ser Tyr Phe Ser Glu Glu Gly Ile Gly Tyr Asn Ile Ile
        275                 280                 285

Arg Val Pro Met Ala Ser Cys Asp Phe Ser Ile Arg Thr Tyr Thr Tyr
    290                 295                 300

Ala Asp Thr Pro Asp Asp Phe Gln Leu Leu Asn Phe Ser Leu Pro Glu
305                 310                 315                 320

Glu Asp Thr Lys Leu Lys Ile Pro Leu Ile His Arg Ala Leu Gln Leu
                325                 330                 335

Ala Gln Arg Pro Val Ser Leu Leu Ala Ser Pro Trp Thr Ser Pro Thr
            340                 345                 350

Trp Leu Lys Thr Asn Gly Ala Val Asn Gly Lys Gly Ser Leu Lys Gly
        355                 360                 365

Gln Pro Gly Asp Ile Tyr His Gln Thr Trp Ala Arg Tyr Phe Val Lys
    370                 375                 380

Phe Leu Asp Ala Tyr Ala Glu His Lys Leu Gln Phe Trp Ala Val Thr
385                 390                 395                 400

Ala Glu Asn Glu Pro Ser Ala Gly Leu Leu Ser Gly Tyr Pro Phe Gln
                405                 410                 415

Cys Leu Gly Phe Thr Pro Glu His Gln Arg Asp Phe Ile Ala Arg Asp
            420                 425                 430

Leu Gly Pro Thr Leu Ala Asn Ser Thr His His Asn Val Arg Leu Leu
        435                 440                 445

Met Leu Asp Asp Gln Arg Leu Leu Leu Pro His Trp Ala Lys Val Val
    450                 455                 460

Leu Thr Asp Pro Glu Ala Ala Lys Tyr Val His Gly Ile Ala Val His
465                 470                 475                 480

Trp Tyr Leu Asp Phe Leu Ala Pro Ala Asn Ala Thr Leu Gly Glu Thr
                485                 490                 495

His Arg Leu Phe Pro Asn Thr Met Leu Phe Ala Ser Glu Ala Cys Val
            500                 505                 510

Gly Ser Lys Phe Trp Glu Gln Ser Val Arg Leu Gly Ser Trp Asp Arg
        515                 520                 525

Gly Met Gln Tyr Ser His Ser Ile Ile Thr Asn Leu Leu Tyr His Val
    530                 535                 540

Val Gly Trp Thr Asp Trp Asn Leu Ala Leu Asn Pro Glu Gly Gly Pro
545                 550                 555                 560

Asn Trp Val Arg Asn Phe Val Asp Ser Pro Ile Ile Val Asp Ile Thr
                565                 570                 575

Lys Asp Thr Phe Tyr Lys Gln Pro Met Phe Tyr His Leu Gly His Phe
            580                 585                 590

Ser Lys Phe Ile Pro Glu Gly Ser Gln Arg Val Gly Leu Val Ala Ser
        595                 600                 605

Gln Lys Asn Asp Leu Asp Ala Val Ala Leu Met His Pro Asp Gly Ser
    610                 615                 620

Ala Val Val Val Leu Asn Arg Ser Ser Lys Asp Val Pro Leu Thr
625                 630                 635                 640

Ile Lys Asp Pro Ala Val Gly Phe Leu Glu Thr Ile Ser Pro Gly Tyr
                645                 650                 655

Ser Ile His Thr Tyr Leu Trp Arg Arg Gln His His His His His His
            660                 665                 670

His His
```

```
<210> SEQ ID NO 56
<211> LENGTH: 842
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 56
```

Met Lys Leu Ser Thr Ile Leu Phe Thr Ala Cys Ala Thr Leu Ala Ala
1               5                   10                  15

Ala Glu Val Gln Leu Val Glu Ser Gly Gly Leu Val Gln Pro Gly
            20                  25                  30

Gly Ser Leu Arg Leu Ser Cys Ala Ala Ser Glu Tyr Pro Ser Asn Phe
        35                  40                  45

Tyr Ala Met Ser Trp Phe Arg Gln Ala Pro Gly Lys Glu Arg Glu Phe
50                  55                  60

Val Ser Gly Val Ser Arg Asp Gly Leu Thr Thr Leu Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Ile Val Ile Thr Gly Val Trp Asn Lys Val Asp Val Asn Ser
        115                 120                 125

Arg Ser Tyr His Tyr Trp Gly Gln Gly Thr Leu Val Thr Val Ser Ser
130                 135                 140

Gly Gly Gly Gly Ser Gly Gly Gly Ser Gly Gly Gly Gly Ser
145                 150                 155                 160

Gly Gly Gly Ser Gly Gly Gly Ser Ser Glu Thr Gln Ala Asn Ser
                165                 170                 175

Thr Thr Asp Ala Leu Asn Val Leu Leu Ile Ile Val Asp Asp Leu Arg
            180                 185                 190

Pro Ser Leu Gly Cys Tyr Gly Asp Lys Leu Val Arg Ser Pro Asn Ile
        195                 200                 205

Asp Gln Leu Ala Ser His Ser Leu Leu Phe Gln Asn Ala Phe Ala Gln
210                 215                 220

Gln Ala Val Cys Ala Pro Ser Arg Val Ser Phe Leu Thr Gly Arg Arg
225                 230                 235                 240

Pro Asp Thr Thr Arg Leu Tyr Asp Phe Asn Ser Tyr Trp Arg Val His
                245                 250                 255

Ala Gly Asn Phe Ser Thr Ile Pro Gln Tyr Phe Lys Glu Asn Gly Tyr
            260                 265                 270

Val Thr Met Ser Val Gly Lys Val Phe His Pro Gly Ile Ser Ser Asn
        275                 280                 285

His Thr Asp Asp Ser Pro Tyr Ser Trp Ser Phe Pro Pro Tyr His Pro
290                 295                 300

Ser Ser Glu Lys Tyr Glu Asn Thr Lys Thr Cys Arg Gly Pro Asp Gly
305                 310                 315                 320

Glu Leu His Ala Asn Leu Leu Cys Pro Val Asp Val Leu Asp Val Pro
                325                 330                 335

```
Glu Gly Thr Leu Pro Asp Lys Gln Ser Thr Glu Gln Ala Ile Gln Leu
            340                 345                 350

Leu Glu Lys Met Lys Thr Ser Ala Ser Pro Phe Phe Leu Ala Val Gly
        355                 360                 365

Tyr His Lys Pro His Ile Pro Phe Arg Tyr Pro Lys Glu Phe Gln Lys
    370                 375                 380

Leu Tyr Pro Leu Glu Asn Ile Thr Leu Ala Pro Asp Pro Glu Val Pro
385                 390                 395                 400

Asp Gly Leu Pro Pro Val Ala Tyr Asn Pro Trp Met Asp Ile Arg Gln
                405                 410                 415

Arg Glu Asp Val Gln Ala Leu Asn Ile Ser Val Pro Tyr Gly Pro Ile
            420                 425                 430

Pro Val Asp Phe Gln Arg Lys Ile Arg Gln Ser Tyr Phe Ala Ser Val
        435                 440                 445

Ser Tyr Leu Asp Thr Gln Val Gly Arg Leu Leu Ser Ala Leu Asp Asp
    450                 455                 460

Leu Gln Leu Ala Asn Ser Thr Ile Ile Ala Phe Thr Ser Asp His Gly
465                 470                 475                 480

Trp Ala Leu Gly Glu His Gly Glu Trp Ala Lys Tyr Ser Asn Phe Asp
                485                 490                 495

Val Ala Thr His Val Pro Leu Ile Phe Tyr Val Pro Gly Arg Thr Ala
            500                 505                 510

Ser Leu Pro Glu Ala Gly Glu Lys Leu Phe Pro Tyr Leu Asp Pro Phe
        515                 520                 525

Asp Ser Ala Ser Gln Leu Met Glu Pro Gly Arg Gln Ser Met Asp Leu
    530                 535                 540

Val Glu Leu Val Ser Leu Phe Pro Thr Leu Ala Gly Leu Ala Gly Leu
545                 550                 555                 560

Gln Val Pro Pro Arg Cys Pro Val Pro Ser Phe His Val Glu Leu Cys
                565                 570                 575

Arg Glu Gly Lys Asn Leu Leu Lys His Phe Arg Phe Arg Asp Leu Glu
            580                 585                 590

Glu Asp Pro Tyr Leu Pro Gly Asn Pro Arg Glu Leu Ile Ala Tyr Ser
        595                 600                 605

Gln Tyr Pro Arg Pro Ser Asp Ile Pro Gln Trp Asn Ser Asp Lys Pro
    610                 615                 620

Ser Leu Lys Asp Ile Lys Ile Met Gly Tyr Ser Ile Arg Thr Ile Asp
625                 630                 635                 640

Tyr Arg Tyr Thr Val Trp Val Gly Phe Asn Pro Asp Glu Phe Leu Ala
                645                 650                 655

Asn Phe Ser Asp Ile His Ala Gly Glu Leu Tyr Phe Val Asp Ser Asp
            660                 665                 670

Pro Leu Gln Asp His Asn Met Tyr Asn Asp Ser Gln Gly Gly Asp Leu
        675                 680                 685

Phe Gln Leu Leu Met Pro Gly Gly Gly Ser Gly Gly Gly Ser
    690                 695                 700

Gly Gly Gly Gly Ser Gly Gly Gly Ser Gly Gly Gly Gly Ser Glu
705                 710                 715                 720

Val Gln Leu Val Glu Ser Gly Gly Leu Val Gln Pro Gly Asn Ser
                725                 730                 735

Leu Arg Leu Ser Cys Ala Ala Ser Gly Phe Thr Phe Ser Phe Gly
            740                 745                 750
```

```
Met Ser Trp Val Arg Gln Ala Pro Gly Lys Gly Leu Glu Trp Val Ser
            755                 760                 765

Ser Ile Ser Gly Ser Gly Ser Asp Thr Leu Tyr Ala Asp Ser Val Lys
    770                 775                 780

Gly Arg Phe Thr Ile Ser Arg Asp Asn Ala Lys Thr Thr Leu Tyr Leu
785                 790                 795                 800

Gln Met Asn Ser Leu Arg Pro Glu Asp Thr Ala Val Tyr Tyr Cys Thr
                805                 810                 815

Ile Gly Gly Ser Leu Ser Arg Ser Ser Gln Gly Thr Leu Val Thr Val
            820                 825                 830

Ser Ser His His His His His His His His
        835                 840

<210> SEQ ID NO 57
<211> LENGTH: 847
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 57

Met Lys Leu Ser Thr Ile Leu Phe Thr Ala Cys Ala Thr Leu Ala Ala
1               5                   10                  15

Ala Gln Val Gln Leu Val Glu Ser Gly Gly Gly Leu Val Gln Pro Gly
            20                  25                  30

Gly Ser Leu Arg Leu Ser Cys Ala Ala Ser Gly Arg Thr Ile Asp Asn
        35                  40                  45

Tyr Ala Met Ala Trp Val Arg Gln Ala Pro Gly Lys Gly Leu Glu Trp
    50                  55                  60

Val Ala Thr Ile Asp Trp Gly Asp Gly Thr Arg Tyr Ala Asn Ser
65                  70                  75                  80

Val Lys Gly Arg Phe Thr Ile Ser Arg Asp Asn Ser Lys Asn Thr Met
                85                  90                  95

Tyr Leu Gln Met Asn Ser Leu Arg Ala Glu Asp Thr Ala Val Tyr Tyr
            100                 105                 110

Cys Ala Met Ala Arg Gln Ser Arg Val Asn Leu Asp Val Ala Arg Tyr
        115                 120                 125

Asp Tyr Trp Gly Gln Gly Thr Leu Val Thr Val Ser Ser Gly Gly Gly
130                 135                 140

Gly Ser Gly Gly Gly Gly Ser Gly Gly Gly Gly Ser Gly Gly Gly Gly
145                 150                 155                 160

Ser Gly Gly Gly Gly Ser Ser Glu Thr Gln Ala Asn Ser Thr Thr Asp
                165                 170                 175

Ala Leu Asn Val Leu Leu Ile Ile Val Asp Asp Leu Arg Pro Ser Leu
            180                 185                 190

Gly Cys Tyr Gly Asp Lys Leu Val Arg Ser Pro Asn Ile Asp Gln Leu
        195                 200                 205

Ala Ser His Ser Leu Leu Phe Gln Asn Ala Phe Ala Gln Gln Ala Val
    210                 215                 220

Cys Ala Pro Ser Arg Val Ser Phe Leu Thr Gly Arg Arg Pro Asp Thr
225                 230                 235                 240
```

```
Thr Arg Leu Tyr Asp Phe Asn Ser Tyr Trp Arg Val His Ala Gly Asn
                245                 250                 255

Phe Ser Thr Ile Pro Gln Tyr Phe Lys Glu Asn Gly Tyr Val Thr Met
            260                 265                 270

Ser Val Gly Lys Val Phe His Pro Gly Ile Ser Ser Asn His Thr Asp
        275                 280                 285

Asp Ser Pro Tyr Ser Trp Ser Phe Pro Pro Tyr His Pro Ser Ser Glu
    290                 295                 300

Lys Tyr Glu Asn Thr Lys Thr Cys Arg Gly Pro Asp Gly Glu Leu His
305                 310                 315                 320

Ala Asn Leu Leu Cys Pro Val Asp Val Leu Asp Val Pro Glu Gly Thr
                325                 330                 335

Leu Pro Asp Lys Gln Ser Thr Glu Gln Ala Ile Gln Leu Leu Glu Lys
            340                 345                 350

Met Lys Thr Ser Ala Ser Pro Phe Phe Leu Ala Val Gly Tyr His Lys
        355                 360                 365

Pro His Ile Pro Phe Arg Tyr Pro Lys Glu Phe Gln Lys Leu Tyr Pro
    370                 375                 380

Leu Glu Asn Ile Thr Leu Ala Pro Asp Pro Glu Val Pro Asp Gly Leu
385                 390                 395                 400

Pro Pro Val Ala Tyr Asn Pro Trp Met Asp Ile Arg Gln Arg Glu Asp
                405                 410                 415

Val Gln Ala Leu Asn Ile Ser Val Pro Tyr Gly Pro Ile Pro Val Asp
            420                 425                 430

Phe Gln Arg Lys Ile Arg Gln Ser Tyr Phe Ala Ser Val Ser Tyr Leu
        435                 440                 445

Asp Thr Gln Val Gly Arg Leu Leu Ser Ala Leu Asp Asp Leu Gln Leu
    450                 455                 460

Ala Asn Ser Thr Ile Ile Ala Phe Thr Ser Asp His Gly Trp Ala Leu
465                 470                 475                 480

Gly Glu His Gly Glu Trp Ala Lys Tyr Ser Asn Phe Asp Val Ala Thr
                485                 490                 495

His Val Pro Leu Ile Phe Tyr Val Pro Gly Arg Thr Ala Ser Leu Pro
            500                 505                 510

Glu Ala Gly Glu Lys Leu Phe Pro Tyr Leu Asp Pro Phe Asp Ser Ala
        515                 520                 525

Ser Gln Leu Met Glu Pro Gly Arg Gln Ser Met Asp Leu Val Glu Leu
    530                 535                 540

Val Ser Leu Phe Pro Thr Leu Ala Gly Leu Ala Gly Leu Gln Val Pro
545                 550                 555                 560

Pro Arg Cys Pro Val Pro Ser Phe His Val Glu Leu Cys Arg Glu Gly
                565                 570                 575

Lys Asn Leu Leu Lys His Phe Arg Phe Arg Asp Leu Glu Glu Asp Pro
            580                 585                 590

Tyr Leu Pro Gly Asn Pro Arg Glu Leu Ile Ala Tyr Ser Gln Tyr Pro
        595                 600                 605

Arg Pro Ser Asp Ile Pro Gln Trp Asn Ser Lys Pro Ser Leu Lys
    610                 615                 620

Asp Ile Lys Ile Met Gly Tyr Ser Ile Arg Thr Ile Asp Tyr Arg Tyr
625                 630                 635                 640

Thr Val Trp Val Gly Phe Asn Pro Asp Glu Phe Leu Ala Asn Phe Ser
                645                 650                 655

Asp Ile His Ala Gly Glu Leu Tyr Phe Val Asp Ser Asp Pro Leu Gln
```

```
                    660                 665                 670
Asp His Asn Met Tyr Asn Asp Ser Gln Gly Gly Asp Leu Phe Gln Leu
                675                 680                 685

Leu Met Pro Gly Gly Gly Ser Gly Gly Gly Ser Gly Gly Gly
        690                 695                 700

Gly Ser Gly Gly Gly Ser Gly Gly Gly Ser Ala Val Gln Leu
705                 710                 715                 720

Val Glu Ser Gly Gly Gly Leu Val Gln Pro Gly Asn Ser Leu Arg Leu
                725                 730                 735

Ser Cys Ala Ala Ser Gly Phe Thr Phe Arg Ser Phe Gly Met Ser Trp
                740                 745                 750

Val Arg Gln Ala Pro Gly Lys Glu Pro Glu Trp Val Ser Ser Ile Ser
                755                 760                 765

Gly Ser Gly Ser Asp Thr Leu Tyr Ala Asp Ser Val Lys Gly Arg Phe
            770                 775                 780

Thr Ile Ser Arg Asp Asn Ala Lys Thr Thr Leu Tyr Leu Gln Met Asn
785                 790                 795                 800

Ser Leu Lys Pro Glu Asp Thr Ala Val Tyr Tyr Cys Thr Ile Gly Gly
                805                 810                 815

Ser Leu Ser Arg Ser Ser Gln Gly Thr Gln Val Thr Val Ser Ser His
                820                 825                 830

His His His His His His Trp Ser His Pro Gln Phe Glu Lys
            835                 840                 845

<210> SEQ ID NO 58
<211> LENGTH: 847
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 58

Met Lys Leu Ser Thr Ile Leu Phe Thr Ala Cys Ala Thr Leu Ala Ala
1               5                   10                  15

Ala Gln Val Gln Leu Val Glu Ser Gly Gly Leu Val Gln Pro Gly
            20                  25                  30

Gly Ser Leu Arg Leu Ser Cys Ala Ala Ser Gly Arg Thr Ile Asp Asn
        35                  40                  45

Tyr Ala Met Ala Trp Val Arg Gln Ala Pro Gly Lys Gly Leu Glu Trp
    50                  55                  60

Val Ala Thr Ile Asp Trp Gly Asp Gly Thr Arg Tyr Ala Asn Ser
65              70                  75                  80

Val Lys Gly Arg Phe Thr Ile Ser Arg Asp Asn Ser Lys Asn Thr Met
                85                  90                  95

Tyr Leu Gln Met Asn Ser Leu Arg Ala Glu Asp Thr Ala Val Tyr Tyr
            100                 105                 110

Cys Ala Met Ala Arg Gln Ser Arg Val Asn Leu Asp Val Ala Arg Tyr
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
```

```
            145                 150                 155                 160
        Ser Gly Gly Gly Ser Ala Val Gln Leu Val Glu Ser Gly Gly
                        165                 170                 175

Leu Val Gln Pro Gly Asn Ser Leu Arg Leu Ser Cys Ala Ala Ser Gly
                        180                 185                 190

Phe Thr Phe Arg Ser Phe Gly Met Ser Trp Val Arg Gln Ala Pro Gly
                        195                 200                 205

Lys Glu Pro Glu Trp Val Ser Ile Ser Gly Ser Gly Ser Asp Thr
            210                 215                 220

Leu Tyr Ala Asp Ser Val Lys Gly Arg Phe Thr Ile Ser Arg Asp Asn
        225                 230                 235                 240

Ala Lys Thr Thr Leu Tyr Leu Gln Met Asn Ser Leu Lys Pro Glu Asp
                        245                 250                 255

Thr Ala Val Tyr Tyr Cys Thr Ile Gly Gly Ser Leu Ser Arg Ser Ser
                        260                 265                 270

Gln Gly Thr Gln Val Thr Val Ser Ser Gly Gly Gly Ser Gly Gly
                        275                 280                 285

Gly Gly Ser Gly Gly Gly Ser Gly Gly Gly Ser Gly Gly Gly
                290                 295                 300

Gly Ser Ser Glu Thr Gln Ala Asn Ser Thr Thr Asp Ala Leu Asn Val
        305                 310                 315                 320

Leu Leu Ile Ile Val Asp Asp Leu Arg Pro Ser Leu Gly Cys Tyr Gly
                        325                 330                 335

Asp Lys Leu Val Arg Ser Pro Asn Ile Asp Gln Leu Ala Ser His Ser
                        340                 345                 350

Leu Leu Phe Gln Asn Ala Phe Ala Gln Gln Ala Val Cys Ala Pro Ser
                        355                 360                 365

Arg Val Ser Phe Leu Thr Gly Arg Arg Pro Asp Thr Thr Arg Leu Tyr
                        370                 375                 380

Asp Phe Asn Ser Tyr Trp Arg Val His Ala Gly Asn Phe Ser Thr Ile
        385                 390                 395                 400

Pro Gln Tyr Phe Lys Glu Asn Gly Tyr Val Thr Met Ser Val Gly Lys
                        405                 410                 415

Val Phe His Pro Gly Ile Ser Ser Asn His Thr Asp Asp Ser Pro Tyr
                        420                 425                 430

Ser Trp Ser Phe Pro Pro Tyr His Pro Ser Ser Glu Lys Tyr Glu Asn
                        435                 440                 445

Thr Lys Thr Cys Arg Gly Pro Asp Gly Glu Leu His Ala Asn Leu Leu
                        450                 455                 460

Cys Pro Val Asp Val Leu Asp Val Pro Glu Gly Thr Leu Pro Asp Lys
        465                 470                 475                 480

Gln Ser Thr Glu Gln Ala Ile Gln Leu Leu Glu Lys Met Lys Thr Ser
                        485                 490                 495

Ala Ser Pro Phe Phe Leu Ala Val Gly Tyr His Lys Pro His Ile Pro
                        500                 505                 510

Phe Arg Tyr Pro Lys Glu Phe Gln Lys Leu Tyr Pro Leu Glu Asn Ile
                        515                 520                 525

Thr Leu Ala Pro Asp Pro Glu Val Pro Asp Gly Leu Pro Pro Val Ala
                        530                 535                 540

Tyr Asn Pro Trp Met Asp Ile Arg Gln Arg Glu Asp Val Gln Ala Leu
        545                 550                 555                 560

Asn Ile Ser Val Pro Tyr Gly Pro Ile Pro Val Asp Phe Gln Arg Lys
                        565                 570                 575
```

-continued

Ile Arg Gln Ser Tyr Phe Ala Ser Val Ser Tyr Leu Asp Thr Gln Val
            580                 585                 590

Gly Arg Leu Leu Ser Ala Leu Asp Asp Leu Gln Leu Ala Asn Ser Thr
            595                 600                 605

Ile Ile Ala Phe Thr Ser Asp His Gly Trp Ala Leu Gly Glu His Gly
610                 615                 620

Glu Trp Ala Lys Tyr Ser Asn Phe Asp Val Ala Thr His Val Pro Leu
625                 630                 635                 640

Ile Phe Tyr Val Pro Gly Arg Thr Ala Ser Leu Pro Glu Ala Gly Glu
            645                 650                 655

Lys Leu Phe Pro Tyr Leu Asp Pro Phe Asp Ser Ala Ser Gln Leu Met
            660                 665                 670

Glu Pro Gly Arg Gln Ser Met Asp Leu Val Glu Leu Val Ser Leu Phe
            675                 680                 685

Pro Thr Leu Ala Gly Leu Ala Gly Leu Gln Val Pro Pro Arg Cys Pro
690                 695                 700

Val Pro Ser Phe His Val Glu Leu Cys Arg Glu Gly Lys Asn Leu Leu
705                 710                 715                 720

Lys His Phe Arg Phe Arg Asp Leu Glu Glu Asp Pro Tyr Leu Pro Gly
            725                 730                 735

Asn Pro Arg Glu Leu Ile Ala Tyr Ser Gln Tyr Pro Arg Pro Ser Asp
            740                 745                 750

Ile Pro Gln Trp Asn Ser Asp Lys Pro Ser Leu Lys Asp Ile Lys Ile
            755                 760                 765

Met Gly Tyr Ser Ile Arg Thr Ile Asp Tyr Arg Tyr Thr Val Trp Val
770                 775                 780

Gly Phe Asn Pro Asp Glu Phe Leu Ala Asn Phe Ser Asp Ile His Ala
785                 790                 795                 800

Gly Glu Leu Tyr Phe Val Asp Ser Asp Pro Leu Gln Asp His Asn Met
            805                 810                 815

Tyr Asn Asp Ser Gln Gly Gly Asp Leu Phe Gln Leu Leu Met Pro His
            820                 825                 830

His His His His His His Trp Ser His Pro Gln Phe Glu Lys
            835                 840                 845

```
<210> SEQ ID NO 59
<211> LENGTH: 847
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 59
```

Met Lys Leu Ser Thr Ile Leu Phe Thr Ala Cys Ala Thr Leu Ala Ala
1               5                   10                  15

Ala Ala Val Gln Leu Val Glu Ser Gly Gly Leu Val Gln Pro Gly
            20                  25                  30

Asn Ser Leu Arg Leu Ser Cys Ala Ala Ser Gly Phe Thr Phe Arg Ser
            35                  40                  45

Phe Gly Met Ser Trp Val Arg Gln Ala Pro Gly Lys Glu Pro Glu Trp
50                  55                  60

```
Val Ser Ser Ile Ser Gly Ser Gly Ser Asp Thr Leu Tyr Ala Asp Ser
 65                  70                  75                  80

Val Lys Gly Arg Phe Thr Ile Ser Arg Asp Asn Ala Lys Thr Thr Leu
                 85                  90                  95

Tyr Leu Gln Met Asn Ser Leu Lys Pro Glu Asp Thr Ala Val Tyr Tyr
            100                 105                 110

Cys Thr Ile Gly Gly Ser Leu Ser Arg Ser Ser Gln Gly Thr Gln Val
            115                 120                 125

Thr Val Ser Ser Gly Gly Gly Gly Ser Gly Gly Gly Gly Ser Gly Gly
        130                 135                 140

Gly Gly Ser Gly Gly Gly Gly Ser Gly Gly Gly Gly Ser Gln Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Arg Thr Ile Asp Asn Tyr Ala Met Ala
            180                 185                 190

Trp Val Arg Gln Ala Pro Gly Lys Gly Leu Glu Trp Val Ala Thr Ile
        195                 200                 205

Asp Trp Gly Asp Gly Gly Thr Arg Tyr Ala Asn Ser Val Lys Gly Arg
210                 215                 220

Phe Thr Ile Ser Arg Asp Asn Ser Lys Asn Thr Met Tyr Leu Gln Met
225                 230                 235                 240

Asn Ser Leu Arg Ala Glu Asp Thr Ala Val Tyr Tyr Cys Ala Met Ala
                245                 250                 255

Arg Gln Ser Arg Val Asn Leu Asp Val Ala Arg Tyr Asp Tyr Trp Gly
            260                 265                 270

Gln Gly Thr Leu Val Thr Val Ser Ser Gly Gly Gly Gly Ser Gly Gly
        275                 280                 285

Gly Gly Ser Gly Gly Gly Gly Ser Gly Gly Gly Gly Ser Gly Gly Gly
290                 295                 300

Gly Ser Ser Glu Thr Gln Ala Asn Ser Thr Thr Asp Ala Leu Asn Val
305                 310                 315                 320

Leu Leu Ile Ile Val Asp Asp Leu Arg Pro Ser Leu Gly Cys Tyr Gly
                325                 330                 335

Asp Lys Leu Val Arg Ser Pro Asn Ile Asp Gln Leu Ala Ser His Ser
            340                 345                 350

Leu Leu Phe Gln Asn Ala Phe Ala Gln Gln Ala Val Cys Ala Pro Ser
        355                 360                 365

Arg Val Ser Phe Leu Thr Gly Arg Arg Pro Asp Thr Thr Arg Leu Tyr
370                 375                 380

Asp Phe Asn Ser Tyr Trp Arg Val His Ala Gly Asn Phe Ser Thr Ile
385                 390                 395                 400

Pro Gln Tyr Phe Lys Glu Asn Gly Tyr Val Thr Met Ser Val Gly Lys
                405                 410                 415

Val Phe His Pro Gly Ile Ser Ser Asn His Thr Asp Asp Ser Pro Tyr
            420                 425                 430

Ser Trp Ser Phe Pro Pro Tyr His Pro Ser Ser Glu Lys Tyr Glu Asn
        435                 440                 445

Thr Lys Thr Cys Arg Gly Pro Asp Gly Glu Leu His Ala Asn Leu Leu
450                 455                 460

Cys Pro Val Asp Val Leu Asp Val Pro Glu Gly Thr Leu Pro Asp Lys
465                 470                 475                 480
```

-continued

```
Gln Ser Thr Glu Gln Ala Ile Gln Leu Leu Glu Lys Met Lys Thr Ser
            485                 490                 495
Ala Ser Pro Phe Phe Leu Ala Val Gly Tyr His Lys Pro His Ile Pro
        500                 505                 510
Phe Arg Tyr Pro Lys Glu Phe Gln Lys Leu Tyr Pro Leu Glu Asn Ile
    515                 520                 525
Thr Leu Ala Pro Asp Pro Glu Val Pro Asp Gly Leu Pro Pro Val Ala
530                 535                 540
Tyr Asn Pro Trp Met Asp Ile Arg Gln Arg Glu Asp Val Gln Ala Leu
545                 550                 555                 560
Asn Ile Ser Val Pro Tyr Gly Pro Ile Pro Val Asp Phe Gln Arg Lys
                565                 570                 575
Ile Arg Gln Ser Tyr Phe Ala Ser Val Ser Tyr Leu Asp Thr Gln Val
            580                 585                 590
Gly Arg Leu Leu Ser Ala Leu Asp Asp Leu Gln Leu Ala Asn Ser Thr
        595                 600                 605
Ile Ile Ala Phe Thr Ser Asp His Gly Trp Ala Leu Gly Glu His Gly
    610                 615                 620
Glu Trp Ala Lys Tyr Ser Asn Phe Asp Val Ala Thr His Val Pro Leu
625                 630                 635                 640
Ile Phe Tyr Val Pro Gly Arg Thr Ala Ser Leu Pro Glu Ala Gly Glu
                645                 650                 655
Lys Leu Phe Pro Tyr Leu Asp Pro Phe Asp Ser Ala Ser Gln Leu Met
            660                 665                 670
Glu Pro Gly Arg Gln Ser Met Asp Leu Val Glu Leu Val Ser Leu Phe
        675                 680                 685
Pro Thr Leu Ala Gly Leu Ala Gly Leu Gln Val Pro Pro Arg Cys Pro
    690                 695                 700
Val Pro Ser Phe His Val Glu Leu Cys Arg Glu Gly Lys Asn Leu Leu
705                 710                 715                 720
Lys His Phe Arg Phe Arg Asp Leu Glu Glu Asp Pro Tyr Leu Pro Gly
                725                 730                 735
Asn Pro Arg Glu Leu Ile Ala Tyr Ser Gln Tyr Pro Arg Pro Ser Asp
            740                 745                 750
Ile Pro Gln Trp Asn Ser Asp Lys Pro Ser Leu Lys Asp Ile Lys Ile
        755                 760                 765
Met Gly Tyr Ser Ile Arg Thr Ile Asp Tyr Arg Tyr Thr Val Trp Val
    770                 775                 780
Gly Phe Asn Pro Asp Glu Phe Leu Ala Asn Phe Ser Asp Ile His Ala
785                 790                 795                 800
Gly Glu Leu Tyr Phe Val Asp Ser Asp Pro Leu Gln Asp His Asn Met
                805                 810                 815
Tyr Asn Asp Ser Gln Gly Gly Asp Leu Phe Gln Leu Leu Met Pro His
            820                 825                 830
His His His His His Trp Ser His Pro Gln Phe Glu Lys
        835                 840                 845
```

<210> SEQ ID NO 60
<211> LENGTH: 1295
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:

<223> OTHER INFORMATION: Homo Sapiens
<220> FEATURE:
<223> OTHER INFORMATION: Yarrowia Lipolytica

<400> SEQUENCE: 60

```
Met Lys Leu Ser Thr Ile Leu Phe Thr Ala Cys Ala Thr Leu Ala Ala
1               5                   10                  15

Ala Gln Val Gln Leu Val Glu Ser Gly Gly Leu Val Gln Pro Gly
            20                  25                  30

Gly Ser Leu Arg Leu Ser Cys Ala Ala Ser Gly Arg Thr Ile Asp Asn
                35                  40                  45

Tyr Ala Met Ala Trp Val Arg Gln Ala Pro Gly Lys Gly Leu Glu Trp
    50                  55                  60

Val Ala Thr Ile Asp Trp Gly Asp Gly Gly Thr Arg Tyr Ala Asn Ser
65                  70                  75                  80

Val Lys Gly Arg Phe Thr Ile Ser Arg Asp Asn Ser Lys Asn Thr Met
                85                  90                  95

Tyr Leu Gln Met Asn Ser Leu Arg Ala Glu Asp Thr Ala Val Tyr Tyr
            100                 105                 110

Cys Ala Met Ala Arg Gln Ser Arg Val Asn Leu Asp Val Ala Arg Tyr
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gly Gly Gly Ser Ser Glu Thr Gln Ala Asn Ser Thr Thr Asp
                165                 170                 175

Ala Leu Asn Val Leu Leu Ile Ile Val Asp Asp Leu Arg Pro Ser Leu
            180                 185                 190

Gly Cys Tyr Gly Asp Lys Leu Val Arg Ser Pro Asn Ile Asp Gln Leu
        195                 200                 205

Ala Ser His Ser Leu Leu Phe Gln Asn Ala Phe Ala Gln Gln Ala Val
    210                 215                 220

Cys Ala Pro Ser Arg Val Ser Phe Leu Thr Gly Arg Arg Pro Asp Thr
225                 230                 235                 240

Thr Arg Leu Tyr Asp Phe Asn Ser Tyr Trp Arg Val His Ala Gly Asn
                245                 250                 255

Phe Ser Thr Ile Pro Gln Tyr Phe Lys Glu Asn Gly Tyr Val Thr Met
            260                 265                 270

Ser Val Gly Lys Val Phe His Pro Gly Ile Ser Ser Asn His Thr Asp
        275                 280                 285

Asp Ser Pro Tyr Ser Trp Ser Phe Pro Pro Tyr His Pro Ser Ser Glu
    290                 295                 300

Lys Tyr Glu Asn Thr Lys Thr Cys Arg Gly Pro Asp Gly Glu Leu His
305                 310                 315                 320

Ala Asn Leu Leu Cys Pro Val Asp Val Leu Asp Val Pro Glu Gly Thr
                325                 330                 335

Leu Pro Asp Lys Gln Ser Thr Glu Gln Ala Ile Gln Leu Leu Glu Lys
            340                 345                 350

Met Lys Thr Ser Ala Ser Pro Phe Phe Leu Ala Val Gly Tyr His Lys
        355                 360                 365

Pro His Ile Pro Phe Arg Tyr Pro Lys Glu Phe Gln Lys Leu Tyr Pro
    370                 375                 380

Leu Glu Asn Ile Thr Leu Ala Pro Asp Pro Glu Val Pro Asp Gly Leu
```

```
            385                 390                 395                 400
        Pro Pro Val Ala Tyr Asn Pro Trp Met Asp Ile Arg Gln Arg Glu Asp
                        405                 410                 415

Val Gln Ala Leu Asn Ile Ser Val Pro Tyr Gly Pro Ile Pro Val Asp
                        420                 425                 430

Phe Gln Arg Lys Ile Arg Gln Ser Tyr Phe Ala Ser Val Ser Tyr Leu
                        435                 440                 445

Asp Thr Gln Val Gly Arg Leu Leu Ser Ala Leu Asp Asp Leu Gln Leu
                    450                 455                 460

Ala Asn Ser Thr Ile Ile Ala Phe Thr Ser Asp His Gly Trp Ala Leu
        465                 470                 475                 480

Gly Glu His Gly Glu Trp Ala Lys Tyr Ser Asn Phe Asp Val Ala Thr
                            485                 490                 495

His Val Pro Leu Ile Phe Tyr Val Pro Gly Arg Thr Ala Ser Leu Pro
                        500                 505                 510

Glu Ala Gly Glu Lys Leu Phe Pro Tyr Leu Asp Pro Phe Asp Ser Ala
                        515                 520                 525

Ser Gln Leu Met Glu Pro Gly Arg Gln Ser Met Asp Leu Val Glu Leu
                    530                 535                 540

Val Ser Leu Phe Pro Thr Leu Ala Gly Leu Ala Gly Leu Gln Val Pro
        545                 550                 555                 560

Pro Arg Cys Pro Val Pro Ser Phe His Val Glu Leu Cys Arg Glu Gly
                            565                 570                 575

Lys Asn Leu Leu Lys His Phe Arg Phe Arg Asp Leu Glu Glu Asp Pro
                        580                 585                 590

Tyr Leu Pro Gly Asn Pro Arg Glu Leu Ile Ala Tyr Ser Gln Tyr Pro
                        595                 600                 605

Arg Pro Ser Asp Ile Pro Gln Trp Asn Ser Asp Lys Pro Ser Leu Lys
                    610                 615                 620

Asp Ile Lys Ile Met Gly Tyr Ser Ile Arg Thr Ile Asp Tyr Arg Tyr
        625                 630                 635                 640

Thr Val Trp Val Gly Phe Asn Pro Asp Glu Phe Leu Ala Asn Phe Ser
                            645                 650                 655

Asp Ile His Ala Gly Glu Leu Tyr Phe Val Asp Ser Asp Pro Leu Gln
                        660                 665                 670

Asp His Asn Met Tyr Asn Asp Ser Gln Gly Gly Asp Leu Phe Gln Leu
                        675                 680                 685

Leu Met Pro Gly Gly Gly Gly Ser Asp Ala His Lys Ser Glu Val Ala
                    690                 695                 700

His Arg Phe Lys Asp Leu Gly Glu Glu Asn Phe Lys Ala Leu Val Leu
        705                 710                 715                 720

Ile Ala Phe Ala Gln Tyr Leu Gln Gln Cys Pro Phe Glu Asp His Val
                            725                 730                 735

Lys Leu Val Asn Glu Val Thr Glu Phe Ala Lys Thr Cys Val Ala Asp
                        740                 745                 750

Glu Ser Ala Glu Asn Cys Asp Lys Ser Leu His Thr Leu Phe Gly Asp
                        755                 760                 765

Lys Leu Cys Thr Val Ala Thr Leu Arg Glu Thr Tyr Gly Glu Met Ala
                    770                 775                 780

Asp Cys Cys Ala Lys Gln Glu Pro Glu Arg Asn Glu Cys Phe Leu Gln
        785                 790                 795                 800

His Lys Asp Asp Asn Pro Asn Leu Pro Arg Leu Val Arg Pro Glu Val
                            805                 810                 815
```

Asp Val Met Cys Thr Ala Phe His Asp Asn Glu Glu Thr Phe Leu Lys
            820                 825                 830

Lys Tyr Leu Tyr Glu Ile Ala Arg Arg His Pro Tyr Phe Tyr Ala Pro
            835                 840                 845

Glu Leu Leu Phe Phe Ala Lys Arg Tyr Lys Ala Ala Phe Thr Glu Cys
            850                 855                 860

Cys Gln Ala Ala Asp Lys Ala Ala Cys Leu Leu Pro Lys Leu Asp Glu
865                 870                 875                 880

Leu Arg Asp Glu Gly Lys Ala Ser Ser Ala Lys Gln Arg Leu Lys Cys
                885                 890                 895

Ala Ser Leu Gln Lys Phe Gly Glu Arg Ala Phe Lys Ala Trp Ala Val
            900                 905                 910

Ala Arg Leu Ser Gln Arg Phe Pro Lys Ala Glu Phe Ala Glu Val Ser
            915                 920                 925

Lys Leu Val Thr Asp Leu Thr Lys Val His Thr Glu Cys Cys His Gly
            930                 935                 940

Asp Leu Leu Glu Cys Ala Asp Asp Arg Ala Asp Leu Ala Lys Tyr Ile
945                 950                 955                 960

Cys Glu Asn Gln Asp Ser Ile Ser Ser Lys Leu Lys Glu Cys Cys Glu
                965                 970                 975

Lys Pro Leu Leu Glu Lys Ser His Cys Ile Ala Glu Val Glu Asn Asp
            980                 985                 990

Glu Met Pro Ala Asp Leu Pro Ser Leu Ala Ala Asp Phe Val Glu Ser
            995                 1000                1005

Lys Asp Val Cys Lys Asn Tyr Ala Glu Ala Lys Asp Val Phe Leu
    1010                1015                1020

Gly Met Phe Leu Tyr Glu Tyr Ala Arg Arg His Pro Asp Tyr Ser
    1025                1030                1035

Val Val Leu Leu Leu Arg Leu Ala Lys Thr Tyr Glu Thr Thr Leu
    1040                1045                1050

Glu Lys Cys Cys Ala Ala Ala Asp Pro His Glu Cys Tyr Ala Lys
    1055                1060                1065

Val Phe Asp Glu Phe Lys Pro Leu Val Glu Glu Pro Gln Asn Leu
    1070                1075                1080

Ile Lys Gln Asn Cys Glu Leu Phe Glu Gln Leu Gly Glu Tyr Lys
    1085                1090                1095

Phe Gln Asn Ala Leu Leu Val Arg Tyr Thr Lys Lys Val Pro Gln
    1100                1105                1110

Val Ser Thr Pro Thr Leu Val Glu Val Ser Arg Asn Leu Gly Lys
    1115                1120                1125

Val Gly Ser Lys Cys Cys Lys His Pro Glu Ala Lys Arg Met Pro
    1130                1135                1140

Cys Ala Glu Asp Tyr Leu Ser Val Val Leu Asn Gln Leu Cys Val
    1145                1150                1155

Leu His Glu Lys Thr Pro Val Ser Asp Arg Val Thr Lys Cys Cys
    1160                1165                1170

Thr Glu Ser Leu Val Asn Arg Arg Pro Cys Phe Ser Ala Leu Glu
    1175                1180                1185

Val Asp Glu Thr Tyr Val Pro Lys Glu Phe Asn Ala Glu Thr Phe
    1190                1195                1200

Thr Phe His Ala Asp Ile Cys Thr Leu Ser Glu Lys Glu Arg Gln
    1205                1210                1215

```
Ile Lys Lys Gln Thr Ala Leu Val Glu Leu Val Lys His Lys Pro
1220                1225                1230

Lys Ala Thr Lys Glu Gln Leu Lys Ala Val Met Asp Asp Phe Ala
1235                1240                1245

Ala Phe Val Glu Lys Cys Cys Lys Ala Asp Asp Lys Glu Thr Cys
1250                1255                1260

Phe Ala Glu Glu Gly Pro Lys Leu Val Ala Ala Ser Gln Ala Ala
1265                1270                1275

Leu Gly Leu His His His His His His Trp Ser His Pro Gln Phe
1280                1285                1290

Glu Lys
1295

<210> SEQ ID NO 61
<211> LENGTH: 700
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 61

Met Lys Leu Ser Thr Ile Leu Phe Thr Ala Cys Ala Thr Leu Ala Ala
1               5                   10                  15

Ala Ser Glu Thr Gln Ala Asn Ser Thr Thr Asp Ala Leu Asn Val Leu
                20                  25                  30

Leu Ile Ile Val Asp Asp Leu Arg Pro Ser Leu Gly Cys Tyr Gly Asp
            35                  40                  45

Lys Leu Val Arg Ser Pro Asn Ile Asp Gln Leu Ala Ser His Ser Leu
        50                  55                  60

Leu Phe Gln Asn Ala Phe Ala Gln Gln Ala Val Cys Ala Pro Ser Arg
65                  70                  75                  80

Val Ser Phe Leu Thr Gly Arg Arg Pro Asp Thr Thr Arg Leu Tyr Asp
                85                  90                  95

Phe Asn Ser Tyr Trp Arg Val His Ala Gly Asn Phe Ser Thr Ile Pro
            100                 105                 110

Gln Tyr Phe Lys Glu Asn Gly Tyr Val Thr Met Ser Val Gly Lys Val
        115                 120                 125

Phe His Pro Gly Ile Ser Ser Asn His Thr Asp Asp Ser Pro Tyr Ser
130                 135                 140

Trp Ser Phe Pro Pro Tyr His Pro Ser Ser Glu Lys Tyr Glu Asn Thr
145                 150                 155                 160

Lys Thr Cys Arg Gly Pro Asp Gly Glu Leu His Ala Asn Leu Leu Cys
                165                 170                 175

Pro Val Asp Val Leu Asp Val Pro Glu Gly Thr Leu Pro Asp Lys Gln
            180                 185                 190

Ser Thr Glu Gln Ala Ile Gln Leu Leu Glu Lys Met Lys Thr Ser Ala
        195                 200                 205

Ser Pro Phe Phe Leu Ala Val Gly Tyr His Lys Pro His Ile Pro Phe
210                 215                 220

Arg Tyr Pro Lys Glu Phe Gln Lys Leu Tyr Pro Leu Glu Asn Ile Thr
225                 230                 235                 240
```

```
Leu Ala Pro Asp Pro Glu Val Pro Asp Gly Leu Pro Val Ala Tyr
                245                 250                 255
Asn Pro Trp Met Asp Ile Arg Gln Arg Glu Asp Val Gln Ala Leu Asn
        260                 265                 270
Ile Ser Val Pro Tyr Gly Pro Ile Pro Val Asp Phe Gln Arg Lys Ile
            275                 280                 285
Arg Gln Ser Tyr Phe Ala Ser Val Ser Tyr Leu Asp Thr Gln Val Gly
        290                 295                 300
Arg Leu Leu Ser Ala Leu Asp Asp Leu Gln Leu Ala Asn Ser Thr Ile
305                 310                 315                 320
Ile Ala Phe Thr Ser Asp His Gly Trp Ala Leu Gly Glu His Gly Glu
                325                 330                 335
Trp Ala Lys Tyr Ser Asn Phe Asp Val Ala Thr His Val Pro Leu Ile
            340                 345                 350
Phe Tyr Val Pro Gly Arg Thr Ala Ser Leu Pro Glu Ala Gly Glu Lys
        355                 360                 365
Leu Phe Pro Tyr Leu Asp Pro Phe Asp Ser Ala Ser Gln Leu Met Glu
        370                 375                 380
Pro Gly Arg Gln Ser Met Asp Leu Val Glu Leu Val Ser Leu Phe Pro
385                 390                 395                 400
Thr Leu Ala Gly Leu Ala Gly Leu Gln Val Pro Pro Arg Cys Pro Val
                405                 410                 415
Pro Ser Phe His Val Glu Leu Cys Arg Glu Gly Lys Asn Leu Leu Lys
            420                 425                 430
His Phe Arg Phe Arg Asp Leu Glu Glu Asp Pro Tyr Leu Pro Gly Asn
        435                 440                 445
Pro Arg Glu Leu Ile Ala Tyr Ser Gln Tyr Pro Arg Pro Ser Asp Ile
        450                 455                 460
Pro Gln Trp Asn Ser Asp Lys Pro Ser Leu Lys Asp Ile Lys Ile Met
465                 470                 475                 480
Gly Tyr Ser Ile Arg Thr Ile Asp Tyr Arg Tyr Thr Val Trp Val Gly
                485                 490                 495
Phe Asn Pro Asp Glu Phe Leu Ala Asn Phe Ser Asp Ile His Ala Gly
            500                 505                 510
Glu Leu Tyr Phe Val Asp Ser Asp Pro Leu Gln Asp His Asn Met Tyr
        515                 520                 525
Asn Asp Ser Gln Gly Gly Asp Leu Phe Gln Leu Leu Met Pro Gly Gly
        530                 535                 540
Gly Gly Ser Gly Gly Gly Ser Gly Gly Gly Ser Gly Gly Gly Gly Gly
545                 550                 555                 560
Gly Ser Gly Gly Gly Ser Gln Val Gln Leu Val Glu Ser Gly Gly
                565                 570                 575
Gly Leu Val Gln Ala Gly Gly Ser Leu Arg Leu Ser Cys Val Ala Ser
            580                 585                 590
Gly Arg Thr Phe Ile Ala Tyr Ala Met Gly Trp Phe Arg Gln Ala Pro
        595                 600                 605
Gly Lys Glu Arg Glu Phe Val Ala Ala Ile Thr Asn Phe Ala Gly Gly
        610                 615                 620
Thr Thr Tyr Tyr Ala Asp Ser Val Lys Gly Arg Phe Thr Ile Ser Arg
625                 630                 635                 640
Asp Asn Ala Lys Thr Thr Val Tyr Leu Gln Met Asn Ser Leu Lys Pro
                645                 650                 655
Glu Asp Thr Ala Leu Tyr Tyr Cys Ala Ala Asp Arg Ser Ala Gln Thr
```

```
                       660                 665                 670
Met Arg Gln Val Arg Pro Val Leu Pro Tyr Trp Gly Gln Gly Thr Gln
                   675                 680                 685

Val Thr Val Ser His His His His His His
               690                 695                 700

<210> SEQ ID NO 62
<211> LENGTH: 699
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 62

Met Lys Leu Ser Thr Ile Leu Phe Thr Ala Cys Ala Thr Leu Ala Ala
1               5                   10                  15

Ala Ser Glu Thr Gln Ala Asn Ser Thr Thr Asp Ala Leu Asn Val Leu
            20                  25                  30

Leu Ile Ile Val Asp Asp Leu Arg Pro Ser Leu Gly Cys Tyr Gly Asp
        35                  40                  45

Lys Leu Val Arg Ser Pro Asn Ile Asp Gln Leu Ala Ser His Ser Leu
    50                  55                  60

Leu Phe Gln Asn Ala Phe Ala Gln Gln Ala Val Cys Ala Pro Ser Arg
65                  70                  75                  80

Val Ser Phe Leu Thr Gly Arg Arg Pro Asp Thr Thr Arg Leu Tyr Asp
                85                  90                  95

Phe Asn Ser Tyr Trp Arg Val His Ala Gly Asn Phe Ser Thr Ile Pro
            100                 105                 110

Gln Tyr Phe Lys Glu Asn Gly Tyr Val Thr Met Ser Val Gly Lys Val
        115                 120                 125

Phe His Pro Gly Ile Ser Ser Asn His Thr Asp Asp Ser Pro Tyr Ser
    130                 135                 140

Trp Ser Phe Pro Pro Tyr His Pro Ser Ser Glu Lys Tyr Glu Asn Thr
145                 150                 155                 160

Lys Thr Cys Arg Gly Pro Asp Gly Glu Leu His Ala Asn Leu Leu Cys
                165                 170                 175

Pro Val Asp Val Leu Asp Val Pro Glu Gly Thr Leu Pro Asp Lys Gln
            180                 185                 190

Ser Thr Glu Gln Ala Ile Gln Leu Leu Glu Lys Met Lys Thr Ser Ala
        195                 200                 205

Ser Pro Phe Phe Leu Ala Val Gly Tyr His Lys Pro His Ile Pro Phe
    210                 215                 220

Arg Tyr Pro Lys Glu Phe Gln Lys Leu Tyr Pro Leu Glu Asn Ile Thr
225                 230                 235                 240

Leu Ala Pro Asp Pro Glu Val Pro Asp Gly Leu Pro Pro Val Ala Tyr
                245                 250                 255

Asn Pro Trp Met Asp Ile Arg Gln Arg Glu Asp Val Gln Ala Leu Asn
            260                 265                 270

Ile Ser Val Pro Tyr Gly Pro Ile Pro Val Asp Phe Gln Arg Lys Ile
        275                 280                 285

Arg Gln Ser Tyr Phe Ala Ser Val Ser Tyr Leu Asp Thr Gln Val Gly
```

```
            290                 295                 300
Arg Leu Leu Ser Ala Leu Asp Leu Gln Leu Ala Asn Ser Thr Ile
305                 310                 315                 320

Ile Ala Phe Thr Ser Asp His Gly Trp Ala Leu Gly Glu His Gly Glu
                325                 330                 335

Trp Ala Lys Tyr Ser Asn Phe Asp Val Ala Thr His Val Pro Leu Ile
                340                 345                 350

Phe Tyr Val Pro Gly Arg Thr Ala Ser Leu Pro Glu Ala Gly Glu Lys
                355                 360                 365

Leu Phe Pro Tyr Leu Asp Pro Phe Asp Ser Ala Ser Gln Leu Met Glu
370                 375                 380

Pro Gly Arg Gln Ser Met Asp Leu Val Glu Leu Val Ser Leu Phe Pro
385                 390                 395                 400

Thr Leu Ala Gly Leu Ala Gly Leu Gln Val Pro Pro Arg Cys Pro Val
                405                 410                 415

Pro Ser Phe His Val Glu Leu Cys Arg Glu Gly Lys Asn Leu Leu Lys
                420                 425                 430

His Phe Arg Phe Arg Asp Leu Glu Glu Asp Pro Tyr Leu Pro Gly Asn
                435                 440                 445

Pro Arg Glu Leu Ile Ala Tyr Ser Gln Tyr Pro Arg Pro Ser Asp Ile
                450                 455                 460

Pro Gln Trp Asn Ser Asp Lys Pro Ser Leu Lys Asp Ile Lys Ile Met
465                 470                 475                 480

Gly Tyr Ser Ile Arg Thr Ile Asp Tyr Arg Tyr Thr Val Trp Val Gly
                485                 490                 495

Phe Asn Pro Asp Glu Phe Leu Ala Asn Phe Ser Asp Ile His Ala Gly
                500                 505                 510

Glu Leu Tyr Phe Val Asp Ser Asp Pro Leu Gln Asp His Asn Met Tyr
                515                 520                 525

Asn Asp Ser Gln Gly Gly Asp Leu Phe Gln Leu Leu Met Pro Gly Gly
530                 535                 540

Gly Gly Ser Gly Gly Gly Ser Gly Gly Gly Ser Gly Gly Gly
545                 550                 555                 560

Gly Ser Gly Gly Gly Gly Ser Gln Val Lys Leu Glu Glu Ser Gly Gly
                565                 570                 575

Gly Leu Val Gln Ala Gly Gly Ser Leu Lys Leu Ser Cys Ala Ala Ser
                580                 585                 590

Gly Ser Thr Phe Ser Ser Ser Val Gly Trp Tyr Arg Gln Ala Pro
                595                 600                 605

Gly Gln Gln Arg Glu Leu Val Ala Ala Ile Thr Ser Gly Gly Ser Thr
610                 615                 620

Asn Thr Ala Asp Ser Val Lys Gly Arg Phe Thr Met Ser Arg Asp Asn
625                 630                 635                 640

Ala Lys Asn Thr Val Tyr Leu Gln Met Arg Asp Leu Lys Pro Glu Asp
                645                 650                 655

Thr Ala Val Tyr Tyr Cys Asn Val Ala Gly Arg Asn Trp Val Pro Ile
                660                 665                 670

Ser Arg Tyr Ser Pro Gly Pro Tyr Trp Gly Gln Gly Thr Gln Val Thr
                675                 680                 685

Val Ser Ser His His His His His His
    690                 695

<210> SEQ ID NO 63
```

<211> LENGTH: 231
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 63

Ser Ser Glu Ser Lys Tyr Gly Pro Pro Cys Pro Ser Cys Pro Ala Pro
1               5                   10                  15

Glu Phe Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Lys Pro Pro Ser Gln Glu Glu Met Thr Lys
    130                 135                 140

Asn Gln Val Ser Leu Ser Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Val Pro Val Leu Asp Ser Asp Gly Ser Phe Arg Leu Ala Ser
            180                 185                 190

Tyr Leu Thr Val Asp Lys Ser Arg Trp Gln Glu Gly Asn Val Phe Ser
        195                 200                 205

Cys Ser Val Met His Glu Ala Leu His Asn His Tyr Thr Gln Lys Ser
    210                 215                 220

Leu Ser Leu Ser Leu Gly Lys
225                 230

<210> SEQ ID NO 64
<211> LENGTH: 920
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 64

Met Lys Leu Ser Thr Ile Leu Phe Thr Ala Cys Ala Thr Leu Ala Ala
1               5                   10                  15

Ala Gln Val Gln Leu Val Glu Ser Gly Gly Gly Leu Val Gln Pro Gly
            20                  25                  30

Gly Ser Leu Arg Leu Ser Cys Ala Ala Ser Gly Arg Thr Ile Asp Asn
        35                  40                  45

```
Tyr Ala Met Ala Trp Val Arg Gln Ala Pro Gly Lys Gly Leu Glu Trp
         50                  55                  60

Val Ala Thr Ile Asp Trp Asp Gly Gly Thr Arg Tyr Ala Asn Ser
 65              70                  75                  80

Val Lys Gly Arg Phe Thr Ile Ser Arg Asp Asn Ser Lys Asn Thr Met
                 85                  90                  95

Tyr Leu Gln Met Asn Ser Leu Arg Ala Glu Asp Thr Ala Val Tyr Tyr
            100                 105                 110

Cys Ala Met Ala Arg Gln Ser Arg Val Asn Leu Asp Val Ala Arg Tyr
            115                 120                 125

Asp Tyr Trp Gly Gln Gly Thr Leu Val Thr Val Ser Ser Glu Ser Lys
    130                 135                 140

Tyr Gly Pro Pro Cys Pro Ser Cys Pro Ala Pro Glu Phe Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser Gln Glu
                180                 185                 190

Asp Pro Glu Val Gln Phe Asn Trp Tyr Val Asp Gly Val Glu Val His
            195                 200                 205

Asn Ala Lys Thr Lys Pro Arg Glu Glu Gln Phe Asn Ser Thr Tyr Arg
210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Lys Pro Pro Ser Gln Glu Glu Met Thr Lys Asn Gln Val Ser Leu
    275                 280                 285

Ser Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Val Pro Val
305                 310                 315                 320

Leu Asp Ser Asp Gly Ser Phe Arg Leu Ala Ser Tyr Leu Thr Val Asp
                325                 330                 335

Lys Ser Arg Trp Gln Glu Gly Asn Val Phe Ser Cys Ser Val Met His
            340                 345                 350

Glu Ala Leu His Asn His Tyr Thr Gln Lys Ser Leu Ser Leu Ser Leu
    355                 360                 365

Gly Lys Gly Gly Gly Gly Ser Gly Gly Gly Ser Gly Gly Gly Gly
370                 375                 380

Ser Gly Gly Gly Ser Gly Gly Gly Ser Ser Glu Thr Gln Ala
385                 390                 395                 400

Asn Ser Thr Thr Asp Ala Leu Asn Val Leu Ile Ile Val Asp Asp
                405                 410                 415

Leu Arg Pro Ser Leu Gly Cys Tyr Gly Asp Lys Leu Val Arg Ser Pro
                420                 425                 430

Asn Ile Asp Gln Leu Ala Ser His Ser Leu Leu Phe Gln Asn Ala Phe
            435                 440                 445

Ala Gln Gln Ala Val Cys Ala Pro Ser Arg Val Ser Phe Leu Thr Gly
    450                 455                 460
```

-continued

```
Arg Arg Pro Asp Thr Thr Arg Leu Tyr Asp Phe Asn Ser Tyr Trp Arg
465                 470                 475                 480

Val His Ala Gly Asn Phe Ser Thr Ile Pro Gln Tyr Phe Lys Glu Asn
                485                 490                 495

Gly Tyr Val Thr Met Ser Val Gly Lys Val Phe His Pro Gly Ile Ser
            500                 505                 510

Ser Asn His Thr Asp Asp Ser Pro Tyr Ser Trp Ser Phe Pro Pro Tyr
        515                 520                 525

His Pro Ser Ser Glu Lys Tyr Glu Asn Thr Lys Thr Cys Arg Gly Pro
    530                 535                 540

Asp Gly Glu Leu His Ala Asn Leu Leu Cys Pro Val Asp Val Leu Asp
545                 550                 555                 560

Val Pro Glu Gly Thr Leu Pro Asp Lys Gln Ser Thr Glu Gln Ala Ile
                565                 570                 575

Gln Leu Leu Glu Lys Met Lys Thr Ser Ala Ser Pro Phe Phe Leu Ala
            580                 585                 590

Val Gly Tyr His Lys Pro His Ile Pro Phe Arg Tyr Pro Lys Glu Phe
        595                 600                 605

Gln Lys Leu Tyr Pro Leu Glu Asn Ile Thr Leu Ala Pro Asp Pro Glu
    610                 615                 620

Val Pro Asp Gly Leu Pro Pro Val Ala Tyr Asn Pro Trp Met Asp Ile
625                 630                 635                 640

Arg Gln Arg Glu Asp Val Gln Ala Leu Asn Ile Ser Val Pro Tyr Gly
                645                 650                 655

Pro Ile Pro Val Asp Phe Gln Arg Lys Ile Arg Gln Ser Tyr Phe Ala
            660                 665                 670

Ser Val Ser Tyr Leu Asp Thr Gln Val Gly Arg Leu Leu Ser Ala Leu
        675                 680                 685

Asp Asp Leu Gln Leu Ala Asn Ser Thr Ile Ile Ala Phe Thr Ser Asp
    690                 695                 700

His Gly Trp Ala Leu Gly Glu His Gly Glu Trp Ala Lys Tyr Ser Asn
705                 710                 715                 720

Phe Asp Val Ala Thr His Val Pro Leu Ile Phe Tyr Val Pro Gly Arg
                725                 730                 735

Thr Ala Ser Leu Pro Glu Ala Gly Glu Lys Leu Phe Pro Tyr Leu Asp
            740                 745                 750

Pro Phe Asp Ser Ala Ser Gln Leu Met Glu Pro Gly Arg Gln Ser Met
        755                 760                 765

Asp Leu Val Glu Leu Val Ser Leu Phe Pro Thr Leu Ala Gly Leu Ala
    770                 775                 780

Gly Leu Gln Val Pro Pro Arg Cys Pro Val Pro Ser Phe His Val Glu
785                 790                 795                 800

Leu Cys Arg Glu Gly Lys Asn Leu Leu Lys His Phe Arg Phe Arg Asp
                805                 810                 815

Leu Glu Glu Asp Pro Tyr Leu Pro Gly Asn Pro Arg Glu Leu Ile Ala
            820                 825                 830

Tyr Ser Gln Tyr Pro Arg Pro Ser Asp Ile Pro Gln Trp Asn Ser Asp
        835                 840                 845

Lys Pro Ser Leu Lys Asp Ile Lys Ile Met Gly Tyr Ser Ile Arg Thr
    850                 855                 860

Ile Asp Tyr Arg Tyr Thr Val Trp Val Gly Phe Asn Pro Asp Glu Phe
865                 870                 875                 880

Leu Ala Asn Phe Ser Asp Ile His Ala Gly Glu Leu Tyr Phe Val Asp
```

885                 890                 895
Ser Asp Pro Leu Gln Asp His Asn Met Tyr Asn Asp Ser Gln Gly Gly
            900                 905                 910

Asp Leu Phe Gln Leu Leu Met Pro
            915                 920

<210> SEQ ID NO 65
<211> LENGTH: 909
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens
<220> FEATURE:
<223> OTHER INFORMATION: Yarrowia Lipolytica

<400> SEQUENCE: 65

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Thr Arg Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Ser Glu Ser Lys Tyr
        115                 120                 125

Gly Pro Pro Cys Pro Ser Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Lys Pro Pro Ser Gln Glu Glu Met Thr Lys Asn Gln Val Ser Leu Ser
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Val Pro Val Leu

```
            290                 295                 300
Asp Ser Asp Gly Ser Phe Arg Leu Ala Ser Tyr Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
                340                 345                 350

Lys Gly Gly Gly Ser Gly Gly Gly Ser Gly Gly Gly Gly Ser
                355                 360                 365

Gly Gly Gly Gly Ser Gly Gly Gly Ser Ser Glu Thr Gln Ala Asn
        370                 375                 380

Ser Thr Thr Asp Ala Leu Asn Val Leu Leu Ile Ile Val Asp Asp Leu
385                 390                 395                 400

Arg Pro Ser Leu Gly Cys Tyr Gly Asp Lys Leu Val Arg Ser Pro Asn
                405                 410                 415

Ile Asp Gln Leu Ala Ser His Ser Leu Leu Phe Gln Asn Ala Phe Ala
                420                 425                 430

Gln Gln Ala Val Cys Ala Pro Ser Arg Val Ser Phe Leu Thr Gly Arg
                435                 440                 445

Arg Pro Asp Thr Thr Arg Leu Tyr Asp Phe Asn Ser Tyr Trp Arg Val
                450                 455                 460

His Ala Gly Asn Phe Ser Thr Ile Pro Gln Tyr Phe Lys Glu Asn Gly
465                 470                 475                 480

Tyr Val Thr Met Ser Val Gly Lys Val Phe His Pro Gly Ile Ser Ser
                485                 490                 495

Asn His Thr Asp Asp Ser Pro Tyr Ser Trp Ser Phe Pro Pro Tyr His
                500                 505                 510

Pro Ser Ser Glu Lys Tyr Glu Asn Thr Lys Thr Cys Arg Gly Pro Asp
                515                 520                 525

Gly Glu Leu His Ala Asn Leu Leu Cys Pro Val Asp Val Leu Asp Val
530                 535                 540

Pro Glu Gly Thr Leu Pro Asp Lys Gln Ser Thr Glu Gln Ala Ile Gln
545                 550                 555                 560

Leu Leu Glu Lys Met Lys Thr Ser Ala Ser Pro Phe Phe Leu Ala Val
                565                 570                 575

Gly Tyr His Lys Pro His Ile Pro Phe Arg Tyr Pro Lys Glu Phe Gln
                580                 585                 590

Lys Leu Tyr Pro Leu Glu Asn Ile Thr Leu Ala Pro Asp Pro Glu Val
                595                 600                 605

Pro Asp Gly Leu Pro Pro Val Ala Tyr Asn Pro Trp Met Asp Ile Arg
610                 615                 620

Gln Arg Glu Asp Val Gln Ala Leu Asn Ile Ser Val Pro Tyr Gly Pro
625                 630                 635                 640

Ile Pro Val Asp Phe Gln Arg Lys Ile Arg Gln Ser Tyr Phe Ala Ser
                645                 650                 655

Val Ser Tyr Leu Asp Thr Gln Val Gly Arg Leu Leu Ser Ala Leu Asp
                660                 665                 670

Asp Leu Gln Leu Ala Asn Ser Thr Ile Ile Ala Phe Thr Ser Asp His
                675                 680                 685

Gly Trp Ala Leu Gly Glu His Gly Glu Trp Ala Lys Tyr Ser Asn Phe
        690                 695                 700

Asp Val Ala Thr His Val Pro Leu Ile Phe Tyr Val Pro Gly Arg Thr
705                 710                 715                 720
```

```
Ala Ser Leu Pro Glu Ala Gly Glu Lys Leu Phe Pro Tyr Leu Asp Pro
            725                 730                 735

Phe Asp Ser Ala Ser Gln Leu Met Glu Pro Gly Arg Gln Ser Met Asp
        740                 745                 750

Leu Val Glu Leu Val Ser Leu Phe Pro Thr Leu Ala Gly Leu Ala Gly
            755                 760                 765

Leu Gln Val Pro Pro Arg Cys Pro Val Pro Ser Phe His Val Glu Leu
770                 775                 780

Cys Arg Glu Gly Lys Asn Leu Leu Lys His Phe Arg Phe Arg Asp Leu
785                 790                 795                 800

Glu Glu Asp Pro Tyr Leu Pro Gly Asn Pro Arg Glu Leu Ile Ala Tyr
                805                 810                 815

Ser Gln Tyr Pro Arg Pro Ser Asp Ile Pro Gln Trp Asn Ser Asp Lys
                820                 825                 830

Pro Ser Leu Lys Asp Ile Lys Ile Met Gly Tyr Ser Ile Arg Thr Ile
            835                 840                 845

Asp Tyr Arg Tyr Thr Val Trp Val Gly Phe Asn Pro Asp Glu Phe Leu
        850                 855                 860

Ala Asn Phe Ser Asp Ile His Ala Gly Glu Leu Tyr Phe Val Asp Ser
865                 870                 875                 880

Asp Pro Leu Gln Asp His Asn Met Tyr Asn Asp Ser Gln Gly Gly Asp
                885                 890                 895

Leu Phe Gln Leu Leu Met Pro His His His His His
            900                 905

<210> SEQ ID NO 66
<211> LENGTH: 517
<212> TYPE: PRT
<213> ORGANISM: Homo sapiens

<400> SEQUENCE: 66

Thr Asp Ala Leu Asn Val Leu Leu Ile Ile Val Asp Asp Leu Arg Pro
1               5                   10                  15

Ser Leu Gly Cys Tyr Gly Asp Lys Leu Val Arg Ser Pro Asn Ile Asp
            20                  25                  30

Gln Leu Ala Ser His Ser Leu Leu Phe Gln Asn Ala Phe Ala Gln Gln
        35                  40                  45

Ala Val Cys Ala Pro Ser Arg Val Ser Phe Leu Thr Gly Arg Arg Pro
    50                  55                  60

Asp Thr Thr Arg Leu Tyr Asp Phe Asn Ser Tyr Trp Arg Val His Ala
65                  70                  75                  80

Gly Asn Phe Ser Thr Ile Pro Gln Tyr Phe Lys Glu Asn Gly Tyr Val
                85                  90                  95

Thr Met Ser Val Gly Lys Val Phe His Pro Gly Ile Ser Ser Asn His
            100                 105                 110

Thr Asp Asp Ser Pro Tyr Ser Trp Ser Phe Pro Pro Tyr His Pro Ser
        115                 120                 125

Ser Glu Lys Tyr Glu Asn Thr Lys Thr Cys Arg Gly Pro Asp Gly Glu
    130                 135                 140

Leu His Ala Asn Leu Leu Cys Pro Val Asp Val Leu Asp Val Pro Glu
145                 150                 155                 160

Gly Thr Leu Pro Asp Lys Gln Ser Thr Glu Gln Ala Ile Gln Leu Leu
                165                 170                 175

Glu Lys Met Lys Thr Ser Ala Ser Pro Phe Phe Leu Ala Val Gly Tyr
```

```
            180                 185                 190
His Lys Pro His Ile Pro Phe Arg Tyr Pro Lys Glu Phe Gln Lys Leu
            195                 200                 205

Tyr Pro Leu Glu Asn Ile Thr Leu Ala Pro Asp Pro Glu Val Pro Asp
    210                 215                 220

Gly Leu Pro Pro Val Ala Tyr Asn Pro Trp Met Asp Ile Arg Gln Arg
225                 230                 235                 240

Glu Asp Val Gln Ala Leu Asn Ile Ser Val Pro Tyr Gly Pro Ile Pro
                245                 250                 255

Val Asp Phe Gln Arg Lys Ile Arg Gln Ser Tyr Phe Ala Ser Val Ser
            260                 265                 270

Tyr Leu Asp Thr Gln Val Gly Arg Leu Leu Ser Ala Leu Asp Asp Leu
    275                 280                 285

Gln Leu Ala Asn Ser Thr Ile Ile Ala Phe Thr Ser Asp His Gly Trp
290                 295                 300

Ala Leu Gly Glu His Gly Glu Trp Ala Lys Tyr Ser Asn Phe Asp Val
305                 310                 315                 320

Ala Thr His Val Pro Leu Ile Phe Tyr Val Pro Gly Arg Thr Ala Ser
                325                 330                 335

Leu Pro Glu Ala Gly Glu Lys Leu Phe Pro Tyr Leu Asp Pro Phe Asp
            340                 345                 350

Ser Ala Ser Gln Leu Met Glu Pro Gly Arg Gln Ser Met Asp Leu Val
    355                 360                 365

Glu Leu Val Ser Leu Phe Pro Thr Leu Ala Gly Leu Ala Gly Leu Gln
370                 375                 380

Val Pro Pro Arg Cys Pro Val Pro Ser Phe His Val Glu Leu Cys Arg
385                 390                 395                 400

Glu Gly Lys Asn Leu Leu Lys His Phe Arg Phe Arg Asp Leu Glu Glu
                405                 410                 415

Asp Pro Tyr Leu Pro Gly Asn Pro Arg Glu Leu Ile Ala Tyr Ser Gln
            420                 425                 430

Tyr Pro Arg Pro Ser Asp Ile Pro Gln Trp Asn Ser Asp Lys Pro Ser
    435                 440                 445

Leu Lys Asp Ile Lys Ile Met Gly Tyr Ser Ile Arg Thr Ile Asp Tyr
    450                 455                 460

Arg Tyr Thr Val Trp Val Gly Phe Asn Pro Asp Glu Phe Leu Ala Asn
465                 470                 475                 480

Phe Ser Asp Ile His Ala Gly Glu Leu Tyr Phe Val Asp Ser Asp Pro
                485                 490                 495

Leu Gln Asp His Asn Met Tyr Asn Asp Ser Gln Gly Gly Asp Leu Phe
            500                 505                 510

Gln Leu Leu Met Pro
            515

<210> SEQ ID NO 67
<211> LENGTH: 585
<212> TYPE: PRT
<213> ORGANISM: Homo sapiens

<400> SEQUENCE: 67

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

```
Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
             100                 105                 110

Pro Arg Leu Val Arg Pro Glu Val Asp Val Met Cys Thr Ala Phe His
             115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                 165                 170                 175

Cys Leu Leu Pro Lys Leu Asp Glu Leu Arg Asp Glu Gly Lys Ala Ser
             180                 185                 190

Ser Ala Lys Gln Arg Leu Lys Cys Ala Ser Leu Gln Lys Phe Gly Glu
         195                 200                 205

Arg Ala Phe Lys Ala Trp Ala Val Ala Arg Leu Ser Gln Arg Phe Pro
     210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                 245                 250                 255

Arg Ala Asp Leu Ala Lys Tyr Ile Cys Glu Asn Gln Asp Ser Ile Ser
             260                 265                 270

Ser Lys Leu Lys Glu Cys Cys Glu Lys Pro Leu Leu Glu Lys Ser His
         275                 280                 285

Cys Ile Ala Glu Val Glu Asn Asp Glu Met Pro Ala Asp Leu Pro Ser
     290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                 325                 330                 335

Arg His Pro Asp Tyr Ser Val Val Leu Leu Leu Arg Leu Ala Lys Thr
             340                 345                 350

Tyr Glu Thr Thr Leu Glu Lys Cys Cys Ala Ala Ala Asp Pro His Glu
         355                 360                 365

Cys Tyr Ala Lys Val Phe Asp Glu Phe Lys Pro Leu Val Glu Glu Pro
     370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                 405                 410                 415

Gln Val Ser Thr Pro Thr Leu Val Glu Val Ser Arg Asn Leu Gly Lys
             420                 425                 430

Val Gly Ser Lys Cys Cys Lys His Pro Glu Ala Lys Arg Met Pro Cys
         435                 440                 445

Ala Glu Asp Tyr Leu Ser Val Val Leu Asn Gln Leu Cys Val Leu His
```

```
                450             455             460
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 68
<211> LENGTH: 497
<212> TYPE: PRT
<213> ORGANISM: Homo sapiens

<400> SEQUENCE: 68

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240
```

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 69
<211> LENGTH: 355
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 69

Gln Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Phe Ser Met Asp
            20                  25                  30

Pro Met Ala Trp Phe Arg Gln Pro Pro Gly Lys Glu Arg Glu Phe Val
        35                  40                  45

Ala Ala Gly Ser Ser Thr Gly Arg Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

-continued

```
Leu Gln Met Asn Ser Leu Lys Pro Glu Asp Thr Ala Val Tyr Tyr Cys
                85                  90                  95

Ala Ala Ala Pro Tyr Gly Ala Asn Trp Tyr Arg Asp Glu Tyr Ala Tyr
            100                 105                 110

Trp Gly Gln Gly Thr Gln Val Thr Val Ser Ser Ala Glu Pro Lys Ser
            115                 120                 125

Ser Asp Lys Thr His Thr Cys Pro Pro Cys Pro Ala Pro Glu Leu Leu
        130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Gly Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly
        355

<210> SEQ ID NO 70
<211> LENGTH: 365
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
<220> FEATURE:
<223> OTHER INFORMATION: Homo Sapiens

<400> SEQUENCE: 70

Ala Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Gly Pro Glu Val Lys Phe Asn Trp Tyr
    50                  55                  60
```

```
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Gly Gly Gly Ser Gly Gly Gly Gly
225                 230                 235                 240

Ser Gln Val Gln Leu Val Glu Ser Gly Gly Gly Leu Val Gln Pro Gly
                245                 250                 255

Gly Ser Leu Arg Leu Ser Cys Ala Ala Ser Gly Arg Thr Ile Asp Asn
            260                 265                 270

Tyr Ala Met Ala Trp Val Arg Gln Ala Pro Gly Lys Gly Leu Glu Trp
        275                 280                 285

Val Ala Thr Ile Asp Trp Gly Asp Gly Gly Thr Arg Tyr Ala Asn Ser
    290                 295                 300

Val Lys Gly Arg Phe Thr Ile Ser Arg Asp Asn Ser Lys Asn Thr Met
305                 310                 315                 320

Tyr Leu Gln Met Asn Ser Leu Arg Ala Glu Asp Thr Ala Val Tyr Tyr
                325                 330                 335

Cys Ala Met Ala Arg Gln Ser Arg Val Asn Leu Asp Val Ala Arg Tyr
            340                 345                 350

Asp Tyr Trp Gly Gln Gly Thr Leu Val Thr Val Ser Ser
        355                 360                 365
```